US007598382B2

(12) United States Patent
Hays et al.

(10) Patent No.: US 7,598,382 B2
(45) Date of Patent: Oct. 6, 2009

(54) ARYL SUBSTITUTED IMIDAZOQUINOLINES

(75) Inventors: David S. Hays, Woodbury, MN (US); Tushar Kshirsagar, Woodbury, MN (US); Philip D. Heppner, Forest Lake, MN (US); Bryon A. Merrill, River Falls, WI (US); Michael E. Danielson, St. Paul, MN (US); John F. Gerster, Woodbury, MI (US); Chad A. Haraldson, Apple Valley, MN (US); Sarah Johannessen, Maplewood, MN (US); Maureen A. Kavanagh, Stanchfield, MN (US); Kyle J. Lindstrom, Houlton, WI (US); Michael J. Rice, Oakdale, MN (US); David J. Squire, Houlton, WI (US); Sarah A. Strong, Eagan, MN (US); Joshua R. Wurst, North St. Paul, MN (US)

(73) Assignee: Coley Pharmaceutical Group, Inc., New York, NY (US)

( * ) Notice: Subject to any disclaimer, the term of this patent is extended or adjusted under 35 U.S.C. 154(b) by 135 days.

(21) Appl. No.: 11/275,553

(22) Filed: Jan. 13, 2006

(65) Prior Publication Data
US 2006/0111387 A1 May 25, 2006

Related U.S. Application Data

(62) Division of application No. 10/739,787, filed on Dec. 18, 2003, now Pat. No. 7,091,214.

(60) Provisional application No. 60/435,889, filed on Dec. 20, 2002, provisional application No. 60/516,331, filed on Oct. 31, 2003.

(51) Int. Cl.
*C07D 471/00* (2006.01)
(52) U.S. Cl. .............................. 546/82; 546/83; 546/84
(58) Field of Classification Search .................... 546/82, 546/83, 84
See application file for complete search history.

(56) References Cited

U.S. PATENT DOCUMENTS

| 3,314,941 | A | 4/1967 | Littell et al. |
|---|---|---|---|
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gerster |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster et al. |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,245,776 | B1 | 6/2001 | Skwierczynski et al. |
| 6,331,539 | B1 * | 12/2001 | Crooks et al. ............ 514/228.5 |
| 6,376,669 | B1 | 4/2002 | Rice et al. |
| 6,451,810 | B1 | 9/2002 | Coleman et al. |
| 6,518,265 | B1 | 2/2003 | Kato et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |

(Continued)

FOREIGN PATENT DOCUMENTS

EP 0 389 302 A1 9/1990

(Continued)

OTHER PUBLICATIONS

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner*—D. Margaret Seaman
*Assistant Examiner*—Nizal S Chandrakumar
(74) *Attorney, Agent, or Firm*—Wolf, Greenfield & Sacks, P.C.

(57) ABSTRACT

Aryl substituted imidazoquinoline compounds, pharmaceutical compositions containing the compounds, intermediates, and methods of use of these compounds as immunomodulators, for inducing or inhibiting cytokine biosynthesis in animals and in the treatment of diseases including viral, and neoplastic, are disclosed.

6 Claims, No Drawings

U.S. PATENT DOCUMENTS

| | | | |
|---|---|---|---|
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 * | 1/2004 | Griesgraber | 514/293 |
| 6,683,088 B2 | 1/2004 | Crooks et al. | |
| 6,696,465 B2 | 2/2004 | Dellaria et al. | |
| 6,706,728 B2 | 3/2004 | Hedenstrom et al. | |
| 6,743,920 B2 | 6/2004 | Lindstrom et al. | |
| 6,797,718 B2 | 9/2004 | Dellaria et al. | |
| 6,818,650 B2 | 11/2004 | Griesgraber | |
| 6,888,000 B2 * | 5/2005 | Crooks et al. | 546/82 |
| 6,894,060 B2 | 5/2005 | Slade | |
| 6,924,293 B2 * | 8/2005 | Lindstrom | 514/293 |
| 2002/0055517 A1 | 5/2002 | Smith | |
| 2002/0058674 A1 | 5/2002 | Hedenstrom et al. | |
| 2002/0110840 A1 | 8/2002 | Tomai et al. | |
| 2002/0193729 A1 | 12/2002 | Cormier et al. | |
| 2003/0130299 A1 | 7/2003 | Crooks et al. | |
| 2003/0133913 A1 | 7/2003 | Tomai et al. | |
| 2003/0139364 A1 | 7/2003 | Krieg et al. | |
| 2003/0161797 A1 | 8/2003 | Miller et al. | |
| 2003/0199538 A1 | 10/2003 | Skwierczynski et al. | |
| 2003/0232852 A1 | 12/2003 | Lindstrom et al. | |
| 2004/0010007 A1 | 1/2004 | Dellaria et al. | |
| 2004/0014779 A1 | 1/2004 | Gorden et al. | |
| 2004/0091491 A1 | 5/2004 | Kedl et al. | |
| 2004/0132079 A1 | 7/2004 | Gupta et al. | |
| 2004/0141950 A1 | 7/2004 | Noelle et al. | |
| 2004/0147543 A1 | 7/2004 | Hays et al. | |
| 2004/0162309 A1 | 8/2004 | Gorden et al. | |
| 2004/0171086 A1 | 9/2004 | Fink et al. | |
| 2004/0175336 A1 | 9/2004 | Egging et al. | |
| 2004/0176367 A1 | 9/2004 | Griesgraber et al. | |
| 2004/0180919 A1 | 9/2004 | Miller et al. | |
| 2004/0181130 A1 | 9/2004 | Miller et al. | |
| 2004/0181211 A1 | 9/2004 | Graham et al. | |
| 2004/0191833 A1 | 9/2004 | Fink et al. | |
| 2004/0192585 A1 | 9/2004 | Fox et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2005/0054590 A1 | 3/2005 | Averett | |

FOREIGN PATENT DOCUMENTS

| | | |
|---|---|---|
| JP | 0 394 026 | 10/1990 |
| JP | 9-208584 | 8/1997 |
| JP | 11-80156 | 3/1999 |
| JP | 11-222432 | 8/1999 |
| JP | 2000-247884 | 9/2000 |
| JP | 1 104 764 | 6/2001 |
| WO | WO 00/76518 | 12/2000 |
| WO | WO 00/76519 A1 | 12/2000 |
| WO | WO 01/74343 | 10/2001 |
| WO | WO 02/24225 | 3/2002 |
| WO | WO 02/36592 | 5/2002 |
| WO | WO 02/46188 A2 | 6/2002 |
| WO | WO 02/46194 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |
| WO | WO 03/045494 | 6/2003 |
| WO | WO 03/077944 | 9/2003 |
| WO | WO 03/080114 | 10/2003 |
| WO | WO 03/097641 | 11/2003 |
| WO | WO 03/103584 A2 | 12/2003 |
| WO | WO 2004/091500 | 10/2004 |
| WO | WO 2005/054237 | 6/2005 |
| WO | WO 2005/054238 | 6/2005 |

OTHER PUBLICATIONS

Brennan, et al, "Automated Bioassay of Interferons in Micro-test Plates", *Biotechniques*, June/July, 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

Berényi, et al, "Ring Transformation of Condensed Dihydro-as-triazines", *J. Heterocyclic Chem.*, 18, pp. 1537-1540 (1981).

Chollet, et al, "Development of a Topically Active Imiquimod Formulation", *Pharmaceutical Development and Technology*, 4(1), pp. 35-43 (1999).

Izumi, et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines", *Bioorganic & Medicinal Chemistry*, 11, pp. 2541-2550 (2003).

Wenjie, Li, et al, "An Improved Protocol for the Preparation of 3-Pyridyl-and Some Arylboronic Acids", *J. Org. Chem.*, 67, pp. 5394-5397, 2002.

Carceller, et al, "Design, Synthesis, and Structure-Activity Relationship Studies of novel 1-[(1-Acyl-4-piperidyl)methyl]-1H-2-methylimidazo[4,5-c]pyridine Derivatives as Potent, Orally Active Platelet-Activating Factor Antagonists", *J. Med. Chem.*, 39, pp. 487-493, 1996.

Buckle, et al, "4-Hydroxy-2-nitro-2-quinolones and Related Compounds as Inhibitors of Allergic Reactions", *Journal of Medicinal Chemistry*, vol. 18, No. 7, pp. 726-732, 1975.

\* cited by examiner

ARYL SUBSTITUTED IMIDAZOQUINOLINES

CROSS-REFERENCE TO RELATED APPLICATIONS

The present application is a divisional of U.S. application Ser. No. 10/739,787, filed on Dec. 18, 2003 now U.S. Pat. No. 7,091,214, now allowed, which claims priority to U.S. Provisional Patent Application Ser. No. 60/435,889, filed on Dec. 20, 2002, and to U.S. Provisional Patent Application Ser. No. 60/516,331, filed on Oct. 31, 2003, which are both incorporated herein by reference in their entirety.

FIELD OF THE INVENTION

This invention relates to derivatives of imidazoquinoline compounds and to pharmaceutical compositions containing the compounds. A further aspect of this invention relates to the use of these compounds as immunomodulators, for inducing cytokine biosynthesis in animals and in the treatment of diseases including viral and neoplastic diseases.

BACKGROUND OF THE INVENTION

The first reliable report on the 1H-imidazo[4,5-c]quinoline ring system, Backman et al., *J. Org. Chem.*, 15, 1278-1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.*, 11, 87-92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.*, 85, 94362 (1976), have reported several 2-oxoimidazo[4,5-c]quinolines, and Berenyi et al., *J. Heterocyclic Chem.*, 18, 1537-1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640.

There continues to be interest in the imidazoquinoline ring system and there is a continuing need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

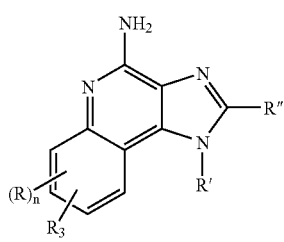

and more specifically of the following Formula (II):

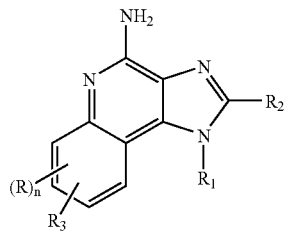

wherein: R, n, R', R", $R_1$, $R_2$, and $R_3$ are as defined below.

The compounds of Formulas I and II are useful as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human PBMC in a culture with the compound(s) at a concentration range of 30 to 0.014 μM and analyzing for interferon ($\alpha$) or tumor necrosis factor ($\alpha$) in the culture supernatant. Compounds can be tested for inhibition of cytokine biosynthesis by incubating mouse macrophage cell line Raw 264.7 in a culture with the compound(s) at a single concentration of, for example, 5 μM and analyzing for tumor necrosis factor ($\alpha$) in the culture supernatant. Compounds can be further tested for dose response by running the test at several compound concentrations, for example, 0.03, 0.1, 0.3, 1, 3, 5, and 10 μM. The ability to modulate cytokine biosynthesis makes the compounds useful in the treatment of a variety of conditions such as viral diseases, neoplastic diseases, and autoimmune diseases that are responsive to such changes in the immune response.

In another aspect, the present invention provides pharmaceutical compositions containing the immune response modifier compounds, and methods of modulating (e.g., inducing or inhibiting) cytokine biosynthesis in an animal, treating a viral disease in an animal, and treating a neoplastic disease in an animal, by administering an effective amount of one or more compounds of Formula I (and more specifically, of Formula II) and/or pharmaceutically acceptable salts thereof to the animal.

In another aspect, the invention provides methods of synthesizing compounds of Formulas I and II and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula (I):

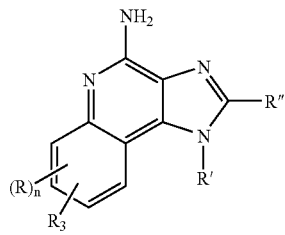

wherein:

R is selected from the group consisting of alkyl, alkoxy, hydroxy, and trifluoromethyl;

n is 0 or 1;

R' and R" are independently selected from the group consisting of hydrogen and non-interfering substitutents;

$R_3$ is selected from the group consisting of:

—Z-Ar,
—Z-Ar'—Y—$R_4$,
—Z-Ar'—X—Y—$R_4$,
—Z-Ar'—$R_5$, and
—Z-Ar'—X—$R_5$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:

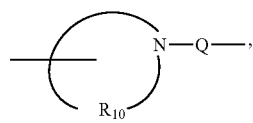

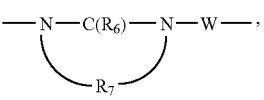

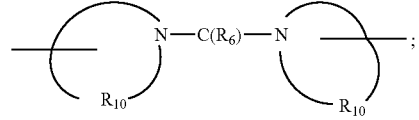

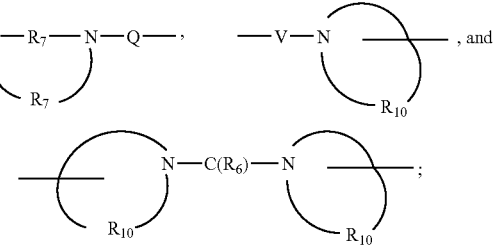

Z is selected from the group consisting of a bond, alkylene, alkenylene, and alkynylene;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

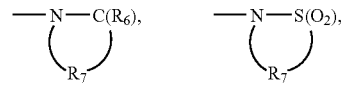

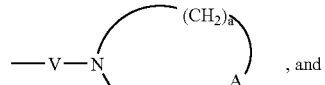

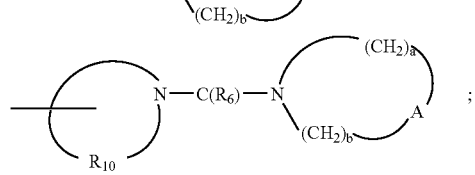

$R_6$ is selected from the group consisting of =O and =S;

each $R_7$ is independently $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

each $R_{10}$ is independently $C_{3-8}$ alkylene;

A is selected from the group consisting of —O—, —C(O)—, —S(O)$_{0-2}$—, —CH$_2$—, and —N($R_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

For certain embodiments of Formula I, n is 0 and —Z— is a bond. For certain embodiments of Formula I, R$_3$ is —Z-Ar, and for certain other embodiments, R$_3$ is —Z-Ar'—Y—R$_4$ or —Z-Ar'—X—Y—R$_4$.

For some embodiments of Formula I, R' is selected from the group consisting of:
—R$_4$,
—X—R$_4$,
—X—Y—R$_4$,
—X—Y—X—Y—R$_4$, and
—X—R$_5$;

wherein each X is independently selected, each Y is independently selected, each R$_4$ is independently selected, and each R$_5$ is independently selected.

For some embodiments of Formula I, R'' is selected from the group consisting of:
—R$_4$,
—X—R$_4$,
—X—Y—R$_4$, and
—X—R$_5$;

wherein each X is independently selected, each Y is independently selected, each R$_4$ is independently selected, and each R$_5$ is independently selected.

The present invention also provides compounds of the following Formula (II):

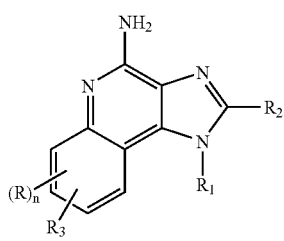

II wherein:
R is selected from the group consisting of alkyl, alkoxy, hydroxy, and trifluoromethyl;
n is 0 or 1;
R$_1$ is selected from the group consisting of:
—R$_4$,
—X—R$_4$,
—X—Y—R$_4$,
—X—Y—X—Y—R$_4$, and
—X—R$_5$;
R$_2$ is selected from the group consisting of:
—R$_4$,
—X—R$_4$,
—X—Y—R$_4$, and
—X—R$_5$;
R$_3$ is selected from the group consisting of:

—Z-Ar,
—Z-Ar'—Y—R$_4$,
—Z-Ar'—X—Y—R$_4$,
—Z-Ar'—R$_5$, and
—Z-Ar'—X—R$_5$;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

—S(O)$_{0-2}$—,   —S(O)$_2$—N(R$_8$)—,
—C(R$_6$)—,   —C(R$_6$)—O—,
—O—C(R$_6$)—,   —O—C(O)—O—,
—N(R$_8$)—Q—,   —C(R$_6$)—N(R$_8$)—,
—O—C(R$_6$)—N(R$_8$)—,   —C(R$_6$)—N(OR$_9$)—,

—N—Q—
  |
  R$_{10}$  (in ring),

—N—C(R$_6$)—N—W—
  |
  R$_7$  (in ring),

—N—R$_7$—N—Q—
  |
  R$_7$  ,   —V—N— , and
                |
                R$_{10}$ (in ring)

—N—C(R$_6$)—N—
  |           |
  R$_{10}$    R$_{10}$  ;

Z is selected from the group consisting of a bond, alkylene, alkenylene, and alkynylene;

each R$_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

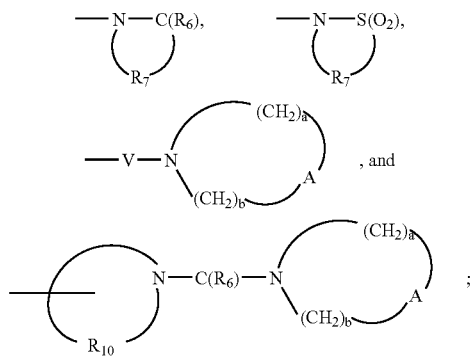

each $R_6$ is independently selected from the group consisting of =O and =S;

each $R_7$ is independently $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

each $R_{10}$ is independently $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

or a pharmaceutically acceptable salt thereof.

In some embodiments of Formula II, $R_1$ is selected from the group consisting of alkyl, arylalkylenyl, aryloxyalkylenyl, hydroxyalkyl, alkylsulfonylalkylenyl, —X—Y—R$_4$, and —X—R$_5$; wherein X is alkylene; Y is selected from the group consisting of —N(R$_8$)—C(O)—, —N(R$_8$)—S(O)$_2$—, —N(R$_8$)—C(O)—N(R$_8$)—, and

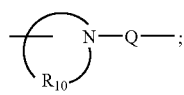

$R_4$ is selected from the group consisting of alkyl, aryl, and heteroaryl; and $R_5$ is selected from the group consisting of

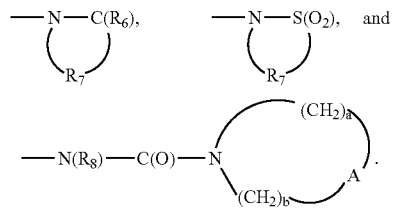

In some embodiments of Formula II, $R_2$ is selected from the group consisting of hydrogen, alkyl, and alkoxyalkylenyl.

For some embodiments of Formula II, n is 0 and —Z— is a bond. For some embodiments of Formula II, $R_3$ is —Z-Ar, and for certain of these embodiments, $R_3$ is selected from the group consisting of phenyl, pyridyl, pyrrolyl, thienyl, and furyl; each of which can be unsubstituted or can be substituted by one or more substituents selected from the group consisting of halogen, alkyl, hydroxy, hydroxyalkyl, alkoxy, carboxy, and cyano.

For some embodiments of Formula II, $R_3$ is —Z-Ar'—Y—R$_4$, —Z-Ar'—X—Y—R$_4$, or —Z-Ar'—R$_5$, and for certain of these embodiments, Ar' is phenyl or pyridyl;

Y is selected from the group consisting of:
—S(O)$_{0-2}$—
—C(O)—,
—N(R$_8$)—Q—,
—C(R$_6$)—N(R$_8$)—, and
—C(R$_6$)—N(OR$_9$)—;

wherein Q is selected from the group consisting of a bond, —C(O)—, and —S(O)$_2$—; $R_8$ is selected from the group consisting of hydrogen, $C_{1-4}$ alkyl, and alkoxyalkylenyl;

X is $C_{1-4}$ alkylene;

$R_4$ is selected from the group consisting of alkyl, aryl, heteroaryl, and heterocyclyl; and $R_5$ is

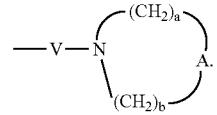

The present invention also provides compounds of the following Formula (IIa):

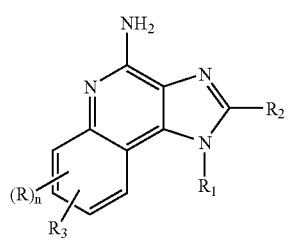

wherein:

R is selected from the group consisting of alkyl, alkoxy, hydroxy, and trifluoromethyl;

n is 0 or 1;

$R_1$ is selected from the group consisting of:
—R$_4$,
—X—R$_4$,

—X—Y—R$_4$,
—X—Y—X—Y—R$_4$, and
—X—R$_5$;
R$_2$ is selected from the group consisting of:
—R$_4$,
—X—R$_4$,
—X—Y—R$_4$, and
—X—R$_5$;
R$_3$ is selected from the group consisting of:
—Z-Ar and
—Z-Ar'—Y—R$_4$;
each X is independently selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups;
each Y is independently selected from the group consisting of:

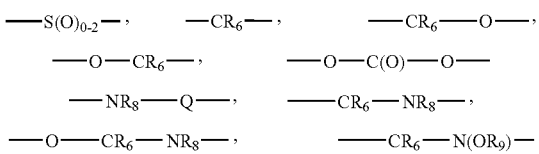

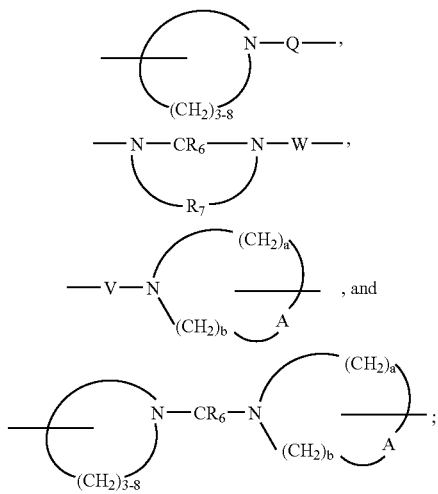

Z is selected from the group consisting of a bond, alkylene, alkenylene, and alkynylene;
Ar is selected from the group consisting of aryl and heteroaryl both of which can be unsubstituted or can be substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
Ar' is selected from the group consisting of arylene and heteroarylene both of which can be unsubstituted or can be substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
each R$_4$ is independently selected from the group consisting of hydrogen, alkyl, alkenyl, alkynyl, aryl, heteroaryl, heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, dialkylamino, and in the case of alkyl, alkenyl, alkynyl, and heterocyclyl, oxo;
each R$_5$ is independently selected from the group consisting of:

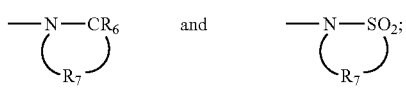

R$_6$ is selected from the group consisting of =O and =S;
R$_7$ is C$_{2-7}$ alkylene;
each R$_8$ present is independently selected from the group consisting of hydrogen, alkyl, and arylalkyl;
R$_9$ is selected from the group consisting of hydrogen and alkyl;
A is selected from the group consisting of —O—, —S(O)$_{0-2}$—, —NR$_4$—, and —CH$_2$—;
Q is selected from the group consisting of —CR$_6$—, —SO$_2$—, —CR$_6$—NR$_8$—W—, —SO$_2$—NR$_8$—, —CR$_6$—O—, and —CR$_6$—N(OR$_9$)—;
V is selected from the group consisting of —CR$_6$—, —O—CR$_6$—, and —NR$_8$—CR$_6$—;
W is selected from the group consisting of a bond, —C(O)—, and —SO$_2$—; and
a and b are independently integers from 1 to 6 with the proviso that a+b is ≦7;
or a pharmaceutically acceptable salt thereof.
For certain embodiments of Formula IIa, n is 0 and the R$_1$, R$_2$, and R$_3$ groups are defined as follows: R$_1$ is R$_4$ or —X—Y—R$_4$, R$_1$ is alkyl or hydroxyalkyl, —X— is C$_{2-6}$ alkylene, and —Y— is —S(O)$_{0-2}$— or —NR$_8$—Q—; R$_2$ is R$_4$ or R$_2$ is alkyl or alkoxyalkyl; R$_3$ is —Z-Ar, —Z— is a bond, -Ar is unsubstituted aryl or heteroaryl, and more particularly -Ar is phenyl, thienyl or pyridyl; and R$_3$ is attached at the 7-position or 8-position per the following numbering scheme.

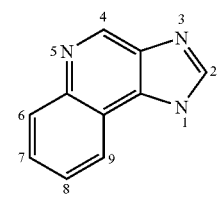

The present invention also provides compounds of the following Formula (III), which include a sulfonamide functional group:

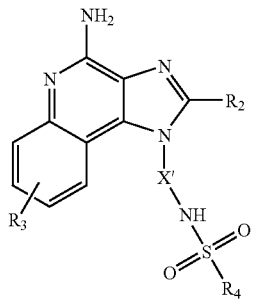

wherein:

R₂ is selected from the group consisting of:
—R₄,
—X—R₄,
—X—Y—R₄, and
—X—R₅;

R₃ is selected from the group consisting of:
—Z-Ar,
—Z-Ar'—Y—R₄,
—Z-Ar'—X—Y—R₄,
—Z-Ar'—R₅, and
—Z-Ar'—X—R₅;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

X' is $C_{2-8}$ alkylene;

each Y is independently selected from the group consisting of:

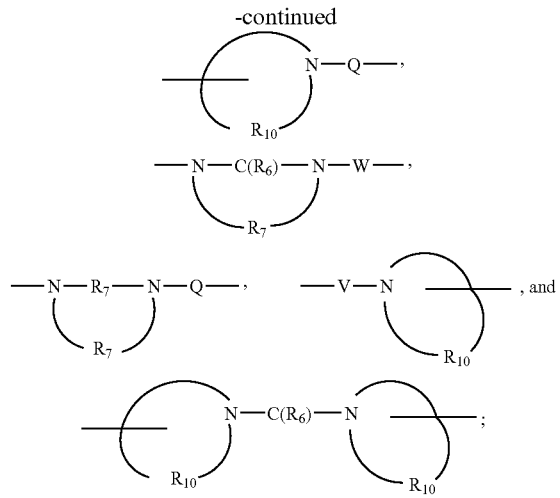

Z is selected from the group consisting of a bond, alkylene, alkenylene, and alkynylene;

each R₄ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each R₅ is independently selected from the group consisting of:

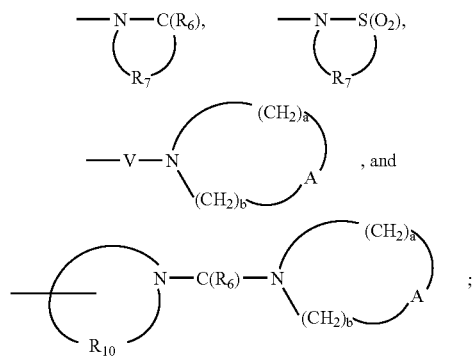

each R₆ is independently selected from the group consisting of =O and =S;

each R₇ is independently $C_{2-7}$ alkylene;

R₈ is selected from the group consisting of hydrogen, alkyl, alkoxyalkylenyl, and arylalkylenyl;

R₉ is selected from the group consisting of hydrogen and alkyl;

each R₁₀ is independently $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

For certain embodiments of Formula III, X' is —CH$_2$—C(CH$_3$)$_2$—.

For certain embodiments of Formula III, R$_2$ is selected from the group consisting of hydrogen, C$_{1-4}$ alkyl, and C$_{1-4}$ alkyl-O—C$_{1-4}$ alkylenyl.

For certain embodiments of Formula III, R$_4$ is selected from the group consisting of alkyl, aryl, and heteroaryl.

For certain embodiments of Formula III, R$_3$ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

The present invention also provides compounds of the following Formula (IV), which include an amide functional group:

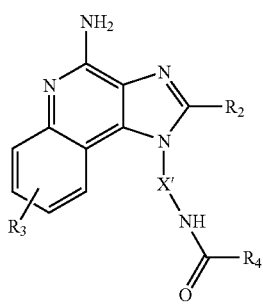

wherein R$_2$, R$_3$, R$_4$, and X' are the same as that for Formula III listed above; or a pharmaceutically acceptable salt thereof.

For certain embodiments of Formula IV, X' is —CH$_2$—C(CH$_3$)$_2$—.

For certain embodiments of Formula IV, R$_2$ is selected from the group consisting of hydrogen, C$_{1-4}$ alkyl, and C$_{1-4}$ alkyl-O—C$_{1-4}$ alkylenyl.

For certain embodiments of Formula IV, R$_4$ is selected from the group consisting of alkyl, aryl, and heteroaryl.

For certain embodiments of Formula IV, R$_3$ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

The present invention also provides compounds of the following Formula (V), which include a urea functional group:

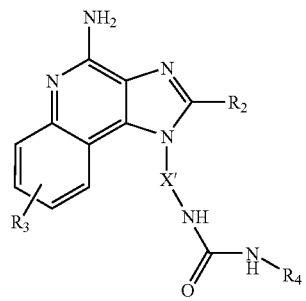

wherein R$_2$, R$_3$, R$_4$, and X' are the same as that for Formula III listed above; or a pharmaceutically acceptable salt thereof.

For certain embodiments of Formula V, X' is —CH$_2$—C(CH$_3$)$_2$—.

For certain embodiments of Formula V, R$_2$ is selected from the group consisting of hydrogen, C$_{1-4}$ alkyl, and C$_{1-4}$ alkyl-O—C$_{1-4}$ alkylenyl.

For certain embodiments of Formula V, R$_4$ is selected from the group consisting of alkyl, aryl, and heteroaryl.

For certain embodiments of Formula V, R$_3$ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

The present invention also provides compounds of the following Formula (VI), which include a piperidine moiety:

wherein R$_2$, R$_3$, R$_4$, Q, and X' are the same as that for Formula III listed above; or a pharmaceutically acceptable salt thereof.

For certain embodiments of Formula VI, Q is selected from the group consisting of —C(O)—, —S(O)$_2$—, and —C(O)—NH—.

For certain embodiments of Formula VI, R$_2$ is selected from the group consisting of hydrogen, C$_{1-4}$ alkyl, and C$_{1-4}$ alkyl-O—C$_{1-4}$ alkylenyl.

For certain embodiments of Formula VI, R₄ is selected from the group consisting of alkyl, aryl, and heteroaryl.

For certain embodiments of Formula VI, R₃ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

The present invention also provides compounds of the following Formula (VII):

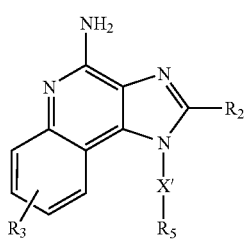

VII wherein R₂, R₃, R₅, and X' are the same as that for Formula III listed above; or a pharmaceutically acceptable salt thereof.

For certain embodiments of Formula VII, R₂ is selected from the group consisting of hydrogen, C$_{1-4}$ alkyl, and C$_{1-4}$ alkyl-O—C$_{1-4}$ alkylenyl.

For certain embodiments of Formula VII, R₃ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

For certain embodiments of Formula VII, R₅ is selected from the group consisting of:

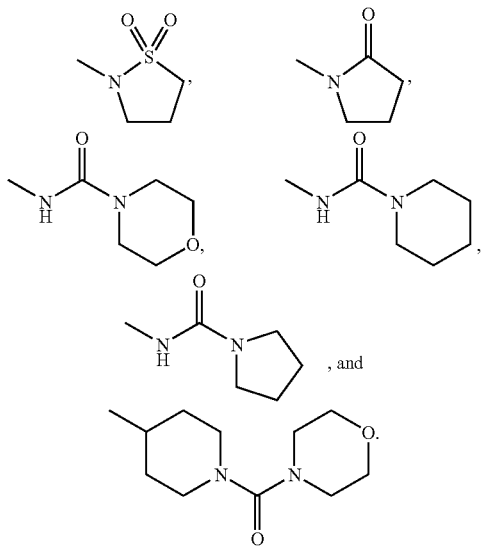

The present invention also provides compounds of the following Formula (VIII):

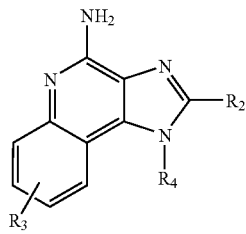

VIII wherein R₂, R₃, and R₄ are the same as that for Formula III listed above; or a pharmaceutically acceptable salt thereof.

For certain embodiments of Formula VIII, R₂ is selected from the group consisting of hydrogen, C$_{1-4}$ alkyl, and C$_{1-4}$ alkyl-O—C$_{1-4}$ alkylenyl.

For certain embodiments of Formula VIII, R₃ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

For certain embodiments of Formula VIII, R₄ is selected from the group consisting of C$_{1-6}$ alkyl, C$_{1-6}$ hydroxyalkyl, C$_{1-4}$ alkyl-O—C$_{1-4}$ alkylenyl, and aryl-O—C$_{1-4}$ alkylenyl.

For certain embodiments of Formula VIII, R₄ is selected from the group consisting of 2-methylpropyl, 2-hydroxy-2-methylpropyl, 3-methoxypropyl, and phenoxyethyl.

The present invention also provides a compound of the following Formula (XLVI):

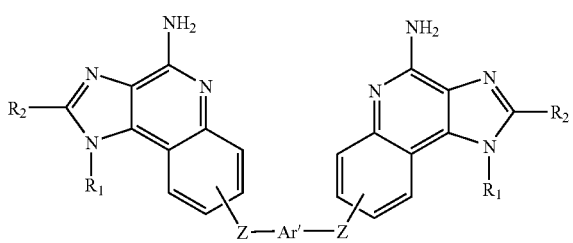

XLVI wherein:
R₁ is selected from the group consisting of:
—R₄,
—X—R₄,
—X—Y—R₄,
—X—Y—X—Y—R₄, and
—X—R₅;
R₂ is selected from the group consisting of:
—R₄,
—X—R₄,
—X—Y—R₄, and
—X—R₅;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:

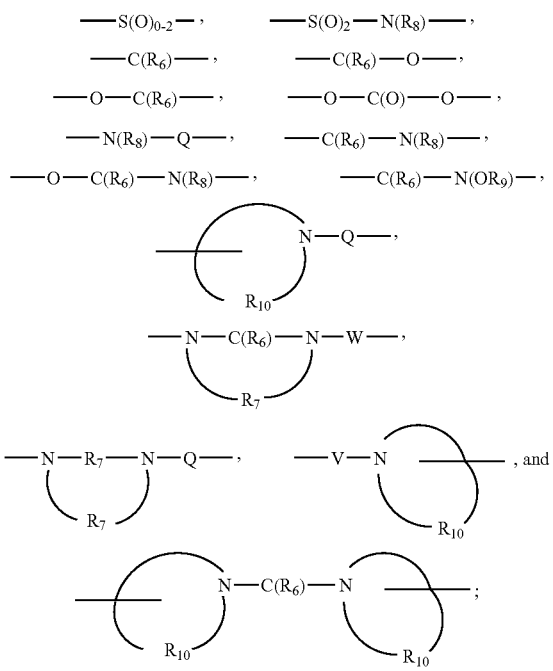

each Z is independently selected from the group consisting of a bond, alkylene, alkenylene, and alkynylene;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

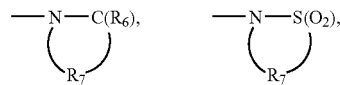

-continued

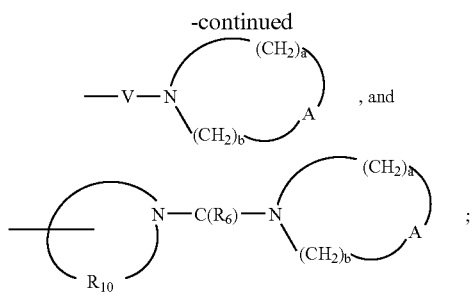

each $R_6$ is independently selected from the group consisting of =O and =S;

each $R_7$ is independently $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl;

each $R_{10}$ is independently $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$), —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is $\leq 7$;

or a pharmaceutically acceptable salt thereof.

For certain embodiments of Formula XLVI, Z is a bond and Ar' is phenylene. For certain embodiments of Formula XLVI, $R_1$ is selected from the group consisting of alkyl, hydroxyalkyl, and —X—Y—R$_4$ wherein X is alkylene, Y is selected from the group consisting of —N(R$_8$)—C(O)—, —N(R$_8$)—S(O)$_2$—, and —N(R$_8$)—C(O)—N(R$_8$)—, and R$_4$ is alkyl. For certain embodiments of Formula XLVI, $R_2$ is selected from the group consisting of hydrogen, alkyl, and alkoxyalkylenyl.

The present invention also provides compounds of the following Formulas XLVII and XLVIII, which are intermediates in the preparation of certain compounds of the present invention:

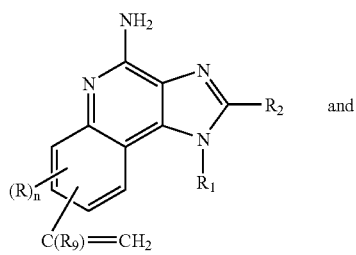

XLVII and

-continued

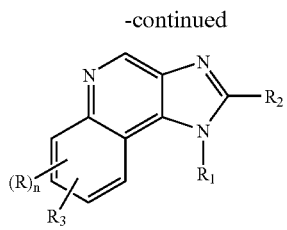

XLVIII wherein:
R is selected from the group consisting of alkyl, alkoxy, hydroxy, and trifluoromethyl;
n is 0 or 1;
$R_1$ is selected from the group consisting of:
—$R_4$,
—X—$R_4$,
—X—Y—$R_4$,
—X—Y—X—Y—$R_4$, and
—X—$R_5$;
$R_2$ is selected from the group consisting of:
—$R_4$,
—X—$R_4$,
—X—Y—$R_4$, and
—X—$R_5$;
$R_3$ is selected from the group consisting of:
—Z-Ar,
—Z-Ar'—Y—$R_4$,
—Z-Ar'—X—Y—$R_4$,
—Z-Ar'—$R_5$, and
—Z-Ar'—X—$R_5$;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
each Y is independently selected from the group consisting of:

—S(O)$_{0-2}$—, —S(O)$_2$—N($R_8$)—,
—C($R_6$)—, —C($R_6$)—O—,
—O—C($R_6$)—, —O—C(O)—O—,
—N($R_8$)—Q—, —C($R_6$)—N($R_8$)—,

—O—C($R_6$)—N($R_8$)—, —C($R_6$)—N(O$R_9$)—, $$\text{—N—Q—}$$
$$R_{10}$$

$$\text{—N—C(R}_6\text{)—N—W—,}$$
$$R_7$$

—N—$R_7$—N—Q—, —V—N     , and
      $R_7$                $R_{10}$

—N—C($R_6$)—N     ;
$R_{10}$            $R_{10}$

Z is selected from the group consisting of a bond, alkylene, alkenylene, and alkynylene;
each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
each $R_5$ is independently selected from the group consisting of:

—N—C($R_6$),   —N—S(O$_2$),
   $R_7$           $R_7$

—V—N—(CH$_2$)$_a$—A    , and
      (CH$_2$)$_b$

—N—C($R_6$)—N—(CH$_2$)$_a$—A  ;
$R_{10}$          (CH$_2$)$_b$ each $R_6$ is independently selected from the group consisting of =O and =S;
each $R_7$ is independently $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
each $R_{10}$ is independently $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

or a pharmaceutically acceptable salt thereof.

Herein, "non-interfering" means that the ability of the compound or salt to modulate (e.g., induce or inhibit) the biosynthesis of one or more cytokines is not destroyed by the non-interfering substitutent. Illustrative non-interfering R' groups include those described above for R$_1$ in Formula II. Illustrative non-interfering R" groups include those described above for R$_2$ in Formula II.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. Likewise, "alkylenyl," "alkenylenyl," and "alkynylenyl" are the divalent forms of the "alkyl," "alkenyl," and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

When a group is present more that once in a Formula I-VIII or XLVI-XLVIII described herein, each group is independently selected, whether specifically stated or not. For example, when more than one Y group is present in a Formula, each Y group is independently selected. Furthermore, subgroups contained within these groups are also independently selected. For example, when each Y group contains an R$_6$, each R$_6$ is also independently selected.

The invention is inclusive of the compounds and salts thereof, described herein in any of their pharmaceutically acceptable forms, including isomers (e.g., diastereomers and enantiomers), solvates, polymorphs, and the like. In particular, if a compound is optically active, the invention specifically includes each of the compound's enantiomers as well as racemic mixtures of the enantiomers.

In some embodiments, compounds of Formulas I-VIII and XLVI induce the biosynthesis of one or more cytokines.

In some embodiments, compounds of Formulas I-VIII and XLVI inhibit the biosynthesis of one or more cytokines.

Preparation of the Compounds

Compounds of the invention can be prepared using known palladium catalyzed coupling reactions such as Suzuki coupling, Stille coupling, Sonogashira coupling, and the Heck reaction.

Suzuki coupling is used in Reaction Scheme I where R$_1$, R$_2$, and R are as defined above, R$_{3a}$ is —Z$_a$-Ar, —Z$_a$—Ar'—Y—R$_4$, or —Z$_a$-Ar'—X—Y—R$_4$ where Z$_a$ is a bond, alkylene or alkenylene, and Hal is bromo, chloro or iodo.

In Reaction Scheme I a halogen substituted imidazoquinoline of Formula IX is coupled with a boronic acid of Formula X to provide an imidazoquinoline of Formula XI which is a subgenus of Formula II. A compound of Formula IX is combined with a boronic acid of Formula X in the presence of palladium (II) acetate, triphenylphosphine and a base such as sodium carbonate in a suitable solvent such as n-propanol. The reaction can be carried out at an elevated temperature (e.g., 80-100° C.).

Reaction Scheme I

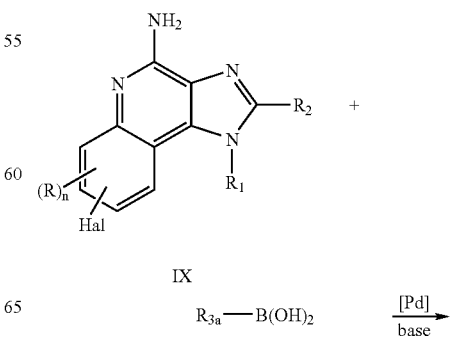

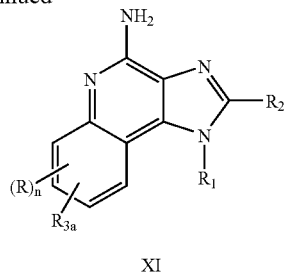

XI

Many compounds of Formula IX are known. See, for example, U.S. Pat. Nos. 4,689,338; 4,929,624; 5,268,376; 5,346,905; 5,389,640; 5,756,747; 6,331,539; and 6,451,810; PCT Publications WO 00/76518; WO 02/46188, WO 02/46189; WO 02/46190; WO 02/46191; WO 02/46192; and WO 02/46193; European Patent Application 1 104 764; and Japanese Patent Application 9-255926. Others can be readily prepared using known synthetic methods. See, for example, U.S. Pat. Nos. 4,988,815; 5,175,296; 5,367,076; 5,395,937; and 5,741,908.

Many boronic acids of Formula X are commercially available; others can be readily prepared using known synthetic methods. See, for example, Li, W. et al, *J. Org. Chem.*, 67, 5394-5397 (2002). The Suzuki coupling reaction can also be carried out using boronic acid esters of Formula $R_{3a}$—B(O-alkyl)$_2$ and anhydrides of boronic acids of Formula X.

Compounds of the invention where Z is alkynylene can be prepared using Stille coupling to couple a halogen substituted imidazoquinoline of Formula IX with a terminal alkyne of the formula —C≡C-Ar.

Compounds of the invention can be prepared according to Reaction Scheme II wherein $R_b$ is selected from alkyl, and alkoxy; $R_{1b}$ and $R_{2b}$ are subsets of $R_1$ and $R_2$ as defined above, which subsets do not include those substituents which one skilled in the art would recognize as being susceptible to oxidation in step (9), examples include substituents containing an —S— or a heteroaryl group; $R_{3b}$ is aryl which may be unsubstituted or substituted by one or more substituents independently selected from alkyl, alkoxy, haloalkyl, haloalkoxy, halogen, nitro, cyano, carboxy, formyl, aryl, aryloxy, arylalkoxy, heterocyclyl, heterocyclylalkyl, amino, alkylamino, and dialkylamino; and n is 0 or 1.

In step (1) of Reaction Scheme II a bromoaniline of Formula XII is coupled with a boronic acid of formula $R_{3b}$—B(OH)$_2$, an anhydride thereof, or a boronic acid ester of Formula $R_{3a}$—B(O-alkyl)$_2$ using the method described in Reaction Scheme I to provide an aryl substituted aniline of Formula XIII. Many bromoanilines of Formula XII are commercially available; others can be readily prepared using known synthetic methods.

In step (2) of Reaction Scheme II an aryl substituted aniline of Formula XIII is reacted with a mixture of triethyl orthoformate and Meldrum's Acid (2,2-dimethyl-1,3-dioxane-4,6-dione) at an elevated temperature (50-55° C.) to provide a compound of Formula XIV.

In step (3) of Reaction Scheme II a quinolin-4-ol of Formula XV is prepared by thermolysis of a compound of Formula XIV. The reaction can be carried out by heating (approximately 215° C.) a solution of the compound of Formula XIV in a heat transfer fluid.

In step (4) of Reaction Scheme II a quinolin-4-ol of Formula XV is nitrated using conventional nitration methods to provide a 3-nitroquinolin-4-ol of Formula XVI. The reaction can be carried out by combining the compound of Formula XV with nitric acid in a suitable solvent such as propionic acid at an elevated temperature (approximately 130° C.).

In step (5) of Reaction Scheme II a 3-nitroquinolin-4-ol of Formula XVI is chlorinated using conventional chlorinating methods to provide a 4-chloro-3-nitroquinoline of Formula XVII. The reaction can be carried out by combining the compound of Formula XVI with phosphorous oxychloride in a suitable solvent such as toluene. The reaction can be carried out at ambient temperature.

In step (6) of Reaction Scheme II a 4-chloro-3-nitroquinoline of Formula XVII is reacted with an amine of Formula $R_{1b}$—NH$_2$ to provide a 3-nitroquinolin-4-amine of Formula XVIII. The reaction can be carried out by adding the amine to a solution of the compound of Formula XVII in a suitable solvent such as N,N-dimethylformamide (DMF) in the presence of a tertiary amine such as triethylamine. The addition can be carried out at a reduced temperature (0° C.) or at ambient temperature.

In step (7) of Reaction Scheme II a 3-nitroquinolin-4-amine of Formula XVIII is reduced to provide a quinoline-3,4-diamine of Formula XIX. The reaction can be carried out using a conventional heterogeneous hydrogenation catalyst such as platinum on carbon or palladium on carbon. The reaction can conveniently be carried out on a Parr apparatus in a suitable solvent such as toluene, isopropanol, or mixtures thereof.

Alternatively the reduction in step (7) can be carried out using sodium dithionite. A solution or suspension of the compound of Formula XVIII in a suitable solvent such as ethanol or isopropanol is treated with an aqueous solution of sodium dithionite. The reaction can be carried out at an elevated temperature (reflux) or at ambient temperature.

In step (8) of Reaction Scheme II a quinoline-3,4-diamine of Formula XIX is reacted with a carboxylic acid or an equivalent thereof to provide a 1H-imidazo[4,5-c]quinoline of Formula XX. Suitable equivalents to carboxylic acid include orthoesters, and 1,1-dialkoxyalkyl alkanoates. The carboxylic acid or equivalent is selected such that it will provide the desired $R_{2b}$ substituent in a compound of Formula XX. For example, triethyl orthoformate will provide a compound where $R_{2b}$ is hydrogen and trimethyl orthovalerate will provide a compound where $R_{2b}$ is butyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (8) can be carried out by (i) reacting a compound of Formula XIX with an acyl halide of formula $R_{2b}$C(O)Cl or $R_{2b}$C(O)Br and then (ii) cyclizing. In part (i) the acyl halide is added to a solution of a compound of Formula XIX in an inert solvent such as acetonitrile, pyridine or dichloromethane. The reaction can be carried out at ambient temperature. Optionally a catalyst such as pyridine hydrochloride can be included. In part (ii) the product of part (i) is heated in pyridine. If step (i) is run in pyridine, then the two steps can be combined into a single step.

In step (9) of Reaction Scheme II a 1H-imidazo[4,5-c]quinoline of Formula XX is oxidized to provide an N-oxide of Formula XXI using a conventional oxidizing agent that is capable of forming N-oxides. The reaction can be carried out by treating a solution of a compound of Formula XX in a suitable solvent such as chloroform or dichloromethane with 3-chloroperoxybenzoic acid at ambient temperature.

In step (10) of Reaction Scheme II an N-oxide of Formula XXI is aminated to provide a 1H-imidazo[4,5-c]quinoline-4- amine of Formula XXII which is a subgenus of Formula II. The reaction is carried out in two parts. In part (i) a compound of Formula XXI is reacted with an acylating agent. Suitable acylating agents include alkyl- or arylsulfonyl chorides (e.g., benzenesulfonyl choride, methanesulfonyl choride, and p-toluenesulfonyl chloride). In part (ii) the product of part (i) is reacted with an excess of an aminating agent. Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula XXI in a suitable solvent such as dichloromethane or chloroform, adding ammonium hydroxide to the solution, and then adding p-toluenesulfonyl chloride. The product or a pharmaceutically acceptable salt thereof can be isolated using conventional methods.

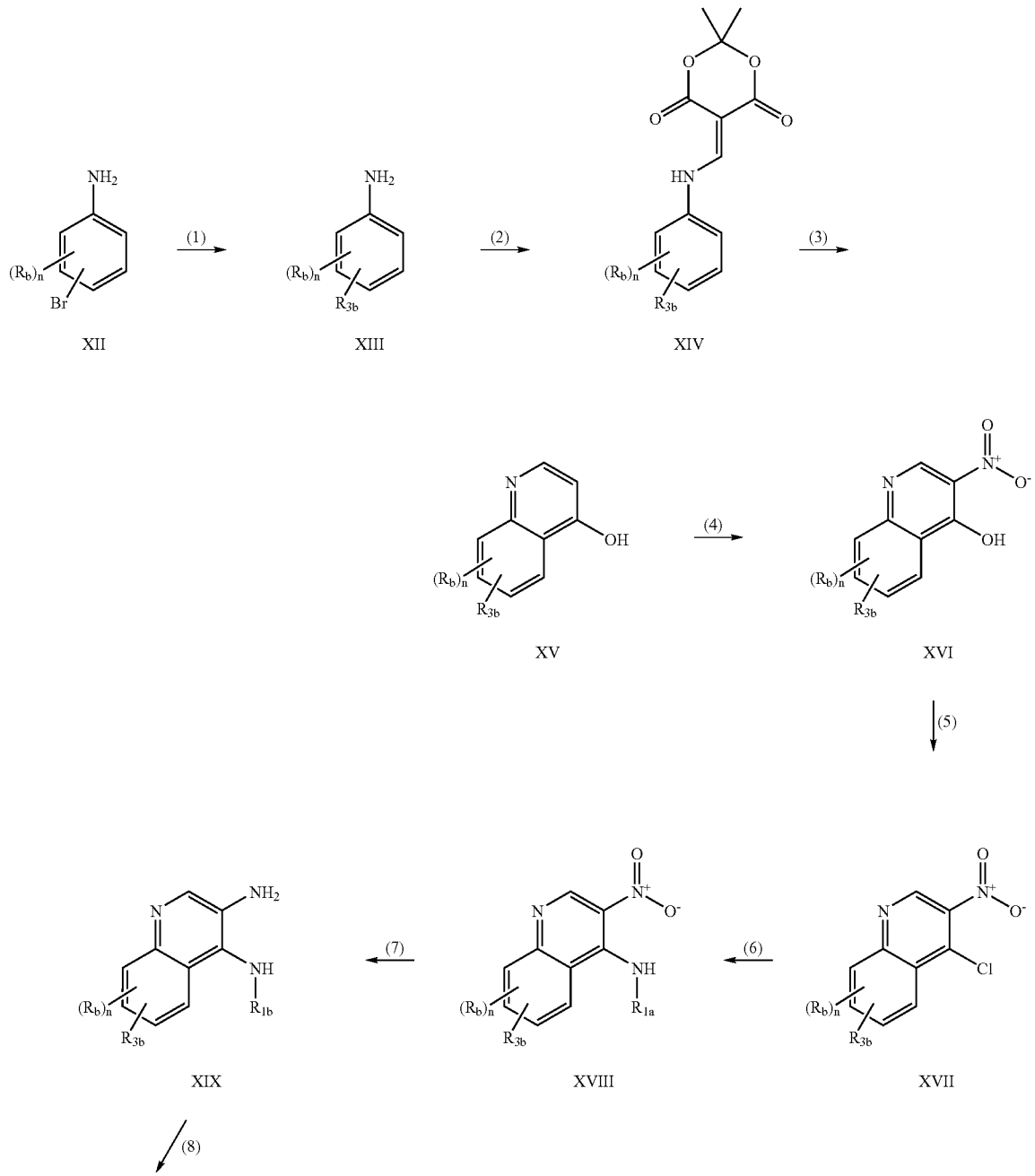

-continued

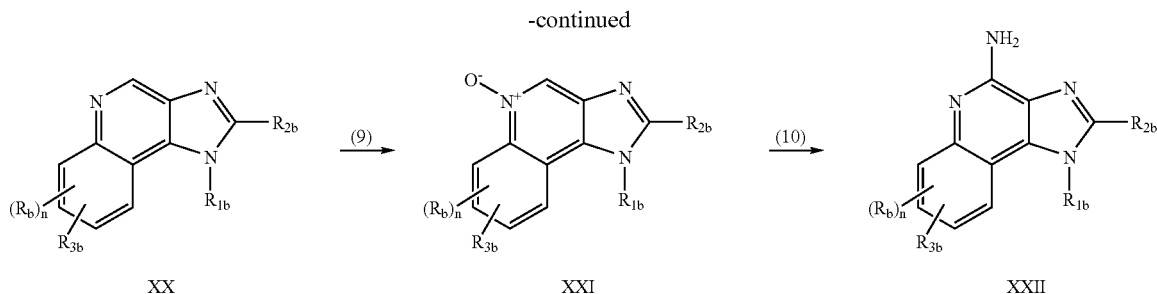

For some embodiments, compounds shown in Reaction Scheme II can be further elaborated using conventional synthetic methods. For example, an amine of Formula $R_{1b}$—$NH_2$, where $R_{1b}$ is $R_{4b}$ and $R_{4b}$ is a subset of $R_4$ that does not include those substitutents which one skilled in the art would recognize as being susceptible to oxidation in step (9), may be substituted by a hydroxy or second amino group, which can be further functionalized before step (7) of Reaction Scheme II. For example, a 3-nitroquinolin-4-amine of Formula XVIII, in which $R_{1b}$ is $R_{4b}$ having an amino substituent, can react with an acid chloride of Formula $R_{4b}C(O)Cl$, a sulfonyl chloride of Formula $R_{4b}S(O)_2Cl$, or a sulfonic anhydride of Formula $(R_{4b}S(O)_2)_2O$ to provide a compound of Formula XVIII in which $R_{1b}$ is —X—Y—$R_{4b}$, where Y is —$N(R_8)$—Q—, $R_8$ is as defined above, and Q is —C(O)— or —$SO_2$—. Numerous acid chlorides, sulfonyl chlorides, and sulfonic anhydrides are commercially available; others can be readily prepared using known synthetic methods. The reaction can be conveniently carried out by adding an acid chloride of Formula $R_{4b}C(O)Cl$, a sulfonyl chloride of Formula $R_{4b}S(O)_2Cl$, or a sulfonic anhydride of Formula $(R_{4b}S(O)_2)_2O$ to a solution of a 3-nitroquinolin-4-amine of Formula XVIII, in which $R_{1b}$ is $R_{4b}$ having an amino substituent, and a base such as triethylamine in a suitable solvent such as dichloromethane. The reaction can be carried out at ambient temperature.

A 3-nitroquinolin-4-amine of Formula XVIII, in which $R_{1b}$ is $R_{4b}$ having an amino substituent, can also react with isocyanates of Formula $R_{4b}N=C=O$ to provide a compound of Formula XVIII in which $R_{1b}$ is —X—Y—$R_{4b}$, where Y is —$N(R_8)$—Q, $R_8$ is as defined above, and Q is —$C(R_6)$—N($R_8$)—W—, $R_6$ is =O, and W is a bond. Numerous isocyanates of Formula $R_{4b}N=C=O$ are commercially available; others can be readily prepared using known synthetic methods. The reaction can be conveniently carried out by adding the isocyanate of Formula $R_{4b}N=C=O$ to a solution of the 3-nitroquinolin-4-amine of Formula XVIII, in which $R_{1b}$ is $R_{4b}$ having an amino substituent, in a suitable solvent such as dichloromethane. The reaction can be carried out at ambient temperature. Alternatively, a compound of Formula XVIII can be treated with an isocyanate of Formula $R_{4b}(CO)N=C=O$, a thioisocyanate of Formula $R_{4b}N=C=S$, a sulfonyl isocyanate of Formula $R_{4b}S(O)_2N=C=O$, or a carbamoyl chloride of Formula $R_{4b}N—(R_8)—C(O)Cl$ or

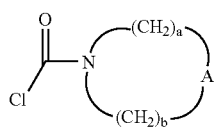

to provide a compound of Formula XVIII, where $R_{1b}$ is —X—$N(R_8)$—Q—$R_{4b}$ or

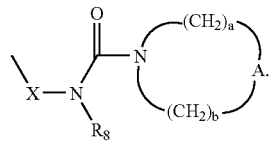

Q is —$C(R_6)$—$N(R_8)$—W—, and $R_6$, $R_8$, and W are as defined above. The product can then be treated according to steps (7) through (10) of Reaction Scheme II to provide 1H-imidazo[4,5-c]quinolin-4-amine of Formula XXII.

Compounds of the invention, where $R_{1c}$ is —X—Y—$R_{4b}$ or —X—$R_5$; Y is —$N(R_8)$—Q—; $R_5$ is

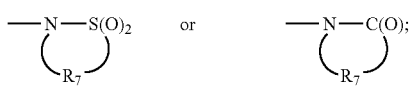

and X, Q, R, $R_2$, $R_{3a}$, $R_{4b}$, and n are as defined above can be prepared according to Reaction Scheme III. Steps (1) through (4) of Reaction Scheme III are carried out as described for steps (2) through (5) of Reaction Scheme II.

In step (5) of Reaction Scheme III, a 4-chloro-3-nitroquinoline of Formula XXVII is treated with a Boc-protected diamine of Formula $(CH_3)_3CO—C(O)—NH—X—NH_2$ to provide a protected 3-nitroquinolin-4-amine of Formula XXVIII. Several Boc-protected diamines of Formula $(CH_3)_3CO—C(O)—NH—X—NH_2$ are commercially available; others can be prepared by known synthetic methods. The reaction is conveniently carried out by adding a solution of the Boc-protected diamine of Formula $(CH_3)_3CO—C(O)—NH—X—NH_2$ to a cooled solution of a 4-chloro-3-nitroquinoline of Formula XXVII in a suitable solvent such as dichloromethane in the presence of a tertiary amine such as triethylamine. The reaction can be carried out at ambient temperature, and the product can be isolated using conventional methods.

In steps (6) and (7) of Reaction Scheme III, a 3-nitroquinolin-4-amine of Formula XXVIII is first reduced to provide a quinoline-3,4-diamine of Formula XXIX, which is converted to 1H-imidazo[4,5-c]quinoline of Formula XXX by reaction with a carboxylic acid equivalent. Steps (6) and (7) of Reaction Scheme III can be carried out as described for steps (7) and (8) of Reaction Scheme II. The sodium dithionite reduction in step (6) can also be conveniently carried out in a mixture of dichloromethane and water at ambient temperature in the presence of potassium carbonate and 1,1'-di-n-octyl-4,4'-bipyridinium dibromide. In part (ii) of step (7), the cyclization can also be carried out in ethanol while heated at reflux.

In step (8) of Reaction Scheme III, the Boc-protecting group of a 1H-imidazo[4,5-c]quinoline of Formula XXX is removed to provide a 1H-imidazo[4,5-c]quinoline of Formula XXXI. The reaction is conveniently carried out by adding hydrochloric acid or a solution of hydrochloric acid in ethanol to a solution of a 1H-imidazo[4,5-c]quinoline of Formula XXX in a suitable solvent such as ethanol. The reaction can be carried out at an elevated temperature, for example, the reflux temperature of the solvent. The product or pharmaceutically acceptable salt thereof can be isolated by conventional methods.

In step (9) of Reaction Scheme III, an amino-substituted 1H-imidazo[4,5-c]quinoline of Formula XXXI is converted to a 1H-imidazo[4,5-c]quinolin-1-yl compound of Formula XXXII, where $R_{1c}$ is as defined above, using conventional methods. For example, a 1H-imidazo[4,5-c]quinoline of Formula XXXI can react with an acid chloride of Formula $R_{4b}C(O)Cl$ to provide a compound of Formula XXXII in which $R_{1c}$ is —X—Y—$R_{4b}$, Y is —N($R_8$)—Q—, and Q is —C(O)—. In addition, a 1H-imidazo[4,5-c]quinoline of Formula XXXI can react with sulfonyl chloride of Formula $R_{4b}S(O)_2Cl$ or a sulfonic anhydride of Formula $(R_{4b}S(O)_2)_2O$ to provide a compound of Formula XXXII in which $R_{1c}$ is —X—Y—$R_{4b}$, Y is —N($R_8$)—Q—, and Q is —$S(O)_2$—. Numerous acid chlorides of Formula $R_{4b}C(O)Cl$, sulfonyl chlorides of Formula $R_{4b}S(O)_2Cl$, and sulfonic anhydrides of Formula $(R_{4b}S(O)_2)_2O$ are commercially available; others can be readily prepared using known synthetic methods. The reaction can be carried out as described above for a compound of Formula XVIII.

Ureas of Formula XXXII, where $R_{1c}$ is —X—Y—$R_{4b}$, Y is —N($R_8$)—Q—, Q is —C($R_6$)—N($R_8$)—W—, and W and $R_8$ are as defined above can be prepared by reacting a 1H-imidazo[4,5-c]quinoline of Formula XXXI with isocyanates of Formula $R_4N=C=O$ or Formula $R_4(CO)N=C=O$, thioisocyanates of Formula $R_4N=C=S$, sulfonyl isocyanates of Formula $R_4S(O)_2N=C=O$, or carbamoyl chlorides of Formula $R_4N—(R_8)—C(O)Cl$. Numerous compounds of these types are commercially available; others can be readily prepared using known synthetic methods. The reaction can be carried out as described above for a compound of Formula XVIII.

Compounds of Formula XXXII where $R_{1c}$ is —X—$R_5$ and $R_5$ is

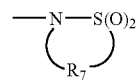

can be prepared by treating an amino-substituted 1H-imidazo[4,5-c]quinoline of Formula XXXI with a chloroalkanesulfonyl chloride of Formula Cl—$R_7S(O)_2Cl$. The reaction is conveniently carried out by adding the chloroalkanesulfonyl chloride to a solution of the amino-substituted 1H-imidazo[4,5-c]quinoline of Formula XXXI in a suitable solvent such as chloroform at ambient temperature. The isolable intermediate chloroalkanesulfonamide can then be treated with a base such as 1,8-diazabicyclo[5.4.0]undec-7-ene at ambient temperature in a suitable solvent such as DMF to effect the cyclization. The product can be isolated using conventional methods.

In steps (10) and (11) of Reaction Scheme III, a 1H-imidazo[4,5-c]quinoline of Formula XXXII is oxidized to afford a 1H-imidazo[4,5-c]quinoline-5N-oxide of Formula XXXIII, which is aminated to provide a 1H-imidazo[4,5-c]quinolin-4-amine of Formula XXXIV. Steps (10) and (11) of Reaction Scheme III can be carried out as described for steps (9) and (10), respectively, of Reaction Scheme II.

In step (12) of Reaction Scheme III, a 1H-imidazo[4,5-c]quinolin-4-amine of Formula XXXIV undergoes a coupling reaction with boronic acid of Formula X, an anhydride thereof, or a boronic acid ester of Formula $R_{3a}—B(O-alkyl)_2$. The Suzuki coupling reaction can be carried out as described in Reaction Scheme I to provide a 1H-imidazo[4,5-c]quinolin-4-amine of Formula XXXV, which is a subgenus of Formula II. The product or pharmaceutically acceptable salt thereof can be isolated using conventional methods.

Reaction Scheme III

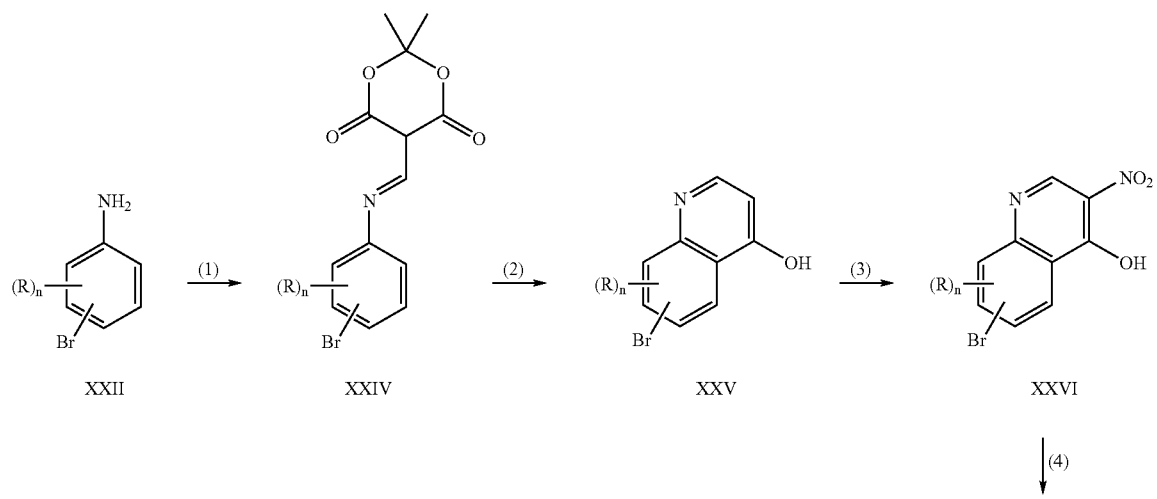

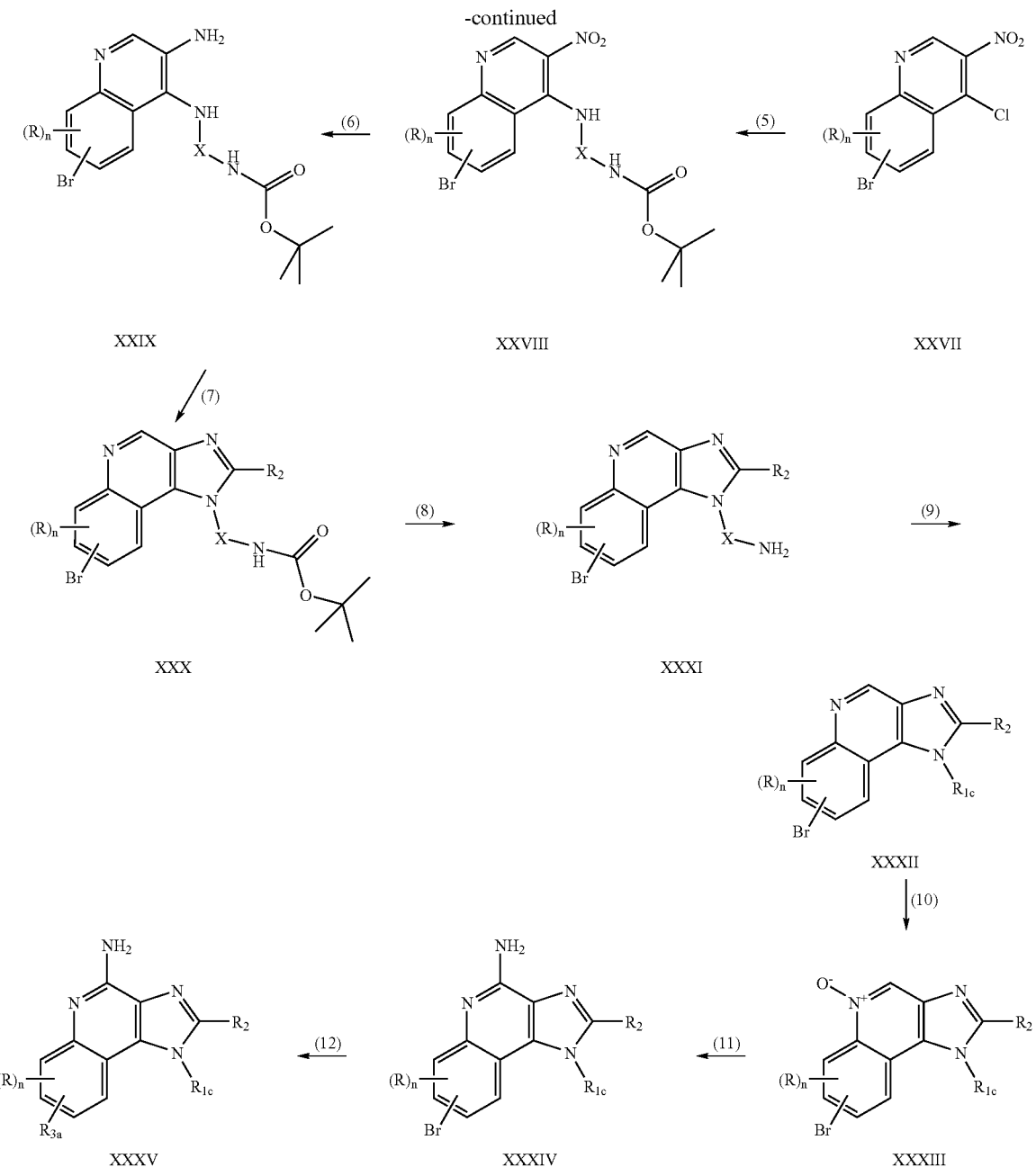

Compounds of the invention can also be prepared according to Reaction Scheme IV, where R, $R_2$, $R_{3a}$, $R_4$, $R_{10}$, X, and Q are as defined above. In step (1) of Reaction Scheme IV, a 4-chloro-3-nitroquinoline of Formula XXVII is treated with a Boc-protected diamine of Formula XXXVI to provide a 3-nitroquinolin-4-amine of Formula XXXVII. Boc-protected diamines of Formula XXXVII are available from the method described by Carceller, E. et al, *J. Med. Chem.*, 39, 487-493 (1996). The reaction can be carried out as described for step (5) of Reaction Scheme III.

In steps (2)-(5) of Reaction Scheme IV, a 3-nitroquinolin-4-amine of Formula XXXVII is first reduced to provide a quinoline-3,4-diamine of Formula XXXVIII, which is converted to 1H-imidazo[4,5-c]quinoline of Formula XXXIX by reaction with a carboxylic acid equivalent. The 1H-imidazo[4,5-c]quinoline of Formula XXXIX is then oxidized to afford a 1H-imidazo[4,5-c]quinoline-5N-oxide of Formula XL, which is aminated to provide a 1H-imidazo[4,5-c]quinolin-4-amine of Formula XLI. Steps (2), (3), (4), and (5) of Reaction Scheme IV can be carried out as described for steps (7), (8), (9), and (10), respectively, of Reaction Scheme II.

In steps (6) of Reaction Scheme IV, the Boc protecting group of a 1H-imidazo[4,5-c]quinolin-4-amine of Formula XLI is removed to provide a 1H-imidazo[4,5-c]quinolin-4-amine of Formula XLII, which is converted to a 1H-imidazo[4,5-c]quinolinyl compound of Formula XLIII in step (7). Steps (6) and (7) of Reaction Scheme IV can be carried out as described for steps (8) and (9) of Reaction Scheme III.

In step (8), the compound of Formula XLIII is then coupled with a boronic acid of Formula X, an anhydride thereof, or boronic acid ester of Formula $R_{3a}$—B(O-alkyl)$_2$ to provide a 1H-imidazo[4,5-c]quinolin-4-amine of Formula XLIV, which is a subgenus of Formula II. The Suzuki coupling reaction can be carried out as described in Reaction Scheme I. In some embodiments, the coupling reaction shown in step (8) is carried out prior to the deprotection and functionalization reactions shown in steps (6) and (7) to provide a compound of Formula XLIV. The product or pharmaceutically acceptable salt thereof can be isolated using conventional methods.

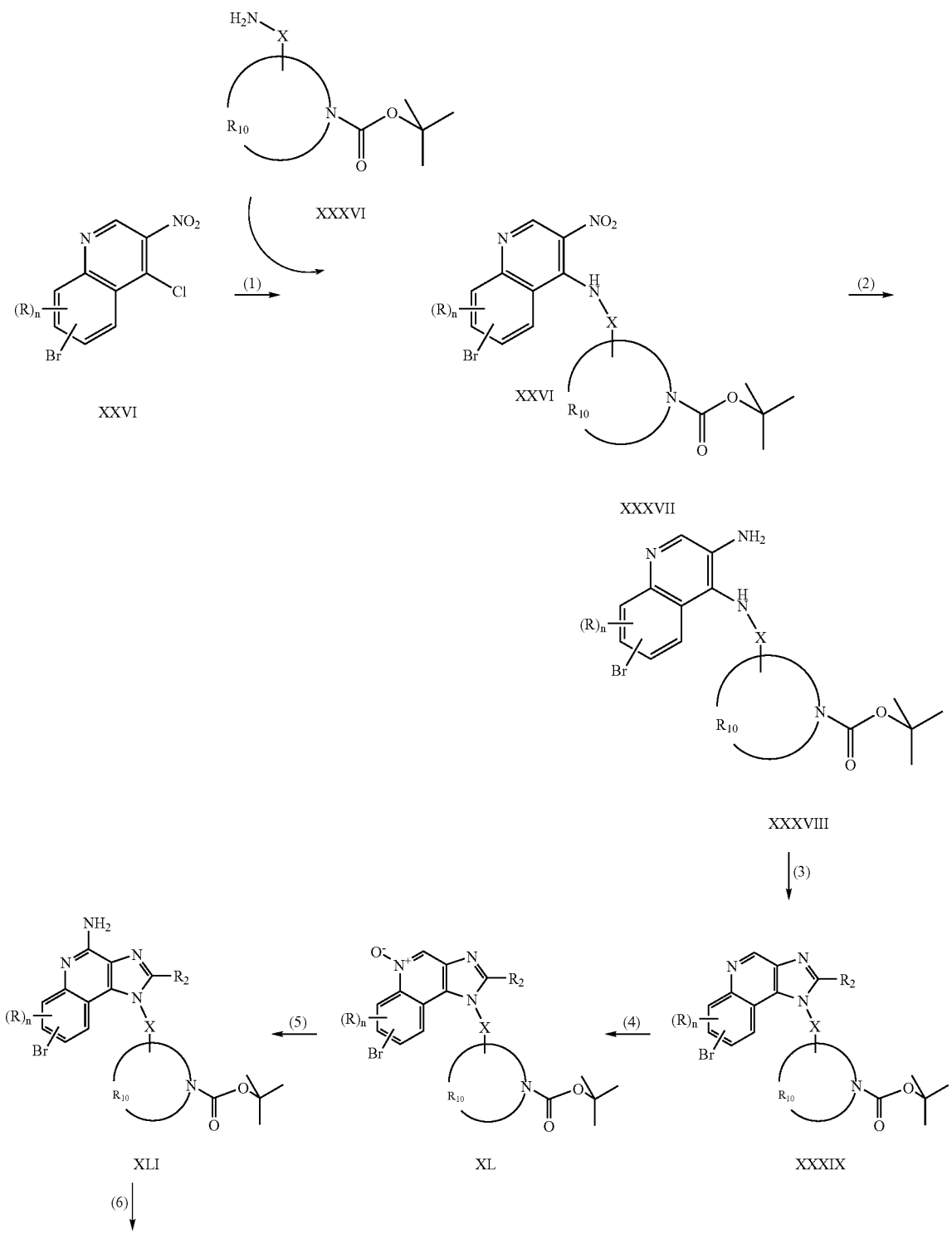

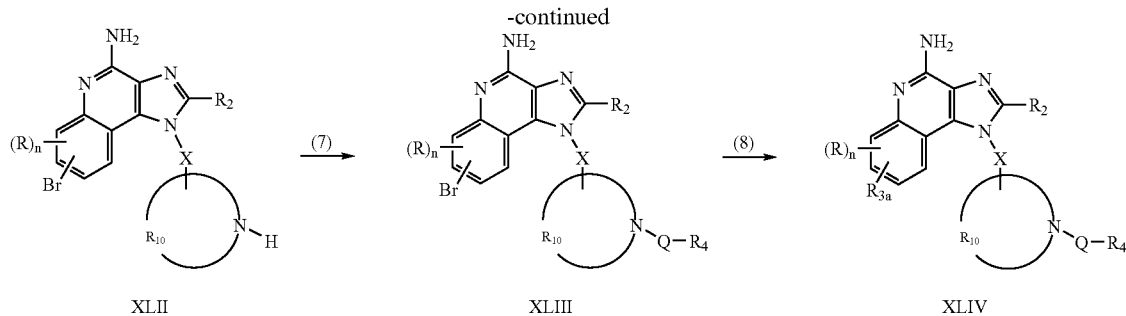

The Heck reaction can be used to prepare compounds of the invention as shown in step (1) of Reaction Scheme V, wherein $R_1$, $R_2$, R, Hal, and n are as defined above and $Ar_a$ is -Ar, -Ar'—Y—$R_4$, or -Ar'—X—Y—$R_4$. In step (1) of Reaction Scheme V, a halogen-substituted imidazoquinolin-4-amine of Formula IX is coupled with a vinyl-substituted compound of Formula L to provide an imidazoquinolin-4-amine of Formula LI, which is a subgenus of Formula II. Alternatively, a compound of Formula L can be coupled with a trifluoromethanesulfonate-substituted imidazoquinolin-4-amine, in which Hal in Formula IX is replaced by —$OSO_2CF_3$— Several compounds of Formula L are commercially available; others can be prepared by known methods. The reaction is conveniently carried out by combining the imidazoquinolin-4-amine of Formula IX and the vinyl-substituted compound of Formula L in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere. The compound or pharmaceutically acceptable salt thereof can be isolated using conventional methods.

In step (2) of Reaction Scheme V, the vinyl group of an imidazoquinolin-4-amine of Formula LI is reduced to provide an imidazoquinolin-4-amine of Formula LII, which is also a subgenus of Formula II. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The compound or pharmaceutically acceptable salt thereof can be isolated using conventional methods.

Reaction Scheme V

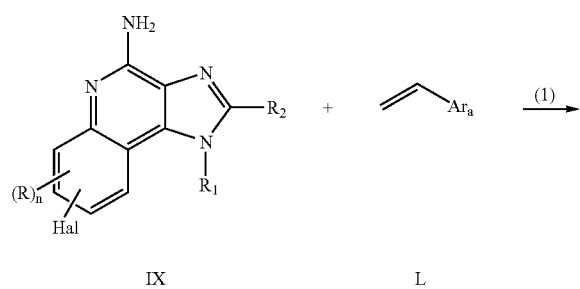

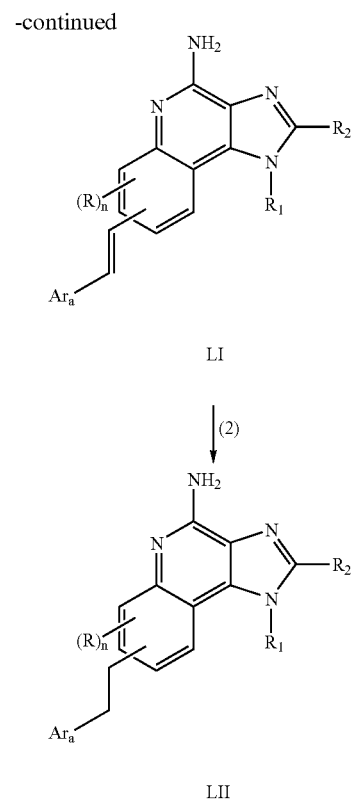

Palladium-catalyzed coupling reactions can also be used to prepare compounds of the invention according to Reaction Scheme VI, wherein $R_1$, $R_2$, $R_9$, R, Hal, $Ar_a$, and n are as defined above. In step (1) of Reaction Scheme VI, a halogen-substituted imidazoquinolin-4-amine of Formula IX undergoes a Suzuki-type coupling with a potassium alkenyltrifluoroborate of Formula LIII to provide an imidazoquinolin-4-amine of Formula XLVII. The reaction is conveniently carried out by combining the imidazoquinolin-4-amine of Formula IX and a compound of Formula LIII, such as potassium vinyltrifluoroborate, in the presence of dichloro[1,1'-bis(diphenylphosphino)ferrocene]palladium (II) dichloromethane adduct and a base such as triethylamine in a suitable solvent such as n-propanol. The reaction can be carried out at an elevated temperature such as the reflux temperature of the solvent under an inert atmosphere. The compound or pharmaceutically acceptable salt thereof can be isolated using conventional methods.

In step (2) of Reaction Scheme VI, the Heck reaction is used to couple a vinylated imidazoquinolin-4-amine of Formula XLVII with an aryl or hetereoaryl halide of Formula $Ar_a$-Hal or a trifluoromethanesulfonate of Formula $Ar_a$—$OSO_2CF_3$. Numerous compounds of Formula $Ar_a$-Hal are commercially available; others can be prepared using known synthetic methods. The reaction is conveniently carried out under the conditions described in step (1) of Reaction Scheme V to provide an imidazoquinolin-4-amine of Formula LI. The product or pharmaceutically acceptable salt thereof can be isolated using conventional methods.

In step (3) of Reaction Scheme VI, the vinyl group of an imidazoquinolin-4-amine of Formula LI is reduced to provide an imidazoquinolin-4-amine of Formula LII. The reaction is conveniently carried out by hydrogenation under the conditions described in step (2) of Reaction Scheme V.

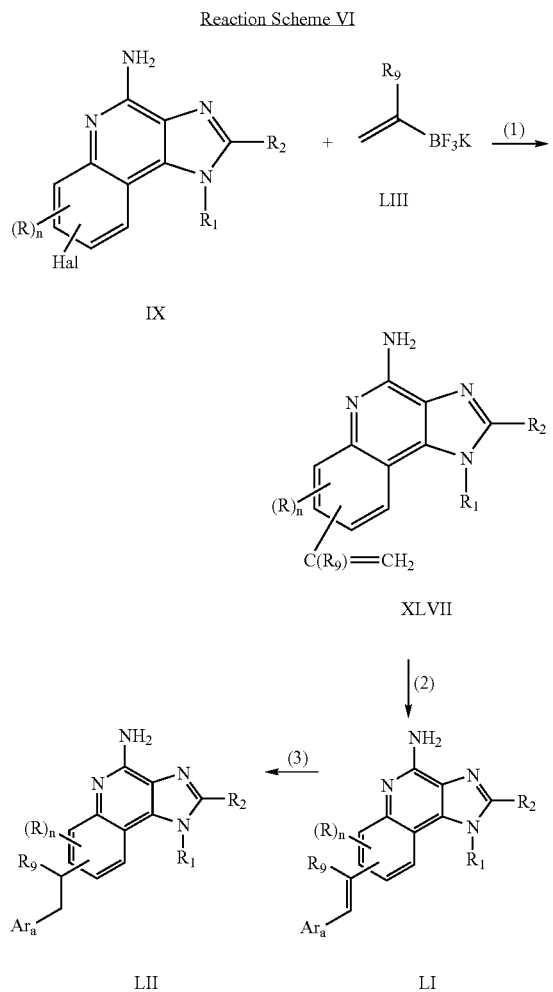

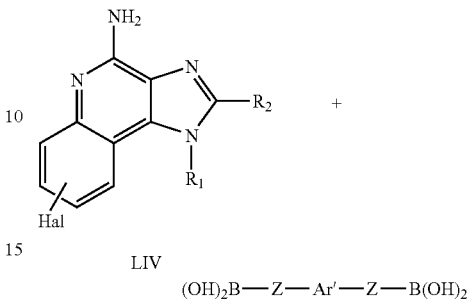

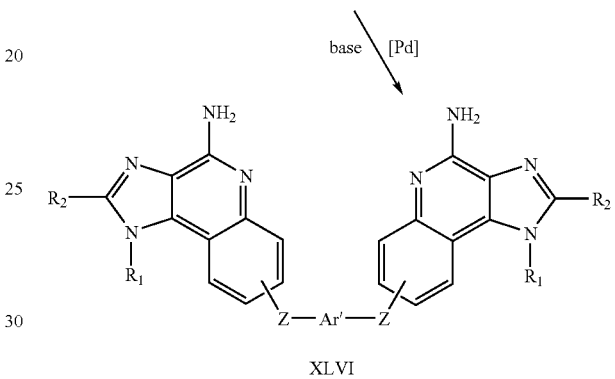

Dimers of the invention can be prepared according to Reaction Scheme VII, wherein $R_1$, $R_2$, Z, Hal, and Ar' are as defined above. In Reaction Scheme VII, a Suzuki coupling is carried out with an imidazoquinolin-4-amine of Formula LIV and a difunctional boronic acid of Formula LV, or an ester or anhydride thereof. Some boronic acids of Formula LV are commercially available; others can be prepared by known synthetic methods. The coupling can be carried out as described in Reaction Scheme I to provide a dimer of Formula XLVI. The compound or pharmaceutically acceptable salt thereof can be isolated using conventional methods.

Compounds of the invention can also be prepared according to Reaction Scheme VIII, wherein R, $R_{3a}$, n, and Hal are as defined above, and $R_{1d}$ and $R_{2d}$ are subsets of $R_1$ and $R_2$ that do not include substituents that one skilled in the art would recognize as being susceptible to nucleophilic attack in step (5). These groups include, for example, esters and ureas. In step (1) of Reaction Scheme VIII, a nitro-substituted quinoline-2,4-diol of Formula LVI is chlorinated to provide a 2,4-dichloroquinoline of Formula LVII. Nitro-substituted quinoline-2,4-diols of Formula LVI can be prepared from substituted anilines according to the methods described in Buckle et al, *J. Med. Chem.*, 18, 726-732 (1975). The chlorination is conveniently carried out by heating the compound of Formula LVI and phenylphosphonic dichloride at an elevated temperature such as 140° C. The reaction can be carried out without solvent, and the product can be isolated using conventional methods.

In step (2) of Reaction Scheme VIII, a 2,4-dichloroquinoline of Formula LVII is reacted with an amine of Formula $R_1$—$NH_2$ to provide a 2-chloro-3-nitroquinolin-4-amine of Formula LVIII. The reaction can be carried out as described in step (6) of Reaction Scheme II.

In step (3) of Reaction Scheme VIII, the nitro group of a 2-chloro-3-nitroquinolin-4-amine of Formula LVIII is reduced to provide a 2-chloroquinoline-3,4-diamine of Formula LIX. The reduction is conveniently carried out with sodium dithionite according to the method described in step (7) of Reaction Scheme II.

In step (4) of Reaction Scheme VIII, a 2-chloroquinoline-3,4-diamine of Formula LIX is treated with a carboxylic acid or an equivalent thereof to provide a 4-chloro-1H-imidazo[4,5-c]quinoline of Formula LX. The reaction can be carried out as described in step (8) of Reaction Scheme II.

In step (5) of Reaction Scheme VIII, a 4-chloro-1H-imidazo[4,5-c]quinoline of Formula LX is aminated to provide a 1H-imidazo[4,5-c]quinolin-4-amine of Formula LXI. The reaction is conveniently carried out by combining the compound of Formula LX with a solution of ammonia in methanol in a bomb reactor and heating at an elevated temperature, such as 120° C. The product or pharmaceutically acceptable salt thereof can be isolated using conventional methods.

In step (6) of Reaction Scheme VIII, a 1H-imidazo[4,5-c]quinolin-4-amine of Formula LXI undergoes a coupling reaction with a boronic acid of Formula X, an anhydride thereof, or a boronic acid ester of Formula $R_{3a}$—B(O-alkyl)$_2$. The Suzuki coupling reaction can be carried out as described in Reaction Scheme I to provide a 1H-imidazo[4,5-c]quinolin-4-amine of Formula LXII, which is a subgenus of Formula II. The product or pharmaceutically acceptable salt thereof can be isolated using conventional methods.

provide a 3-nitroquinolin-4-amine of Formula LXIV. The reaction can be carried out as described for step (5) of Reaction Scheme III.

In steps (2) and (3) of Reaction Scheme IX, a 3-nitroquinolin-4-amine of Formula LXIV is first reduced to provide a quinoline-3,4-diamine of Formula LXV, which is converted to 1H-imidazo[4,5-c]quinoline of Formula LXVI by reaction with a carboxylic acid equivalent. Step (2) of Reaction Scheme IX can be carried out as described for step (7) of Reaction Scheme II or step (8) of Reaction Scheme III. Step (3) of Reaction Scheme IX can be carried out as described for step (8) of Reaction Scheme II.

The 1H-imidazo[4,5-c]quinoline of Formula LXVI is then oxidized in step (4) of Reaction Scheme IX to afford a dioxido-1H-imidazo[4,5-c]quinoline of Formula LXVII. The oxidation reaction is conveniently carried out in a similar manner to step (9) of Reaction Scheme II but with additional

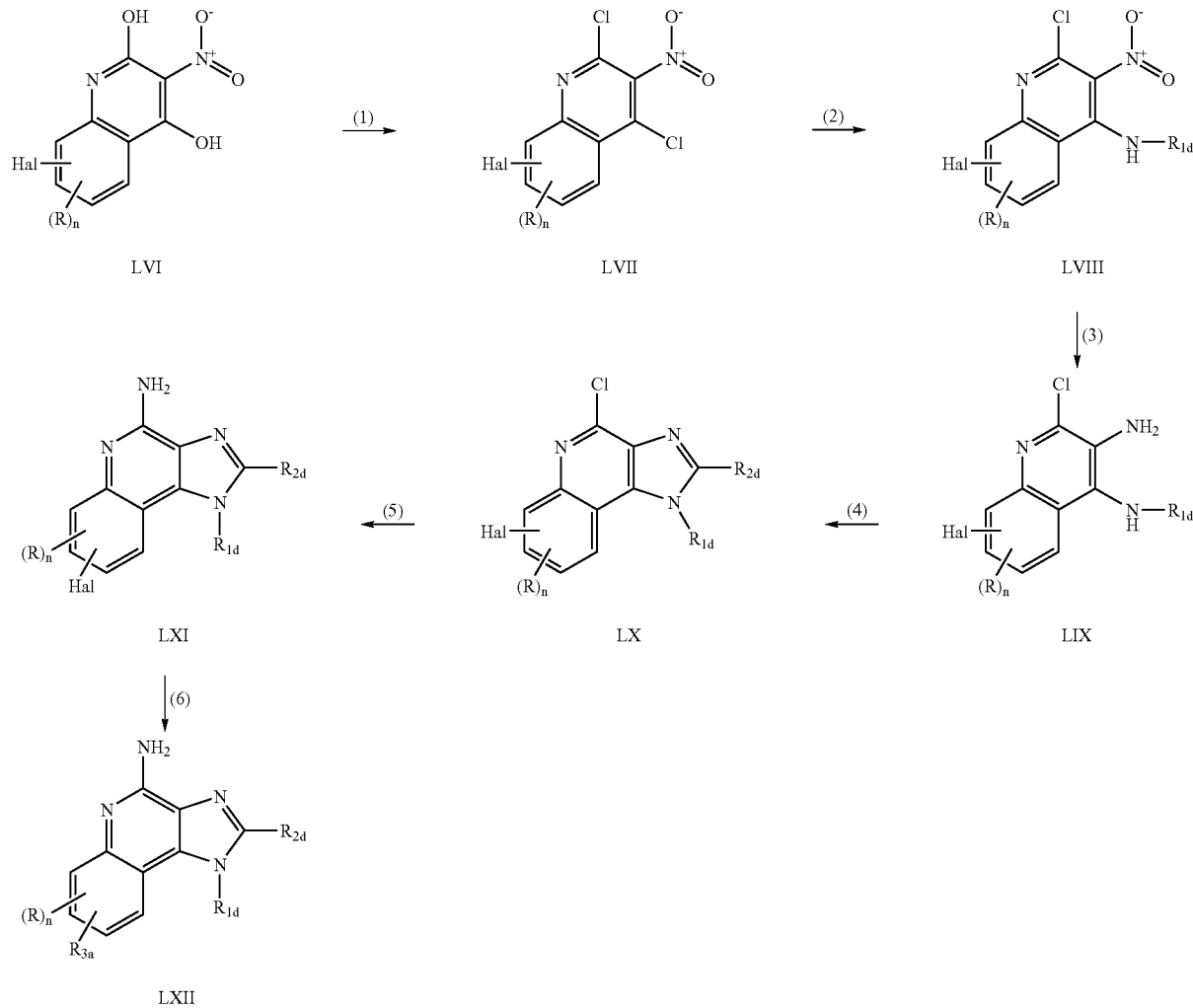

Reaction Scheme VIII

For some embodiments, compounds of the invention are prepared according to Reaction Scheme IX, where R, $R_2$, $R_{3a}$, $R_4$, X, Q, and n are as defined above. In step (1) of Reaction Scheme IX, a 4-chloro-3-nitroquinoline of Formula XXVII is treated with a Boc-protected piperazine of Formula LXIII to equivalents of 3-chloroperoxybenzoic acid. The product can be isolated using conventional methods.

In step (5) of Reaction Scheme IX, a dioxido-1H-imidazo[4,5-c]quinoline of Formula LXVII is aminated to provide a 1H-imidazo[4,5-c]quinolin-4-amine of Formula LXVIII.

Step (5) of Reaction Scheme IX can be carried out as described for step (10) of Reaction Scheme II.

In step (6) of Reaction Scheme IX, the piperazine N-oxide of the 1H-imidazo[4,5-c]quinolin-4-amine of Formula LXVIII is reduced to provide a 1H-imidazo[4,5-c]quinolin-4-amine of Formula LXIX. The reaction is conveniently carried out by adding phosphorous trichloride to an N-oxide of Formula LXVIII in a suitable solvent such as chloroform. The reaction can be carried out at a subambient temperature, such as 4° C. The product can be isolated using conventional methods.

In step (7) of Reaction Scheme IX, the Boc protecting group of a 1H-imidazo[4,5-c]quinolin-4-amine of Formula LXIX is removed to provide a 1H-imidazo[4,5-c]quinolin-4-amine of Formula LXX. The deprotection can be carried out as described in step (8) of Reaction Scheme III.

In step (8) of Reaction Scheme IX, a 1H-imidazo[4,5-c]quinolin-4-amine of Formula LXX is coupled with a boronic acid of Formula X, an anhydride thereof, or boronic acid ester of Formula $R_{3a}$—$B(O\text{-alkyl})_2$ to provide a 1H-imidazo[4,5-c]quinolin-4-amine of Formula LXXI, which is a subgenus of Formula II. The Suzuki coupling reaction can be carried out as described in Reaction Scheme I. The product or pharmaceutically acceptable salt thereof can be isolated using conventional methods.

In step (9) of Reaction Scheme IX, a 1H-imidazo[4,5-c]quinolin-4-amine of Formula LXXI is converted to a 1H-imidazo[4,5-c]quinolinyl compound of Formula LXXII. Step (9) can be carried out as described for step (9) of Reaction Scheme III, and the product or pharmaceutically acceptable salt thereof can be isolated using conventional methods.

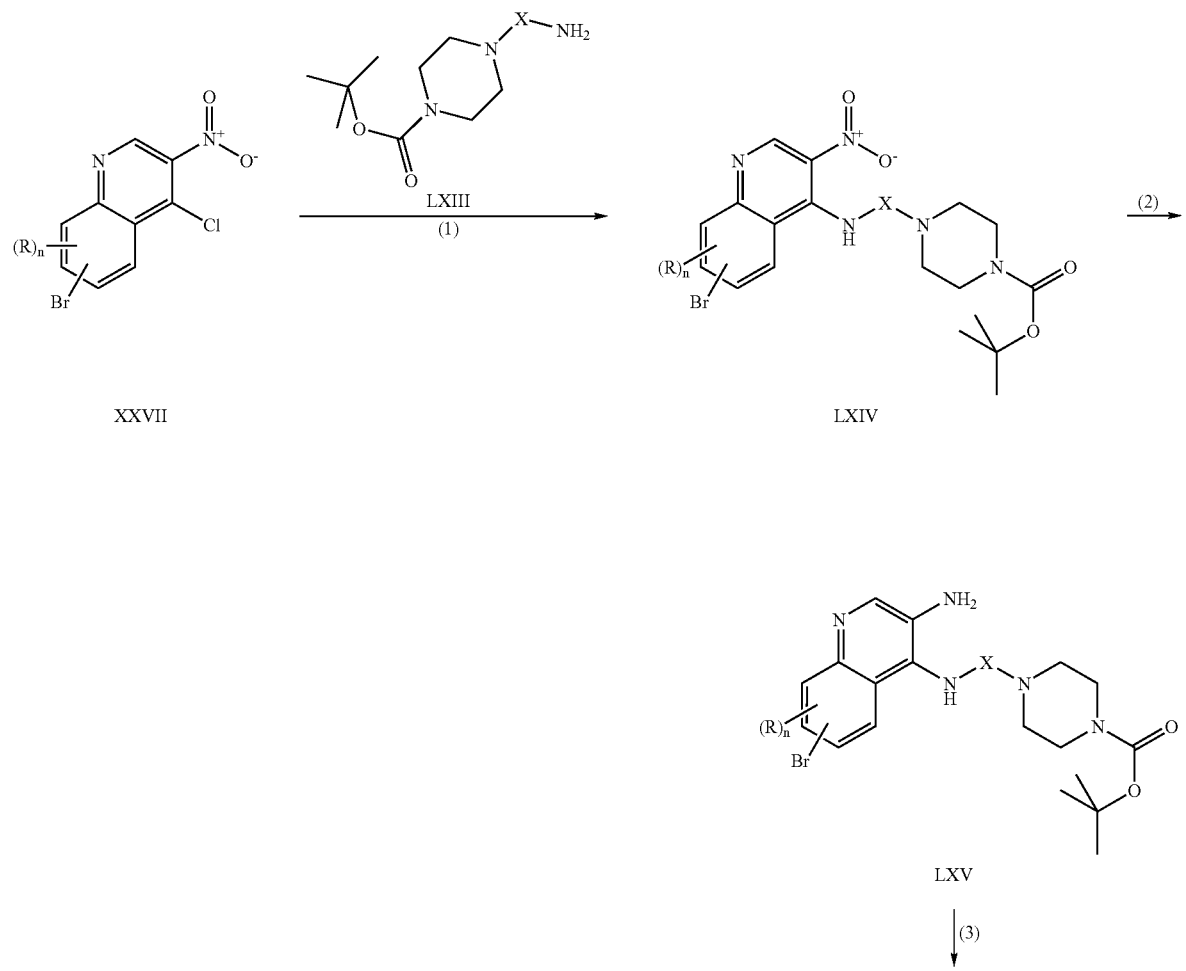

-continued

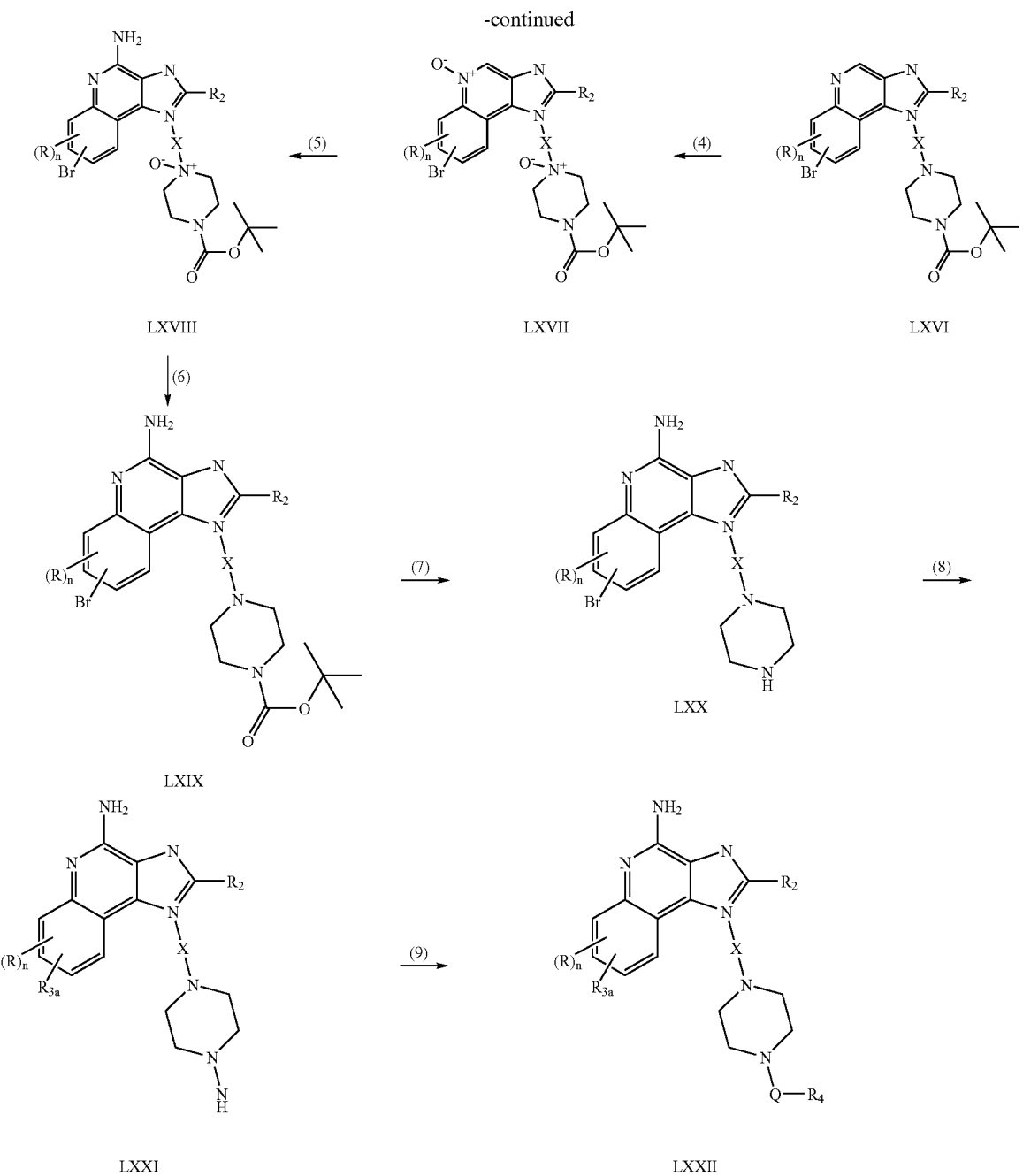

For certain embodiments, compounds of the invention can be prepared according to Reaction Scheme X, where R, $R_2$, $R_4$, X, Hal, and n are as defined above and $X_{1-1}$ is selected from the group consisting of $C_{1-10}$alkylene, $C_{4-10}$alkenylene, and $C_{4-10}$alkynylene, wherein the terminal carbon atoms of alkenylene and alkynylene are tetrahedral. In step (1) a 3-nitroquinolin-4-amine of Formula LXXIII is reduced to provide a quinoline-3,4-diamine of Formula LXXIV. The reaction can be carried out as in step (7) of Reaction Scheme II. The product or a pharmaceutically acceptable salt thereof can be isolated by conventional methods. Many 3-nitroquinolin-4-amines of Formula LXXIII are known or can be prepared using known synthetic methods, see for example, U.S. Pat. Nos. 4,689,338; 5,175,296; and 5,389,640; and the references cited therein.

In step (2) of Reaction Scheme X, a quinoline-3,4-diamine of Formula LXXIV is reacted with a carboxylic acid or an equivalent thereof to provide a 1H-imidazo[4,5-c]quinoline of Formula LXXV. The reaction can be conveniently carried out as described in step (8) of Reaction Scheme II. The product or a pharmaceutically acceptable salt thereof can be isolated by conventional methods.

In step (3) of Reaction Scheme X, a 1H-imidazo[4,5-c] quinoline of Formula LXXV is reacted with sodium hydride to form an alkoxide, which is reacted with a vinyl sulfone to provide a 1H-imidazo[4,5-c]quinoline of Formula LXXVI. The reaction can be carried out by adding catalytic sodium hydride dispersed in mineral oil to a solution of a 1H-imidazo[4,5-c]quinoline of Formula LXXV and a vinyl sulfone of the formula $CH_2=CH-S(O)_2-R_4$ in a suitable solvent such as ried out as described in Reaction Scheme I to provide a 1H-imidazo[4,5-c]quinolin-4-amine of Formula LXXIX, which is a subgenus of Formula II. The product or pharmaceutically acceptable salt thereof can be isolated using conventional methods.

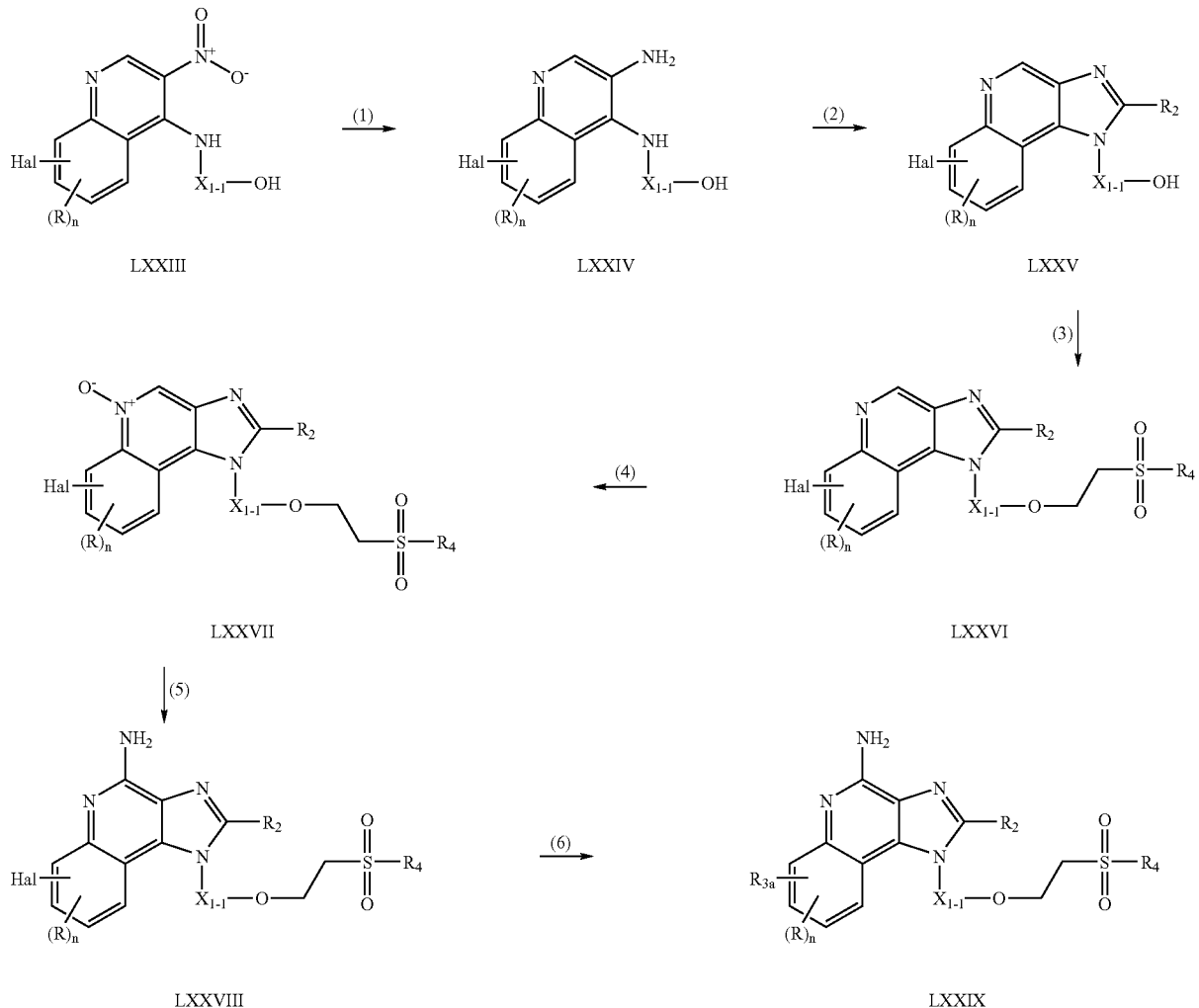

DMF or tetrahydrofuran. The reaction can be run at ambient temperature. The product or a pharmaceutically acceptable salt thereof can be isolated by conventional methods.

In step (4) of Reaction Scheme X, a 1H-imidazo[4,5-c]quinoline of Formula LXXVI is oxidized to provide an N-oxide of Formula LXXVII. The reaction can be conveniently carried out as in step (9) of Reaction Scheme II.

In step (5) an N-oxide of Formula LXXVII is aminated to provide a 1H-imidazo[4,5-c]quinoline-4-amine of Formula LXXVIII. The reaction is carried as in step (10) of Reaction Scheme II. The product or a pharmaceutically acceptable salt thereof can be isolated by conventional methods.

In step (6) of Reaction Scheme X, a halogen-substituted 1H-imidazo[4,5-c]quinoline-4-amine of Formula LXXVIII undergoes a coupling reaction with a boronic acid of Formula X, an anhydride thereof, or a boronic acid ester of Formula $R_{3a}-B(O-alkyl)_2$. The Suzuki coupling reaction can be car- For other embodiments, compounds of the invention can be prepared according to Reaction Scheme XI, where R, $R_2$, $R_4$, $R_8$, X, Hal, and n are as defined above. In step (1) of Reaction Scheme XI, the hydroxy group of a 3-nitroquinolin-4-amine of Formula LXXX is chlorinated using conventional methods to provide a 3-nitroquinolin-4-amine of Formula LXXXI. Many 3-nitroquinolin-4-amines of Formula LXXIII are known or can be prepared using known synthetic methods, see for example, U.S. Pat. Nos. 4,689,338; 5,175,296; and 5,389,640; and the references cited therein. The chlorination is conveniently carried out by adding thionyl chloride to a solution of the 3-nitroquinolin-4-amine of Formula LXXX in a suitable solvent such as dichloromethane. The reaction can be carried out at ambient temperature, and the product can be isolated using conventional methods.

In step (2) of Reaction Scheme XI, a 3-nitroquinolin-4-amine of Formula LXXXI is reduced to provide a quinoline- 3,4-diamine of Formula LXXXII. The reduction can be carried out with sodium dithionite as described in step (7) of Reaction Scheme II. The product can be isolated by conventional methods.

In step (3) of Reaction Scheme XI, a quinoline-3,4-diamine of Formula LXXXII is reacted with a carboxylic acid or an equivalent thereof to provide a 1H-imidazo[4,5-c]quinoline of Formula LXXXIII. The reaction can be conveniently carried out as described in step (8) of Reaction Scheme II; the product can be isolated by conventional methods.

In step (4) of Reaction Scheme XI, the chloro group of a 1H-imidazo[4,5-c]quinoline of Formula LXXXIII is displaced with potassium thioacetate to provide a 1H-imidazo[4,5-c]quinoline of Formula LXXXIV. The reaction is conveniently carried out by adding potassium thioacetate to a solution of a 1H-imidazo[4,5-c]quinoline of Formula LXXXIII in a suitable solvent such as DMF. The reaction can be carried out at ambient temperature, and the product can be isolated using conventional methods.

In step (5) of Reaction Scheme XI, the thioacetate group of a 1H-imidazo[4,5-c]quinoline of Formula LXXXIV is hydrolyzed under basic conditions to provide a thiol-substituted 1H-imidazo[4,5-c]quinoline of Formula LXXXV. The reaction is conveniently carried out by adding a solution of sodium methoxide in methanol to a solution of a 1H-imidazo[4,5-c]quinoline of Formula LXXXIV in methanol. The reaction can be carried out at ambient temperature, and the product can be isolated using conventional methods.

In step (6) of Reaction Scheme XI, the thiol group of a 1H-imidazo[4,5-c]quinoline of Formula LXXXV is oxidized to a sulfonyl chloride of Formula LXXXVI. The reaction is conveniently carried out by adding a solution of sodium chlorate in a suitable solvent such as water to a solution of a thiol-substituted 1H-imidazo[4,5-c]quinoline of Formula LXXXV in hydrochloric acid. The reaction can be carried out at a subambient temperature such as 0° C., and the product can be isolated using conventional methods.

Alternatively, steps (4), (5), and (6) can be replaced with steps (4a) and (5a) of Reaction Scheme XI. In step (4a), the chloro group of a 1H-imidazo[4,5-c]quinoline of Formula LXXXIII is displaced with thiourea to provide a 1H-imidazo[4,5-c]quinoline of Formula LXXXVII. The reaction is conveniently carried out by adding thiourea and a catalytic amount of potassium iodide to a solution of a 1H-imidazo[4,5-c]quinoline of Formula LXXXIII in a suitable solvent such as DMF. The reaction can be carried out at an elevated temperature, such as 110° C., and the product can be isolated using conventional methods.

In step (5a) of Reaction Scheme XI, the thiourea group of a 1H-imidazo[4,5-c]quinoline of Formula LXXXVII is converted to a sulfonyl chloride of Formula LXXXVI under the conditions described in step (6).

In step (7) of Reaction Scheme XI, the sulfonyl chloride of Formula LXXXVI is treated with an amine or an amine salt to provide a sulfonamide of Formula LXXXVIII. The reaction is conveniently carried out by adding an amine of Formula $NH(R_4)(R_8)$ to a sulfonyl chloride of Formula LXXXVI in a suitable solvent such as dichloromethane. The reaction can be carried out at ambient temperature, and the product can be isolated using conventional methods. Alternatively, step (7) can be carried out by adding an amine hydrochloride of Formula $(R_4)(R_8)NH.HCl$ followed by aqueous potassium carbonate to a solution of a sulfonyl chloride of Formula LXXXVI in a suitable solvent such as dichloromethane. The reaction can be carried out at ambient temperature, and the product can be isolated using conventional methods.

In steps (8) and (9) of Reaction Scheme XI, a sulfonamide-substituted 1H-imidazo[4,5-c]quinoline of Formula LXXXVIII is oxidized in step (8) to afford a 1H-imidazo[4,5-c]quinoline-5N-oxide of Formula LXXXIX, which is aminated in step (9) to provide a 1H-imidazo[4,5-c]quinolin-4-amine of Formula XC. Steps (8) and (9) of Reaction Scheme XI can be carried out as described in steps (9) and (10) of Reaction Scheme II.

In step (10) of Reaction Scheme XI, a 1H-imidazo[4,5-c]quinolin-4-amine of Formula XC is coupled with a boronic acid of Formula X, an anhydride thereof, or boronic acid ester of Formula $R_{3a}$—$B(O\text{-alkyl})_2$ to provide a 1H-imidazo[4,5-c]quinolin-4-amine of Formula XCI, which is a subgenus of Formula II. Step (10) can be carried out as described in Reaction Scheme I. The product or pharmaceutically acceptable salt thereof can be isolated using conventional methods.

Reaction Scheme XI

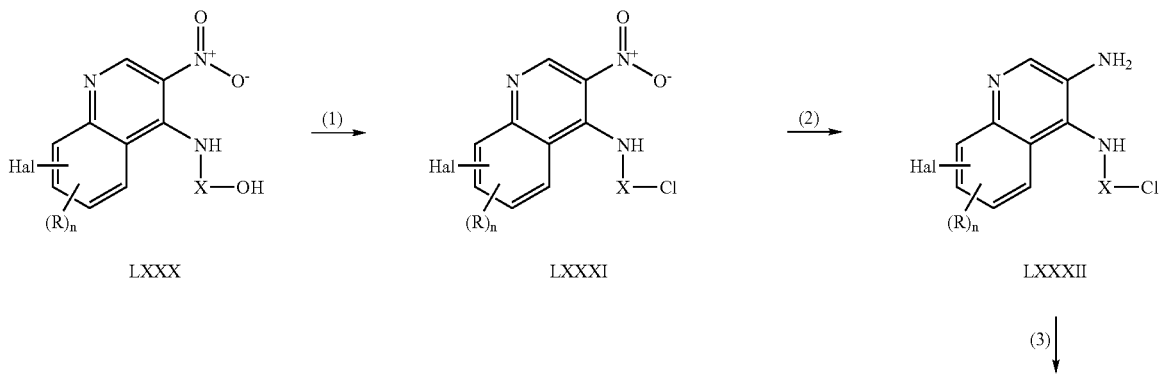

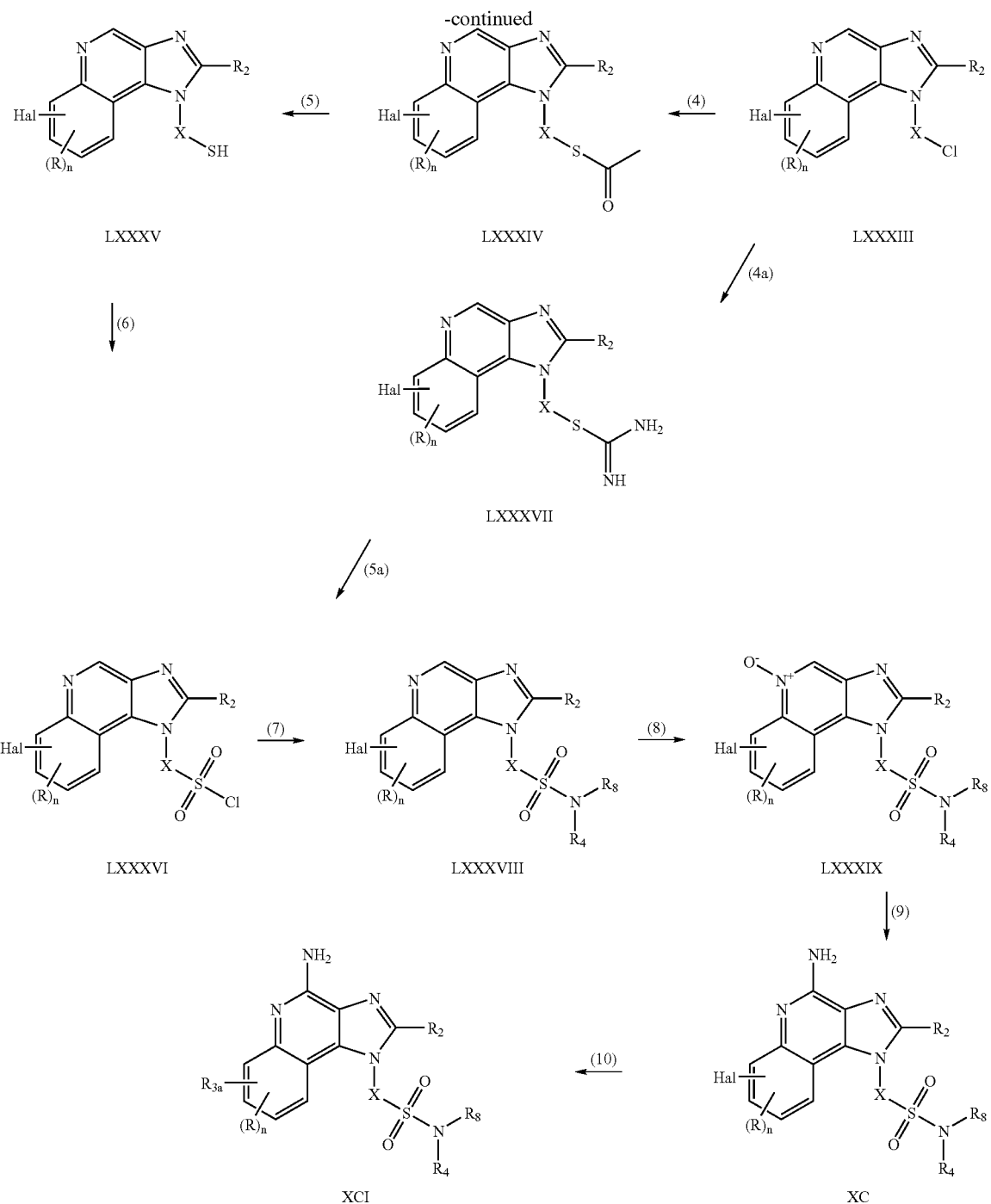

For other embodiments, compounds of the invention can be prepared according to Reaction Scheme XII, wherein R, $R_1$, $R_2$, Hal, and n are as defined above, and HA is a heteroaryl group attached at a nitrogen atom. In Reaction Scheme XII, a halogen-substituted imidazoquinolin-4-amine of Formula IX undergoes a copper-catalyzed amination with a nitrogen-containing heteroaryl compound to provide an imidazoquinolin-4-amine of Formula XCII, which is a subgenus of Formula II. Several nitrogen-containing heteroaryl compounds, such as imidazole and pyrazole, are commercially available; others can be prepared by known methods. The reaction is conveniently carried out by combining the imidazoquinolin-4-amine of Formula IX and the nitrogen-containing heteroaryl compound in the presence of copper (I) iodide, potassium phosphate, and trans-1,2-diaminocyclohexane in a suitable solvent such as 1,4-dioxane. The reaction can be carried out at an elevated temperature such as 110° C. The compound or pharmaceutically acceptable salt thereof can be isolated using conventional methods.

Reaction Scheme XII

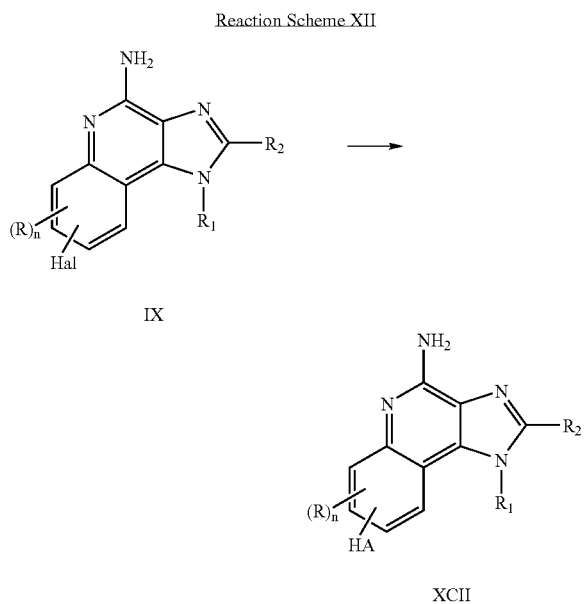

Pharmaceutical Compositions and Biological Activity

Pharmaceutical compositions of the invention contain a therapeutically effective amount of a compound of the invention as described above in combination with a pharmaceutically acceptable carrier.

The term "therapeutically effective amount" or "effective amount" means an amount of the compound sufficient to induce a therapeutic or prophylactic effect, such as cytokine induction, cytokine inhibition, immunomodulation, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. A variety of dosage forms may be used, such as tablets, lozenges, capsules, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, antibodies, proteins, peptides, oligonucleotides, etc.

Compounds of the invention have been shown to modulate (e.g., induce or inhibit) the production of certain cytokines in experiments performed according to the tests set forth below. These results indicate that compounds of the invention are useful as immune response modifiers that can modulate the immune response in a number of different ways, rendering them useful in the treatment of a variety of disorders.

Cytokines whose production may be induced by the administration of certain compounds according to the invention generally include interferon-α (IFN-α) and/or tumor necrosis factor-α (TNF-α) as well as certain interleukins (IL). Cytokines whose biosynthesis may be induced by certain compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and neoplastic diseases. Accordingly, the invention provides a method of inducing cytokine biosynthesis in an animal comprising administering an effective amount of a compound or composition of the invention to the animal. The animal to which the compound or composition is administered for induction of cytokine biosynthesis may have a disease as described infra, for example a viral disease or a neoplastic disease, and administration of the compound may provide therapeutic treatment. Alternatively, the compound may be administered to the animal prior to the animal aquiring the disease so that administration of the compound may provide a prophylactic treatment.

In addition to the ability to induce the production of cytokines, certain compounds of the invention affect other aspects of the innate immune response. For example, natural killer cell activity may be stimulated, an effect that may be due to cytokine induction. Certain compounds may also activate macrophages, which in turn stimulate secretion of nitric oxide and the production of additional cytokines. Further, certain compounds may cause proliferation and differentiation of B-lymphocytes.

Certain compounds of the invention also have an effect on the acquired immune response. For example, the production of the T helper type 1 ($T_H1$) cytokine IFN-γ is induced indirectly and the production of the T helper type 2 ($T_H2$) cytokines IL-4, IL-5 and IL-13 are inhibited upon administration of compounds of the invention.

Other cytokines whose production is inhibited by the administration of certain compounds according to the invention include tumor necrosis factor-α (TNF-α). Among other effects, inhibition of TNF-α production can provide prophylaxis or therapeutic treatment of diseases in animals in which TNF is mediated, making the compounds useful in the treatment of, for example, autoimmune diseases. Accordingly, the invention provides a method of inhibiting TNF-α biosynthesis in an animal comprising administering an effective amount of a compound or composition of the invention to the animal. The animal to which the compound or composition is administered for inhibition of TNF-α biosynthesis may have a disease as described infra, for example an autoimmune disease, and administration of the compound may provide therapeutic treatment. Alternatively, the compound may be administered to the animal prior to the animal aquiring the disease so that administration of the compound may provide a prophylactic treatment.

Whether for prophylaxis or therapeutic treatment of a disease, and whether for effecting innate or acquired immunity, the compound or composition may be administered alone or in combination with one or more active components as in, for example, a vaccine adjuvant. When administered with other components, the compound and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection; and (d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, renal cell carcinoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers; and (e) $T_H2$-mediated, atopic, and autoimmune diseases, such as atopic dermatitis or eczema, eosinophilia, asthma, allergy, allergic rhinitis, systemic lupus erythematosus, essential thrombocytopaenia, multiple sclerosis, Ommen's syndrome, discoid lupus, alopecia greata, inhibition of keloid formation and other types of scarring, and enhancing would healing, including chronic wounds.

IRMs identified herein also may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

IRMs may also be particularly helpful in individuals having compromised immune function. For example, IRM compounds may be used for treating the opportunistic infections and tumors that occur after suppression of cell mediated immunity in, for example, transplant patients, cancer patients and HIV patients.

Thus, one or more of the above diseases or types of diseases, for example, a viral disease, a neoplastic disease, may be treated in an animal in need there of (having the disease) by administering a therapeutically effective amount of a compound or salt of Formula I, II, III, IV, V, VI, VII, VIII, XLVI, or a combination thereof to the animal.

An amount of a compound effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944, WO 03/080114, WO 03/045494, WO 02/024225, WO 02/036592, U.S. Pat. No. 6,245,776, and U.S. Publication Nos. 2002/0193729 and 2003/0139364.

Objects and advantages of this invention are further illustrated by the following examples, but the particular materials and amounts thereof recited in these examples, as well as other conditions and details, should not be construed to unduly limit this invention.

EXAMPLES

In the examples below some of the compounds were purified by preparative high performance liquid chromatography (prep HPLC) using a Waters Fraction Lynx automated purification system. The prep HPLC fractions were analyzed using a Micromass LC-TOFMS and the appropriate fractions were combined and centrifuge evaporated to provide the trifluoroacetate salt of the desired compound. In order to maximize purity, the compounds were sent through the purification process twice. Column: Phenomenex Luna C18(2), 21.2×50 millimeters (mm), 10 micron particle size, 100 Angstrom (Å) pore; flow rate: 25 milliliters per minutes (mL/min); non-linear gradient elution from 5-95% B in 9 min (first purification run) and from 5-65% B in 16 min (second purification run), then hold at 95% B for 2 min, where A is 0.05% trifluoroacetic acid/water and B is 0.05% trifluoroactic acid/acetonitrile; fraction collection by mass-selective triggering.

A variety of chromatographic conditions were used for the prep HPLC purification of other compounds shown in the examples below using either the Phenomenex Luna C18(2) column (21.2×50 millimeters (mm), 10 micron particle size) or a Waters Xterra C18 column (19×50 mm, 5 micron particle size). Elution was carried out in a non-linear gradient from 95:5 to 5:95 A:B, where A is 0.05% trifluoroacetic acid/water and B is 0.05% trifluoroactic acid/acetonitrile; fraction collection was performed by mass-selective triggering.

Some of the compounds prepared by Suzuki coupling were passed through a Waters Oasis Sample Extractions Cartridge MCX (6 cc) prior to prep HPLC purification. The following procedure was used. The product from the coupling reaction was dissolved in 1N hydrochloric acid (3 mL) to adjust to pH 5-7 and passed through the cartridge optionally using light nitrogen pressure. The cartridge was washed with methanol (5 mL) optionally using light nitrogen pressure and transferred to a clean test tube. A solution of 1% ammonia in methanol (2×5 mL) was then passed through the cartridge optionally using light nitrogen pressure, and the basic solution was collected and concentrated.

Example 1

2-Butyl-1-isobutyl-7-(thiophen-3-yl)-1H-imidazo[4,5-c]quinolin-4-amine

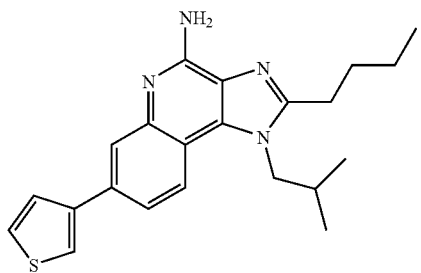

Part A

A mixture of triethyl orthoformate (154 grams (g), 1.04 moles (mol) and Meldrum's acid (142 g, 0.983 mol) was heated to 55° C. for 4 hours (h). After cooling to 50° C., a solution of 3-bromoaniline (162.6 g, 0.945 mol) in ethanol (300 mL) was added such that the temperature of the reaction was maintained between 50-55° C. After half of the 3-bromoaniline had been added, stirring became difficult due to the formation of solids, so more ethanol (1 liter (L)) was added to facilitate stirring. Upon complete addition, the reaction was cooled to room temperature (RT), and the solids were collected by filtration. The filter cake was washed with ice cold ethanol until the washings were nearly colorless, and the product was dried at 65° C. under vacuum to afford 287 g of 5-[(3-bromophenylamino)methylene]-2,2-dimethyl-[1,3]dioxane-4,6-dione as an off-white solid.

$^1$H NMR (300 MHz, CDCl$_3$) δ 11.19 (brd, J=12.8 Hz, 1H), 8.60 (d, J=14.0 Hz, 1H), 7.44-7.38 (m, 2H), 7.30 (t, J=8.0 Hz, 1H), 7.18 (ddd, J=8.0, 2.2, 0.9 Hz, 1H), 1.75 (s, 6H).

Part B

7-Bromoquinolin-4-ol was prepared in accordance with the literature procedure (D. Dibyendu et al., *J. Med. Chem.*, 41, 4918-4926 (1998)) or by thermolysis of 5-[(3-bromophenylamino)methylene]-2,2-dimethyl-[1,3]dioxane-4,6-dione in DOWTHERM A heat transfer fluid and had the following spectral properties:

$^1$H NMR (300 MHz, d$_6$-DMSO) δ 11.70 (brs, 1H), 8.00 (d, J=8.7 Hz, 1H), 7.92 (d, J=7.5 Hz, 1H), 7.74 (d, J=1.9 Hz, 1H), 7.44 (dd, J=8.7, 1.9 Hz, 1H), 6.05 (d, J=7.5 Hz, 1H).

Part C

A stirred suspension of 7-bromoquinolin-4-ol (162 g, 0.723 mol) in propionic acid (1500 mL) was brought to 110° C. 70% Nitric acid (85 g) was added dropwise over 1 h such that the temperature was maintained between 110-115° C. After half of the nitric acid had been added, stirring became difficult due to the formation of solids and an additional 200 mL of propionic acid was added. Upon complete addition, the reaction was stirred for 1 h at 110° C., cooled to room temperature, and the solid was collected by filtration. The filter cake was washed with ice cold ethanol until the washings were nearly colorless (800 mL), and the product was dried at 60° C. under vacuum to afford 152 g of 7-bromo-3-nitroquinolin-4-ol as a pale yellow solid.

$^1$H NMR (300 MHz, d$_6$-DMSO) δ 13.0 (brs, 1H), 9.22 (s, 1H), 8.15 (d, J=8.4 Hz, 1H), 7.90 (d, J=1.6 Hz, 1H), 7.66 (dd, J=8.7, 1.9 Hz, 1H).

Part D

7-Bromo-3-nitroquinolin-4-ol (42 g, 156 millimoles (mmol)) was suspended in POCl$_3$ (130 mL) and brought to 102° C. under an atmosphere of N$_2$. After 45 min, all of the solids had dissolved, so the reaction was cooled to room temperature (RT). The resulting solids were collected by filtration, washed with H$_2$O, and then partitioned with CH$_2$Cl$_2$ (3 L) and 2M Na$_2$CO$_3$ (500 mL). The organic layer was separated, washed with H$_2$O (1×), dried over Na$_2$SO$_4$, filtered, and concentrated to afford 33.7 g of 7-bromo-4-chloro-3-nitroquinoline as a beige solid.

$^1$H NMR (300 MHz, CDCl$_3$) δ 9.26 (s, 1H), 8.41 (d, J=1.8 Hz, 1H), 8.30 (d, J=9.0 Hz, 1H), 7.90 (dd, J=8.9, 2.1 Hz, 1H).

Part E

7-Bromo-4-chloro-3-nitroquinoline (33.5 g, 117 mmol) and Et$_3$N (13.0 g, 128 mmol) were dissolved in CH$_2$Cl$_2$ (500 mL) and cooled on an ice bath. Isobutylamine (9.36 g, 128 mmol) was added in one portion and then the reaction was allowed to warm to room temperature. After 2 h, the reaction mixture was washed with water (500 mL), and the aqueous layer was extracted with CH$_2$Cl$_2$ (2×100 mL). The combined organic layers were dried over MgSO$_4$, filtered, and concentrated to afford 38.0 g of a yellow solid. Recrystallization from refluxing isopropanol (1.1 L) afforded 34.0 g of (7-bromo-3-nitroquinolin-4-yl)isobutylamine as yellow needles.

$^1$H NMR (300 MHz, CDCl$_3$) δ 9.79 (brs, 1H), 9.35 (s, 1H), 8.16 (d, J=9.1 Hz, 1H), 8.16 (d, J=2.2 Hz, 1H), 7.57 (dd, J=9.1, 2.2 Hz, 1H), 3.75 (dd, J=6.6, 5.0 Hz, 2H), 2.14-2.01 (m, 1H), 1.10 (d, J=6.9 Hz, 6H).

Part F

A solution of Na$_2$S$_2$O$_4$ (193 g) in H$_2$O (1 L) was added to a boiling solution of (7-bromo-3-nitroquinolin-4-yl)isobutylamine (32.0 g, 99 mmol) in isopropanol (1 L). Upon complete addition, the reaction mixture was cooled to room temperature and the bulk of the isopropanol was removed on a rotary evaporator. The resulting mixture was extracted with CH$_2$Cl$_2$ (3×), and the combined organic layers were dried over Na$_2$SO$_4$, filtered, and concentrated to afford 39.5 g of the crude 7-bromo-N$^4$-isobutylquinoline-3,4-diamine as a yellow solid.

Part G

7-Bromo-N$^4$-isobutylquinoline-3,4-diamine (39.4 g of crude material), trimethyl orthovalerate (32 g, 0.20 mol), and pyridine hydrochloride (0.31 g, 2.7 mmol) were combined with anhydrous toluene (500 mL) and heated to reflux for 30 min. The reaction was cooled to room temperature, concentrated, and the residue was purified by chromatography on silica gel (75% ethyl acetate in hexane to 100% ethyl acetate gradient) to afford 21.2 g of 7-bromo-2-butyl-1-isobutyl-1H-imidazo[4,5-c]quinoline as a yellow solid.

$^1$H NMR (300 MHz, CDCl$_3$) δ 9.28 (s, 1H), 8.43 (d, J=2.2 Hz, 1H), 7.95 (d, J=8.7 Hz, 1H), 7.70 (dd, J=9.1, 2.2 Hz, 1H), 4.29 (d, J=7.5 Hz, 2H), 2.97-2.91 (m, 2H), 2.40-2.26 (m, 1H), 2.01-1.90 (m, 2H), 1.52 (sextet, J=7.5 Hz, 2H), 1.02 (d, J=6.9 Hz, 6H), 1.01 (t, J=7.3 Hz, 3H);

MS m/z (M+1$^+$) calcd 362.1, obsd 362.1.

Part H

To a solution of 7-bromo-2-butyl-1-isobutyl-1H-imidazo [4,5-c]quinoline (10.8 g, 30.0 mmol) in CH$_2$Cl$_2$ (300 mL) was added 3-chloroperoxybenzoic acid (10.4 g of approximately 77% purity). The reaction was allowed to stir overnight and was washed with 2M Na$_2$CO$_3$ (200 mL). The aqueous layer was extracted with CH$_2$Cl$_2$ (2×200 mL), and the combined organic layers were dried (MgSO$_4$), filtered, and concentrated to afford 13.6 g orange solid. Recrystallization from boiling ethyl acetate (300 mL) afforded 8.25 g of 7-bromo-2-butyl-1-isobutyl-1H-imidazo[4,5-c]quinoline 5-oxide as a yellow powder.

$^1$H NMR (300 MHz, CDCl$_3$) δ 9.24 (d, J=1.9 Hz, 1H), 9.00 (s, 1H), 7.93 (d, J=8.7 Hz, 1H), 7.81 (dd, J=9.1, 2.2 Hz, 1H), 4.26 (d, J=7.5 Hz, 2H), 2.94-2.89 (m, 2H), 2.37-2.23 (m, 1H), 1.97-1.87 (m, 2H), 1.51 (sextet, J=7.4 Hz, 2H), 1.03 (d, J=6.6 Hz, 6H), 1.01 (t, J=7.3 Hz, 3H);

MS m/z (M+1$^+$) calcd 378.1, obsd 378.1.

Part I

To a vigorously stirred mixture of 7-bromo-2-butyl-1-isobutyl-1H-imidazo[4,5-c]quinoline 5-oxide (345 mg, 0.92 mmol) in CH$_2$Cl$_2$ (7 mL) and NH$_4$OH (0.50 mL of 30%) was added p-toluenesulfonyl chloride (175 mg, 0.92 mmol) in one portion. After 15 h, the reaction mixture was diluted with CH$_2$Cl$_2$ and washed with 2 M Na$_2$CO$_3$. The aqueous layer was extracted with CH$_2$Cl$_2$ (2×), and the combined organic layers were dried (Na$_2$SO$_4$), filtered, and concentrated to afford 331 mg of a yellow solid. Recrystallization from boiling isopropanol (3 mL) followed by purification on silica gel (40% acetone in toluene to 50% acetone in toluene gradient) afforded 208 mg of 7-bromo-2-butyl-1-isobutyl-1H-imidazo [4,5-c]quinolin-4-amine as a white solid, m.p. 198-200° C.

$^1$H NMR (300 MHz, CDCl$_3$) δ 7.98 (d, J=2.2 Hz, 1H), 7.73 (d, J=8.7 Hz, 1H), 7.40 (dd, J=8.7, 1.9 Hz, 1H), 5.44 (s, 2H), 4.22 (d, J=7.8 Hz, 2H), 2.92-2.86 (m, 2H), 2.38-2.24 (m, 1H), 1.93-1.83 (m, 2H), 1.50 (sextet, J=7.5 Hz, 2H), 1.00 (d, J=6.9 Hz, 6H), 1.00 (t, J=7.3 Hz, 3H);

$^{13}$C NMR (75 MHz, CDCl$_3$) δ 154.4, 152.0, 146.2, 133.3, 129.9, 127.2, 125.2, 121.1, 120.5, 114.6, 52.8, 30.3, 29.4, 27.7, 22.8, 20.0, 14.1;

MS m/z (M+1$^+$) calcd 375.1, obsd 375.2;

Anal. Calcd for C$_{18}$H$_{23}$BrN$_4$: C, 57.60; H, 6.18; N, 14.93. Found: C, 57.54; H, 6.17; N, 14.98.

Part J

7-Bromo-2-butyl-1-isobutyl-1H-imidazo[4,5-c]quinolin-4-amine (751 mg, 2.00 mmol), thiophene-3-boronic acid (269 mg, 2.10 mmol), and n-propanol (3.6 mL) were combined in a reaction vessel and placed under an atmosphere of N$_2$. Pd(OAc)$_2$ (1.3 mg, 0.0060 mmol), triphenylphosphine (4.7 mg, 0.018 mmol), Na$_2$CO$_3$ (1.2 mL of a 2 M solution, 2.4 mmol), and H$_2$O (0.7 mL) were added, and the reaction mixture was heated to reflux in an oil bath for 2.5 h. Upon cooling to RT, the solid product was collected by filtration and washed with H$_2$O and ethanol. Purification on silica gel (5%-6% methanol (MeOH) in CH$_2$Cl$_2$ gradient) afforded 700 mg of product which was recrystallized from boiling isopropanol (20 mL) to yield 535 mg of 2-butyl-1-isobutyl-7-(thiophen-3-yl)-1H-imidazo[4,5-c]quinolin-4-amine as an off-white powder, m.p. 229-230° C.

$^1$H NMR (300 MHz, CDCl$_3$) δ 8.08 (d, J=1.9 Hz, 1H), 7.91 (d, J=8.7 Hz, 1H), 7.61-7.58 (m, 2H), 7.55 (dd, J=5.2, 1.4 Hz, 1H), 7.42 (dd, J=5.2, 3.0 Hz, 1H), 5.39 (s, 2H), 4.26 (d, J=7.5 Hz, 2H), 2.93-2.88 (m, 2H), 2.46-2.32 (m, 1H), 1.94-1.84 (m, 2H), 1.51 (sextet, J=7.4 Hz, 2H), 1.03 (d, J=6.6 Hz, 6H), 1.01 (t, J=7.5 Hz, 3H);

$^{13}$C NMR (75 MHz, CDCl$_3$) δ 154.1, 151.7, 145.5, 142.3, 134.3, 133.6, 127.2, 126.53, 126.47, 124.6, 121.0, 120.6, 120.4, 114.8, 52.8, 30.4, 29.5, 27.8, 22.9, 20.0, 14.1;

MS m/z (M+1$^+$) calcd 379.1956, obsd 379.1943;

Anal. Calcd for C$_{22}$H$_{26}$N$_4$S: C, 69.80; H, 6.92; N, 14.80; S, 8.47. Found: C, 69.45; H, 7.10; N, 14.90; S, 8.44.

Example 2

2-Butyl-1-isobutyl-7-phenyl-1H-imidazo[4,5-c] quinolin-4-amine

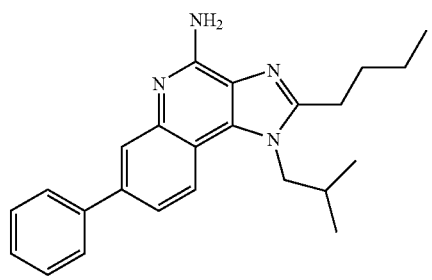

7-Bromo-2-butyl-1-isobutyl-1H-imidazo[4,5-c]quinolin-4-amine and benzeneboronic acid were coupled according to the general procedure described in Part J of Example 1. Purification by chromatography on silica gel (20% acetone in toluene to 60% acetone in toluene gradient) afforded 2-butyl-1-isobutyl-7-phenyl-1H-imidazo[4,5-c]quinolin-4-amine as a white solid, m.p.>250° C.

$^1$H NMR (300 MHz, CDCl$_3$) δ 8.09 (d, J=1.9 Hz, 1H), 7.96 (d, J=8.7 Hz, 1H), 7.77-7.74 (m, 2H), 7.61 (dd, J=8.4, 1.9 Hz, 1H), 7.50-7.45 (m, 2H), 7.36 (tt, J=7.3, 1.5 Hz, 1H), 5.40 (s, 2H), 4.28 (d, J=7.5 Hz, 2H), 2.94-2.89 (m, 2H), 2.48-2.34 (m, 1H), 1.95-1.84 (m, 2H), 1.52 (sextet, J=7.4 Hz, 2H), 1.04 (d, J=6.6 Hz, 6H), 1.01 (t, J=7.3 Hz, 3H);

$^{13}$C NMR (75 MHz, CDCl$_3$) δ 154.2, 151.7, 145.3, 141.0, 139.6, 133.6, 129.1, 127.6, 127.4, 127.2, 125.4, 121.6, 120.4, 114.9, 52.9, 30.4, 29.5, 27.8, 22.9, 20.0, 14.1;

MS m/z (M+1$^+$) calcd 373.2, obsd 373.2;

Anal. Calcd for C$_{24}$H$_{28}$N$_4$: C, 77.38; H, 7.58; N, 15.04. Found: C, 77.16; H, 7.62; N, 14.95.

Example 3

2-Butyl-7-(2,4-dimethoxyphenyl)-1-isobutyl-1H-imidazo[4,5-c]quinolin-4-amine

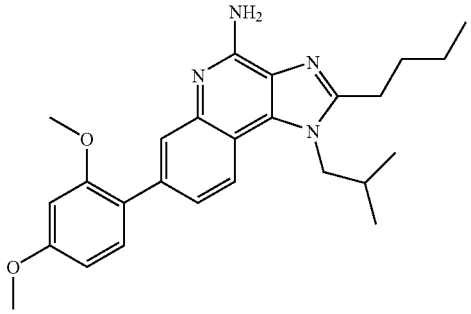

7-Bromo-2-butyl-1-isobutyl-1H-imidazo[4,5-c]quinoline and 2,4-dimethoxybenzeneboronic acid were coupled according to the general procedure described in Part J of Example 1. The resulting 2-butyl-7-(2,4-dimethoxyphenyl)-1-isobutyl-1H-imidazo[4,5-c]quinoline was oxidized and then aminated according to the general procedures described in Parts H and I of Example 1 and purified by chromatography on silica gel (8% methanol in $CH_2Cl_2$ to 10% methanol in $CH_2Cl_2$ gradient) followed by recrystallization from 1/1 ethyl acetate/hexane to afford 2-butyl-7-(2,4-dimethoxyphenyl)-1-isobutyl-1H-imidazo[4,5-c]quinolin-4-amine as a pale orange solid, m.p. 187-189° C.

$^1$H NMR (300 MHz, $CDCl_3$) δ 7.96 (d, J=1.6 Hz, 1H), 7.89 (d, J=8.7 Hz, 1H), 7.53 (dd, J=8.4, 1.9 Hz, 1H), 7.40-7.37 (m, 1H), 6.62-6.58 (m, 2H), 5.38 (s, 2H), 4.25 (d, J=7.5 Hz, 2H), 3.87 (s, 3H), 3.83 (s, 3H), 2.93-2.88 (m, 2H), 2.50-2.36 (m, 1H), 1.94-1.84 (m, 2H), 1.51 (sextet, J=7.4 Hz, 2H), 1.02 (d, J=6.6 Hz, 6H), 1.01 (t, J=7.2 Hz, 3H);

$^{13}$C NMR (75 MHz, $CDCl_3$) δ 160.6, 157.8, 152.9, 151.4, 145.0, 137.2, 133.6, 131.7, 127.7, 127.1, 124.3, 123.5, 119.3, 114.3, 105.0, 99.3, 55.8, 55.6, 52.8, 30.3, 29.4, 27.7, 22.9, 20.0, 14.1;

MS m/z (M+1$^+$) calcd 433.2604, obsd 433.2600;

Anal. Calcd for $C_{26}H_{32}N_4O_2 \cdot 0.17H_2O$: C, 71.67; H, 7.48; N, 12.86. Found: C, 71.25; H, 7.46; N, 12.81. Water content determined by Karl-Fischer analysis.

Example 4

2-Butyl-7-(4-tert-butylphenyl)-1-isobutyl-1H-imidazo[4,5-c]quinolin-4-amine

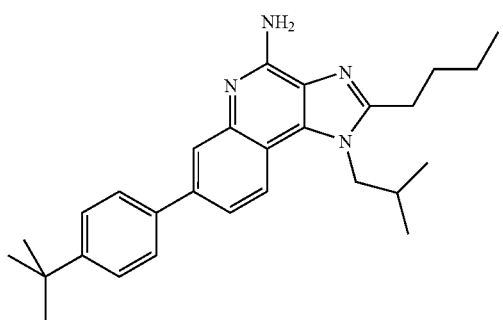

7-Bromo-2-butyl-1-isobutyl-1H-imidazo[4,5-c]quinolin-4-amine and 4-tert-butylbenzeneboronic were coupled according to the general procedure described in Part J of Example 1. Purification by chromatography on silica gel (5% methanol in $CH_2Cl_2$ to 6% methanol in $CH_2Cl_2$ gradient) followed by recrystallization from ethyl acetate afforded 2-butyl-7-(4-tert-butylphenyl)-1-isobutyl-1H-imidazo[4,5-c]quinolin-4-amine as a white solid, m.p. 219-220° C.

$^1$H NMR (300 MHz, $CDCl_3$) δ 8.09 (d, J=1.9 Hz, 1H), 7.94 (d, J=8.7 Hz, 1H), 7.71 (dm, J=8.4 Hz, 2H), 7.60 (dd, J=8.6, 2.1 Hz, 1H), 7.51 (dm, J=8.7 Hz, 2H), 5.38 (s, 2H), 4.27 (d, J=7.5 Hz, 2H), 2.94-2.89 (m, 2H), 2.48-2.35 (m, 1H), 1.92-1.84 (m, 2H), 1.51 (sextet, J=7.4 Hz, 2H), 1.38 (s, 9H), 1.03 (d, J=6.6 Hz, 6H), 1.01 (t, J=7.3 Hz, 3H);

$^{13}$C NMR (100 MHz, $CDCl_3$) δ 154.1, 151.6, 150.6, 145.4, 139.4, 138.0, 133.6, 127.1, 127.0, 126.0, 125.1, 121.5, 120.3, 114.8, 52.8, 34.8, 31.6, 30.4, 29.4, 27.8, 22.9, 20.0, 14.1;

MS m/z (M+1$^+$) calcd 429.3, obsd 429.5;

Anal. Calcd for $C_{28}H_{36}N_4$: C, 78.46; H, 8.47; N, 13.07. Found: C, 78.10; H, 8.45; N, 13.02.

Example 5

2-Butyl-1-isobutyl-7-(4-propoxyphenyl)-1H-imidazo[4,5-c]quinolin-4-amine

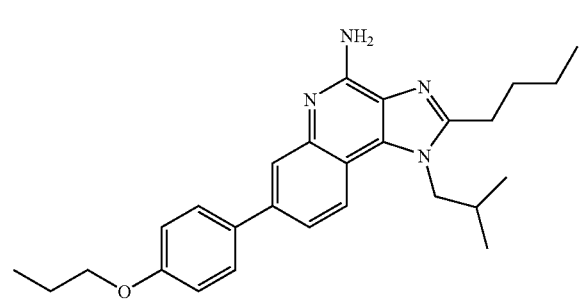

7-Bromo-2-butyl-1-isobutyl-1H-imidazo[4,5-c]quinolin-4-amine and 4-propoxybenzeneboronic acid were coupled according to the general procedure described in Part J of Example 1. The product was recrystallized from isopropanol, collected by filtration, dissolved in $CH_2Cl_2$, and then precipitated with hexanes to afford 2-butyl-1-isobutyl-7-(4-propoxyphenyl)-1H-imidazo[4,5-c]quinolin-4-amine as a pale yellow solid, m.p. 194-197° C.

$^1$H NMR (300 MHz, $CDCl_3$) δ 8.03 (d, J=1.9 Hz, 1H), 7.92 (d, J=8.4 Hz, 1H), 7.69 (dm, J=8.7 Hz, 2H), 7.55 (dd, J=8.4, 1.9 Hz, 1H), 7.01 (dm, J=9.0 Hz, 2H), 5.42 (s, 2H), 4.25 (d, J=7.5 Hz, 2H), 3.98 (t, J=6.7 Hz, 2H), 2.93-2.88 (m, 2H), 2.40 (septet, J=6.9 Hz, 1H), 1.94-1.79 (m, 4H), 1.51 (sextet, J=7.4 Hz, 2H), 1.06 (t, J=7.5 Hz, 3H), 1.02 (d, J=7.2 Hz, 6H), 1.01 (t, J=7.5 Hz, 3H);

$^{13}$C NMR (75 MHz, $CDCl_3$) δ 159.0, 154.0, 151.6, 145.5, 139.3, 133.6, 133.3, 128.3, 127.1, 124.8, 121.2, 120.3, 115.1, 114.5, 69.8, 52.8, 30.4, 29.4, 27.7, 22.87, 22.84, 20.0, 14.1, 10.8;

MS m/z (M+1$^+$) calcd 431.2811, obsd 431.2821;

Anal. Calcd for $C_{27}H_{34}N_4O$: C, 75.31; H, 7.96; N, 13.01. Found: C, 75.20; H, 8.18; N, 12.96.

Example 6

2-Butyl-1-isobutyl-7-(2-propoxyphenyl)-1H-imidazo[4,5-c]quinolin-4-amine

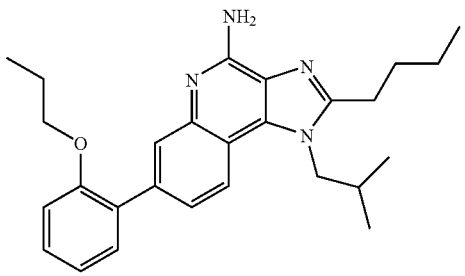

7-Bromo-2-butyl-1-isobutyl-1H-imidazo[4,5-c]quinolin-4-amine and 2-propoxybenzeneboronic acid were coupled according to the general procedure described in Part J of Example 1. The product was recrystallized from isopropanol, collected by filtration, dissolved in $CH_2Cl_2$, and then precipitated with hexanes to afford 2-butyl-1-isobutyl-7-(2-propoxyphenyl)-1H-imidazo[4,5-c]quinolin-4-amine as a white powder, m.p. 174.5-176.0° C.

$^1$H NMR (300 MHz, $CDCl_3$) δ 7.98 (d, J=1.9 Hz, 1H), 7.89 (d, J=8.7 Hz, 1H), 7.61 (dd, J=8.7, 1.9 Hz, 1H), 7.47 (dd, J=7.5, 1.9 Hz, 1H), 7.34-7.29 (m, 1H), 7.07-7.00 (m, 2H), 5.46 (s, 2H), 4.27 (d, J=7.5 Hz, 2H), 3.96 (t, J=6.6 Hz, 2H), 2.94-2.88 (m, 2H), 2.41 (septet, J=6.8 Hz, 1H), 1.94-1.84 (m, 2H), 1.76 (sextet, J=7.1 Hz, 2H), 1.51 (sextet, J=7.4 Hz, 2H), 1.03-0.93 (m, 12H);

$^{13}$C NMR (75 MHz, $CDCl_3$) δ 156.4, 153.9, 151.4, 145.1, 137.6, 133.6, 131.3, 131.0, 128.8, 127.9, 127.2, 124.5, 121.1, 118.9, 114.5, 113.0, 70.4, 52.8, 30.4, 29.4, 27.8, 22.9, 22.8, 20.0, 14.1, 10.9;

MS m/z (M+1$^+$) calcd 431.2811, obsd 431.2809;

Anal. Calcd for $C_{27}H_{34}N_4O \cdot 0.16H_2O$: C, 74.82; H, 7.98; N, 12.93. Found: C, 74.64; H, 7.99; N, 12.78. Water content determined by Karl-Fischer titration.

Example 7

2-Butyl-1-isobutyl-7-[(E)-2-phenylethenyl]-1H-imidazo[4,5-c]quinolin-4-amine

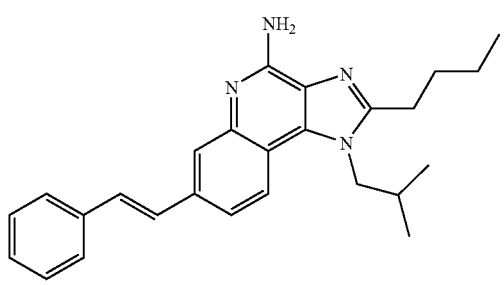

7-Bromo-2-butyl-1-isobutyl-1H-imidazo[4,5-c]quinolin-4-amine and trans-2-phenylvinylboronic acid were coupled according to the general procedure described in Part J of Example 1. Recrystallization from toluene followed by chromatography on silica gel (8% methanol in $CH_2Cl_2$) afforded 2-butyl-1-isobutyl-7-[(E)-2-phenylethenyl]-1H-imidazo[4,5-c]quinolin-4-amine, m.p. 215-216° C.

$^1$H NMR (300 MHz, $CDCl_3$) δ 7.92 (d, J=1.6 Hz, 1H), 7.87 (d, J=8.7 Hz, 1H), 7.57-7.52 (m, 3H), 7.40-7.35 (m, 2H), 7.30-7.24 (m, 3H), 5.44 (s, 2H), 4.24 (d, J=7.5 Hz, 2H), 2.93-2.87 (m, 2H), 2.37 (septet, J=6.9 Hz, 1H), 1.94-1.83 (m, 2H), 1.51 (sextet, J=7.4 Hz, 2H), 1.02 (d, J=7.2 Hz, 6H), 1.00 (t, J=7.5 Hz, 3H);

$^1$H NMR (500 MHz, $CDCl_3$) δ 7.24 (center of AB pattern, J=16.4 Hz);

$^{13}$C NMR (100 MHz, $CDCl_3$) δ 154.2, 151.6, 145.1, 137.6, 136.0, 133.6, 129.2, 128.9, 128.8, 127.9, 127.1, 126.8, 125.6, 120.5, 120.2, 115.1, 52.8, 30.4, 29.4, 27.7, 22.9, 20.0, 14.1;

MS m/z (M+1$^+$) calcd 399.3, obsd 399.2;

Anal. Calcd for $C_{26}H_{30}N_4$: C, 78.36; H, 7.59; N, 14.06. Found: C, 78.05; H, 7.61; N, 14.01.

Example 8

2-Butyl-1-isobutyl-7-phenethyl-1H-imidazo[4,5-c]quinolin-4-amine

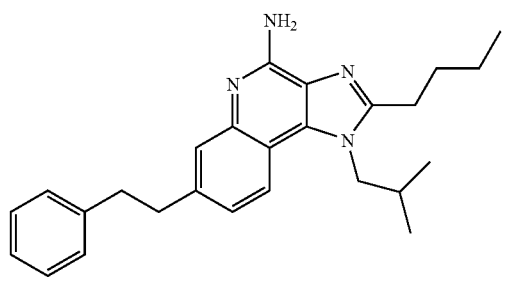

2-Butyl-1-isobutyl-7-[(E)-2-phenylethenyl]-1H-imidazo[4,5-c]quinolin-4-amine (562 mg, 1.41 mmol) was hydrogenated in a Parr bottle over palladium on carbon (10%) until the starting material was consumed as judged by high performance liquid chromatography (HPLC) and thin layer chromatography (TLC) analyses. Purification on silica (5% to 10% methanol in $CH_2Cl_2$ gradient) followed by recrystallization from boiling $CH_3CN$ afforded 150 mg of 2-butyl-1-isobutyl-7-phenethyl-1H-imidazo[4,5-c]quinolin-4-amine, m.p. 181-182° C.

$^1$H NMR (300 MHz, $CDCl_3$) δ 7.80 (d, J=8.4 Hz, 1H), 7.70 (d, J=1.6 Hz, 1H), 7.32-7.14 (m, 6H), 5.44 (s, 2H), 4.23 (d, J=7.5 Hz, 2H), 3.11-3.00 (m, 4H), 2.92-2.87 (m, 2H), 2.43-2.30 (m, 1H), 1.93-1.83 (m, 2H), 1.50 (sextet, J=7.4 Hz, 2H), 1.00 (d, J=6.6 Hz, 6H), 1.00 (t, J=7.3 Hz, 3H);

$^{13}$C NMR (75 MHz, $CDCl_3$) δ 153.9, 151.4, 145.1, 142.1, 140.8, 133.7, 128.7, 128.6, 126.8, 126.5, 126.1, 123.4, 119.8, 114.0, 52.8, 38.1, 38.0, 30.4, 29.4, 27.7, 22.9, 20.0, 14.1;

MS m/z (M+1$^+$) calcd 401.2705, obsd 401.2705;

Anal. Calcd for $C_{26}H_{32}N_4$: C, 77.96; H, 8.05; N, 13.99. Found: C, 77.95; H, 8.02; N, 14.04.

Example 9

2-Ethoxymethyl-1-isobutyl-7-(thiophen-3-yl)-1H-imidazo[4,5-c]quinolin-4-amine

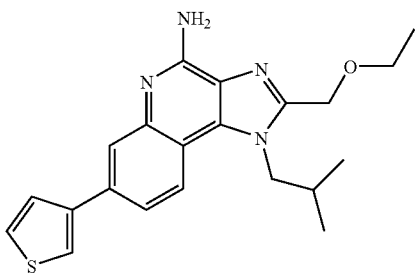

Part A

A solution of 7-bromo-$N^4$-isobutylquinoline-3,4-diamine (85 g, prepared according to Part F of Example 1) in anhydrous pyridine (413 mL) was immersed in an ice bath, and ethoxyacetyl chloride (36.9 g, 300 mmol) was added. The reaction was allowed to warm to room temperature and was then heated in an oil bath held at 85° C. for 3.5 h. The reaction mixture was concentrated under vacuum, and the residue was taken up in diethyl ether and washed with 2M $Na_2CO_3$ (2×) followed by $H_2O$ (1×). The organic layer was dried ($MgSO_4$), filtered, and concentrated. Recrystallization of the resulting solid from boiling 15% ethyl acetate in hexanes afforded 43.0 g of 7-bromo-2-ethoxymethyl-1-isobutyl-1H-imidazo[4,5-c]quinoline as brown crystals.

$^1$H NMR (300 MHz, CDCl$_3$) δ 9.28 (s, 1H), 8.45 (d, J=1.9 Hz, 1H), 7.99 (d, J=9.1 Hz, 1H), 7.74 (dd, J=8.7, 2.2 Hz, 1H), 4.88 (s, 2H), 4.49 (d, J=7.5 Hz, 2H), 3.61 (q, J=7.1 Hz, 2H), 2.45-2.31 (m, 1H), 1.24 (t, J=7.0 Hz, 3H), 1.01 (d, J=6.6 Hz, 6H);

MS m/z (M+1$^+$) calcd 364.1, obsd 364.1.

Part B

7-Bromo-2-ethoxymethyl-1-isobutyl-1H-imidazo[4,5-c]quinoline was oxidized and then aminated according to the general procedures described in Parts H and I of Example 1. Purification by recrystallization from isopropanol afforded 7-bromo-2-ethoxymethyl-1-isobutyl-1H-imidazo[4,5-c]quinolin-4-amine as yellow needles.

$^1$H NMR (300 MHz, CDCl$_3$) δ 7.96 (d, J=2.2 Hz, 1H), 7.73 (d, J=8.7 Hz, 1H), 7.39 (dd, J=8.7, 2.2 Hz, 1H), 5.80 (s, 2H), 4.80 (s, 2H), 4.38 (d, J=7.5 Hz, 2H), 3.60 (q, J=7.1 Hz, 2H), 2.42-2.28 (m, 1H), 1.24 (t, J=6.9 Hz, 3H), 0.99 (d, J=6.6 Hz, 6H);

$^{13}$C NMR (75 MHz, CDCl$_3$) δ 152.4, 149.9, 146.5, 134.1, 129.8, 127.1, 125.3, 121.5, 121.1, 114.5, 66.5, 65.5, 53.1, 29.2, 20.0, 15.2;

Anal. Calcd for $C_{17}H_{21}BrN_4O$: C, 54.12; H, 5.61; N, 14.85. Found: C, 54.16; H, 5.61; N, 14.67.

Part C

7-Bromo-2-ethoxymethyl-1-isobutyl-1H-imidazo[4,5-c]quinolin-4-amine and thiophene-3-boronic acid were coupled according to the general procedure described in Part J of Example 1. Recrystallization from isopropanol followed by purification on silica gel (5% methanol in $CH_2Cl_2$ to 7% methanol in $CH_2Cl_2$ gradient) afforded 2-ethoxymethyl-1-isobutyl-7-(thiophen-3-yl)-1H-imidazo[4,5-c]quinolin-4-amine as a pale yellow solid, m.p. 187-189° C.

$^1$H NMR (300 MHz, CDCl$_3$) δ 8.08 (d, J=1.9 Hz, 1H), 7.94 (d, J=8.4 Hz, 1H), 7.63-7.60 (m, 2H), 7.55 (dd, J=5.2, 1.4 Hz, 1H), 7.43 (dd, J=5.2, 3.0 Hz, 1H), 5.44 (s, 2H), 4.83 (s, 2H), 4.45 (d, J=7.5 Hz, 2H), 3.61 (q, J=7.1 Hz, 2H), 2.44 (septet, J=6.8 Hz, 1H), 1.25 (t, J=7.0 Hz, 3H), 1.04 (d, J=6.9 Hz, 6H);

$^{13}$C NMR (125 MHz, CDCl$_3$) δ 152.0, 149.7, 145.8, 142.2, 134.9, 134.5, 127.1, 126.5, 124.6, 121.1, 120.84, 120.82, 114.8, 66.5, 65.6, 53.1, 29.3, 20.1, 15.3;

MS m/z (M+1$^+$) calcd 381.1749, obsd 381.1763;

Anal. Calcd for $C_{21}H_{24}N_4OS$: C, 66.29; H, 6.36; N, 14.72. Found: C, 66.54; H, 6.37; N, 14.73.

Example 10

2-Butyl-1-(3-methanesulfonylpropyl)-7-phenyl-1H-imidazo[4,5-c]quinolin-4-amine

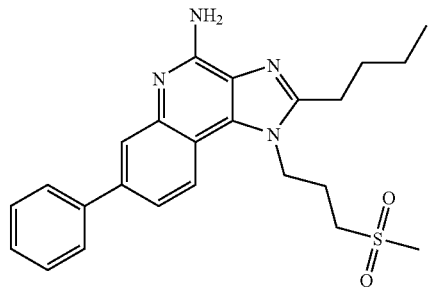

Part A

A solution of 3-bromoaniline (344 g, 2.00 mol) and phenyl boronic acid (268 g, 2.2 mol) in n-propanol (3.5 L) was sparged with $N_2$ for 10 min. To this solution was added Pd(OAc)$_2$ (1.35 g, 6.0 mmol), triphenylphosphine (4.72 g, 18.0 mmol), $Na_2CO_3$ (1.2 L of a 2 M solution, 2.4 mol), and $H_2O$ (700 mL). The reaction was brought to reflux under a $N_2$ atmosphere over a period of 45 min and then cooled to RT and transferred to a separatory funnel. The clear aqueous layer was drawn off (1.1 L), and the organic layer was washed with brine (3×500 mL). The organic layer was treated with charcoal (90 g of Darco G-60) and $MgSO_4$ (160 g) and was filtered through CELITE filter agent, washing with ethyl acetate. The filtrate was concentrated (420 g of an orange oil), dissolved in 1.1 L of 1/1 hexane/isopropanol, filtered to remove insoluble solid and then diluted with an additional 1.9 L of 1/1 hexane/isopropanol. The resulting solution was cooled in an ice bath and then anhydrous HCl in ether (1.05 L of a 2 M solution, 2.1 mol) was added. The solid was collected by filtration, washed with 700 mL diethyl ether (Et$_2$O), and dried at RT in a vacuum oven to obtain 345 g of the HCl salt of biphenyl-3-ylamine as yellow crystals. The free base was obtained by shaking the solid with tert-butyl methyl ether and 1 N NaOH followed by isolation in the usual fashion.

$^1$H NMR (300 MHz, CDCl$_3$): consistent with literature data (C. N. Carrigan et al., *J. Med. Chem.*, 45, 2260-2276 (2002)).

Part B

Triethyl orthoformate (148 g, 1.00 mol), Meldrum's acid (137 g, 0.95 mol), and biphenyl-3-ylamine (155 g, 0.916 mol) were combined and treated according to the general procedure described in Part A of Example 1 to obtain 283 g of 5-(biphenyl-3-ylaminomethylene)-2,2-dimethyl-[1,3]dioxane-4,6-dione as a yellow solid.

$^1$H NMR (300 MHz, CDCl$_3$) δ 11.33 (brd, J=14.0 Hz, 1H), 8.72 (d, J=15.0 Hz, 1H), 7.60-7.56 (m, 2H), 7.51-7.37 (m, 6H), 7.25-7.21 (m, 1H), 1.77 (s, 6H).

Part C 5-(Biphenyl-3-ylaminomethylene)-2,2-dimethyl-[1,3]dioxane-4,6-dione (160.2 g, 496 mmol) was dissolved in 800 mL of DOWTHERM A heat transfer fluid at 100° C. and added over 40 min by way of a cannula line to 1.3 L of preheated DOWTHERM A heat transfer fluid to 215° C. After complete addition, the reaction was held at 215° C. for 90 min and then cooled to RT. The resulting solid was collected by filtration, sequentially washed with diethyl ether (1.7 L) and acetone (500 mL), and then dried in a vacuum oven at 70° C. overnight. The resulting product (74.5 g) contained approximately 5% of the undesired isomer. This product was combined with material from a separate run (51.4 g) and slurried in 440 mL of refluxing ethanol. Filtration of the slurry while hot followed by sequential ethanol and diethyl ether rinses afforded 106.1 g of 7-phenylquinolin-4-ol as a tan solid.

$^1$H NMR (300 MHz, d$_6$-DMSO) δ 11.77 (brs, 1H), 8.16 (d, J=8.4 Hz, 1H), 7.95-7.91 (m, 1H), 7.75-7.70 (m, 3H), 7.61 (dd, J=8.4, 1.6 Hz, 1H), 7.56-7.50 (m, 2H), 7.47-7.42 (m, 1H), 6.05 (d, J=7.5 Hz, 1H).

Part D

A stirred suspension of 7-phenylquinolin-4-ol (84.9 g, 384 mmol) in propionic acid (850 mL) was heated to 129° C. Nitric acid (70%, 45.0 g) was added dropwise over 25 min, during which the temperature dropped to 124° C. The reaction was stirred an additional 3 h at that temperature and then cooled to 5° C. on an ice bath. The resulting solid was collected by filtration, washed with ice cold ethanol (until washings were nearly colorless) and dried at 70° C. in a vacuum oven overnight to obtain 83.2 g of 3-nitro-7-phenylquinolin-4-ol as a beige powder.

$^1$H NMR (300 MHz, d$_6$-DMSO) δ 13.00 (brs, 1H), 9.23 (s, 1H), 8.33 (d, J=8.4 Hz, 1H), 7.94 (d, J=1.3 Hz, 1H), 7.83 (dd, J=8.4, 1.9 Hz, 1H), 7.77-7.74 (m, 2H), 7.59-7.53 (m, 2H), 7.51-7.45 (m, 1H);

MS m/z (M+1$^+$) calcd 267.1, obsd 267.1.

Part E

A solution of phosphorous oxychloride (3.1 g, 20 mmol) in anhydrous N,N-dimethylformamide (DMF, 14 mL) was added to a suspension of 3-nitro-7-phenylquinolin-4-ol (5.0 g, 18.8 mmol) in 80 mL of DMF over 3 min. The reaction was allowed to stir for 1.5 h and then poured into 250 mL crushed ice. The resulting precipitate was collected by filtration, washed with H$_2$O, and dried under vacuum for 2 h. The crude 4-chloro-3-nitro-7-phenylquinoline thus obtained was used without further purification.

Part F

4-Chloro-3-nitro-7-phenylquinoline (5.3 g, 18.8 mmol) and 3-methylsulfanyl-propylamine (2.17 g, 20.6 mmol) were combined and treated according to the general procedure described in Part E of Example 1. Recrystallization from isopropanol afforded 6.2 g of (3-methylsulfanylpropyl)-(3-nitro-7-phenylquinolin-4-yl)amine as gold plates.

Part G (3-Methylsulfanylpropyl)-(3-nitro-7-phenylquinolin-4-yl)amine (3.0 g, 8.5 mmol) was hydrogenated in a Parr bottle over Pt/C (0.3 g of 5%) in 42 mL of toluene for 1 h. The reaction mixture was filtered through CELITE filter agent, washed with methanol (100 mL) and CHCl$_3$ (50 mL), and then concentrated to afford 2.75 g of N$^4$-(3-methylsulfanylpropyl)-7-phenylquinoline-3,4-diamine as a brown oil.

Part H

N$^4$-(3-Methylsulfanylpropyl)-7-phenylquinoline-3,4-diamine (2.75 g, 8.49 mmol), trimethyl orthovalerate (1.7 g, 10 mmol), and pyridine hydrochloride (0.3 g) were dissolved in toluene (28 mL) and heated to reflux for 1.5 h, collecting the volatiles in a Dean-Stark trap. Upon cooling to room temperature, the solvent was removed under vacuum. The resulting solid was slurried in hexanes (100 mL) for 1 h and then collected by filtration to afford 3.0 g of 2-butyl-1-(3-methylsulfanylpropyl)-7-phenyl-1H-imidazo[4,5-c]quinoline.

Part I

To a solution of 2-butyl-1-(3-methylsulfanylpropyl)-7-phenyl-1H-imidazo[4,5-c]quinoline (3.0 g, 7.70 mmol) in CHCl$_3$ (39 mL) was added 3-chloroperoxybenzoic acid (6.74 g of approximately 77% purity) over 20 min. Aqueous NH$_4$OH (39 mL, 30%) was added, and to the resulting rapidly stirred biphasic suspension was added p-toluenesulfonyl chloride (1.8 g, 9.44 mmol) in one portion. After monitoring by thin layer chromatography indicated that no starting material remained, the reaction mixture was sequentially washed with 1% Na$_2$CO$_3$ (2×50 mL) and brine (50 mL); then dried (Na$_2$SO$_4$); filtered; and concentrated to a brown solid. Purification on silica (5% methanol in CH$_2$Cl$_2$) followed by recrystallization from CH$_3$CN afforded 0.50 g of 2-butyl-1-(3-methanesulfonylpropyl)-7-phenyl-1H-imidazo[4,5-c]quinolin-4-amine as colorless needles, m.p. 214-216° C.

$^1$H NMR (300 MHz, d$_6$-DMSO) δ 8.21 (d, J=8.7 Hz, 1H), 7.87 (d, J=1.9 Hz, 1H), 7.78-7.75 (m, 2H), 7.57-7.48 (m, 3H), 7.41-7.36 (m, 1H), 6.52 (s, 2H), 4.69 (t, J=7.5 Hz, 2H), 3.41 (t, J=7.6 Hz, 2H), 3.02 (s, 3H), 2.95 (t, J=7.8 Hz, 2H), 2.30-2.20 (m, 2H), 1.82 (pentet, J=7.6 Hz, 2H), 1.47 (sextet, J=7.5 Hz, 2H), 0.97 (t, J=7.3 Hz, 3H);

MS m/z (M+1$^+$) calcd 437.2, obsd 437.3;

Anal. Calcd for C$_{24}$H$_{28}$N$_4$O$_2$S: C, 66.03; H, 6.46; N, 12.86. Found: C, 66.09; H, 6.43; N, 12.57.

Example 11

8-(4-tert-Butylphenyl)-1-isobutyl-1H-imidazo[4,5-c]quinolin-4-amine

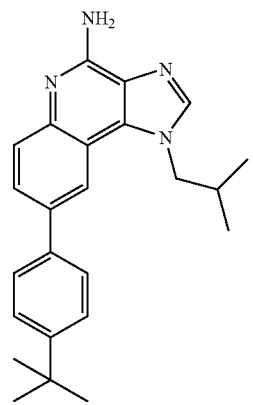

Part A

To a solution of 1-isobutyl-1H-imidazo[4,5-c]quinolin-4-amine (10.0 g, 41.6 mmol) in acetic acid (150 mL) was added Br$_2$ (10.0 g, 62.6 mmol), and after 24 h, the resulting solid was collected by filtration and washed with H$_2$O. The orange solid was suspended in a saturated aqueous solution of NaHSO$_3$, after which it was again collected and stirred with a 2 M solution of Na$_2$CO$_3$ for 18 h. The solid was collected by filtration, washed with H$_2$O, and azeotropically dried with toluene on a rotary evaporator. Purification on silica gel (7%-10% methanol in CH$_2$Cl$_2$ gradient) afforded 3.4 g of 8-bromo-1-isobutyl-1H-imidazo[4,5-c]quinolin-4-amine.

$^1$H NMR (400 MHz, CDCl$_3$) δ 8.00 (d, J=2.2 Hz, 1H), 7.79 (s, 1H), 7.69 (d, J=9.0 Hz, 1H), 7.59 (dd, J=8.8, 2.2 Hz, 1H), 5.60 (s, 2H), 4.26 (d, J=7.4 Hz, 2H), 2.37-2.27 (m, 1H), 1.05 (d, J=6.6 Hz, 6H).

Part B

8-Bromo-1-isobutyl-1H-imidazo[4,5-c]quinolin-4-amine and 4-tert-butylbenzeneboronic acid were coupled according to the general procedure described in Part J of Example 1. Recrystallization from isopropanol followed by chromatography on silica gel (7% methanol in CH$_2$Cl$_2$) afforded 8-(4-tert-butylphenyl)-1-isobutyl-1H-imidazo[4,5-c]quinolin-4-amine as a white solid, m.p.>250° C.

$^1$H NMR (400 MHz, d$_6$-DMSO) δ 8.21 (s, 1H), 8.16 (d, J=2.0 Hz, 1H), 7.75 (dd, J=8.8, 2.1 Hz, 1H), 7.70-7.67 (m, 3H), 7.52 (dt, J=8.6, 2.1 Hz, 2H), 6.68 (s, 2H), 4.49 (d, J=7.2 Hz, 2H), 2.28 (septet, J=6.8 Hz, 1H), 1.33 (s, 9H), 0.97 (d, J=6.6 Hz, 6H);

$^{13}$C NMR (125 MHz, d$_6$-DMSO) δ 152.2, 149.4, 144.3, 143.4, 137.6, 132.7, 131.7, 128.5, 126.7, 126.2, 125.8, 125.5, 118.0, 115.1, 53.5, 34.2, 31.1, 28.5, 19.4;

Anal. Calcd for C$_{24}$H$_{28}$N$_4$: C, 77.38; H, 7.58; N, 15.04. Found: C, 77.17; H, 7.57; N, 14.99.

Example 12

1-Isobutyl-8-(thiophen-3-yl)-1H-imidazo[4,5-c]quinolin-4-amine

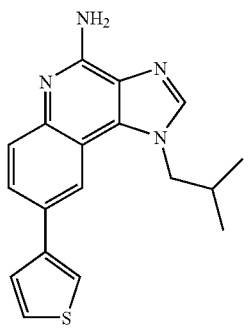

8-Bromo-1-isobutyl-1H-imidazo[4,5-c]quinolin-4-amine and thiophene-3-boronic acid were coupled according to the general procedure described in Part J of Example 1. Recrystallization from isopropanol followed by chromatography on silica gel (7% methanol in CH$_2$Cl$_2$) afforded 1-isobutyl-8-(thiophen-3-yl)-1H-imidazo[4,5-c]quinolin-4-amine as a white solid, m.p. 235-236° C.

$^1$H NMR (400 MHz, d$_6$-DMSO) δ 8.20 (s, 1H), 8.19 (d, J=2.0 Hz, 1H), 7.88 (dd, J=3.0, 1.4 Hz, 1H), 7.81 (dd, J=8.7, 2.0 Hz, 1H), 7.70 (dd, J=5.1, 3.0 Hz, 1H), 7.64-7.62 (m, 2H), 6.66 (s, 2H), 4.51 (d, J=7.4 Hz, 2H), 2.23 (septet, J=6.9 Hz, 1H), 0.96 (d, J=6.6 Hz, 6H);

$^{13}$C NMR (125 MHz, d$_6$-DMSO) δ 152.1, 144.2, 143.4, 141.8, 131.7, 128.5, 128.1, 127.2, 126.6, 126.1, 125.3, 119.9, 117.5, 115.0, 53.5, 28.4, 19.4;

Anal. Calcd for C$_{18}$H$_{18}$N$_4$S: C, 67.05; H, 5.63; N, 17.38. Found: C, 66.74; H, 5.46; N, 17.32.

Example 13

8-(2,4-Dimethoxyphenyl)-1-isobutyl-1H-imidazo[4,5-c]quinolin-4-amine

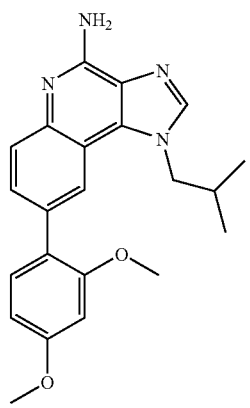

8-Bromo-1-isobutyl-1H-imidazo[4,5-c]quinolin-4-amine and 2,4-dimethoxybenzeneboronic acid were coupled according to the general procedure described in Part J of Example 1. Purification by chromatography on silica gel (7% methanol in CH$_2$Cl$_2$) afforded 8-(2,4-dimethoxyphenyl)-1-isobutyl-1H-imidazo[4,5-c]quinolin-4-amine as a white solid, m.p. 223-227° C.

$^1$H NMR (400 MHz, d$_6$-DMSO) δ 8.18 (s, 1H), 8.08 (d, J=2.0 Hz, 1H), 7.62 (d, J=8.6 Hz, 1H), 7.52 (dd, J=8.6, 2.0 Hz, 1H), 7.34 (d, J=8.4 Hz, 1H), 6.71 (d, J=2.4 Hz, 1H), 6.66 (dd, J=8.3, 2.4 Hz, 1H), 6.61 (s, 2H), 4.36 (d, J=7.5 Hz, 2H), 3.82 (s, 3H), 3.80 (s, 3H), 2.34-2.24 (m, 1H), 0.93 (d, J=6.6 Hz, 6H);

$^{13}$C NMR (100 MHz, d$_6$-DMSO) δ 159.8, 157.1, 152.0, 143.6, 143.2, 131.7, 130.9, 130.5, 128.3, 128.1, 125.7, 122.5, 120.8, 114.4, 105.4, 99.0, 55.6, 55.3, 55.4, 28.2, 19.3;

Anal. Calcd for C$_{22}$H$_{24}$N$_4$O$_2$: C, 70.19; H, 6.43; N, 14.88. Found: C, 69.92; H, 6.41; N, 14.67.

Example 14

1-Isobutyl-8-(pyridin-3-yl)-1H-imidazo[4,5-c]quinolin-4-amine

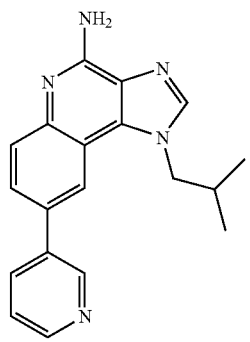

8-Bromo-1-isobutyl-1H-imidazo[4,5-c]quinolin-4-amine and pyridine-3-boronic acid were coupled according to the general procedure described in Part J of Example 1. Purification by chromatography on silica gel (7%-10% methanol in $CH_2Cl_2$ gradient) afforded 1-isobutyl-8-(pyridin-3-yl)-1H-imidazo[4,5-c]quinolin-4-amine as a white solid, m.p. 244-246° C.

$^1$H NMR (400 MHz, $d_6$-DMSO) δ 9.01 (dd, J=2.3, 0.8 Hz, 1H), 8.57 (dd, J=4.7, 1.6 Hz, 1H), 8.22 (s, 1H), 8.22 (d, J=2.0 Hz, 1H), 8.18 (ddd, J=8.0, 2.5, 1.6 Hz, 1H), 7.82 (dd, J=8.7, 2.1 Hz, 1H), 7.72 (d, J=8.6 Hz, 1H), 7.52 (ddd, J=8.0, 4.7, 0.8 Hz, 1H), 6.76 (s, 2H), 4.52 (d, J=7.2 Hz, 2H), 2.29-2.22 (m, 1H), 0.95 (d, J=6.6 Hz, 6H);

$^{13}$C NMR (125 MHz, $d_6$-DMSO) δ 152.5, 147.9, 147.6, 144.8, 143.5, 135.9, 133.8, 131.7, 129.5, 128.5, 126.9, 125.5, 123.9, 118.7, 115.2, 53.4, 28.4, 19.4;

Anal. Calcd for $C_{19}H_{19}N_5$: C, 71.90; H, 6.03; N, 22.07. Found: C, 71.73; H, 5.91; N, 21.86.

Example 15

1-Isobutyl-8-phenyl-1H-imidazo[4,5-c]quinolin-4-amine

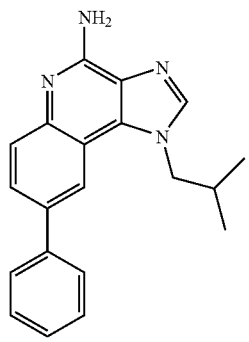

8-Bromo-1-isobutyl-1H-imidazo[4,5-c]quinolin-4-amine and benzeneboronic acid were coupled according to the general procedure described in Part J of Example 1. Recrystallization from isopropanol followed by recrystallization from methanol afforded 1-isobutyl-8-phenyl-1H-imidazo[4,5-c]quinolin-4-amine as a beige solid, m.p. 203-204° C.

$^1$H NMR (400 MHz, $d_6$-DMSO) δ 8.21 (s, 1H), 8.17 (d, J=2.0 Hz, 1H), 7.78-7.76 (m, 3H), 7.69 (d, J=8.6 Hz, 1H), 7.52-7.48 (m, 2H), 7.36 (tt, J=7.4, 1.2 Hz, 1H), 6.71 (s, 2H), 4.49 (d, J=7.4 Hz, 2H), 2.32-2.21 (m, 1H), 0.96 (d, J=6.6 Hz, 6H);

$^{13}$C NMR (100 MHz, $d_6$-DMSO) δ 152.3, 144.4, 143.4, 140.5, 132.8, 131.8, 129.0, 128.5, 126.9, 126.7, 126.5, 125.6, 118.4, 115.1, 53.6, 28.5, 19.4;

Anal. Calcd for $C_{20}H_{20}N_4$: C, 75.92; H, 6.37; N, 17.71. Found: C, 75.80; H, 6.26; N, 17.68.

Example 16

2-Ethyl-1-isobutyl-8-phenyl-1H-imidazo[4,5-c]quinolin-4-amine

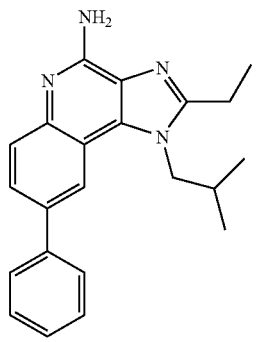

Part A

To a solution of 2-ethyl-1-isobutyl-1H-imidazo[4,5-c]quinolin-4-amine (805 mg, 3.00 mmol) in acetic acid (10 mL) was added $Br_2$ (719 mg, 4.50 mmol), and after 20 h, the resulting solid was collected by filtration and washed with $H_2O$. The orange solid was suspended in $NaHSO_3$ (25 mL of a saturated solution) and stirred for 23 h, after which it was again collected and stirred with $NaHCO_3$ (20 mL of a saturated solution) and $CH_2Cl_2$. The organic layer was drawn off, washed with $H_2O$, dried ($Na_2SO_4$), filtered, and concentrated to afford 858 mg of a yellow solid. Purification on silica gel (5%-7% MeOH in $CH_2Cl_2$ gradient) afforded 450 mg of 8-bromo-2-ethyl-1-isobutyl-1H-imidazo[4,5-c]quinolin-4-amine as a yellow solid. Additional purification on silica as before followed by recrystallization from boiling isopropanol (10 mL) afforded 316 mg of white needles, m.p. 222-223° C.

$^1$H NMR (400 MHz, $d_6$-DMSO) δ 8.02 (s, 1H), 7.52 (s, 2H), 6.65 (s, 2H), 4.33 (d, J=7.0 Hz, 2H), 2.94 (q, J=7.5 Hz, 2H), 2.18-2.07 (m, 1H), 1.37 (t, J=7.5 Hz, 3H), 0.94 (d, J=6.8 Hz, 6H);

$^{13}$C NMR (100 MHz, $d_6$-DMSO) δ 155.1, 152.1, 143.6, 131.4, 128.9, 128.3, 127.0, 122.3, 116.2, 112.8, 51.3, 28.9, 20.2, 19.2, 12.1;

Anal. Calcd for $C_{16}H_{19}BrN_4$: C, 55.34; H, 5.52; N, 16.13. Found: C, 55.26; H, 5.36; N, 16.14.

Part B

8-Bromo-2-ethyl-1-isobutyl-1H-imidazo[4,5-c]quinolin-4-amine and benzeneboronic acid were coupled according to the general procedure described in Part J of Example 1. Chromatography on silica gel (5%-7% methanol in $CH_2Cl_2$ gradient) afforded 2-ethyl-1-isobutyl-8-phenyl-1H-imidazo[4,5-c]quinolin-4-amine as a white solid, m.p. 233-235° C.

$^1$H NMR (400 MHz, $d_6$-DMSO) δ 8.15 (d, J=1.8 Hz, 1H), 7.77-7.72 (m, 3H), 7.68 (d, J=8.6 Hz, 1H), 7.52-7.48 (m, 2H), 7.36 (tt, J=7.4, 1.1 Hz, 1H), 6.57 (s, 2H), 4.42 (d, J=6.6 Hz, 2H), 2.96 (q, J=7.5 Hz, 2H), 2.35-2.24 (m, 1H), 1.39 (t, J=7.5 Hz, 3H), 0.98 (d, J=6.6 Hz, 6H);

$^{13}$C NMR (100 MHz, $d_6$-DMSO) δ 154.6, 151.9, 144.2, 140.7, 132.7, 132.5, 129.0, 126.9, 126.8, 126.6, 125.1, 118.2, 115.1, 51.5, 28.9, 20.2, 19.3, 12.1;

Anal. Calcd for $C_{22}H_{24}N_4$: C, 76.71; H, 7.02; N, 16.27. Found: C, 76.52; H, 6.89; N, 16.30.

Example 17

2-Ethyl-1-isobutyl-8-(pyridin-3-yl)-1H-imidazo[4,5-c]quinolin-4-amine

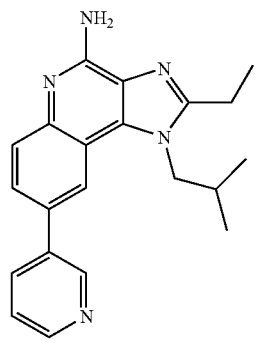

8-Bromo-2-ethyl-1-isobutyl-1H-imidazo[4,5-c]quinolin-4-amine and pyridine-3-boronic acid were coupled according to the general procedure described in Part J of Example 1. Chromatography on silica gel (5%-7% methanol in $CH_2Cl_2$ gradient) followed by recrystallization from isopropanol afforded 2-ethyl-1-isobutyl-8-(pyridin-3-yl)-1H-imidazo[4,5-c]quinolin-4-amine as white crystals, m.p.>250° C.

$^1$H NMR (400 MHz, $d_6$-DMSO) δ 9.00 (d, J=2.4 Hz, 1H), 8.57 (dd, J=4.8, 1.5 Hz, 1H), 8.19 (d, J=2.0 Hz, 1H), 8.16 (dt, J=7.9, 1.7 Hz, 1H), 7.78 (dd, J=8.6, 2.0 Hz, 1H), 7.71 (d, J=8.6 Hz, 1H), 7.53 (dd, J=7.9, 4.8 Hz, 1H), 6.63 (s, 2H), 4.45 (d, J=6.8 Hz, 2H), 2.96 (q, J=7.5 Hz, 2H), 2.33-2.23 (m, 1H), 1.39 (t, J=7.5 Hz, 3H), 0.96 (d, J=6.4 Hz, 6H);

$^{13}$C NMR (100 MHz, $d_6$-DMSO) δ 154.7, 152.2, 147.9, 147.6, 144.7, 136.1, 133.9, 132.4, 129.4, 127.0, 126.9, 125.1, 124.0, 118.6, 115.2, 51.4, 28.9, 20.3, 19.3, 12.1;

Anal. Calcd for $C_{21}H_{23}N_5$: C, 73.02; H, 6.71; N, 20.27. Found: C, 73.24; H, 6.77; N, 20.65.

Example 18

1-Butyl-2-ethoxymethyl-8-phenyl-1H-imidazo[4,5-c]quinolin-4-amine

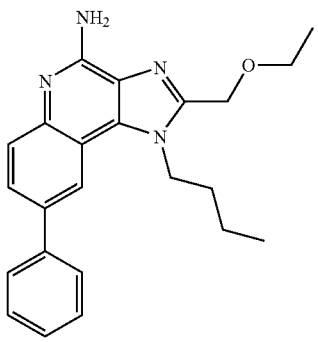

Part A
1-Butyl-2-ethoxymethyl-1H-imidazo[4,5-c]quinolin-4-amine was brominated according to the general procedure described in Part A of Example 11. Purification on silica gel (6%-10% methanol in $CH_2Cl_2$) followed by recrystallization from isopropanol afforded 8-bromo-1-butyl-2-ethoxymethyl-1H-imidazo[4,5-c]quinolin-4-amine as yellow needles, m.p. 182-183° C.

$^1$H NMR (300 MHz, CDCl$_3$) δ 8.07 (d, J=2.2 Hz, 1H), 7.68 (d, J=8.7 Hz, 1H), 7.58 (dd, J=8.7, 2.2 Hz, 1H), 5.44 (s, 2H), 4.80 (s, 2H), 4.56-4.51 (m, 2H), 3.61 (q, J=7.0 Hz, 2H), 2.02-1.93 (m, 2H), 1.57 (sextet, J=7.4 Hz, 2H), 1.25 (t, J=6.9 Hz, 3H), 1.07 (t, J=7.3 Hz, 3H);

$^{13}$C NMR (75 MHz, CDCl$_3$) δ 151.8, 149.7, 144.0, 133.3, 130.6, 129.1, 127.3, 122.7, 117.0, 115.5, 66.6, 65.4, 46.2, 32.3, 20.3, 15.3, 13.9;

MS m/z (M+1$^+$) calcd 379.1, obsd 379.0;

Anal. Calcd for $C_{17}H_{21}BrN_4O$: C, 54.12; H, 5.61; N, 14.85. Found: C, 54.01; H, 5.50; N, 14.83.

Part B
8-Bromo-1-butyl-2-ethoxymethyl-1H-imidazo[4,5-c]quinolin-4-amine and benzeneboronic acid were coupled according to the general procedure described in Part J of Example 1. Chromatography on silica gel (10% methanol in $CH_2Cl_2$) followed by recrystallization from isopropanol afforded 1-butyl-2-ethoxymethyl-8-phenyl-1H-imidazo[4,5-c]quinolin-4-amine as an off-white solid, m.p. 186-187° C.

$^1$H NMR (300 MHz, CDCl$_3$) δ 8.17 (d, J=1.9 Hz, 1H), 7.89 (d, J=8.7 Hz, 1H), 7.79 (dd, J=8.7, 1.9 Hz, 1H), 7.69-7.66 (m, 2H), 7.52-7.47 (m, 2H), 7.37 (tt, J=7.3, 1.3 Hz, 1H), 5.46 (s, 2H), 4.82 (s, 2H), 4.64-4.58 (m, 2H), 3.62 (q, J=7.0 Hz, 2H), 2.11-2.01 (m, 2H), 1.58 (sextet, J=7.5 Hz, 2H), 1.26 (t, J=7.0 Hz, 3H), 1.05 (t, J=7.3 Hz, 3H);

$^{13}$C NMR (75 MHz, CDCl$_3$) δ 151.7, 149.2, 144.7, 141.5, 135.4, 134.5, 129.1, 127.8, 127.3, 127.2, 126.9, 118.5, 115.9, 66.5, 65.4, 46.4, 32.5, 20.4, 15.3, 13.9;

MS m/z (M+1$^+$) calcd 375.2, obsd 375.2;

Anal. Calcd for $C_{23}H_{26}N_4O$: C, 73.77; H, 7.00; N, 14.96. Found: C, 73.76; H, 7.15; N, 14.95.

Example 19

1-Butyl-2-ethoxymethyl-8-(pyridin-3-yl)-1H-imidazo[4,5-c]quinolin-4-amine

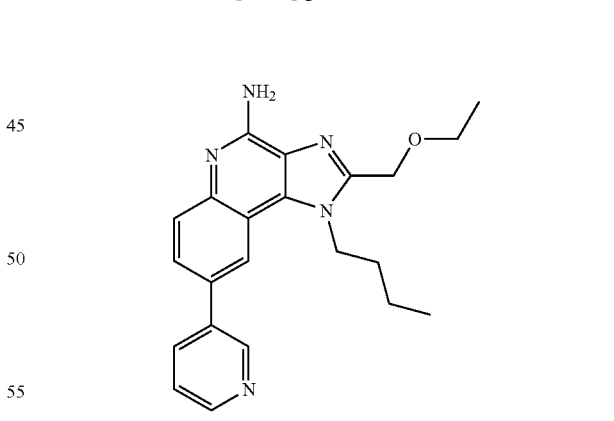

8-Bromo-1-butyl-2-ethoxymethyl-1H-imidazo[4,5-c]quinolin-4-amine and pyridine-3-boronic acid were coupled according to the general procedure described in Part J of Example 1. Chromatography on silica gel (8%-10% methanol in $CH_2Cl_2$ gradient) followed by recrystallization from isopropanol (3×) and chromatography as above afforded 1-butyl-2-ethoxymethyl-8-(pyridin-3-yl)-1H-imidazo[4,5-c]quinolin-4-amine as a white solid, m.p. 220-222° C.

$^1$H NMR (300 MHz, CDCl$_3$) δ 8.95 (dd, J=2.3, 0.8 Hz, 1H), 8.63 (dd, J=4.7, 1.6 Hz, 1H), 8.17 (d, J=2.2 Hz, 1H), 7.96

(ddd, J=7.8, 2.5, 1.6 Hz, 1H), 7.92 (d, J=8.7 Hz, 1H), 7.76 (dd, J=8.7, 1.9 Hz, 1H), 7.42 (ddd, J=8.0, 4.8, 0.8 Hz, 1H), 5.47 (s, 2H), 4.83 (s, 2H), 4.65-4.60 (m, 2H), 3.63 (q, J=7.0 Hz, 2H), 2.10-1.99 (m, 2H), 1.57 (sextet, J=7.5 Hz, 2H), 1.26 (t, J=7.0 Hz, 3H), 1.04 (t, J=7.3 Hz, 3H);

$^{13}$C NMR (125 MHz, CDCl$_3$) δ 152.0, 149.5, 148.49, 148.51, 145.2, 137.0, 134.4, 134.3, 131.8, 128.3, 127.4, 126.6, 123.9, 118.7, 116.2, 66.6, 65.4, 46.5, 32.5, 20.4, 15.3, 14.0;

MS m/z (M+1$^+$) calcd 376.2, obsd 376.2;

Anal. Calcd for C$_{22}$H$_{25}$N$_5$O: C, 70.37; H, 6.71; N, 18.66. Found: C, 70.00; H, 6.49; N, 18.64.

Examples 20-65

The compounds in the table below were prepared according to the following method. 8-Bromo-1-isobutyl-1H-imidazo[4,5-c]quinoline-4-amine (25 mg) was dissolved in 1:1 volume:volume (v:v) dichloromethane:methanol. An aliquot (2 mL, 1.0 equivalents (eq.)) was placed in a 2 dram (7.4 mL) vial. The solvent was removed by vacuum centrifugation. The vial was charged with the appropriate boronic acid (1.25 eq.), palladium (II) acetate (0.1 eq.), and n-propanol (900 μL) and then sonicated for 30 seconds. The vial was then charged with 2M aqueous sodium carbonate solution (313 μL), deionized water (63 μL), and a solution of triphenylphosphine in n-propanol (63 μL, 0.15 eq.). The vial was capped and then heated to 80° C. for 5 hours in a sand bath. The vial was allowed to cool to room temperature and then the solvent was removed by vacuum centrifugation. The residue was purified by preparative high performance liquid chromatography using the method described above to provide the trifluoroacetate salt of the desired compound. The table below shows the structure of the free base and the measured mass (M+H).

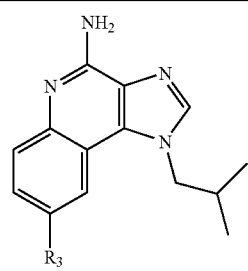

| Example Number | R$_3$ | Measured Mass (M + H) |
|---|---|---|
| 20 | ![phenyl] | 317.1774 |
| 21 | ![2-thienyl] | 323.1330 |

-continued

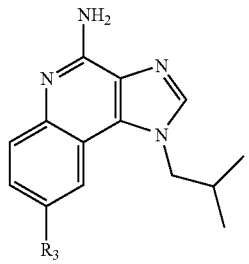

| Example Number | R$_3$ | Measured Mass (M + H) |
|---|---|---|
| 22 | 2-methylphenyl | 331.1920 |
| 23 | 3-methylphenyl | 331.1905 |
| 24 | 4-methylphenyl | 331.1945 |
| 25 | 3-aminophenyl | 332.1877 |
| 26 | 2-fluorophenyl | 335.1661 |
| 27 | 3-fluorophenyl | 335.1678 |
| 28 | 4-fluorophenyl | 335.1677 |

-continued

Structure: 4-amino-1-isobutyl-imidazoquinoline with R₃ substituent at 8-position.

| Example Number | R₃ | Measured Mass (M + H) |
|---|---|---|
| 29 | 4-vinylphenyl | 343.1921 |
| 30 | 3,4-dimethylphenyl | 345.2095 |
| 31 | 3,5-dimethylphenyl | 345.2093 |
| 32 | 4-ethylphenyl | 345.2099 |
| 33 | 2-methoxyphenyl | 347.1888 |
| 34 | 3-methoxyphenyl | 347.1874 |
| 35 | 4-(hydroxymethyl)phenyl | 347.1892 |
| 36 | 4-methoxyphenyl | 347.1865 |
| 37 | 2-chlorophenyl | 351.1367 |
| 38 | 3-chlorophenyl | 351.1375 |
| 39 | 4-chlorophenyl | 351.1375 |
| 40 | 2,4-difluorophenyl | 353.1594 |
| 41 | 2,6-difluorophenyl | 353.1577 |

-continued
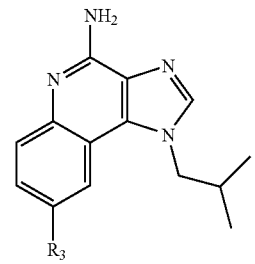
| Example Number | R₃ | Measured Mass (M + H) |
|---|---|---|
| 42 | 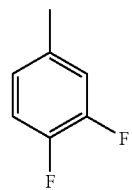 | 353.1579 |
| 43 | 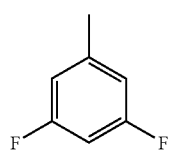 | 353.1587 |
| 44 | 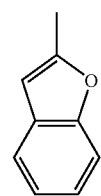 | 357.1731 |
| 45 | 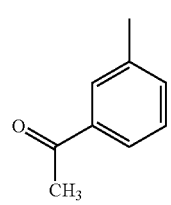 | 359.1873 |
| 46 | 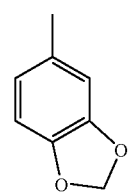 | 361.1670 |
| 47 | 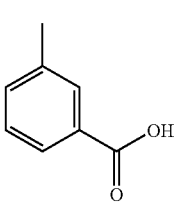 | 361.1639 |
-continued
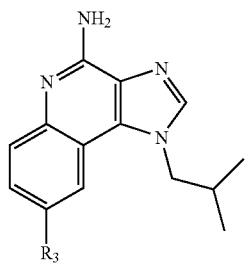
| Example Number | R₃ | Measured Mass (M + H) |
|---|---|---|
| 48 | 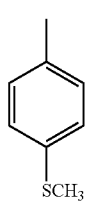 | 363.1652 |
| 49 | 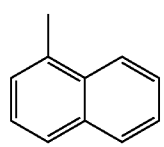 | 367.1932 |
| 50 | 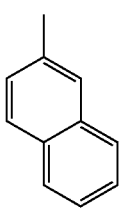 | 367.1942 |
| 51 | 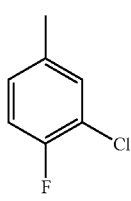 | 369.1288 |
| 52 | 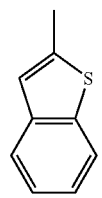 | 373.1484 |
| 53 | 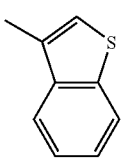 | 373.1494 |

-continued
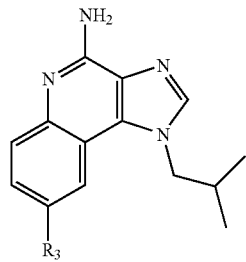
| Example Number | R₃ | Measured Mass (M + H) |
|---|---|---|
| 54 | 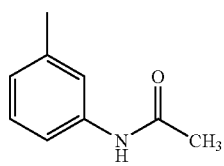 | 374.1965 |
| 55 | 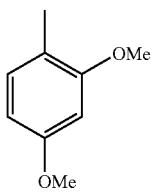 | 377.1985 |
| 56 | 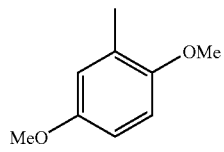 | 377.2000 |
| 57 | 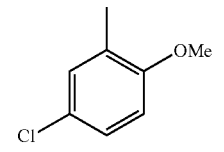 | 381.1507 |
| 58 | 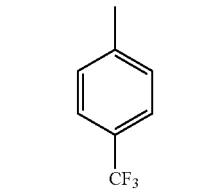 | 385.1658 |
| 59 | 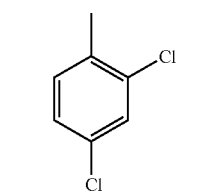 | 385.0974 |
| 60 | 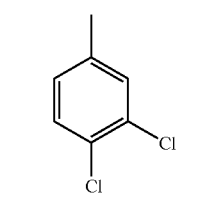 | 385.0998 |
-continued
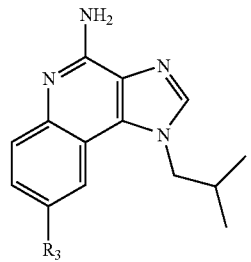
| Example Number | R₃ | Measured Mass (M + H) |
|---|---|---|
| 61 | 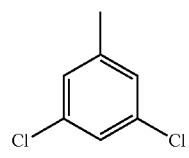 | 385.0982 |
| 62 | 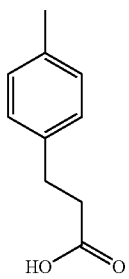 | 389.1980 |
| 63 | 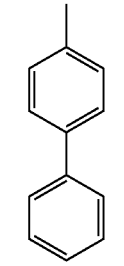 | 393.2057 |
| 64 | 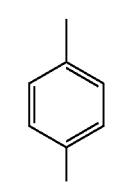 | 401.1596 |
| 65 | 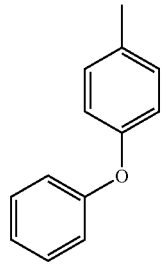 | 409.2036 |

Examples 66-105
The compounds in the table below were prepared according to the method of Examples 20-65 above using 7-bromo-2-butyl-1-isobutyl-1H-imidazo[4,5-c]quinoline-4-amine as the starting material. The table below shows the structure of the free base and the measured mass (M+H).
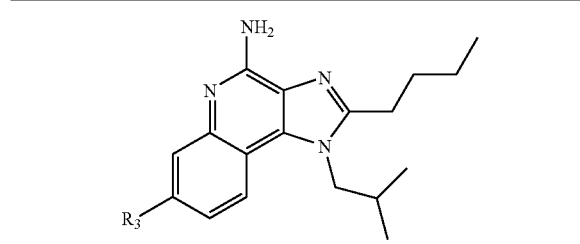
| Example Number | R₃ | Measured Mass (M + H) |
|---|---|---|
| 66 |  | 373.2385 |
| 67 | 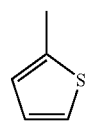 | 379.1978 |
| 68 | 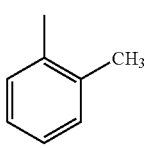 | 387.2582 |
| 69 | 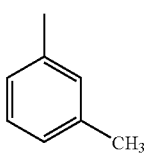 | 387.2550 |
| 70 | 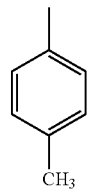 | 387.2545 |
| 71 | 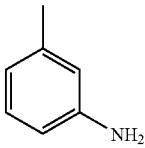 | 388.2536 |
-continued
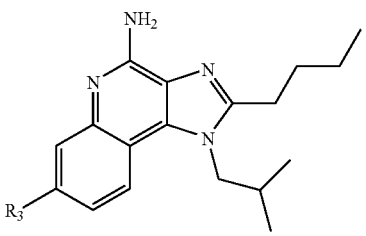
| Example Number | R₃ | Measured Mass (M + H) |
|---|---|---|
| 72 | 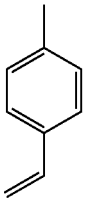 | 399.2577 |
| 73 | 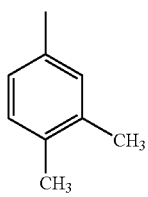 | 401.2712 |
| 74 | 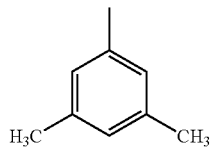 | 401.2686 |
| 75 | 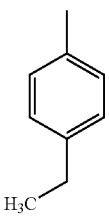 | 401.2719 |
| 76 | 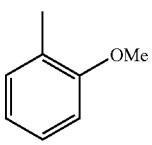 | 403.2483 |
| 77 | 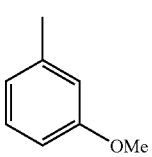 | 403.2507 |

-continued

Structure: 4-amino-2-butyl-1-isobutyl-1H-imidazo[4,5-c]quinoline with R₃ substituent on the benzo ring.

| Example Number | R₃ | Measured Mass (M + H) |
|---|---|---|
| 78 | 4-(hydroxymethyl)phenyl | 403.2516 |
| 79 | 4-methoxyphenyl | 403.2505 |
| 80 | 2-chlorophenyl | 407.2021 |
| 81 | 3-chlorophenyl | 407.2024 |
| 82 | 4-chlorophenyl | 407.2008 |
| 83 | 2,4-difluorophenyl | 409.2214 |
| 84 | 3,4-difluorophenyl | 409.2227 |
| 85 | 3,5-difluorophenyl | 409.2241 |
| 86 | 2-benzofuranyl | 413.2376 |
| 87 | 1,3-benzodioxol-5-yl | 417.2313 |
| 88 | 2-nitrophenyl | 418.2268 |
| 89 | 2-(methylthio)phenyl | 419.2299 |
| 90 | 4-(methylthio)phenyl | 419.2283 |

-continued

[Structure: 4-amino-2-butyl-1-isobutyl-1H-imidazo[4,5-c]quinoline with R₃ substituent]

| Example Number | R₃ | Measured Mass (M + H) |
|---|---|---|
| 91 | 1-naphthyl (methyl-attached) | 423.2552 |
| 92 | 2-naphthyl | 423.2559 |
| 93 | 3-chloro-4-fluorophenyl | 425.1915 |
| 94 | benzothiophen-2-yl | 429.2125 |
| 95 | benzothiophen-3-yl | 429.2142 |
| 96 | 2,5-dimethoxyphenyl (2-OMe, 5-OMe) | 433.2633 |
| 97 | 3,4-dimethoxyphenyl | 433.2613 |

-continued

[Structure: 4-amino-2-butyl-1-isobutyl-1H-imidazo[4,5-c]quinoline with R₃ substituent]

| Example Number | R₃ | Measured Mass (M + H) |
|---|---|---|
| 98 | 4-chloro-2-methoxyphenyl | 437.2122 |
| 99 | 4-(trifluoromethyl)phenyl | 441.2265 |
| 100 | 2,4-dichlorophenyl | 441.1620 |
| 101 | 3,4-dichlorophenyl | 441.1646 |
| 102 | 3,5-dichlorophenyl | 441.1586 |
| 103 | biphenyl-4-yl | 449.2728 |

-continued

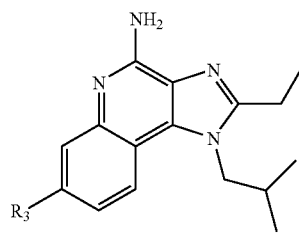

| Example Number | R₃ | Measured Mass (M + H) |
|---|---|---|
| 104 | 4-methylphenoxy (via OCH₃-substituted phenyl) | 457.2203 |
| 105 | 4-(trifluoromethoxy)benzyl-4-phenoxy | 465.2656 |

Examples 106-116

7-Bromo-2-ethoxymethyl-1-(2-methylpropyl)-1H-imidazo[4,5-c]quinolin-4-amine and the boronic acid or boronic acid ester from the table below were coupled according to the general procedure described in Part J of Example 1. The reaction was heated at reflux overnight unless otherwise indicated below the table. The solid collected from the reaction was washed with hexanes. Samples that were recrystallized from isopropanol and then dichloromethane:hexanes were dried under high vacuum overnight. Samples that were recrystallized from acetonitrile were then washed with hexanes and dried overnight in a vacuum oven at 75-80° C. The purification for Examples 115 and 116 is described below the table.

Examples 106-116

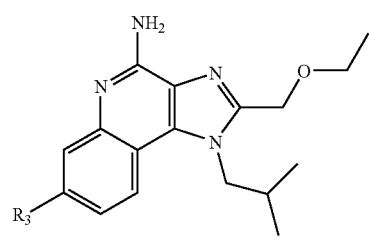

| Example | Boronic Acid or Ester | Recrystallization Solvent | R₃ |
|---|---|---|---|
| 106 | 3-Propoxyphenylboronic acid | Isopropanol then dichloromethane: hexanes | 3-propoxyphenyl |
| 107 | 4-Propoxyphenylboronic acid | Isopropanol then dichloromethane: hexanes | 4-propoxyphenyl |
| 108 | Phenylboronic acid | Isopropanol then dichloromethane: hexanes | phenyl |

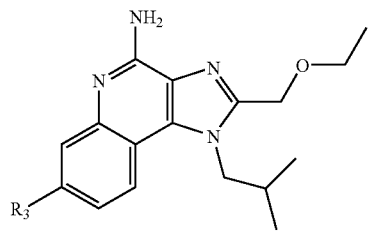

| Example | Boronic Acid or Ester | Recrystallization Solvent | $R_3$ |
|---|---|---|---|
| 109 | 2-Propoxyphenylboronic acid | Isopropanol, then acetonitrile | |
| 110 | 4-Cyanophenylboronic acid | Acetonitrile | |
| 111 | 3-Cyanophenylboronic acid | Acetonitrile | |
| 112 | trans-2-[4-(Trifluoromethyl)-phenyl]vinylboronic acid | Acetonitrile | |
| 113 | Pyridine-3-boronic acid 1,3-propanediol cyclic ester | Acetonitrile | |
| 114 | 4-(Dimethylamino)phenyl boronic acid | Acetonitrile | |
| 115 | 5-(tert-Butyldimethylsilanyloxymethyl) pyridine-3-boronic acid | Not used | |
| 116 | Pyridine-4-boronic acid pinacol ester | Acetonitrile | |

Example 106

2-Ethoxymethyl-1-(2-methylpropyl)-7-(3-propoxyphenyl)-1H-imidazo[4,5-c]quinolin-4-amine The product was obtained as an off-white powder, mp 140.0-141.0° C.

Anal. Calcd for $C_{26}H_{32}N_4O_2$: C, 72.19; H, 7.46; N, 12.95. Found: C, 71.88; H, 7.36; N, 12.72.

Example 107

2-Ethoxymethyl-1-(2-methylpropyl)-7-(4-propoxyphenyl)-1H-imidazo[4,5-c]quinolin-4-amine The product was obtained as a white solid, mp 209.0-210.0° C.

Anal. Calcd for $C_{26}H_{32}N_4O_2$: C, 72.19; H, 7.46; N, 12.95. Found: C, 71.93; H, 7.41; N, 12.76.

Example 108

2-Ethoxymethyl-1-(2-methylpropyl)-7-phenyl-1H-imidazo[4,5-c]quinolin-4-amine

The product was obtained as a white solid, mp 176.5-178.0° C.
Anal. Calcd for $C_{23}H_{26}N_4O$: C, 73.77; H, 7.00; N, 14.96. Found: C, 73.65; H, 6.90; N, 14.80.

Example 109

2-Ethoxymethyl-1-(2-methylpropyl)-7-(2-propoxyphenyl)-1H-imidazo[4,5-c]quinolin-4-amine The product was obtained as light-yellow needles, mp 168.0-169.0° C.
Anal. Calcd for $C_{26}H_{32}N_4O_2$: C, 72.19; H, 7.46; N, 12.95. Found: C, 71.96; H, 7.40; N, 13.13.

Example 110

4-(4-Amino-2-ethoxymethyl-1-(2-methylpropyl)-1H-imidazo[4,5-c]quinolin-7-yl)benzonitrile The product was obtained as an off-white solid, mp 211.0-212.0° C.
Anal. Calcd for $C_{24}H_{25}N_5O$: C, 72.16; H, 6.31; N, 17.53. Found: C, 71.87; H, 6.22; N, 17.40.

Example 111

3-(4-Amino-2-ethoxymethyl-1-(2-methylpropyl)-1H-imidazo[4,5-c]quinolin-7-yl)benzonitrile The product was obtained as light-brown crystals, mp 210.0-211.0° C.
Anal. Calcd for $C_{24}H_{25}N_5O$: C, 72.16; H, 6.31; N, 17.53. Found: C, 71.88; H, 6.06; N, 17.63.

Example 112

2-Ethoxymethyl-1-(2-methylpropyl)-7-{(E)-2-[(4-trifluoromethyl)phenyl]vinyl}-1H-imidazo[4,5-c]quinolin-4-amine The product was obtained as light-yellow needles, mp 193.0-194.0° C.
Anal. Calcd for $C_{26}H_{27}F_3N_4O$: C, 66.65; H, 5.81; N, 11.96. Found: C, 66.51; H, 5.76; N, 11.96.

Example 113

2-Ethoxymethyl-1-(2-methylpropyl)-7-(pyridin-3-yl)-1H-imidazo[4,5-c]quinolin-4-amine Following recrystallization from acetonitrile, the crystals were purified by flash column chromatography on silica gel. The polar component of the eluent was a mixture of chloroform:methanol:ammonium hydroxide 80:18:2 (CMA). The chromatographic separation was carried out eluting sequentially with 95:5, 90:10, 85:15, 80:20, and 75:25 chloroform:CMA. The fractions containing the product were combined, dried over magnesium sulfate, filtered, and concentrated under reduced pressure until a precipitate began to form. Hexanes were added, and the resulting solid was isolated by filtration to provide 2-ethoxymethyl-1-(2-methylpropyl)-7-pyridin-3-yl-1H-imidazo[4,5-c]quinolin-4-amine as a white solid, mp 179.5-181.5° C.
Anal. Calcd for $C_{22}H_{25}N_5O$: C, 70.38; H, 6.71; N, 18.65. Found: C, 70.07; H, 6.87; N, 18.57.

Example 114

7-(4-Dimethylaminophenyl)-2-ethoxymethyl-1-(2-methylpropyl)-1H-imidazo[4,5-c]quinolin-4-amine The product was obtained as a yellow solid, mp 214.5-215.5° C.
Anal. Calcd for $C_{25}H_{31}N_5O$: C, 71.91; H, 7.48; N, 16.77. Found: C, 71.66; H, 7.40; N, 16.71.

Example 115

{5-[4-Amino-2-ethoxymethyl-1-(2-methylpropyl)-1H-imidazo[4,5-c]quinolin-7-yl]pyridin-3-yl}methanol Part A
3-Bromo-5-(tert-butyldimethylsilanyloxymethyl)pyridine was prepared according to the published procedure (Zhang, N. et al, *J. Med. Chem.*, 45, 2832-2840 (2002)). Under a nitrogen atmosphere, a solution of 3-bromo-5-(tert-butyldimethylsilanyloxymethyl)pyridine (28.70 g, 94.94 mmol) and triisopropyl borate (26.3 mL, 114 mmol) in dry THF was cooled to −70° C. n-Butyllithium (45.6 mL, 114 mmol) was added dropwise over a period of 1.5 hours. The reaction was stirred for an additional 30 minutes and then allowed to warm to −20° C. Dilute aqueous ammonium chloride was added, and the mixture was allowed to warm to ambient temperature. The aqueous layer was separated and extracted with diethyl ether. The combined organic fractions were concentrated under reduced pressure, and methanol was added to the resulting oil. A solid formed, which was stirred with water for two days, isolated by filtration, and dried under reduced pressure to provide 18.19 g of 5-(tert-butyldimethylsilanyloxymethyl)pyridine-3-boronic acid as a white solid.

Part B
The coupling reaction was heated at reflux for four days, and the product was purified on a Biotage HORIZON High-Performance Flash Chromatography instrument (HPFC) (eluting with chloroform:CMA in a gradient from 100:0 to 55:45.) The fractions containing the product were combined and concentrated under reduced pressure until a precipitate began to form. Hexanes were added, and the resulting solid was isolated by filtration and dried overnight in an oven at 70° C. to provide [5-(4-amino-2-ethoxymethyl-1-(2-methylpropyl)-1H-imidazo[4,5-c]quinolin-7-yl)pyridin-3-yl]methanol as an off-white powder, mp 211.0-212.0° C.
Anal. Calcd for $C_{23}H_{27}N_5O_2$: C, 68.13; H, 6.71; N, 17.27. Found: C, 68.04; H, 7.07; N, 17.21.

Example 116

2-Ethoxymethyl-1-(2-methylpropyl)-(7-pyridin-4-yl)-1H-imidazo[4,5-c]quinolin-4-amine The reaction was heated at reflux for 48 hours, and the reaction mixture was partitioned between aqueous sodium chloride and dichloromethane. The aqueous layer was extracted twice with dichloromethane, and the combined organic fractions were dried over magnesium sulfate, filtered, and concentrated under reduced pressure. The residue was purified by flash column chromatography on silica gel (eluting with chloroform:CMA in a gradient from 95:5 to 80:20) followed by recrystallization from acetonitrile to provide 2-ethoxymethyl-1-(2-methylpropyl)-(7-pyridin-4-yl)-1H-imidazo[4,5-c]quinolin-4-amine as a white solid, mp 211-213° C.

Anal. Calcd for $C_{22}H_{25}N_5O$: C, 70.38; H, 6.71; N, 18.65. Found: C, 70.33; H, 6.76; N, 18.69.

Example 117

2-Ethoxymethyl-1-(2-methylpropyl)-7-{2-[(trifluoromethyl)phenyl]ethyl}-1H-imidazo[4,5-c]quinolin-4-amine

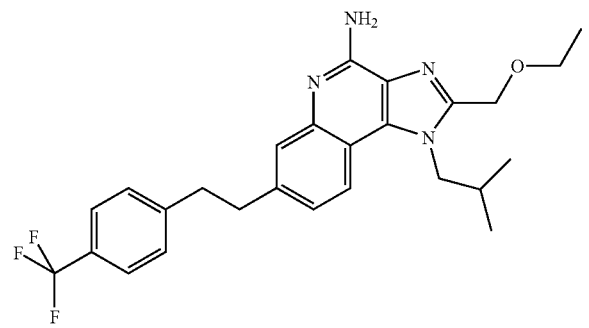

A solution of 2-ethoxymethyl-1-(2-methylpropyl)-7-{(E)-2-[(4-trifluoromethyl)phenyl]vinyl}-1H-imidazo[4,5-c]quinolin-4-amine (0.47 g, 1.0 mmol) in ethyl acetate (200 mL) was added to a Parr vessel charged with 10% palladium on carbon (0.30 g). The reaction was placed under hydrogen pressure (50 psi, $3.4 \times 10^5$ Pa) for seven days. The reaction mixture was filtered, and the filter cake was washed with ethyl acetate. The filtrate was concentrated under reduced pressure to provide 0.22 g of 2-ethoxymethyl-1-(2-methylpropyl)-7-{2-[(4-trifluoromethyl)phenyl]ethyl}-1H-imidazo[4,5-c]quinolin-4-amine as a white powder, mp 175.5-178° C.

Anal. Calcd for $C_{26}H_{29}F_3N_4O$: C, 66.37; H, 6.21; N, 11.91. Found: C, 66.09; H, 6.39; N, 11.53.

Examples 118-122

For Examples 118-121, triphenylphosphine (31 mg, 0.12 mmol) and palladium (II) acetate (9 mg, 0.04 mmol) were added to a mixture of 8-bromo-1-(2-methylpropyl)-1H-imidazo[4,5-c]quinolin-4-amine (1.28 g, 4.00 mmol), the boronic acid from the table below (6.00 mmol, 1.5 equivalents), n-propanol (7 mL), aqueous sodium carbonate (5.0 mL of 2 M), and water (1.4 mL). The reaction was purged with nitrogen and heated at reflux under a nitrogen atmosphere for one to two hours. Upon cooling to ambient temperature, a solid formed and was isolated by filtration and washed with water. The crude product was recrystallized from methanol and dried overnight at 1.33 Pa and 98° C. to provide the products listed below the table.

For Example 122, 8-bromo-1-(2-methylpropyl)-1H-imidazo[4,5-c]quinolin-4-amine and the boronic acid from the table below were coupled according to the general procedure described in Part J of Example 1. The reaction was heated at reflux overnight. The crude product was recrystallized from methanol.

Examples 118-122

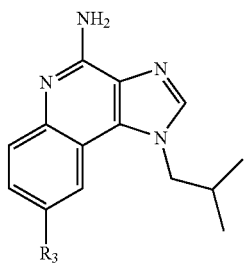

| Example | Boronic acid or ester | $R_3$ |
|---|---|---|
| 118 | 4-Ethylphenylboronic acid | |
| 119 | 3,4-Dimethylphenylboronic acid | |
| 120 | 3-Acetylphenylboronic acid | |
| 121 | Thianaphthene-3-boronic acid | |
| 122 | trans-2-Phenylvinylboronic acid | |

Example 118

8-(4-Ethylphenyl)-1-(2-methylpropyl)-1H-imidazo[4,5-c]quinolin-4-amine

The product was obtained as pale yellow needles, mp 238-240° C.

Anal. Calcd for $C_{22}H_{24}N_4$: C, 76.71; H, 7.02; N, 16.26. Found: C, 76.67; H, 7.00; N, 16.31.

Example 119

8-(3,4-Dimethylphenyl)-1-(2-methylpropyl)-1H-imidazo[4,5-c]quinolin-4-amine

The product was obtained as pale yellow needles, mp 204-205° C.

Anal. Calcd for $C_{22}H_{24}N_4$: C, 76.71; H, 7.02; N, 16.26. Found: C, 76.33; H, 7.28; N, 16.21.

Example 120

1-{3-[4-Amino-1-(2-methylpropyl)-1H-imidazo[4,5-c]quinolin-8-yl]phenyl}ethanone

The product was obtained as a white solid, mp 217-218° C.

Anal. Calcd for $C_{22}H_{22}N_4O$: C, 73.72; H, 6.19; N, 15.63. Found: C, 73.87; H, 6.24; N, 15.75.

Example 121

8-Benzo[b]thiophen-3-yl-1-(2-methylpropyl)-1H-imidazo[4,5-c]quinolin-4-amine

The product was obtained as pale yellow needles, mp 247-248° C.

Anal. Calcd for $C_{22}H_{20}N_4S \cdot 0.14H_2O$: C, 70.46; H, 5.45; N, 14.94. Found: C, 70.28; H, 5.26; N, 14.91.

Example 122

1-(2-Methylpropyl)-8-styryl-1H-imidazo[4,5-c]quinolin-4-amine

The product was obtained as pale yellow crystals, mp 228-230° C.

Anal. Calcd for $C_{22}H_{22}N_4 \cdot 1.5H_2O$: C, 71.52; H, 6.82; N, 15.16. Found: C, 71.34; H, 6.63; N, 15.20.

Example 123

1-(2-Methylpropyl)-8-phenethyl-1H-imidazo[4,5-c]quinolin-4-amine

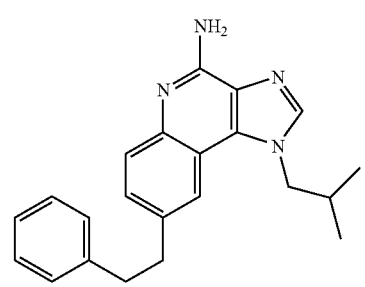

A solution of 1-(2-methylpropyl)-8-styryl-1H-imidazo[4,5-c]quinolin-4-amine (1.37 g, 4.00 mmol) in ethanol (40 mL) was added to a Parr vessel charged with 10% palladium on carbon (137 mg). The reaction was placed under hydrogen pressure (40 psi, $2.8 \times 10^5$ Pa) for six days. The reaction mixture was filtered through a layer of CELITE filter aid, and the filter cake was washed with ethanol. The filtrate was concentrated under reduced pressure, and the residue was recrystallized from methanol to provide 0.300 g of 1-(2-methylpropyl)-8-phenethyl-1H-imidazo[4,5-c]quinolin-4-amine as a white solid, mp 175-178° C.

Anal. Calcd for $C_{22}H_{24}N_4 \cdot 0.75H_2O$: C, 73.82; H, 7.18; N, 15.65. Found: C, 73.45; H, 7.32; N, 15.33.

Example 124

2-Methyl-1-(3-methanesulfonylpropyl)-7-phenyl-1H-imidazo[4,5-c]quinolin-4-amine

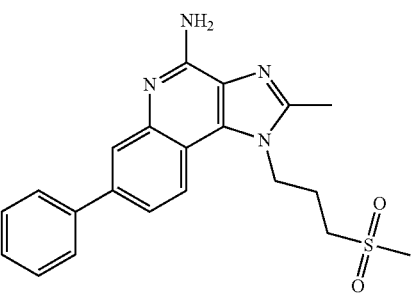

Part A $N^4$-(3-Methylsulfanylpropyl)-7-phenylquinoline-3,4-diamine and trimethyl orthoacetate were reacted according to the general method described in Part H of Example 10. The crude product was purified by column chromatography on silica gel (eluting with 95:5 dichloromethane:methanol) to provide 2-methyl-1-(3-methanesulfanylpropyl)-7-phenyl-1H-imidazo[4,5-c]quinolin-4-amine as a light brown solid.

Part B

The method described in Part I of Example 10 was followed. The crude product was recrystallized from acetonitrile (67 mL/g) and then from methanol (106 mL/g). The crystals were purified by column chromatography on silica gel (eluting with 90:10 dichloromethane:methanol), and the resulting solid was recrystallized from acetonitrile (220 mL/g) and dried for 17 hours under vacuum at 85° C. to provide 2-methyl-1-(3-methanesulfonylpropyl)-7-phenyl-1H-imidazo[4,5-c]quinolin-4-amine as a white powder, mp mp 203-205° C.

Anal. Calcd for $C_{21}H_{22}N_4O_2S$: C, 63.94; H, 5.62: N, 14.20. Found: C, 63.81; H, 5.47; N, 14.14.

Examples 125-135

Part A

Triethylamine (17.35 mL, 124 mmol) was added to a solution of 7-bromo-4-chloro-3-nitroquinoline (29.84 g, 104 mmol) in dichloromethane (253 mL), and the reaction was cooled to 0° C. 1-Amino-2-methylpropan-2-ol (10.17 g, 114 mmol) was added dropwise, and then the reaction was allowed to warm to ambient temperature and stirred overnight. A precipitate formed and was isolated by filtration and washed with water. The crude solid was recrystallized from a mixture of isopropanol and acetonitrile to provide 27.78 g of 1-(7-bromo-3-nitroquinolin-4-ylamino)-2-methylpropan-2-ol as a solid.

Part B

A solution of 1-(7-bromo-3-nitroquinolin-4-ylamino)-2-methylpropan-2-ol (27.78 g, 81.66 mmol) in acetonitrile (1.2 L) was added to a Parr vessel charged with 5% platinum on carbon (0.84 g), and the reaction was placed under hydrogen pressure (50 psi, $3.4 \times 10^5$ Pa) for two days. The reaction mixture was filtered through a layer of CELITE filter aid, and the filter cake was washed with ethanol (1 L). The filtrate was concentrated under reduced pressure to provide 21.70 g of 1-(3-amino-7-bromoquinolin-4-ylamino)-2-methylpropan-2-ol as a yellow oil.

97

Part C

A solution of 1-(3-amino-7-bromoquinolin-4-ylamino)-2-methylpropan-2-ol (158.19 g, 0.510 mol) in dichloromethane (1.2 L) was cooled to 0° C. Ethoxyacetyl chloride (62.50 g, 0.510 mol) was added dropwise, and then the reaction was allowed to warm to ambient temperature and stirred overnight. A precipitate formed and was isolated by filtration to provide N-[7-bromo-4-(2-hydroxy-2-methylpropylamino)quinolin-3-yl]-2-ethoxyacetamide as a solid.

Part D

A solution of sodium hydroxide (25 g, 0.625 mol) in water (205 mL) was added to a solution of N-[7-bromo-4-(2-hydroxy-2-methylpropylamino)quinolin-3-yl]-2-ethoxyacetamide (170.88 g, 0.431 mol) in ethanol (700 mL), and the reaction was heated at reflux under a nitrogen atmosphere for two hours. Upon cooling the reaction, a precipitate formed and was isolated by filtration. The solid was purified by flash column chromatography on silica gel (eluting sequentially with chloroform, 99:1 chloroform:methanol, and 97:3 chloroform:methanol) to provide 80.31 g of 1-(7-bromo-2-ethoxymethyl-1H-imidazo[4,5-c]quinolin-1-yl)-2-methylpropan-2-ol as a tan solid.

Part E

3-Chloroperoxybenzoic acid (73.27 g of 50% pure material, 0.212 mol) was added in four portions over a period of 30 minutes to a solution of 1-(7-bromo-2-ethoxymethyl-1H-imidazo[4,5-c]quinolin-1-yl)-2-methylpropan-2-ol (80.31 g, 0.212 mol) in dichloromethane (950 mL), and the reaction was stirred overnight at ambient temperature. The reaction mixture was washed twice with aqueous sodium carbonate (2 M) and then diluted with additional dichloromethane (1.5 L total volume). The solution was cooled to 0° C., and concentrated ammonium hydroxide (83 mL) was added. p-Toluenesulfonyl chloride (48.56 g, 0.254 mol) was then added over a period of 20 minutes, and the reaction was allowed to warm to ambient temperature and stirred overnight. A precipitate formed and was isolated by filtration and washed sequentially with 2 M aqueous sodium carbonate and water. The crude product was recrystallized from 2:1 isopropanol:acetonitrile and collected in two crops to provide 58.4 g of 1-(4-amino-7-bromo-2-ethoxymethyl-1H-imidazo[4,5-c]quinolin-1-yl)-2-methylpropan-2-ol as a solid.

Part F 1-(4-Amino-7-bromo-2-ethoxymethyl-1H-imidazo[4,5-c]quinolin-1-yl)-2-methylpropan-2-ol and the boronic acid or boronic acid ester from the table below were coupled according to the general procedure described in Part J of Example 1. The reaction was heated at reflux for between 1.5 and 27 hours. The reaction mixture was partitioned between brine and chloroform. The aqueous layer was extracted twice with chloroform, and the combined organic fractions were dried over magnesium sulfate, filtered, and concentrated under reduced pressure. The purification and characterization of each compound is given below the table.

98

Examples 125-135

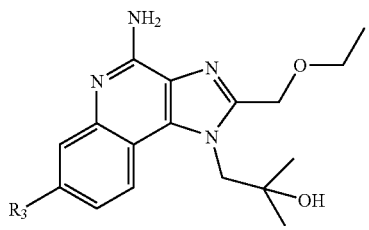

| Example | Boronic acid or ester | $R_3$ |
|---|---|---|
| 125 | Thiophene-3-boronic acid | |
| 126 | Pyridine-3-boronic acid 1,3-propanediol cyclic ester | |
| 127 | Pyridine-4-boronic acid pinacol ester | |
| 128 | 1H-Pyrazole-4-boronic acid pinacol ester | |
| 129 | 3-(Pyrrolidine-1-carbonyl)phenylboronic acid | |
| 130 | 3-(Morpholine-4-carbonyl)phenylboronic acid | |
| 131 | Phenylboronic acid | |
| 132 | 4-(N,O-Dimethyl-hydroxylamino-carbonyl)phenyl boronic acid | |
| 133 | 5-(tert-Butyldimethyl-silanyloxymethyl)pyridine-3-boronic acid | |

-continued

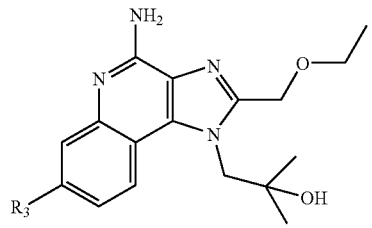

| Example | Boronic acid or ester | R3 |
|---|---|---|
| 134 | 5-Ethoxymethylpyridin-3-ylboronic acid | 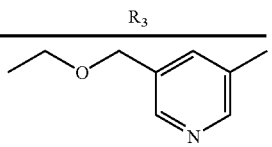 |
| 135 | 3-Carboxyphenyl-boronic acid | 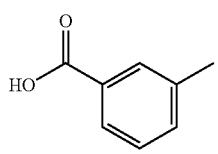 |

Example 125

1-[4-Amino-2-ethoxymethyl-7-(thiophen-3-yl)-1H-imidazo[4,5-c]quinolin-1-yl]-2-methylpropan-2-ol The crude product was recrystallized from 2-butanone and then purified by flash column chromatography on silica gel (eluting with chloroform:CMA in a gradient from 90:10 to 65:35). The resulting solid was recrystallized from acetonitrile to provide 1-[4-amino-2-ethoxymethyl-7-(thiophen-3-yl)-1H-imidazo[4,5-c]quinolin-1-yl]-2-methylpropan-2-ol as white crystals, mp 204-205° C.
Anal. Calcd for $C_{21}H_{24}N_4O_2S$: C, 63.61; H, 6.10; N, 14.13. Found: C, 63.71; H, 6.23; N, 14.31.

Example 126

1-[4-Amino-2-ethoxymethyl-7-(pyridin-3-yl)-1H-imidazo[4,5-c]quinolin-1-yl]-2-methylpropan-2-ol The crude product was purified three times by HPFC (eluting with chloroform:CMA in a gradient from 90:10 to 70:30). The resulting solid was recrystallized from acetonitrile and dried overnight at 1.33 Pa and 98° C. to provide 1-[4-amino-2-ethoxymethyl-7-(pyridin-3-yl)-1H-imidazo[4,5-c]quinolin-1-yl]-2-methylpropan-2-ol as a white solid, mp 197-199° C.
Anal. Calcd for $C_{22}H_{25}N_5O_2.0.28H_2O$: C, 66.63; H, 6.50; N, 17.66. Found: C, 66.63; H, 6.55; N, 17.88.

Example 127

1-[4-Amino-2-ethoxymethyl-7-(pyridin-4-yl)-1H-imidazo[4,5-c]quinolin-1-yl]-2-methylpropan-2-ol The crude product was purified twice by HPFC (eluting with chloroform:CMA in a gradient from 100:0 to 55:45). The fractions containing the pure product were concentrated under reduced pressure until a precipitate formed. Hexanes were added, and the resulting solid was isolated by filtration and dried overnight under vacuum to provide 1-[4-amino-2-ethoxymethyl-7-(pyridin-4-yl)-1H-imidazo[4,5-c]quinolin-1-yl]-2-methylpropan-2-ol as a pale yellow solid, mp 220-221° C.
Anal. Calcd for $C_{22}H_{25}N_5O_2.0.39H_2O$: C, 66.31; H, 6.52; N, 17.57. Found: C, 65.95; H, 6.32; N, 17.44.

Example 128

1-[4-Amino-2-ethoxymethyl-7-(1H-pyrazol-4-yl)-1H-imidazo[4,5-c]quinolin-1-yl]-2-methylpropan-2-ol The crude product was purified by HPFC (eluting with chloroform:CMA in a gradient from 100:0 to 40:60) followed by recrystallization from methanol to provide 1-[4-amino-2-ethoxymethyl-7-(1H-pyrazol-4-yl)-1H-imidazo[4,5-c]quinolin-1-yl]-2-methylpropan-2-ol as white, granular crystals, mp>250° C.
Anal. Calcd for $C_{20}H_{24}N_6O_2$: C, 63.14; H, 6.36; N, 22.09. Found: C, 62.89; H, 6.35; N, 21.94.

Example 129

{3-[4-Amino-2-ethoxymethyl-1-(2-hydroxy-2-methylpropyl)-1H-imidazo[4,5-c]quinolin-7-yl]phenyl}pyrrolidin-1-ylmethanone The crude product was purified by HPFC (eluting with chloroform:CMA in a gradient from 100:0 to 65:35) followed by recrystallizations from isopropanol and acetonitrile to provide {3-[4-amino-2-ethoxymethyl-1-(2-hydroxy-2-methylpropyl)-1H-imidazo[4,5-c]quinolin-7-yl]phenyl}pyrrolidin-1-ylmethanone as a white powder, mp 216.5-217.5° C.
Anal. Calcd for $C_{28}H_{33}N_5O_3$: C, 68.97; H, 6.82; N, 14.36. Found: C, 68.67; H, 7.01; N, 14.42.

Example 130

{3-[4-Amino-2-ethoxymethyl-1-(2-hydroxy-2-methylpropyl)-1H-imidazo[4,5-c]quinolin-7-yl]phenyl}morpholin-4-ylmethanone The crude product was purified by HPFC (eluting with chloroform:CMA in a gradient from 100:0 to 70:30) followed by recrystallizations from isopropanol, dichloromethane:hexanes, and isopropanol. The crystals were dried under vacuum with heating to provide {3-[4-amino-2-ethoxymethyl-1-(2-hydroxy-2-methylpropyl)-1H-imidazo[4,5-c]quinolin-7-yl]phenyl}morpholin-4-ylmethanone as a white powder, mp 152.0-154.0° C.
Anal. Calcd for $C_{28}H_{33}N_5O_4.0.5H_2O$: C, 65.61; H, 6.69; N, 13.66. Found: C, 65.67; H, 7.09; N, 13.72.

Example 131

1-(4-Amino-2-ethoxymethyl-7-phenyl-1H-imidazo[4,5-c]quinolin-1-yl)-2-methylpropan-2-ol The crude product was recrystallized from methanol:water and then purified by HPFC (eluting with chloroform:CMA in a gradient from 100:0 to 70:30) to provide 1-(4-amino-2-ethoxymethyl-7-phenyl-1H-imidazo[4,5-c]quinolin-1-yl)-2-methylpropan-2-ol as a white solid, mp 211-212° C.
$^1$H NMR (500 mHz, DMSO-$d_6$) δ 8.34 (d, J=8.5 Hz, 1H), 7.83 (d, J=2 Hz, 1H), 7.76-7.73 (m, 2H), 7.52-7.46 (m, 3H), 7.38-7.35 (m, 1H), 6.58 (br s, 2H), 4.88 (s, 3H), 4.68 (br s, 2H), 3.52 (q, J=7 Hz, 2H), 1.19 (br s, 6H), 1.13 (t, J=7 Hz, 3H);

HRMS (ESI) m/z 391.2124 (391.2134 calcd for $C_{23}H_{26}N_4O_2$, (M+H).

Example 132

4-[4-Amino-2-ethoxymethyl-1-(2-hydroxy-2-methylpropyl)-1H-imidazo[4,5-c]quinolin-7-yl]-N-methoxy-N-methylbenzamide

The crude product was purified three times by HPFC (eluting with chloroform:CMA in gradients from 100:0 to 70:30). The fractions containing the pure product were concentrated under reduced pressure until a precipitate formed. Hexanes were added, and the resulting solid was isolated by filtration and dried overnight in a vacuum oven at 80° C. and then heated to melting under vacuum to provide 4-[4-amino-2-ethoxymethyl-1-(2-hydroxy-2-methylpropyl)-1H-imidazo[4,5-c]quinolin-7-yl]-N-methoxy-N-methylbenzamide as a light green solid.

$^{13}C$ NMR (75 MHz, DMSO-$d_6$) δ 168.7, 152.3, 151.0, 145.5, 141.9, 137.0, 133.9, 133.0, 128.5, 126.2, 123.7, 122.2, 119.1, 114.8, 70.6, 65.2, 64.8, 60.7, 54.8, 33.2, 27.6, 14.9;

HRMS (EI) m/z 478.2446 (478.2454 calcd for $C_{26}H_{31}N_5O_4$).

Example 133

1-[4-Amino-2-ethoxymethyl-7-(5-hydroxymethylpyridin-3-yl)-1H-imidazo[4,5-c]quinolin-1-yl]-2-methylpropan-2-ol

The reaction was heated at reflux for three hours and then allowed to cool and stand at ambient temperature for several days. The crude product was purified by HPFC (eluting with chloroform:CMA in a gradient from 100:0 to 65:35). The solid (3.73 g) was dissolved in tetrahydrofuran (THF) (5 mL), water (5 mL), and acetic acid (15 mL). The solution was allowed to stand at room temperature for three days, and then the solvents were removed under reduced pressure. The residue was partitioned between chloroform and 2 M aqueous sodium carbonate:brine, and the aqueous layer was extracted with chloroform (7×). The combined organic fractions were concentrated under reduced pressure. The residue was then purified by HPFC (eluting with chloroform:CMA in a gradient from 100:0 to 35:65) followed by recrystallization from acetonitrile to provide 1-[4-amino-2-ethoxymethyl-7-(5-hydroxymethylpyridin-3-yl)-1H-imidazo[4,5-c]quinolin-1-yl]-2-methylpropan-2-ol as a white powder, mp 188-190° C.

Anal. Calcd for $C_{23}H_{27}N_5O_3$: C, 65.54; H, 6.46; N, 16.62. Found: C, 65.22; H, 6.66; N, 16.56.

Example 134

1-[4-Amino-2-ethoxymethyl-7-(5-ethoxymethylpyridin-3-yl)-1H-imidazo[4,5-c]quinolin-1-yl]-2-methylpropan-2-ol

Part A (5-Bromopyridin-3-yl)methanol was prepared according to the published procedure (Zhang, N. et al, *J. Med. Chem.*, 45, 2832-2840 (2002)). A solution of (5-bromopyridin-3-yl)methanol (7.39 g, 39.3 mmol) in THF was cooled to 0° C. Sodium bis(trimethylsilyl)amide (39.3 mL of a 1.0 M solution in THF) was added, and the reaction was stirred for 20 minutes. Iodoethane (3.46 mL, 43.2 mmol) and DMF were added, and the reaction was allowed to warm to ambient temperature and stirred overnight. Brine was added, and the aqueous layer was extracted twice with hexanes. The combined organic fractions were concentrated under reduced pressure, and the residue was purified by HPFC (eluting with hexanes:ethyl acetate in a gradient from 100:0 to 70:30) to provide 5.11 g of 3-bromo-5-ethoxymethylpyridine as a colorless oil.

Part B

The method described in Part A of Example 115 was used to convert 3-bromo-5-ethoxymethylpyridine (5.11 g, 23.6 mmol) to 5-ethoxymethylpyridin-3-ylboronic acid, which was obtained as a white solid.

Part C

The crude product from the coupling reaction was recrystallized from dichloromethane:hexanes and then purified twice by HPFC (eluting with chloroform:CMA in a gradient from 100:0 to 70:30). The resulting solid was recrystallized from dichloromethane:hexanes to provide 1-[4-amino-2-ethoxymethyl-7-(5-ethoxymethylpyridin-3-yl)-1H-imidazo[4,5-c]quinolin-1-yl]-2-methylpropan-2-ol as a white powder, mp 156.0-156.5° C.

Anal. Calcd for $C_{25}H_{31}N_5O_3$: C, 66.79; H, 6.95; N, 15.58. Found: C, 66.46; H, 6.98; N, 15.51.

Example 135

3-[4-Amino-2-ethoxymethyl-1-(2-hydroxy-2-methylpropyl)-1H-imidazo[4,5-c]quinolin-7-yl]benzoic acid

The crude product was isolated as a solid from the reaction mixture, recrystallized from dimethyl sulfoxide, stirred with methanol:water, and isolated by filtration to provide 3-[4-amino-2-ethoxymethyl-1-(2-hydroxy-2-methylpropyl)-1H-imidazo[4,5-c]quinolin-7-yl]benzoic acid as a white powder, mp>250° C.

HRMS (ESI) m/z 435.2016 (435.2032 calcd for $C_{24}H_{26}N_4O_4$, (M+H).

Examples 136-141

Part A

The method described in Part A of Example 9 was used to react 1-(3-amino-7-bromoquinolin-4-ylamino)-2-methylpropan-2-ol (29.0 g, 93.5 mmol) with 3-methoxypropionyl chloride (11.5 g, 93.5 mmol). The crude product was recrystallized from 2:1 ethyl acetate:hexane and then purified by flash column chromatography on silica gel (eluting sequentially with 60:40 acetone:toluene and acetone). The resulting solid was recrystallized from 3:1 ethyl acetate hexane to provide 13.3 g of 1-[7-bromo-2-(2-methoxyethyl)-1H-imidazo[4,5-c]quinolin-1-yl]-2-methylpropan-2-ol as translucent crystals.

Part B

1-[7-Bromo-2-(2-methoxyethyl)-1H-imidazo[4,5-c]quinolin-1-yl]-2-methylpropan-2-ol was oxidized and then aminated according to the methods described in Parts H and I of Example 1. After recrystallization from ethanol, 1-[4-amino-7-bromo-2-(2-methoxyethyl)-1H-imidazo[4,5-c]quinolin-1-yl]-2-methylpropan-2-ol was obtained as a pale orange solid.

Part C

1-[4-Amino-7-bromo-2-(2-methoxyethyl)-1H-imidazo[4,5-c]quinolin-1-yl]-2-methylpropan-2-ol and the boronic acid or boronic acid ester from the table below were coupled according to the general procedure described in Part J of Example 1. The reaction was heated at reflux for between three hours and overnight. For Example 136, a solid formed upon cooling to room temperature and was isolated by filtration and washed with hexanes. For Examples 137-141, the reaction mixture was partitioned between brine and chloroform. The aqueous layer was extracted twice with chloroform, and the combined organic fractions were dried over magnesium sulfate, filtered, and concentrated under reduced pressure. The purification and characterization of each compound is given below the table.

Examples 136-141

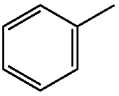

| Example | Boronic acid or ester | $R_3$ |
|---|---|---|
| 136 | Phenylboronic acid | 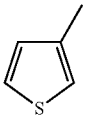 |
| 137 | Thiophene-3-boronic acid | 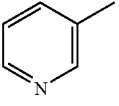 |
| 138 | Pyridine-3-boronic acid 1,3-propanediol cyclic ester | 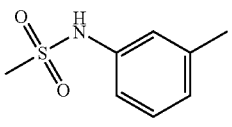 |
| 139 | 3-(Methylsulfonylamino)phenyl-boronic acid | 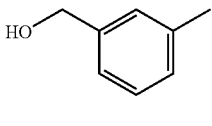 |
| 140 | 3-(Hydroxymethyl)phenyl-boronic acid | 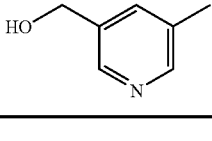 |
| 141 | 5-(tert-Butyldimethyl-silanyloxymethyl)pyridine-3-boronic acid |  |

Example 136

1-[4-Amino-2-(2-methoxyethyl)-7-phenyl-1H-imidazo[4,5-c]quinolin-1-yl]-2-methylpropan-2-ol The crude product was recrystallized twice from isopropanol and then from dichloromethane:hexanes and dried overnight under vacuum to provide 1-[4-amino-2-(2-methoxyethyl)-7-phenyl-1H-imidazo[4,5-c]quinolin-1-yl]-2-methylpropan-2-ol as a white solid, mp 226-227° C.
Anal. Calcd for $C_{23}H_{26}N_4O_2$: C, 70.75; H, 6.71; N, 14.35. Found: C, 70.49; H, 6.56; N, 14.28.

Example 137

1-[4-Amino-2-(2-methoxyethyl)-7-(thiophen-3-yl)-1H-imidazo[4,5-c]quinolin-1-yl]-2-methylpropan-2-ol The crude product purified by flash column chromatography on silica gel (eluting with chloroform:CMA in a gradient from 85:15 to 70:30). The resulting solid was recrystallized from ethanol to provide 1-[4-amino-2-(2-methoxyethyl)-7-(thiophen-3-yl)-1H-imidazo[4,5-c]quinolin-1-yl]-2-methylpropan-2-ol as white crystals, mp 233-234° C.
Anal. Calcd for $C_{21}H_{24}N_4O_2S$: C, 63.61; H, 6.10; N, 14.13. Found: C, 63.45; H, 6.21; N, 14.07.

Example 138

1-[4-Amino-2-(2-methoxyethyl)-7-(pyridin-3-yl)-1H-imidazo[4,5-c]quinolin-1-yl]-2-methylpropan-2-ol The crude product was purified by flash column chromatography on silica gel (eluting with chloroform:CMA in a gradient from 90:10 to 70:30). The resulting solid was recrystallized from methanol to provide 1-[4-amino-2-(2-methoxyethyl)-7-(pyridin-3-yl)-1H-imidazo[4,5-c]quinolin-1-yl]-2-methylpropan-2-ol as white needles, mp 158-160° C.
Anal. Calcd for $C_{22}H_{25}N_5O_2 \cdot 1.10H_2O$: C, 64.26; H, 6.67; N, 17.03. Found: C, 64.12; H, 7.02; N, 17.27.

Example 139

N-{3-[4-Amino-1-(2-hydroxy-2-methylpropyl)-2-(2-methoxyethyl)-1H-imidazo[4,5-c]quinolin-7-yl]phenyl}methanesulfamide The crude product was purified by flash column chromatography on silica gel (eluting with chloroform:CMA in a gradient from 90:10 to 80:20) to provide N-{3-[4-amino-1-(2-hydroxy-2-methylpropyl)-2-(2-methoxyethyl)-1H-imidazo[4,5-c]quinolin-7-yl]phenyl}methanesulfamide as a white powder, mp 156-158° C.
Anal. Calcd for $C_{24}H_{29}N_5O_4S \cdot 3.0H_2O$: C, 53.62; H, 6.56; N, 13.03. Found: C, 53.50; H, 6.49; N, 12.95.

Example 140

1-[4-Amino-7-(3-hydroxymethylphenyl)-2-(2-methoxyethyl)-1H-imidazo[4,5-c]quinolin-1-yl]-2-methylpropan-2-ol The crude product was purified by flash column chromatography on silica gel (eluting with chloroform:CMA in a gradient from 90:10 to 80:20) to provide 1-[4-amino-7-(3- hydroxymethylphenyl)-2-(2-methoxyethyl)-1H-imidazo[4,5-c]quinolin-1-yl]-2-methylpropan-2-ol as a white powder, mp 212-213° C.

Anal. Calcd for $C_{24}H_{28}N_4O_3 \cdot 0.17H_2O$: C, 68.06; H, 6.74; N, 13.22. Found: C, 67.73; H, 6.63; N, 13.04.

Example 141

1-[4-Amino-7-(5-hydroxymethylpyridin-3-yl)-2-(2-methoxyethyl)-1H-imidazo[4,5-c]quinolin-1-yl]-2-methylpropan-2-ol The crude product was purified by flash column chromatography on silica gel (eluting with chloroform:CMA in a gradient from 90:10 to 80:20) to provide 1-[4-amino-7-(5-hydroxymethylpyridin-3-yl)-2-(2-methoxyethyl)-1H-imidazo[4,5-c]quinolin-1-yl]-2-methylpropan-2-ol as a yellow solid, mp 210-211° C.

Anal. Calcd for $C_{23}H_{27}N_5O_3 \cdot 1.0H_2O$: C, 62.85; H, 6.65; N, 15.93. Found: C, 62.47; H, 6.33; N, 15.83.

Examples 142-144

Part A

Triethyl orthopropionate (12.9 g, 73.2 mmol) and pyridine hydrochloride (220 mg) were added to a solution of 1-(3-amino-7-bromoquinolin-4-ylamino)-2-methylpropan-2-ol (22.1 g, 70.6 mmol) in anhydrous toluene (300 mL), and the reaction was heated at reflux for three hours. The reaction was allowed to cool to ambient temperature and stand overnight; a precipitate formed. The precipitate was isolated by filtration, washed with toluene, and air-dried to provide 18.42 g of 1-(7-bromo-2-ethyl-1H-imidazo[4,5-c]quinolin-1-yl)-2-methylpropan-2-ol as beige crystals.

Part B 1-(7-Bromo-2-ethyl-1H-imidazo[4,5-c]quinolin-1-yl)-2-methylpropan-2-ol was oxidized and then aminated according to the methods described in Parts H and I of Example 1. The product from amination was isolated by filtration from the reaction mixture and stirred with 2 M aqueous sodium carbonate and chloroform for ten minutes. The resulting solid was isolated by filtration and washed with water to provide 1-(4-amino-7-bromo-2-methoxyethyl-1H-imidazo[4,5-c]quinolin-1-yl)-2-methylpropan-2-ol as a white solid, which was used without further purification.

Part C 1-(4-Amino-7-bromo-2-ethyl-1H-imidazo[4,5-c]quinolin-1-yl)-2-methylpropan-2-ol and the boronic acid or boronic acid ester from the table below were coupled according to the general procedure described in Part J of Example 1. The reaction was heated at reflux between 12 and 54 hours. The work-up procedure described in Part F of Examples 125-131 was followed, and the purification and characterization of each compound is described below the table.

Examples 142-144

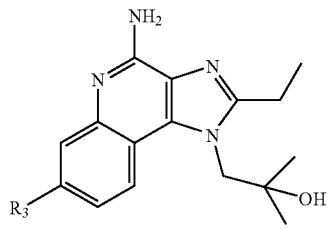

| Example | Boronic acid or ester | $R_3$ |
|---|---|---|
| 142 | Pyridine-3-boronic acid 1,3-propanediol cyclic ester | |
| 143 | Pyridine-4-boronic acid pinacol ester | |
| 144 | 5-(tert-Butyldimethyl-silanyloxymethyl) pyridine-3-boronic acid | |

Example 142

1-[4-Amino-2-ethyl-7-(pyridin-3-yl)-1H-imidazo[4,5-c]quinolin-1-yl]-2-methylpropan-2-ol The crude product was purified by HPFC (eluting with chloroform:CMA in a gradient from 100:0 to 55:45). The resulting solid was dissolved in chloroform and precipitated with hexane, recrystallized twice from acetonitrile, and finally recrystallized from 3:1 acetonitrile:methanol and dried at 1.33 Pa and 80° C. to provide 1-[4-amino-2-ethyl-7-(pyridin-3-yl)-1H-imidazo[4,5-c]quinolin-1-yl]-2-methylpropan-2-ol as white needles, mp 245-247° C.

Anal. Calcd for $C_{21}H_{23}N_5O$: C, 69.78; H, 6.41; N, 19.38. Found: C, 69.60; H, 6.53; N, 19.58.

Example 143

1-[4-Amino-2-ethyl-7-(pyridin-4-yl)-1H-imidazo[4,5-c]quinolin-1-yl]-2-methylpropan-2-ol The crude product was purified by HPFC (eluting with chloroform:CMA in a gradient from 100:0 to 65:35) The resulting solid was recrystallized from acetonitrile:methanol and air-dried to provide 1-[4-amino-2-ethyl-7-(pyridin-4-yl)-1H-imidazo[4,5-c]quinolin-1-yl]-2-methylpropan-2-ol as a white solid, mp>250° C.

Anal. Calcd for $C_{21}H_{23}N_5O$: C, 69.78; H, 6.41; N, 19.38. Found: C, 69.68; H, 6.54; N, 19.43.

Example 144

1-[4-Amino-2-ethyl-7-(5-hydroxymethylpyridin-3-yl)-1H-imidazo[4,5-c]quinolin-1-yl]-2-methylpropan-2-ol

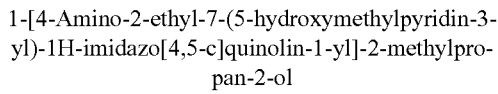

The crude product was purified by HPFC, and the resulting solid was dissolved in THF (5 mL), water (5 mL), and acetic acid (15 mL). The solution was allowed to stand at room temperature for three days, and 5 M aqueous sodium hydroxide and 2 M aqueous sodium carbonate were added to adjust to pH 11. A solid was present and was isolated by filtration and purified by HPFC™ (eluting with chloroform:CMA in a gradient from 100:0 to 35:65). The resulting solid was recrystallized from 3:1 methanol:acetonitrile and dried overnight at 1.33 Pa and 80° C. to provide 1-[4-amino-2-ethyl-7-(5-hydroxymethylpyridin-3-yl)-1H-imidazo[4,5-c]quinolin-1-yl]-2-methylpropan-2-ol as white crystals, mp>250

Anal. Calcd for $C_{22}H_{25}N_5O_2$: C, 67.50; H, 6.44; N, 17.89. Found: C, 67.28; H, 6.71; N, 18.06.

Example 145

2-(2-Methoxyethyl)-1-(2-methylpropyl)-7-(pyridin-3-yl)-1H-imidazo[4,5-c]quinolin-4-amine

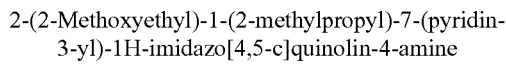

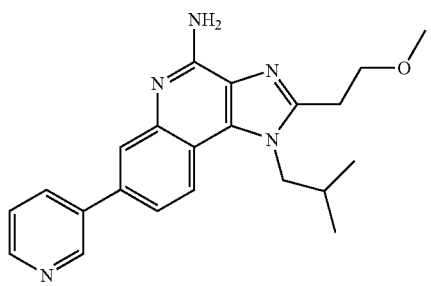

7-Bromo-2-(2-methoxyethyl)-1-(2-methylpropyl)-1H-imidazo[4,5-c]quinolin-4-amine was prepared according to the procedures described in Parts A and B of Example 9 using methoxypropanoyl chloride instead of ethoxyacetyl chloride. 7-Bromo-2-(2-methoxyethyl)-1-(2-methylpropyl)-1H-imidazo[4,5-c]quinolin-4-amine was coupled with pyridine-3-boronic acid 1,3-propanediol cyclic ester according to the method described in Examples 118-121. The reaction was heated at reflux overnight, and the work-up procedure described in Part F of Examples 125-131 was followed. The crude product was purified by flash column chromatography on silica gel (eluting with chloroform:CMA in a gradient from 90:10 to 76:24) followed by recrystallization from methanol. The crystals were dried at 1.33 Pa and 98° C. to provide 2-(2-methoxyethyl)-1-(2-methylpropyl)-7-(pyridin-3-yl)-1H-imidazo[4,5-c]quinolin-4-amine as white needles, mp 207-208° C.

Anal. Calcd for $C_{22}H_{25}N_5O$: C, 70.38; H, 6.71; N, 18.65. Found: C, 70.31; H, 6.76; N, 18.76.

Example 146

{5-[4-Amino-2-(2-methoxyethyl)-1-(2-methylpropyl)-1H-imidazo[4,5-c]quinolin-7-yl]pyridin-3-yl}methanol

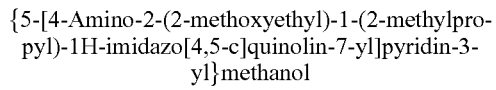

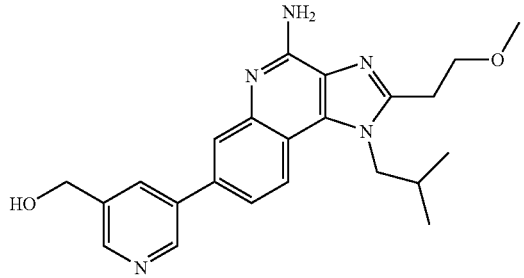

7-Bromo-2-(2-methoxyethyl)-1-(2-methylpropyl)-1H-imidazo[4,5-c]quinolin-4-amine was coupled with 5-(tert-butyldimethylsilanyloxymethyl)pyridine-3-boronic acid according to the method described in Examples 118-121. The reaction was heated at reflux for 2.25 hours, and the work-up procedure described in Part F of Examples 125-131 was followed. The crude product was purified and deprotected according to the procedure described in Example 144. The resulting solid was purified by HPFC (eluting with chloroform:CMA in a gradient from 100:0 to 55:45) followed by recrystallization from acetonitrile to provide {5-[4-amino-2-(2-methoxyethyl)-1-(2-methylpropyl)-1H-imidazo[4,5-c]quinolin-7-yl]pyridin-3-yl}methanol as white needles, mp 202-204° C.

Anal. Calcd for $C_{23}H_{27}N_5O_2$: C, 68.13; H, 6.71; N, 17.27. Found: C, 67.89; H, 6.62; N, 17.26.

Examples 147-150

Part A
6-Bromo-4-chloro-3-nitroquinoline, prepared from 4-bromoaniline according to the methods described in Parts A-D of Example 1, was treated according to the methods described in Parts A and B of Examples 125-135 to provide 1-(3-amino-6-bromoquinolin-4-ylamino)-2-methylpropan-2-ol.

Part B
1-(3-Amino-6-bromoquinolin-4-ylamino)-2-methylpropan-2-ol was treated according to the method described in Parts A and B of Example 9 to provide 1-(4-amino-8-bromo-2-ethoxymethyl-1H-imidazo[4,5-c]quinolin-1-yl)-2-methylpropan-2-ol.

Part C
1-(4-Amino-8-bromo-2-ethoxymethyl-1H-imidazo[4,5-c]quinolin-1-yl)-2-methylpropan-2-ol and the boronic acid or boronic acid ester from the table below were coupled according to the general procedure described in Part J of Example 1. The reaction was stirred overnight. The crude product was purified by flash column chromatography on silica gel (eluting sequentially with 95:5 and 90:10 dichloromethane:methanol) followed by recrystallization from methanol to provide the products shown in the table below.

For Example 150, the product from the coupling reaction (1.5 g, 2.8 mmol) was dissolved in THF (25 mL). Tetrabutylammonium fluoride (3.64 mL of a 1.0 M solution in THF) was added, and the reaction was stirred for one hour at ambient temperature. Saturated ammonium chloride (20 mL) was added, and the aqueous layer was separated and extracted with dichloromethane (3×50 mL). The combined organic fractions were dried over sodium sulfate and filtered. A precipitate formed in the filtrate and was isolated by filtration. The solid was washed with dichloromethane, stirred with methanol, isolated by filtration, and washed with methanol to provide the product shown in the table below.

Examples 147-150

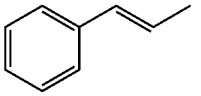

| Example | Boronic Acid or Ester | R₃ |
|---|---|---|
| 147 | trans-2-Phenylvinylboronic acid | 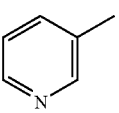 |
| 148 | Pyridine-3-boronic acid | 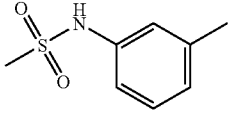 |
| 149 | 3-(Methylsulfonylamino)phenylboronic acid | 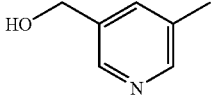 |
| 150 | 5-(tert-Butyldimethyl-silanyloxymethyl)pyridine-3-boronic acid | |

Examples 147-150

Example 151

1-(4-Amino-2-ethoxymethyl-8-phenethyl-1H-imidazo[4,5-c]quinolin-1-yl)-2-methylpropan-2-ol

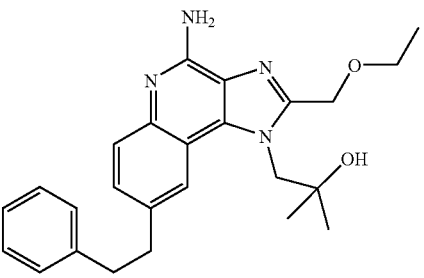

1-(4-Amino-2-ethoxymethyl-8-styryl-1H-imidazo[4,5-c]quinolin-1-yl)-2-methylpropan-2-ol (1.0 g, 2.4 mmol) was treated according to the method described in Example 123. The crude product was purified by flash column chromatography on silica gel (eluting with 95:5 dichloromethane:methanol) prior to recrystallization from methanol to provide 0.500 g of 1-(4-amino-2-ethoxymethyl-8-phenethyl-1H-imidazo[4,5-c]quinolin-1-yl)-2-methylpropan-2-ol as white crystals, mp 175-176° C.

Anal. Calcd for $C_{25}H_{30}N_4O_2$: C, 70.38; H, 7.30; N, 13.13. Found: C, 70.27; H, 7.26; N, 13.11.

Examples 152-156

Part A

A solution of tert-butoxy N-(4-aminobutyl)carbamate (15.38 g, 81.7 mmol) in dichloromethane (100 mL) was added dropwise over a period of 30 minutes to a solution of 7-bromo-4-chloro-3-nitroquinoline (74.3 mmol) and triethylamine (20.6 mL, 149 mmol) in dichloromethane (400 mL), and the reaction was stirred overnight at ambient temperature. The reaction was diluted with dichloromethane (500 mL), washed sequentially with water and brine, dried over magnesium sulfate, filtered, and concentrated under reduced pressure. The residue was recrystallized from isopropanol to pro-

| Example | Name | Form | mp (° C.) | Anal. |
|---|---|---|---|---|
| 147 | 1-(4-Amino-2-ethoxymethyl-8-styryl-1H-imidazo[4,5-c]quinolin-1-yl)-2-methylpropan-2-ol | Pale yellow powder | 217-218 | Calcd for $C_{25}H_{28}N_4O_2$: C, 72.09; H, 6.78; N, 13.45. Found: C, 71.71; H, 6.97; N, 13.46. |
| 148 | 1-[4-Amino-2-ethoxymethyl-8-(pyridin-3-yl)-1H-imidazo[4,5-c]quinolin-1-yl]-2-methylpropan-2-ol | White crystals | 222-223 | Calcd for $C_{22}H_{25}N_5O_2$: C, 67.50; H, 6.44; N, 17.89. Found: C, 67.23; H, 6.55; N, 17.85. |
| 149 | N-{3-[4-Amino-2-ethoxymethyl-1-(2-hydroxy-2-methylpropyl)-1H-imidazo[4,5-c]quinolin-8-yl]phenyl}methanesulfamide | Off-white crystals | 221-222 | Calcd for $C_{24}H_{29}N_5O_4S \cdot 0.33H_2O$: C, 58.89; H, 6.11; N, 14.31. Found: C, 58.81; H, 5.80; N, 14.30. |
| 150 | 1-[4-Amino-2-ethoxymethyl-8-(5-hydroxymethylpyridin-3-yl)-1H-imidazo[4,5-c]quinolin-1-yl]-2-methylpropan-2-ol | White powder | 230-232 | Calcd for $C_{23}H_{27}N_5O_3$: C, 65.54; H, 6.46; N, 16.62. Found: C, 65.25; H, 6.24; N, 16.65. | vide tert-butyl [4-(7-bromo-3-nitroquinolin-4-ylamino) butyl]carbamate as a yellow solid.

Part B

A solution of sodium hydrosulfite (43.35 g, 249 mmol) and potassium carbonate (38.28 g, 277 mmol) in water (300 mL) was added to a mixture of tert-butyl [4-(7-bromo-3-nitroquinolin-4-ylamino)butyl]carbamate (24.3 g, 55.3 mmol) and 1,1'-diethyl-4,4'-bipyridinium dibromide (1.03 g, 2.76 mmol) in dichloromethane (368 mL) and water (40 mL), and the reaction was stirred overnight at ambient temperature. The reaction mixture was filtered through a layer of CELITE filter aid. The aqueous filtrate was extracted with dichloromethane, and the combined organic fractions were dried over magnesium sulfate, filtered, and concentrated under reduced pressure to provide 22.4 g of tert-butyl [4-(3-amino-7-bromoquinolin-4-ylamino)butyl]carbamate as a brown powder.

Part C tert-Butyl [4-(3-amino-7-bromoquinolin-4-ylamino)butyl]carbamate (24.3 g, 59.4 mmol) was treated with ethoxyacetyl chloride (7.28 g, 59.4 mmol) according to the method described in Part C of Examples 125-135.

Part D

A solution of the material from Part C and triethylamine (33.1 mL, 238 mmol) in ethanol (295 mL) was heated at reflux for two hours. The reaction was then allowed to cool to ambient temperature, and the solvent was removed under reduced pressure. The residue was dissolved in dichloromethane, and the resulting solution was washed sequentially with water and brine, dried over magnesium sulfate, filtered, and concentrated under reduced pressure. The crude product was purified by flash chromatography on silica gel (eluting sequentially with 90:10 and 85:15 chloroform:CMA) to provide 23.6 g of tert-butyl [4-(7-bromo-2-ethoxymethyl-1H-imidazo[4,5-c]quinolin-1-yl)butyl]carbamate as a tan solid.

Part E

Concentrated hydrochloric acid (15.6 mL, 0.194 mol) was added to a solution of tert-butyl [4-(7-bromo-2-ethoxymethyl-1H-imidazo[4,5-c]quinolin-1-yl)butyl]carbamate (23.2 g, 48 mmol) in ethanol, and the reaction was heated at reflux for 20 minutes. A precipitate formed, and the reaction was allowed to cool to ambient temperature overnight. The solid was isolated by filtration, washed with ethanol, and dissolved in water. The solution was washed with dichloromethane and then made basic with the addition of 50% aqueous sodium hydroxide. The basic solution was extracted with dichloromethane (3×300 mL), and the combined extracts were dried over magnesium sulfate, filtered, and concentrated under reduced pressure to provide 17 g of 4-(7-bromo-2-ethoxymethyl-1H-imidazo[4,5-c]quinolin-1-yl)butylamine as an off-white solid.

Part F

3-Chloropropanesulfonyl chloride (5.45 mL, 44.8 mmol) was added dropwise over a period of four minutes to a solution of 4-(7-bromo-2-ethoxymethyl-1H-imidazo[4,5-c]quinolin-1-yl)butylamine (16.9 g, 44.8 mmoL) and triethylamine (9.42 mL, 67.6 mmol) in dichloromethane (300 mL), and the reaction was stirred at ambient temperature for 30 minutes. The reaction was poured into water, and the organic layer was washed with brine and dried over magnesium sulfate, filtered, and concentrated under reduced pressure. The resulting solid was dissolved in N,N-dimethylformamide (DMF) (300 mL), and 1,8-diazabicyclo[5.4.0]undec-7-ene (DBU) (10.1 mL, 67.6 mmol) was added. The reaction was stirred overnight at ambient temperature under a nitrogen atmosphere. Additional DBU (5 mL) was added, and the reaction was stirred for an additional four hours. The solvent was removed under reduced pressure, and the residue was dissolved in dichloromethane. The resulting solution was washed with water (2×200 mL) and brine, dried over magnesium sulfate, filtered, and concentrated under reduced pressure to provide 7-bromo-1-[4-(1,1-dioxidoisothiazolidin-2-yl)-2-ethoxymethyl-1H-imidazo[4,5-c]quinoline as an oil.

Part G

7-Bromo-1-[4-(1,1-dioxidoisothiazolidin-2-yl)-2-ethoxymethyl-1H-imidazo[4,5-c]quinoline was oxidized and then aminated according to the methods described in Parts H and I of Example 1. The oxidation was carried out in chloroform, and several equivalents of 3-chloroperoxybenzoic acid were used. The product from amination was purified by column chromatography on silica gel (eluting with chloroform:CMA in a gradient from 98:2 to 85:15) followed by recrystallization from acetonitrile to provide 7-bromo-1-[4-(1,1-dioxidoisothiazolidin-2-yl)-2-ethoxymethyl-1H-imidazo[4,5-c]quinolin-4-amine as a white solid.

Part H

7-Bromo-1-[4-(1,1-dioxidoisothiazolidin-2-yl)-2-ethoxymethyl-1H-imidazo[4,5-c]quinolin-4-amine and the boronic acid or boronic acid ester from the table below were coupled according to the general procedure described in Part J of Example 1. The reaction was heated at reflux until an analysis by HPLC indicated the reaction was complete. The work-up procedure described in Part F of Examples 125-135 was followed, and the crude product was purified by column chromatography on silica gel (eluting with a gradient of chloroform:CMA) followed by recrystallization using the solvent indicated in the table below.

For Example 155, the reaction was heated at reflux for three hours. Following chromatographic purification, the residue was deprotected according to the method described in Example 144, purified by column chromatography, and recrystallized from acetonitrile.

For Example 156, the coupling was carried out using tri (ortho-tolyl)phosphine instead of triphenylphosphine.

Examples 152-156

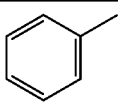

| Example | Boronic acid or ester | Recrystallization solvent | $R_3$ |
|---------|------------------------|----------------------------|-------|
| 152 | Phenylboronic acid | Acetonitrile | phenyl |

-continued

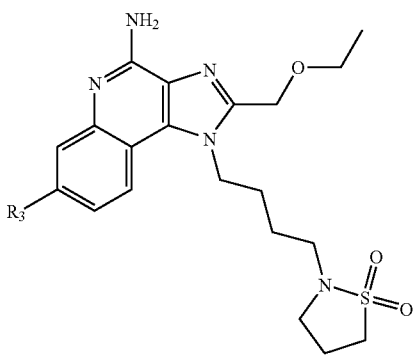

| Example | Boronic acid or ester | Recrystallization solvent | R₃ |
|---|---|---|---|
| 153 | Pyridine-3-boronic acid 1,3-propanediol cyclic ester | Isopropanol | pyridin-3-yl |
| 154 | Pyridine-4-boronic acid pinacol ester | Methanol then Isopropanol | pyridin-4-yl |
| 155 | 5-(tert-Butyl-dimethyl-silanyloxymethyl)pyridine-3-boronic acid | Acetonitrile | 5-(hydroxymethyl)pyridin-3-yl |
| 156 | 3-(Hydroxymethyl)phenyl-boronic acid | Acetonitrile (twice) | 3-(hydroxymethyl)phenyl |

Example 152

1-[4-(1,1-Dioxidoisothiazolidin-2-yl)butyl]-2-ethoxymethyl-7-phenyl-1H-imidazo[4,5-c]quinolin-4-amine The product was obtained as white crystals, mp 167-168.5° C.
$^{13}$C NMR (75 MHz, DMSO-$d_6$) δ 152.3, 148.9, 145.6, 140.1, 138.5, 132.8, 129.0, 127.4, 126.7, 126.4, 123.8, 121.0, 120.1, 113.8, 65.4, 64.1, 46.5, 46.1, 45.1, 43.8, 27.2, 24.3, 18.3, 14.9;
MS (APCI) m/z 494.2213 (494.2226 calcd for $C_{26}H_{31}N_5O_3S$, M+H);
Anal. Calcd for $C_{26}H_{31}N_5O_3S$: C, 63.26; H, 6.33; N, 14.19; S, 6.50. Found: C, 62.66; H, 6.34; N, 14.10; S, 6.45.

Example 153

1-[4-(1,1-Dioxidoisothiazolidin-2-yl)-butyl]-2-ethoxymethyl-7-(pyridin-3-yl)-1H-imidazo[4,5-c]quinolin-4-amine The product was obtained as white, flocculent crystals, mp 171-173° C.
Anal. Calcd for $C_{25}H_{30}N_6O_3S$: C, 60.71; H, 6.11; N, 16.99. Found: C, 60.56; H, 6.18; N, 16.92.

Example 154

1-[4-(1,1-Dioxidoisothiazolidin-2-yl)-butyl]-2-ethoxymethyl-7-(pyridin-4-yl)-1H-imidazo[4,5-c]quinolin-4-amine The product was obtained as a white, crystalline solid, mp 186-187.5° C.
Anal. Calcd for $C_{25}H_{30}N_6O_3S$: C, 60.71; H, 6.11; N, 16.99; S, 6.48. Found: C, 60.36; H, 6.38; N, 16.88; S, 6.42.

Example 155

(5-{4-Amino-1-[4-(1,1-dioxidoisothiazolidin-2-yl)butyl]-2-ethoxymethyl-1H-imidazo[4,5-c]quinolin-7-yl}pyridin-3-yl)methanol The product was obtained as a white, powdery solid, mp 184.5-186° C.
Anal. Calcd for $C_{26}H_{32}N_6O_4S$: C, 59.52; H, 6.15; N, 16.02; S, 6.11. Found: C, 59.53; H, 6.01; N, 16.06; S, 6.04.

Example 156

(5-{4-Amino-1-[4-(1,1-dioxidoisothiazolidin-2-yl)butyl]-2-ethoxymethyl-1H-imidazo[4,5-c]quinolin-7-yl}phenyl)methanol The product was obtained as a white powder, mp 158-161° C.
$^{13}$C NMR (75 MHz, DMSO-$d_6$) δ 152.3, 148.9, 145.4, 143.3, 139.9, 138.7, 132.9, 128.7, 126.3, 125.5, 125.0, 124.8, 123.6, 121.0, 120.1, 113.7, 65.4, 64.1, 62.9, 46.5, 46.1, 45.1, 43.8, 27.2, 24.3, 18.3, 14.9;
MS (APCI) m/z 524.2 (524.2 calcd for $C_{27}H_{33}N_5O_4S$, M+H);
Anal. Calcd for $C_{27}H_{33}N_5O_4S$·0.3$H_2O$: C, 61.93; H, 6.35; N, 13.37; S, 6.12. Found: C, 61.51; H, 6.78; N, 13.24; S, 6.12.

Example 157 tert-Butyl {4-[4-amino-2-ethoxymethyl-7-(pyridin-3-yl)-1H-imidazo[4,5-c]quinolin-1-yl]butyl}carbamate

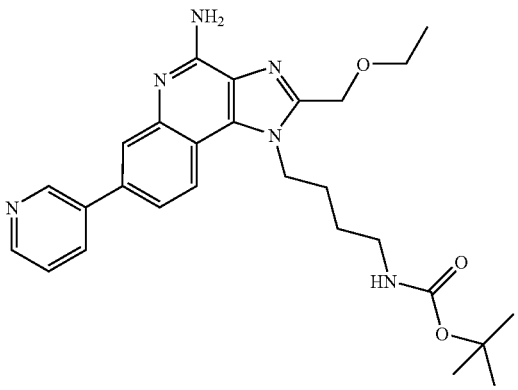

tert-Butyl [4-(7-bromo-2-ethoxymethyl-1H-imidazo[4,5-c]quinolin-1-yl)butyl]carbamate was oxidized and aminated according to the methods described in Parts H and I of Example 1 to afford tert-butyl [4-(4-amino-7-bromo-2-ethoxymethyl-1H-imidazo[4,5-c]quinolin-1-yl)butyl]carbamate, which was coupled with 3-pyridylboronic acid according to the method described in Part J of Example 1. The reaction was heated at reflux for four hours, and the work-up procedure described in Part F of Examples 125-135 was followed. The crude product was recrystallized from acetonitrile (1 mL/g) to provide tert-butyl {4-[4-amino-2-ethoxymethyl-7-(pyridin-3-yl)-1H-imidazo[4,5-c]quinolin-1-yl]butyl}carbamate as a white solid, mp 117-119° C.

Anal. Calcd for $C_{27}H_{34}N_6O_3$: C, 64.33; H, 7.10; N, 16.67. Found: C, 64.35; H, 7.42; N, 16.71.

Example 158 tert-Butyl {4-[4-amino-2-propyl-7-(pyridin-3-yl)-1H-imidazo[4,5-c]quinolin-1-yl]butyl}carbamate

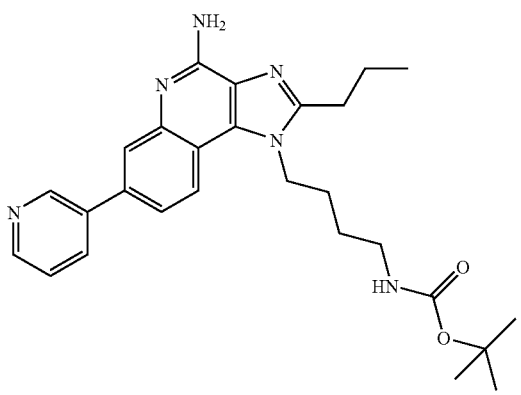

tert-Butyl [4-(3-amino-7-bromoquinolin-4-ylamino)butyl]carbamate was treated with butyryl chloride and cyclized according to the methods described in Part C and D of Examples 125-135. The resulting product, tert-butyl [4-(7-bromo-2-propyl-1H-imidazo[4,5-c]quinolin-1-yl)butyl]carbamate was oxidized and aminated according to the methods described in Parts H and I of Example 1 to afford tert-butyl [4-(4-amino-7-bromo-2-propyl-1H-imidazo[4,5-c]quinolin-1-yl)butyl]carbamate, which was coupled with 3-pyridylboronic acid according to the method described in Part J of Example 1. The reaction was heated at reflux for four hours, and the work-up procedure described in Part F of Examples 125-135 was followed. The crude product was recrystallized from toluene (1 mL/g) to provide tert-butyl {4-[4-amino-2-propyl-7-(pyridin-3-yl)-1H-imidazo[4,5-c]quinolin-1-yl]butyl}carbamate as a tan powder, mp 136-138° C.

Anal. Calcd for $C_{27}H_{34}N_6O_2$: C, 65.83; H, 7.37; N, 17.06. Found: C, 65.92; H, 7.61; N, 16.92.

Examples 159-161

Part A

7-Bromo-4-chloro-3-nitroquinoline (39.85 g, 138.6 mmol) was reacted with 2,2-dimethyl-1,3-dioxolane-4-methanamine (20.0 g, 152 mmol) according to the method described in Part A of Examples 125-135 to provide 48.35 g of (7-bromo-3-nitroquinolin-4-yl)-2,2-dimethyl-1,3-dioxolan-4-ylmethyl)amine as a yellow solid. The product was not recrystallized.

Part B

The methods described in Parts B, C, and D of Examples 152-156 were used to convert (7-bromo-3-nitroquinolin-4-yl)-2,2-dimethyl-1,3-dioxolan-4-ylmethyl)amine to 7-bromo-1-[(2,2-dimethyl-1,3-dioxolan-4-yl)methyl]-2-ethoxymethyl-1H-imidazo[4,5-c]quinoline, which was obtained as an off-white solid, mp 138-140° C. In Part B, 1,1'-di-n-octyl-4,4'-bipyridinium dibromide was used instead of 1,1'-diethyl-4,4'-bipyridinium dibromide. Triethylamine (1.1 equivalents) was added in Part C.

Anal. Calcd for $C_{19}H_{22}BrN_3O_3$: C, 54.30; H, 5.28; N, 10.00. Found: C, 54.07; H, 5.25; N, 9.90.

Part C

7-Bromo-1-[(2,2-dimethyl-1,3-dioxolan-4-yl)methyl]-2-ethoxymethyl-1H-imidazo[4,5-c]quinoline was oxidized and then aminated according to the methods described in Parts H and I of Example 1. The oxidation product was not recrystallized. The product from amination was purified by column chromatography on silica gel (eluting with chloroform:CMA in a gradient from 95:5 to 85:15) followed by recrystallization from acetonitrile to provide 7-bromo-1-[(2,2-dimethyl-1,3-dioxolan-4-yl)methyl]-2-ethoxymethyl-1H-imidazo[4,5-c]quinolin-4-amine as a white solid, mp 174-175° C.

Anal. Calcd for $C_{19}H_{23}BrN_4O_3$: C, 52.42; H, 5.33; N, 12.87. Found: C, 52.41; H, 5.25; N, 12.81.

Part D

7-Bromo-1-[(2,2-dimethyl-1,3-dioxolan-4-yl)methyl]-2-ethoxymethyl-1H-imidazo[4,5-c]quinolin-4-amine and the boronic acid or ester from the table below were coupled according to the method described in Examples 118-121. The work-up procedure described in Part F of Examples 125-135 was followed. For Examples 159 and 160, the crude product was purified by flash chromatography (eluting with a gradient of chloroform:CMA) followed by recrystallization from the solvent indicated in the table below. For Example 161, the crude product was dissolved in hot methanol, filtered, concentrated under reduced pressure, triturated with ethyl acetate, isolated by filtration, and then recrystallized from methanol.

Examples 159-161

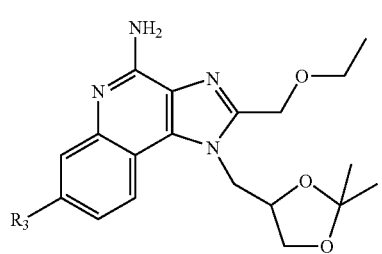

| Example | Boronic acid or ester | Recrystallization solvent | R³ |
|---|---|---|---|
| 159 | Pyridine-3-boronic acid 1,3-propanediol cyclic ester | Acetonitrile (twice) | 3-pyridyl |
| 160 | 4-(Hydroxymethyl)phenylboronic acid | Ethanol | 4-(hydroxymethyl)phenyl |
| 161 | Phenylboronic acid | Methanol | phenyl |

| Example | Name | Form | mp | Anal. |
|---|---|---|---|---|
| 159 | 1-[(2,2-Dimethyl-1,3-dioxolan-4-yl)methyl]-2-ethoxymethyl-7-(pyridin-3-yl)-1H-imidazo[4,5-c]quinolin-4-amine | White crystals | 181–182° C. | Calcd for $C_{24}H_{27}N_5O_3$: C, 65.65; H, 6.33; N, 15.95. Found: C, 65.77; H, 6.33; N, 15.96. |
| 160 | 1-[(2,2-Dimethyl-1,3-dioxolan-4-yl)methyl]-2-ethoxymethyl-7-(4-hydroxymethylphenyl)-1H-imidazo[4,5-c]quinolin-4-amine | Off-white crystals | 219–220° C. | Calcd for $C_{26}H_{30}N_4O_4$: C, 67.51; H, 6.54; N, 12.11. Found: C, 67.47; H, 6.21; N, 11.98. |
| 161 | 1-[(2,2-Dimethyl-1,3-dioxolan-4-yl)methyl]-2-ethoxymethyl-7-phenyl-1H-imidazo[4,5-c]quinolin-4-amine | Light yellow crystals | 168–170° C. | Calcd for $C_{25}H_{28}N_4O_3$: C, 69.42; H, 6.53; N, 12.95. Found: C, 69.37; H, 6.62; N, 13.04. |

Example 162

3-[4-Amino-2-ethoxymethyl-7-(pyridin-3-yl)-1H-imidazo[4,5-c]quinolin-1-yl]propane-1,2-diol

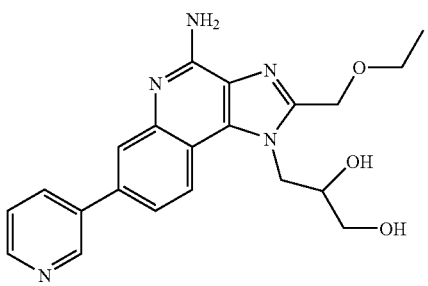

Hydrochloric acid (12 mL of 1 N) was added to a solution of 1-[(2,2-dimethyl-1,3-dioxolan-4-yl)methyl]-2-ethoxymethyl-7-(pyridin-3-yl)-1H-imidazo[4,5-c]quinolin-4-amine (0.75 g, 1.73 mmol) in THF, and the reaction was stirred overnight at ambient temperature. The THF was removed under reduced pressure, and 1% aqueous sodium hydroxide was added to the remaining solution to adjust to pH 9. A precipitate formed, was isolated by filtration, washed with water, and dried in an oven at 60° C. to provide 0.61 g of 3-[4-amino-2-ethoxymethyl-7-(pyridin-3-yl)-1H-imidazo[4,5-c]quinolin-1-yl]propane-1,2-diol as a white solid, mp 218-220° C.

Anal. Calcd for $C_{21}H_{23}N_5O_3$: C, 62.68; H, 6.01; N, 17.40. Found: C, 62.58; H, 5.99; N, 17.29.

Examples 163-175

Part A

7-Bromo-4-chloro-3-nitroquinoline (29.54 g, 102.7 mmol) was reacted with 3-methoxy propyl amine (10.07 g, 113.0 mmol) according to the method described in Part A of Examples 125-135 to provide 32.9 g of (7-bromo-3-nitroquinolin-4-yl)-(3-methoxypropyl)amine as a yellow solid. The product was not recrystallized.

Part B

The methods described in Parts B, C, and D of Examples 152-156 were used to convert (7-bromo-3-nitroquinolin-4-yl)-(3-methoxypropyl)amine to 7-bromo-2-ethoxymethyl-1-(3-methoxypropyl)-1H-imidazo[4,5-c]quinoline, which was obtained as a white solid. In Part B, 1,1'-di-n-octyl-4,4'-bipyridinium dibromide was used instead of 1,1'-diethyl-4,4'-bipyridinium dibromide. Triethylamine (1.1 equivalents) was added in Part C. The chromatographic purification in Part D was carried out using ethyl acetate:acetone as the eluent.

Part C

7-Bromo-2-ethoxymethyl-1-(3-methoxypropyl)-1H-imidazo[4,5-c]quinoline was oxidized and then aminated according to the methods described in Parts H and I of Example 1. The oxidation product was not recrystallized. The product from amination was purified as described in Part C of Examples 159-161 to provide 7-bromo-2-ethoxymethyl-1-(3-methoxypropyl)-1H-imidazo[4,5-c]quinolin-4-amine as off-white crystals.

Part D

7-Bromo-2-ethoxymethyl-1-(3-methoxypropyl)-1H-imidazo[4,5-c]quinolin-4-amine and the boronic acid or ester from the table below were coupled according to the method described in Examples 118-121 or in Part J of Example 1. For Example 159, the product was isolated as a solid and recrystallized from ethanol. For the remaining examples, the crude product was purified by flash chromatography (eluting with a gradient of chloroform:CMA) followed by recrystallization from the solvent indicated in the table below.

For Example 167, following chromatographic purification the product was deprotected according to the method described in Example 144. The crude deprotected product was recrystallized from isopropanol and then from acetonitrile to provide the product shown in the table below.

Examples 163-175

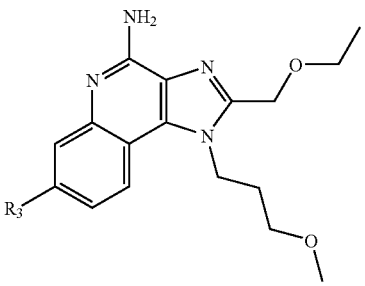

| Ex. | Boronic acid or ester | Recrystallization solvent | $R_3$ |
|---|---|---|---|
| 163 | Phenylboronic acid | Isopropanol then acetonitrile | (phenyl) |

-continued

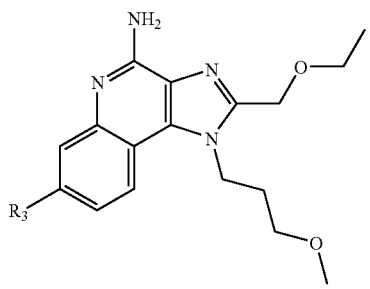

| Ex. | Boronic acid or ester | Recrystallization solvent | R₃ |
|---|---|---|---|
| 164 | Pyridine-3-boronic acid 1,3-propanediol cyclic ester | Acetonitrile (twice) | pyridin-3-yl |
| 165 | Pyridine-4-boronic acid pinacol ester | Ethanol (twice) | pyridin-4-yl |
| 166 | 4-(Hydroxymethyl)phenylboronic acid | Ethanol | 4-(hydroxymethyl)phenyl |
| 167 | 5-(tert-butyldimethyl-silanyloxymethyl)pyridine-3-boronic acid | Isopropanol then Acetonitrile | 5-(hydroxymethyl)pyridin-3-yl |
| 168 | Furan-2-boronic acid | Acetonitrile | furan-2-yl |
| 169 | 4-Chlorophenylboronic acid | Ethanol (twice) | 4-chlorophenyl |
| 170 | 4-(Morpholine-4-carbonyl)phenylboronic acid | Ethanol | 4-(morpholine-4-carbonyl)phenyl |
| 171 | 3-(iso-Butylaminocarbonyl)phenylboronic acid | Ethanol (twice) | 3-(iso-butylaminocarbonyl)phenyl |
| 172 | 4-(Ethylsulfonyl)phenylboronic acid | Ethanol | 4-(ethylsulfonyl)phenyl |

-continued

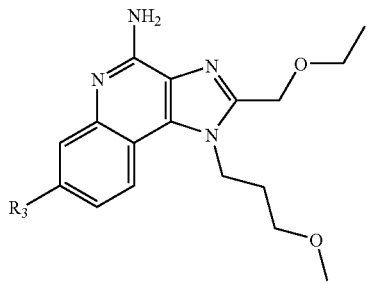

| Ex. | Boronic acid or ester | Recrystallization solvent | R₃ |
|---|---|---|---|
| 173 | 4-(iso-Propoxyphenyl)boronic acid | Acetonitrile | (4-isopropoxyphenyl) |
| 174 | 3-(Morpholine-4-carbonyl)phenylboronic acid | Acetonitrile | (3-(morpholine-4-carbonyl)phenyl) |
| 175 | 3-(Pyrrolidine-1-carbonyl)phenylboronic acid | Ethyl acetate | (3-(pyrrolidine-1-carbonyl)phenyl) |

Examples 163-175

| Example | Name | Form | Mp (° C.) | Anal. |
|---|---|---|---|---|
| 163 | 2-Ethoxymethyl-1-(3-methoxypropyl)-7-phenyl-1H-imidazo[4,5-c]quinolin-4-amine | White crystals | 146-147 | Calcd for $C_{23}H_{26}N_4O_2$: C, 70.75; H, 6.71; N, 14.35. Found: C, 70.73; H, 6.70; N, 14.34. |
| 164 | 2-Ethoxymethyl-1-(3-methoxypropyl)-7-(pyridin-3-yl)-1H-imidazo[4,5-c]quinolin-4-amine | White crystals | 151-152 | Calcd for $C_{22}H_{25}N_5O_2$: C, 67.50; H, 6.44; N, 17.89. Found: C, 67.21; H, 6.46; N, 17.97. |
| 165 | 2-Ethoxymethyl-1-(3-methoxypropyl)-7-(pyridin-4-yl)-1H-imidazo[4,5-c]quinolin-4-amine | White, crystalline solid | 225-226 | Calcd for $C_{22}H_{25}N_5O_2$: C, 67.50; H, 6.44; N, 17.89. Found: C, 67.29; H, 6.37; N, 17.64. |
| 166 | 2-Ethoxymethyl-1-(3-methoxypropyl)-7-(4-hydroxymethylphenyl)-1H-imidazo[4,5-c]quinolin-4-amine | White, crystalline solid | 228-229 | Calcd for $C_{24}H_{28}N_4O_3$: C, 68.55; H, 6.71; N, 13.32. Found: C, 68.36; H, 6.86; N, 13.06. |
| 167 | 2-Ethoxymethyl-1-(3-methoxypropyl)-7-(5-hydroxymethylpyridin-3-yl)-1H-imidazo[4,5-c]quinolin-4-amine | White solid | 198-199 | Calcd for $C_{23}H_{27}N_5O_3$: C, 65.54; H, 6.46; N, 16.62. Found: C, 65.41; H, 6.40; N, 16.63. |
| 168 | 2-Ethoxymethyl-7-(furan-2-yl)-1-(3-methoxypropyl)-1H-imidazo[4,5-c]quinolin-4-amine | Off-white solid | 144-145 | Calcd for $C_{21}H_{24}N_4O_3$: C, 66.30; H, 6.36; N, 14.73. Found: C, 65.96; H, 6.16; N, 14.56. |
| 169 | 7-(4-Chlorophenyl)-2-ethoxymethyl-1-(3-methoxypropyl)-1H-imidazo[4,5-c]quinolin-4-amine | White solid | 188-190 | Calcd for $C_{23}H_{25}ClN_4O_2$: C, 65.01; H, 5.93; N, 13.18. Found: C, 64.72; H, 5.93; N, 13.04. |
| 170 | {4-[4-Amino-2-ethoxymethyl-1-(3-methoxypropyl)-1H-imidazo[4,5-c]quinolin-7-yl]phenyl}morpholin-4-ylmethanone | White solid | 163-165 | Calcd for $C_{28}H_{33}N_5O_4$: C, 66.78; H, 6.61; N, 13.91. Found: C, 66.52; H, 6.59; N, 13.71. |
| 171 | 3-[4-Amino-2-ethoxymethyl-1-(3-methoxypropyl)-1H-imidazo[4,5-c]quinolin-7-yl]-N-(2-methylpropyl)benzamide | Off-white solid | 209-210 | Calcd for $C_{28}H_{35}N_5O_3$: C, 68.69; H, 7.21; N, 14.30. Found: C, 68.52; H, 7.44; N, 14.23. |

-continued

| Example | Name | Form | Mp (° C.) | Anal. |
|---|---|---|---|---|
| 172 | 7-[(4-Ethanesulfonyl)phenyl]-2-ethoxymethyl-1-(3-methoxypropyl)-1H-imidazo[4,5-c]quinolin-4-amine | White solid | 156-158 | Calcd for $C_{25}H_{30}N_4O_4S$: C, 62.22; H, 6.27; N, 11.61. Found: C, 61.99; H, 5.98; N, 11.47. |
| 173 | 2-Ethoxymethyl-7-[4-(2-propoxy)phenyl]-1-(3-methoxypropyl)-1H-imidazo[4,5-c]quinolin-4-amine | Off-white crystals | 175-177 | Calcd for $C_{26}H_{32}N_4O_3$: C, 69.62; H, 7.19; N, 12.49. Found: C, 69.70; H, 7.45; N, 12.60. |
| 174 | {3-[4-Amino-2-ethoxymethyl-1-(3-methoxypropyl)-1H-imidazo[4,5-c]quinolin-7-yl]phenyl}morpholin-4-ylmethanone | Off-white crystals | 174-176 | Calcd for $C_{28}H_{33}N_5O_4$: C, 66.78; H, 6.61; N, 13.91. Found: C, 66.55; H, 6.53; N, 13.97. |
| 175 | {3-[4-Amino-2-ethoxymethyl-1-(3-methoxypropyl)-1H-imidazo[4,5-c]quinolin-7-yl]phenyl}pyrrolidin-1-ylmethanone | White solid | 145-146 | Calcd for $C_{28}H_{33}N_5O_3$•0.85HCl: C, 64.85; H, 5.81; N, 6.58. Found: C, 64.90; H, 5.74; N, 6.61. |

Example 176 tert-Butyl 4-{[4-amino-2-ethoxymethyl-7-(pyridin-3-yl)-1H-imidazo[4,5-c]quinolin-1-yl]methyl}piperidine-1-carboxylate

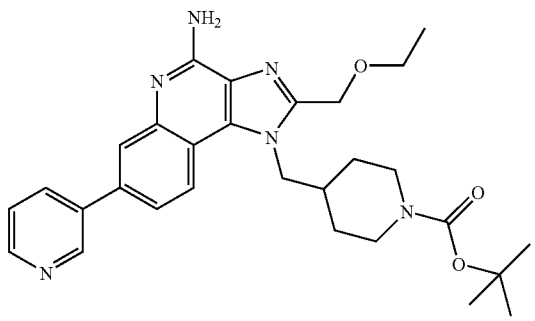

Part A

7-Bromo-4-chloro-3-nitroquinoline was treated according to the methods described in Parts A through D of Examples 152-156 using 1-(tert-butoxycarbonyl)-4-(aminomethyl)piperidine (Carceller, E. et al, *J. Med. Chem.*, 39, 487-493 (1996)) in Part A. In Part B, 1,1'-di-n-octyl-4,4'-bipyridinium dibromide was used instead of 1,1'-diethyl-4,4'-bipyridinium dibromide. Triethylamine (1.1 equivalents) was added to the reaction in Part C. Following chromatographic purification in Part D (eluting with 95:5 chloroform:CMA), tert-butyl 4-[(7-bromo-2-ethoxymethyl-1H-imidazo[4,5-c]quinolin-1-yl)methyl]piperidine-1-carboxylate was obtained as an off-white solid. A small portion of the product was recrystallized from acetonitrile to provide a white solid, mp 169-170° C.

Anal. Calcd for $C_{24}H_{31}BrN_4O_3$: C, 57.26; H, 6.21; N, 11.13. Found: C, 57.31; H, 6.29; N, 11.07.

Part B tert-Butyl 4-[(7-bromo-2-ethoxymethyl-1H-imidazo[4,5-c]quinolin-1-yl)methyl]piperidine-1-carboxylate was oxidized and then aminated according to the methods described in Parts H and I of Example 1. The oxidation product was not recrystallized. The product from amination was purified as described in Part C of Examples 159-161 to provide tert-butyl 4-[(4-amino-7-bromo-2-ethoxymethyl-1H-imidazo[4,5-c]quinolin-1-yl)methyl]piperidine-1-carboxylate as a tan solid.

Part C tert-Butyl 4-[(4-amino-7-bromo-2-ethoxymethyl-1H-imidazo[4,5-c]quinolin-1-yl)methyl]piperidine-1-carboxylate (12.79 g, 24.67 mmol) and pyrdine-3-boronic acid 1,3-propanediol cyclic ester (4.42 g, 27.14 mmol) were coupled according to the method described in Examples 118-121. The work-up procedure described in Part F of Examples 125-135 was followed. The crude product was recrystallized twice from ethyl acetate to provide 10.89 g of tert-butyl 4-{[4-amino-2-ethoxymethyl-7-(pyridin-3-yl)-1H-imidazo[4,5-c]quinolin-1-yl]methyl}piperidine-1-carboxylate as an off-white solid, mp 197-198° C.

Anal. Calcd for $C_{29}H_{36}N_6O_3$.0.5$H_2O$: C, 66.26; H, 7.10; N, 15.99. Found: C, 66.47; H, 7.47; N, 16.00.

Example 177

2-Ethoxymethyl-1-(piperidin-4-ylmethyl)-7-(pyridin-3-yl)-1H-imidazo[4,5-c]quinolin-4-amine trihydrochloride

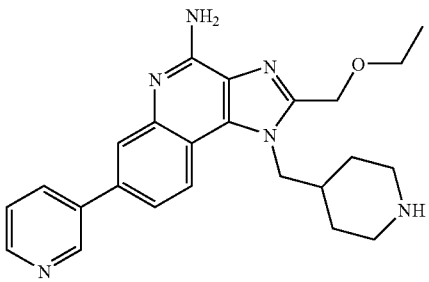

Ethanolic hydrochloric acid (17.68 mL of 4.25 M) was added to a solution of tert-butyl 4-{[4-amino-2-ethoxymethyl-7-(pyridin-3-yl)-1H-imidazo[4,5-c]quinolin-1-yl]methyl}piperidine-1-carboxylate (9.71 g, 18.8 mmol) in anhydrous ethanol, and the reaction was heated at reflux for two hours. A precipitate formed, and the reaction was allowed to cool to ambient temperature. The solid was isolated by filtration, washed with a small volume of cold ethanol, and dried under reduced pressure to provide 7.1 g of 2-ethoxymethyl-1-(piperidin-4-ylmethyl)-7-(pyridin-3-yl)-1H-imidazo[4,5-c]quinolin-4-amine trihydrochloride as an off-white solid, mp>250° C.

Anal. Calcd for $C_{24}H_{28}N_6O\cdot3HCl\cdot1.17H_2O$: C, 52.70; H, 6.14; N, 15.36. Found: C, 53.11; H, 6.48; N, 15.07.

Examples 178-181

A 0.02-0.03 M solution of 2-ethoxymethyl-1-(piperidin-4-ylmethyl)-7-(pyridin-3-yl)-1H-imidazo[4,5-c]quinolin-4-amine trihydrochloride (1 equivalent) and triethylamine (5 equivalents) in the solvent indicated in the table below was cooled to 4° C. The reagent from the table below (1 equivalent) was added dropwise, and the reaction was allowed to warm to ambient temperature and stirred for between two and 24 hours. The reaction mixture was diluted with chloroform, and the resulting solution was washed sequentially with water, 4% aqueous sodium carbonate (2×), water, and brine and then concentrated under reduced pressure. For Examples 178, 179, and 181, the residue was purified by flash column chromatography on silica gel (eluting with chloroform: CMA) followed by recrystallization from the solvent indicated in the table below. For Example 180, the crude product was recystallized from ethyl acetate. The structures of the products are shown in the table.

Examples 178-181

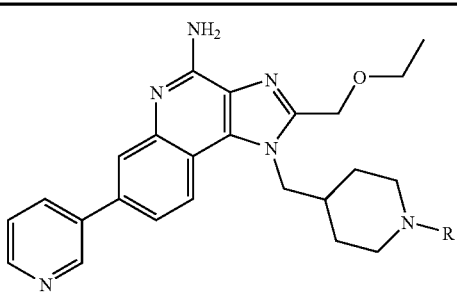

| Example | Reagent | Reaction solvent | Recrystallization solvent | R |
|---|---|---|---|---|
| 178 | Methanesulfonyl chloride | Chloroform | Acetonitrile then ethyl acetate | ![S(=O)(=O)CH3] |
| 179 | Isobutyryl chloride | 1-Methyl-2-pyrrolidinone | Ethyl Acetate | ![C(=O)CH(CH3)2] |
| 180 | 4-Morpholine-carbonyl chloride | Chloroform | Ethyl acetate | ![C(=O)-morpholine] |
| 181 | Palmitoyl chloride | Chloroform | Chloroform:hexanes | ![C(=O)C15H31] |

Examples 178-181

| Example | Name | Form | Mp (° C.) | Anal. |
|---|---|---|---|---|
| 178 | 2-Ethoxymethyl-1-{[1-(methanesulfonyl)piperidin-4-yl]methyl}-7-(pyridin-3-yl)-1H-imidazo[4,5-c]quinolin-4-amine | Off-white powder | 254-255 | Calcd for $C_{25}H_{30}N_6O_3S\cdot0.4HCl$: C, 58.97; H, 6.02; N, 16.50; Cl, 2.78. Found: C, 58.94; H, 5.78; N, 16.34; Cl, 3.06. |
| 179 | 2-Ethoxymethyl-1-[(1-isobutyrylpiperidin-4-yl)methyl]-7-(pyridin-3-yl)- | Beige powder | 130-132 | Calcd for $C_{28}H_{34}N_6O_2\cdot0.375H_2O$: C, 68.16; H, 7.10; N, 17.03. Found: C, |

| Example | Name | Form | Mp (° C.) | Anal. |
|---|---|---|---|---|
| | 1H-imidazo[4,5-c]quinolin-4-amine | | | 67.84; H, 7.14; N, 16.82. |
| 180 | 2-Ethoxymethyl-1-{[1-(morpholin-4-ylcarbonyl)piperidin-4-yl]methyl}-7-(pyridin-3-yl)-1H-imidazo[4,5-c]quinolin-4-amine | Tan solid | 224-225 | Calcd for $C_{29}H_{35}N_7O_3 \cdot 0.125H_2O$: C, 65.49; H, 6.68; N, 18.43. Found: C, 65.12; H, 6.40; N, 18.19. |
| 181 | 2-Ethoxymethyl-1-[(1-palmitoylpiperidin-4-yl)methyl]-7-(pyridin-3-yl)-1H-imidazo[4,5-c]quinolin-4-amine | Off-white crystalline solid | 72-75 | Calcd for $C_{40}H_{58}N_6O_2 \cdot 0.1H_2O$: C, 73.15; H, 8.93; N, 12.80. Found: C, 72.83; H, 8.84; N, 12.75 |

Example 182

2-Ethoxymethyl-7-(pyridin-3-yl)-1-{[1-(tetrahydrofuran-2-ylcarbonyl)piperidin-4-yl]methyl}-1H-imidazo[4,5-c]quinolin-4-amine

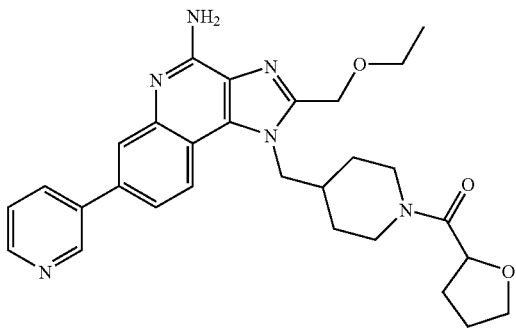

A solution of 2-ethoxymethyl-1-(piperidin-4-ylmethyl)-7-(pyridin-3-yl)-1H-imidazo[4,5-c]quinolin-4-amine trihydrochloride (1.0 g, 1.90 mmol) and triethylamine (1.35 mL, 9.50 mmol) in chloroform (80 mL) was cooled to 4° C. 2-Tetrahydrofuroic acid (0.243 g, 2.09 mmol) and 1-(3-dimethoxyaminopropyl)-3-ethylcarbodiimide hydrochloride (0.401 g, 2.09 mmol) were sequentially added, and the reaction was stirred for two hours. The reaction was incomplete as determined by thin layer chromatography (TLC) analysis. The reaction was cooled to 4° C., and 1-hydroxybenzotriazole (0.283 g, 2.09 mmol) was added. The reaction was allowed to warm to ambient temperature, stirred for 16 hours, and then diluted with chloroform (100 mL). The resulting solution was washed sequentially with water (100 mL), 4% aqueous sodium carbonate (2×100 mL), water (200 mL), and brine (150 mL); dried over sodium sulfate; filtered; and concentrated under reduced pressure. The residue was purified by HPFC followed by recrystallization from ethyl acetate to provide 0.68 g of 2-ethoxymethyl-7-(pyridin-3-yl)-1-{[1-(tetrahydrofuran-2-ylcarbonyl)piperidin-4-yl]methyl}-1H-imidazo[4,5-c]quinolin-4-amine as a white, crystalline solid, mp 191-192° C.

Anal. Calcd for $C_{29}H_{34}N_6O_3 \cdot 0.3H_2O$: C, 66.98; H, 6.71; N, 16.16. Found: C, 66.87; H, 6.70; N, 15.77.

Example 183-186

Part A

7-Bromo-4-chloro-3-nitroquinoline (35.26 g, 123.8 mmol) was treated with 1-(3-aminopropyl)pyrrolidin-2-one (19.1 mL, 136.2 mmol) according to the method described in Part E of Example 1 to provide 40.87 g of 1-[3-(7-bromo-3-nitroquinolin-4-ylamino)propyl]pyrrolidin-2-one as a yellow solid.

Part B

1-[3-(7-Bromo3-nitroquinolin-4-ylamino)propyl]pyrrolidin-2-one was treated according to the methods described in Parts B, C, and D of Examples 152-156. 3-Methoxypropionyl chloride was used in Part C, and triethylamine (1.3 equivalents) was added to the reaction mixture. The crude product obtained in Part D was purified by flash chromatography on silica gel (eluting sequentially with 100:0 and 92.5:7.5 chloroform:methanol) followed by recrystallization from acetonitrile. The crystals were washed with acetonitrile and diethyl ether and dried in a vacuum oven at 60° C. to provide 1-{3-[7-bromo-2-(2-methoxyethyl)-1H-imidazo[4,5-c]quinolin-1-yl]propyl}pyrrolidin-2-one as a light grey solid.

Part C

1-{3-[7-Bromo-2-(2-methoxyethyl)-1H-imidazo[4,5-c]quinolin-1-yl]propyl}pyrrolidin-2-one was oxidized and then aminated according to the methods described in Parts H and I of Example 1. The product from amination was recrystallized from isopropanol and then from ethanol. The crystals were washed with cold ethanol and diethyl ether and dried overnight in a vacuum oven at 60° C. to provide 1-{3-[4-amino-7-bromo-2-(2-methoxyethyl)-1H-imidazo[4,5-c]quinolin-1-yl]propyl}pyrrolidin-2-one as a white solid, mp 228-231° C.

Anal. Calcd for $C_{20}H_{24}N_5O_2Br$: C, 53.82; H, 5.42; N, 15.69. Found: C, 53.48; H, 5.37; N, 15.45.

Part D

1-{3-[4-Amino-7-bromo-2-(2-methoxyethyl)-1H-imidazo[4,5-c]quinolin-1-yl]propyl}pyrrolidin-2-one and the boronic acid or ester from the table below were coupled according to the method described in Examples 118-121. The work-up procedure described in Part F of Examples 125-135 was followed. The crude product was purified by HPFC (eluting with chloroform:CMA in a gradient from 100:00 to 70:30) followed by recrystallization from the solvent listed in the table below to provide the product shown in the table.

Examples 183-186

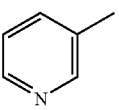

| Example | Boronic acid or ester | Recrystallization solvent | R₃ |
|---|---|---|---|
| 183 | 3-Pyridine boronic acid | Ethanol | 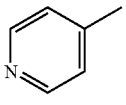 |
| 184 | Pyridine-4-boronic acid pinacol ester | Acetonitrile | 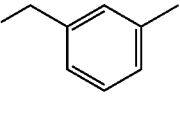 |
| 185 | 3-(Hydroxymethyl)phenylboronic acid | Ethanol | 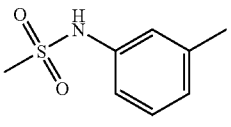 |
| 186 | [3-(Methylsulfonyl)amino-phenyl]boronic acid | Not used |  |

Examples 183-186

Examples 187-190

Part A

6-Bromo-4-chloro-3-nitroquinoline (50.62 g, 177.8 mmol), prepared from 4-bromoaniline according to the methods described in Parts A-D of Example 1, was treated with 1-(3-aminopropyl)pyrrolidin-2-one (27.5 mL, 196 mmol) according to the method described in Part E of Example 1 to provide 61.41 g of 1-[3-(6-bromo-3-nitroquinolin-4-ylamino)propyl]pyrrolidin-2-one as a solid.

Part B

1-[3-(6-Bromo3-nitroquinolin-4-ylamino)propyl]pyrrolidin-2-one was treated according to the methods described in Parts B, C, and D of Examples 152-156. 3-Methoxypropionyl chloride was used in Part C. The crude product obtained in Part D was recrystallized from acetonitrile. The crystals were washed with cold acetonitrile and diethyl ether and dried in a vacuum oven at 60° C. to provide 1-{3-[8-bromo-2-(2-methoxyethyl)-1H-imidazo[4,5-c]quinolin-1-yl]propyl}pyrrolidin-2-one as a light grey solid.

Part C

1-{3-[8-Bromo-2-(2-methoxyethyl)-1H-imidazo[4,5-c]quinolin-1-yl]propyl}pyrrolidin-2-one was oxidized and then aminated according to the methods described in Parts H and I of Example 1. The product from amination was recrystallized twice from isopropanol. The crystals were washed with cold isopropanol and dried in a vacuum oven at 60° C. to provide 1-{3-[4-amino-8-bromo-2-(2-methoxyethyl)-1H-imidazo[4,5-c]quinolin-1-yl]propyl}pyrrolidin-2-one as a white solid, mp 185-188° C.

Anal. Calcd for $C_{20}H_{24}N_5O_2Br$: C, 53.82; H, 5.42; N, 15.69. Found: C, 53.67; H, 5.28; N, 15.45.

Part D

1-{3-[4-Amino-8-bromo-2-(2-methoxyethyl)-1H-imidazo[4,5-c]quinolin-1-yl]propyl}pyrrolidin-2-one and the boronic acid or ester from the table below were coupled according to the method described in Examples 118-121. The reaction was heated at reflux overnight. The work-up procedure described in Part F of Examples 125-135 was followed.

| Example | Name | Form | Mp (° C.) | Anal. |
|---|---|---|---|---|
| 183 | 1-{3-[4-Amino-2-(2-methoxyethyl)-7-(pyridin-3-yl)-1H-imidazo[4,5-c]quinolin-1-yl]propyl}pyrrolidin-2-one | White solid | 218-221 | Calcd for $C_{25}H_{28}N_6O_2$: C, 67.55; H, 6.35; N, 18.91. Found: C, 67.30; H, 6.37; N, 18.79. |
| 184 | 1-{3-[4-Amino-2-(2-methoxyethyl)-7-(pyridin-4-yl)-1H-imidazo[4,5-c]quinolin-1-yl]propyl}pyrrolidin-2-one | Off-white solid | 232-235 | Calcd for $C_{25}H_{28}N_6O_2$: C, 67.55; H, 6.35; N, 18.91. Found: C, 67.18; H, 6.49; N, 18.77. |
| 185 | 1-{3-[4-Amino-7-(3-hydroxymethylphenyl)-2-(2-methoxyethyl)-1H-imidazo[4,5-c]quinolin-1-yl]propyl}pyrrolidin-2-one | Off-white needles | 184-187 | Calcd for $C_{27}H_{31}N_5O_3 \cdot 1.2H_2O$: C, 65.49; H, 6.80; N, 14.14. Found: C, 65.46; H, 6.82; N, 14.14. |
| 186 | N-(3-{4-Amino-2-(2-methoxyethyl)-1-[3-(2-oxopyrrolidin-1-yl)propyl]-1H-imidazo[4,5-c]quinolin-7-yl}phenyl)methanesulfonamide | White powder | 210-213 | Calcd for $C_{27}H_{32}N_6O_4S$: C, 60.43; H, 6.01; N, 15.66. Found: C, 60.17; H, 6.15; N, 15.66. |

For Examples 1-3, the crude product was recrystallized from the solvent indicated in the table below. For Example 4, the crude product was purified by HPFC™ (eluting with chloroform:CMA in a gradient from 100:00 to 75:25) followed by recrystallization from the solvents listed in the table below to provide the product shown in the table.

Examples 187-190

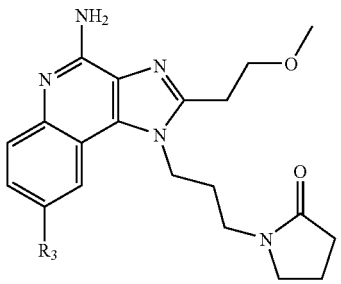

| Example | Boronic acid or ester | Recrystallization solvent | R₃ |
|---|---|---|---|
| 187 | Phenylboronic acid | Isopropanol | (phenyl) |
| 188 | 3-Pyridine boronic acid | Ethanol (twice) | (pyridin-3-yl) |
| 189 | 3-Acetylphenyl boronic acid | Acetonitrile | (3-acetylphenyl) |
| 190 | Thianaphthene-3-boronic acid | Propyl acetate then toluene | (benzo[b]thiophen-3-yl) |

Examples 187-190

| Example | Name | Form | Mp (° C.) | Anal. |
|---|---|---|---|---|
| 187 | 1-{3-[4-Amino-2-(2-methoxyethyl)-8-phenyl-1H-imidazo[4,5-c]quinolin-1-yl]propyl}pyrrolidin-2-one | Off-white solid | 207-210 | Calcd for $C_{26}H_{29}N_5O_2 \cdot 0.2H_2O$: C, 69.85; H, 6.63; N, 15.67. Found: C, 69.51; H, 7.00; N, 15.42. |
| 188 | 1-{3-[4-Amino-2-(2-methoxyethyl)-8-(pyridin-3-yl)-1H-imidazo[4,5-c]quinolin-1-yl]propyl}pyrrolidin-2-one | Yellow solid | 221-224 | Calcd for $C_{25}H_{28}N_6O_2$: C, 67.55; H, 6.35; N, 18.91. Found: C, 67.30; H, 5.99; N, 18.91. |
| 189 | 1-{3-[8-(3-Acetylphenyl)-4-amino-2-(2-methoxyethyl)-1H-imidazo[4,5-c]quinolin-1-yl]propyl}pyrrolidin-2-one | Yellow solid | 164-167 | Calcd for $C_{28}H_{31}N_5O_3 \cdot 0.3H_2O$: C, 68.50; H, 6.49; N, 14.27. Found: C, 68.16; H, 6.43; N, 14.37. |
| 190 | 1-{3-[4-amino-8-(benzo[b]thiophen-3-yl)-2-(2-methoxyethyl)-1H-imidazo[4,5-c]quinolin-1-yl]propyl}pyrrolidin-2-one | White solid | 202-205 | Calcd for $C_{28}H_{29}N_5O_2S$: C, 67.31; H, 5.85; N, 14.02. Found: C, 67.07; H, 5.66; N, 13.88. |

Example 191 tert-Butyl 4-[(4-amino-2-ethoxymethyl-7-phenyl-1H-imidazo[4,5-c]quinolin-1-yl)methyl]piperidine-1-carboxylate

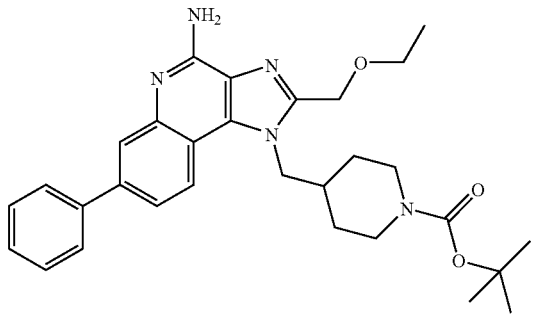

Part A

4-Chloro-3-nitro-7-phenylquinoline (8.35 g, 29.3 mmol) was treated with 1-(tert-butoxycarbonyl)-4-(aminomethyl)piperidine (7.54 g, 35.2 mmol) according to the method described in Part A of Examples 152-156. The crude solid was triturated with water, isolated by filtration, sonicated with diethyl ether, isolated by filtration, and dried for four hours in a vacuum oven at 40° C. to provide 12.78 g of tert-butyl 4-[(3-nitro-7-phenylquinolin-4-ylamino)methyl]piperidine-1-carboxylate as a yellow solid, mp 153-154° C.

Part B tert-Butyl 4-[(3-nitro-7-phenylquinolin-4-ylamino)methyl]piperidine-1-carboxylate was treated according to the methods described in Parts B-D of Example 152-156. In Part B, 1,1'-di-n-octyl-4,4'-bipyridinium dibromide was used instead of 1,1'-diethyl-4,4'-bipyridinium dibromide. Triethylamine (1.1 equivalents) was added to the reaction in Part C. The crude product from Part D was purified by flash column chromatography on silica gel (eluting with 95:5 chloroform:CMA) followed by recrystallization from dichloromethane:diethyl ether to provide tert-butyl 4-[(2-ethoxymethyl-7-phenyl-1H-imidazo[4,5-c]quinolin-1-yl)methyl]piperidine-1-carboxylate as a white powder, mp 166-167° C.

Anal. Calcd for $C_{30}H_{36}N_4O_3$: C, 71.97; H, 7.25; N, 11.19. Found: C, 71.86; H, 7.20; N, 11.11.

Part C tert-Butyl 4-[(2-ethoxymethyl-7-phenyl-1H-imidazo[4,5-c]quinolin-1-yl)methyl]piperidine-1-carboxylate was oxidized and then aminated according to the methods described in Parts H and I of Example 1. The oxidation product was not recrystallized. The product from amination was purified by column chromatography on silica gel (eluting with 90:10 chloroform:CMA) followed by recrystallization from ethyl acetate to provide tert-butyl 4-[(4-amino-2-ethoxymethyl-7-phenyl-1H-imidazo[4,5-c]quinolin-1-yl)methyl]piperidine-1-carboxylate as a white powder, mp 194-195° C.

Anal. Calcd for $C_{30}H_{37}N_5O_3$: C, 69.88; H, 7.23; N, 13.58. Found: C, 69.85; H, 7.16; N, 13.43.

Example 192

2-Ethoxymethyl-7-phenyl-1-(piperidin-4-ylmethyl)-1H-imidazo[4,5-c]quinolin-4-amine

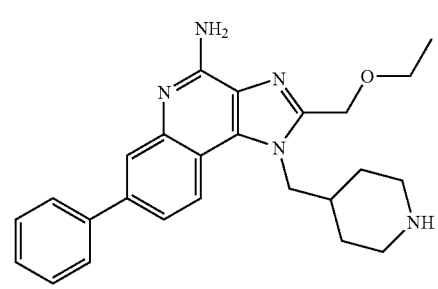

tert-Butyl 4-[(4-amino-2-ethoxymethyl-7-phenyl-1H-imidazo[4,5-c]quinolin-1-yl)methyl]piperidine-1-carboxylate (0.64 g) was deprotected according to the method described in Example 177. The crude solid was dissolved in water (10 mL), and ammonium hydroxide was added until the solution was basic. The mixture was then extracted with chloroform (2×10 mL), and the combined extracts were dried over magnesium sulfate, filtered, and concentrated under reduced pressure. The residue was recrystallized from acetonitrile and dried for 16 hours in a vacuum oven at 60° C. to provide 0.28 g of 2-ethoxymethyl-7-phenyl-1-(piperidin-4-ylmethyl)-1H-imidazo[4,5-c]quinolin-4-amine as a white, crystalline solid, mp 142-143° C.

Anal. Calcd for $C_{25}H_{29}N_5O \cdot 0.5H_2O$: C, 70.73; H, 7.12; N, 16.50. Found: C, 70.58; H, 7.24; N, 16.61.

Examples 193-195

2-Ethoxymethyl-7-phenyl-1-(piperidin-4-ylmethyl)-1H-imidazo[4,5-c]quinolin-4-amine dihydrochloride was prepared according to the method described in Example 177. A solution of 2-ethoxymethyl-7-phenyl-1-(piperidin-4-ylmethyl)-1H-imidazo[4,5-c]quinolin-4-amine dihydrochloride (1.0 g, 2.05 mmol) and triethylamine (1.14 mL, 8.20 mmol) in dichloromethane (35 mL) was cooled to 4° C. The reagent from the table below (2.05 mmol) was added dropwise, and the reaction was allowed to warm to ambient temperature and stirred for between one and three hours. The reaction mixture was diluted with chloroform, and the resulting solution was washed sequentially with water, 4% aqueous sodium carbonate (2×), water, and brine and then concentrated under reduced pressure. The crude product was recrystallized from the solvent listed in the table below to provide the compound shown in the table.

Example 193-195

Examples 193-195

| Example | Reagent | Recrystallization solvent | R |
|---|---|---|---|
| 193 | Methanesulfonyl chloride | Ethyl acetate | S(=O)(=O)CH₃ |
| 194 | Isobutyryl chloride | Ethyl acetate then acetonitrile | C(=O)CH(CH₃)CH₃ |
| 195 | 4-Morpholine-carbonyl chloride | Ethyl acetate | C(=O)-morpholine |

Examples 196-198

Part A

4-Chloro-3-nitro-7-phenylquinoline (6.0 g, 21 mmol) was treated with 2-phenoxyethylamine (3.18 g, 23.2 mmol) according to the method described in Part A of Examples 125-135. The crude solid was triturated with water (100 mL), isolated by filtration, sonicated with diethyl ether, isolated by filtration, and dried for two hours in a vacuum oven at 40° C. to provide 8.12 g of (3-nitro-7-phenylquinolin-4-yl)-(2-phenoxyethyl)amine as a yellow solid.

Part B

A solution of (3-nitro-7-phenylquinolin-4-yl)-(2-phenoxyethyl)amine (7.25 g, 18.8 mmol) in methanol (150 mL) was added to a Parr vessel charged with 5% platinum on carbon (0.84 g), and the reaction was placed under hydrogen pressure (50 psi, $3.4 \times 10^5$ Pa) for three hours. The reaction mixture was filtered through a layer of CELITE filter aid, and the filtrate was concentrated under reduced pressure, dissolved in toluene (2×25 mL), and concentrated under reduced pressure to provide $N^4$-(2-phenoxyethyl)-7-phenylquinoline-3,4-diamine as a yellow semi-solid.

Part C

A modification of the method described in Part C of Examples 125-135 was followed. A 0.2 M solution of the material from Part B and triethylamine (1 equivalent) in dichloromethane was treated with the acid chloride (1 equivalent) indicated in the table below.

Part D

The material from Part C was cyclized according to the method described in Part D of Examples 152-156. The crude product was purified by flash chromatography on silica gel (eluting with 95:5 chloroform:CMA) followed by recrystallization from ethyl acetate or ethyl acetate:diethyl ether to provide the following products.

Example 196

2-Cyclopropylmethyl-1-(2-phenoxyethyl)-7-phenyl-1H-imidazo[4,5-c]quinoline was obtained as a white powder, mp

| Example | Name | Form | Mp (° C.) | Anal. |
|---|---|---|---|---|
| 193 | 2-Ethoxymethyl-1-{[1-(methanesulfonyl)piperidin-4-yl]methyl}-7-phenyl-1H-imidazo[4,5-c]quinolin-4-amine | White solid | 224-225 | Calcd for $C_{26}H_{31}N_5O_3S$: C, 63.26; H, 6.33; N, 14.19. Found: C, 62.99; H, 6.49; N, 14.05. |
| 194 | 2-Ethoxymethyl-1-[(1-isobutyrylpiperidin-4-yl)methyl]-7-phenyl-1H-imidazo[4,5-c]quinolin-4-amine | White, crystalline solid | 156-158 | Calcd for $C_{29}H_{35}N_5O_2 \cdot 0.5H_2O$: C, 70.42; H, 7.34; N, 14.16. Found: C, 70.17; H, 7.49; N, 14.13. |
| 195 | 2-Ethoxymethyl-1-{[1-(morpholin-4-ylcarbonyl)piperidin-4-yl]methyl}-7-phenyl-1H-imidazo[4,5-c]quinolin-4-amine | White solid | 208-209 | Calcd for $C_{30}H_{36}N_6O_3$: C, 68.16; H, 6.86; N, 15.90. Found: C, 67.82; H, 6.99; N, 15.71. |

175-176° C. Anal. Calcd for $C_{28}H_{25}N_3O$: C, 80.16; H, 6.01; N, 10.02. Found: C, 79.87; H, 5.92; N, 9.85.

Example 197

2-Ethoxymethyl-1-(2-phenoxyethyl)-7-phenyl-1H-imidazo[4,5-c]quinoline was obtained as a yellow, crystalline solid, mp 137-138° C. Anal. Calcd for $C_{27}H_{25}N_3O_2$: C, 76.57; H, 5.95; N, 9.92. Found: C, 76.60; H, 6.10; N, 9.66.

Example 198

2-(4-Methoxybenzyl)-1-(2-phenoxyethyl)-7-phenyl-1H-imidazo[4,5-c]quinoline was obtained as a white, crystalline powder, mp 205-206° C. Anal. Calcd for $C_{32}H_{27}N_3O_2$: C, 79.15; H, 5.60; N, 8.65. Found: C, 78.87; H, 5.65; N, 8.60.

Part E

The material from Part D was oxidized and then aminated according to the methods described in Parts H and I of Example 1. The oxidation product was not recrystallized. The product from amination was purified by column chromatography on silica gel (eluting with 95:5 or 90:10 chloroform:CMA) followed by recrystallization from ethyl acetate to provide the products shown in the table below.

Examples 196-198

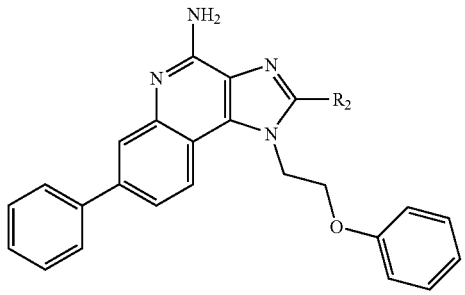

| Example | Acid Chloride | R₂ |
|---|---|---|
| 196 | Cyclopropylacetyl chloride | (cyclopropylmethyl) |
| 197 | Ethoxyacetyl chloride | (ethoxymethyl) |
| 198 | 4-Methoxyphenylacetyl chloride | (4-methoxybenzyl) |

Examples 196-198

| Example | Name | Form | Mp (° C.) | Anal. |
|---|---|---|---|---|
| 196 | 2-Cyclopropylmethyl-1-(2-phenoxyethyl)-7-phenyl-1H-imidazo[4,5-c]quinolin-4-amine | White solid | 188-189 | Calcd for $C_{28}H_{26}N_4O$: C, 77.39; H, 6.03; N, 12.89. Found: C, 77.10; H, 6.03; N, 12.85. |
| 197 | 2-Ethoxymethyl-1-(2-phenoxyethyl)-7-phenyl-1H-imidazo[4,5-c]quinolin-4-amine | White, crystalline solid | 159-160 | Calcd for $C_{27}H_{26}N_4O_2$: C, 73.95; H, 5.98; N, 12.78. Found: C, 73.72; H, 5.94; N, 12.78. |
| 198 | 2-(4-Methoxybenzyl)-1-(2-phenoxyethyl)-7-phenyl-1H-imidazo[4,5-c]quinolin-4-amine | Fluffy, white powder | 197-198 | Calcd for $C_{32}H_{28}N_4O_2$: C, 76.78; H, 5.64; N, 11.19. Found: C, 76.55; H, 5.75; N, 11.12. |

Example 199

N-{4-[4-Amino-2-(2-methoxyethyl)-7-phenyl-1H-imidazo[4,5-c]quinolin-1-yl]butyl}methanesulfonamide

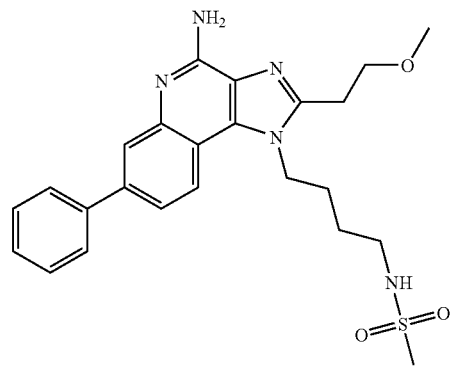

Part A

Under a nitrogen atmosphere, a solution of tert-butyl N-(4-aminobutyl)carbamate (13.8 g, 73.4 mmol) and triethylamine (15.3 mL, 110 mmol) was cooled to 0° C. Methanesulfonyl chloride (6.3 mL, 81 mmol) was added, and the reaction was allowed to warm to ambient temperature and stirred overnight. Aqueous acetic acid (200 mL of 10%) was added. The organic layer was then separated and washed with water (200 mL), saturated aqueous sodium bicarbonate (200 mL), water (200 mL), and brine; dried over sodium sulfate; filtered; and concentrated under reduced pressure to provide 18.9 g of tert-butyl [4-(methanesulfonylamino)butyl]carbamate as an off-white solid.

Part B

A solution of hydrochloric acid in ethanol was added to a solution of tert-butyl [4-(methanesulfonylamino)butyl]carbamate (18.9 g, 71.1 mmol) in ethanol (100 mL), and the reaction was heated at 100° C. for two hours. The solvent was removed under reduced pressure. A mixture of dichloromethane:hexanes was added to the resulting oil and removed under reduced pressure; this process was repeated several times. The residue was dried for three days under vacuum to provide 14.3 g of N-(4-aminobutyl)methanesulfonamide hydrochloride as a tan solid.

Part C

N-(4-aminobutyl)methanesulfonamide hydrochloride (7.8 g, 39 mmol) was added to a suspension of 4-chloro-3-nitro-7-phenylquinoline (35 mmol) and triethylamine (8.0 g, 79 mmol) in NMP (80 mL), and the reaction was stirred at ambient temperature overnight. The resulting solution was poured into water (350 mL) to form a solid, which was isolated by filtration, washed with water, air-dried, and recrystallized from acetonitrile to provide 12.0 g of N-[4-(3-nitro-7-phenylquinolin-4-ylamino)butyl]methanesulfonamide as yellow plates.

Part D

The method described in Part B of Examples 125-135 was used to convert N-[4-(3-nitro-7-phenylquinolin-4-ylamino)butyl]methanesulfonamide (12.0 g, 29.0 mmol) to N-[4-(3-amino-7-phenylquinolin-4-ylamino)butyl]methanesulfonamide, which was isolated as a brown solid.

Part E

The material from Part D was treated according to the method described in Part A of Example 9. The crude product was recrystallized from methyl ethyl ketone and then purified twice by flash column chromatography on silica gel (eluting with chloroform:CMA in a gradient from 95:5 to 75:25 and eluting with acetone:methanol in a gradient from 100:0 to 95:5).

Part F

N-{4-[2-(2-methoxyethyl)-7-phenyl-1H-imidazo[4,5-c]quinolin-1-yl]butyl}methanesulfonamide was oxidized and then aminated according to the methods described in Parts H and I of Example 1. Both reactions were carried out in chloroform. The oxidation product was recrystallized from 5:1 acetonitrile:ethyl acetate and dried under vacuum overnight at 45° C. The amination product was recrystallized from acetonitrile and dried in a vacuum oven at 70° C. to provide N-{4-[4-amino-2-(2-methoxyethyl)-7-phenyl-1H-imidazo[4,5-c]quinolin-1-yl]butyl}methanesulfonamide as a white solid, mp 201-202° C.

Anal. Calcd for $C_{24}H_{29}N_5O_3S$: C, 61.65; H, 6.25; N, 14.98. Found: C, 61.55; H, 6.11; N, 15.01.

Example 200

N-[2-(4-Amino-7-phenyl-2-propyl-1H-imidazo[4,5-c]quinolin-1-yl)-1,1-dimethylethyl]methanesulfonamide

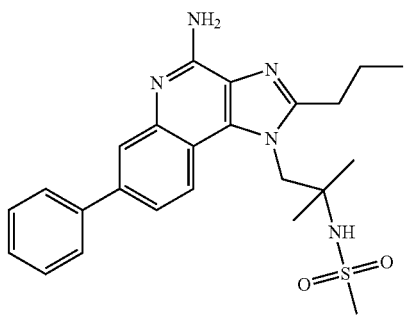

Part A

A solution of 1,2-diamino-2-methylpropane (9.3 mL, 88.9 mmol) and triethylamine (5.0 mL, 35.5 mmol) in dichloromethane (100 mL) was cooled to 0° C. A solution of 4-chloro-3-nitro-7-phenylquinoline (5.06 g, 17.8 mmol) in dichloromethane (50 mL) was added over a period of 45 minutes, and then the reaction was allowed to warm to ambient temperature. The solution was washed sequentially with water (2×100 mL) and brine (150 mL), dried over sodium sulfate, filtered, and concentrated under reduced pressure to provide $N^1$-(3-nitro-7-phenylquinolin-4-yl)-2-methylpropane-1,2-diamine as an orange solid.

Part B

A solution of $N^1$-(3-nitro-7-phenylquinolin-4-yl)-2-methylpropane-1,2-diamine (5.85 g, 17.4 mmol) in dichloromethane (200 mL) was cooled to 0° C. Triethylamine (3.6 mL, 26 mmol) and methanesulfonic anhydride (3.03, 17.4 mmol) were sequentially added. The reaction was allowed to warm to ambient temperature and stirred for two hours. Additional methanesulfonic anhydride (0.76 g, 4.4 mmol) was added, and the reaction was stirred overnight. A precipitate was present and was isolated by filtration, washed with water, and dried for two hours under high vacuum at 75° C. The filtrate was washed sequentially with water (2×100 mL) and brine (100 mL), dried over sodium sulfate, filtered, concentrated under reduced pressure, and recrystallized from dichloroethane. The two solids were combined to provide 5.26 g of N-[1,1-dimethyl-2-(3-nitro-7-phenylquinolin-4-ylamino)ethyl]methanesulfonamide as a yellow powder.

Part C

The method described in Part B of Examples 125-135 was used to convert N-[1,1-dimethyl-2-(3-nitro-7-phenylquinolin-4-ylamino)ethyl]methanesulfonamide (5.26 g, 12.6 mmol) to 4.53 g of N-[2-(3-amino-7-phenylquinolin-4-ylamino)-1,1-dimethylethyl]methanesulfonamide, which was isolated as a yellow-orange solid.

Part D

N-[2-(3-Amino-7-phenylquinolin-4-ylamino)-1,1-dimethylethyl]methanesulfonamide (2.20 g, 5.04 mmol) was treated with trimethyl orthobutyrate (0.90 mL, 5.5 mmol) according to the method described in Part G of Example 1. The chromatographic purification was carried out eluting with 92.5:7.5 dichloromethane:methanol to provide 1.8 g of N-[2-(7-phenyl-2-propyl-1H-imidazo[4,5-c]quinolin-1-yl)-1,1-dimethylethyl]methanesulfonamide as a tan solid.

Part E

N-[2-(7-Phenyl-2-propyl-1H-imidazo[4,5-c]quinolin-1-yl)-1,1-dimethylethyl]methanesulfonamide was oxidized and then aminated according to the methods described in Parts H and I of Example 1. The oxidation reaction was carried out in chloroform, and the product was not recrystallized. The product from amination was recrystallized from ethanol, and isolated by filtration. The solid was recrystallized from acetonitrile, and the crystals were dissolved in dichloromethane:methanol, concentrated under reduced pressure, and dried under high vacuum at 60° C. to provide N-[2-(4-amino-7-phenyl-2-propyl-1H-imidazo[4,5-c]quinolin-1-yl)-1,1-dimethylethyl]methanesulfonamide as a white, crystalline solid, mp 135-141° C.

Anal. Calcd for $C_{24}H_{29}N_5O_2S$: C, 63.83; H, 6.47; N, 15.51. Found: C, 63.48; H, 6.80; N, 15.34.

Example 201

N-[2-(4-Amino-2-ethoxymethyl-7-phenyl-1H-imidazo[4,5-c]quinolin-1-yl)-1,1-dimethylethyl]methanesulfonamide

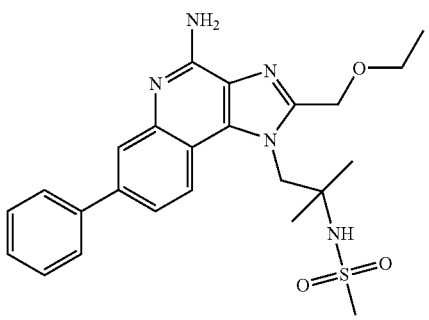

Part A

A modification of the method described in Part C of Examples 125-135 was used to treat N-[1,1-dimethyl-2-(3-amino-7-phenylquinolin-4-ylamino)ethyl]methanesulfonamide (2.33 g, 5.33 mmol) with ethoxyacetyl chloride (0.72 g, 5.87 mmol). Triethylamine (1.5 mL, 11 mmol) was added to the reaction, which was stirred overnight.

Part B

A solution of the material from Part A and triethylamine (1.5 mL, 11 mmol) in anhydrous toluene (100 mL) was heated at reflux overnight. The solvent was then removed under reduced pressure, and the residue was dissolved in dichloromethane (100 mL). The resulting solution was washed sequentially with 1% aqueous sodium carbonate (2×100 mL) and brine (100 mL), dried over sodium sulfate, filtered, and concentrated under reduced pressure. The crude product was purified by column chromatography on silica gel (eluting with 95:5 dichloromethane:methanol) to provide 2.07 g of N-[2-(2-ethoxymethyl-7-phenyl-1H-imidazo[4,5-c]quinolin-1-yl)-1,1-dimethylethyl]methanesulfonamide as a yellow solid.

Part C

N-[2-(2-Ethoxymethyl-7-phenyl-1H-imidazo[4,5-c]quinolin-1-yl)-1,1-dimethylethyl]methanesulfonamide was oxidized and then aminated according to the methods described in Parts H and I or Example 1. The oxidation reaction was carried out in chloroform, and the product was not recrystallized. The product from amination was recrystallized from acetonitrile, and the crystals were dissolved in dichloromethane:methanol, concentrated under reduced pressure, and dried in a vacuum oven to provide N-[2-(4-amino-2-ethoxymethyl-7-phenyl-1H-imidazo[4,5-c]quinolin-1-yl)-1,1-dimethylethyl]methanesulfonamide as a white powder, mp 239-242° C.

Anal. Calcd for $C_{24}H_{29}N_5O_2S \cdot 0.3H_2O$: C, 60.94; H, 6.31; N, 14.81. Found: C, 60.91; H, 6.03; N, 14.71.

Example 202

Cyclohexane N-[2-(4-amino-2-ethoxymethyl-7-phenyl-1H-imidazo[4,5-c]quinolin-1-yl)-1,1-dimethylethyl]carboxamide

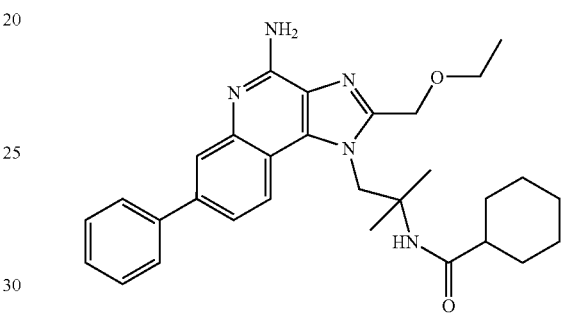

Part A

A solution of $N^1$-(3-nitro-7-phenylquinolin-4-yl)-2-methylpropane-1,2-diamine (3.56 g, 10.6 mmol) in dichloromethane (100 mL) was cooled to 0° C. Triethylamine (3.0 mL, 21 mmol) and cyclohexanecarbonyl chloride (1.55 mL, 11.6 mmol) were sequentially added. The reaction was allowed to warm to ambient temperature and stirred for two hours. The reaction was washed sequentially with water (2×100 mL) and brine (100 mL), dried over sodium sulfate, filtered, and concentrated under reduced pressure. The crude product was purified by column chromatography on silica gel (eluting with 65:35 hexanes:ethyl acetate) to provide 3.33 g of cyclohexane N-[1,1-dimethyl-2-(3-nitro-7-phenylquinolin-4-ylamino)ethyl]carboxamide as a yellow solid.

Part B

The method described in Part B of Examples 125-135 was used to convert cyclohexane N-[1,1-dimethyl-2-(3-nitro-7-phenylquinolin-4-ylamino)ethyl]carboxamide (3.33 g, 7.46 mmol) to 3.06 g of cyclohexane N-[2-(3-amino-7-phenylquinolin-4-ylamino)-1,1-dimethylethyl]carboxamide, which was isolated as an orange solid.

Part C

Cyclohexane N-[2-(3-amino-7-phenylquinolin-4-ylamino)-1,1-dimethylethyl]carboxamide was treated according to the methods described in Parts A-C Example 201. The product from amination was purified by column chromatography on silica gel (eluting with 92.5:7.5 dichloromethane:methanol) followed by recrystallization from isopropanol. The crystals were dissolved in dichloromethane:methanol, concentrated under reduced pressure, and dried for two days under high vacuum at 65° C. to provide cyclohexane N-[2-(4-amino-2-ethoxymethyl-7-phenyl-1H-imidazo[4,5-c]quinolin-1-yl)-1,1-dimethylethyl]carboxamide as a white powder, mp 195-198° C.

Anal. Calcd for $C_{30}H_{37}N_5O_2 \cdot 0.25H_2O$: C, 71.47; H, 7.50; N, 13.89. Found: C, 71.49; H, 7.54; N, 13.88.

Example 203

N-[2-(4-Amino-2-ethoxymethyl-7-phenyl-1H-imidazo[4,5-c]quinolin-1-yl)-1,1-dimethylethyl]-N'-cyclohexylurea

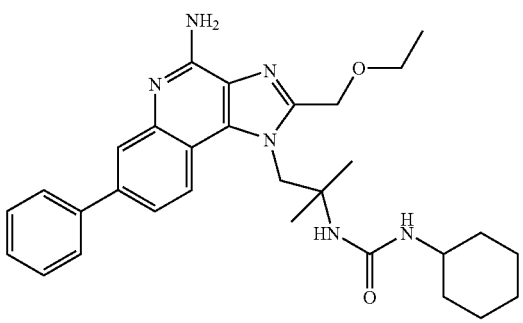

Part A

A solution of $N^1$-(3-nitro-7-phenylquinolin-4-yl)-2-methylpropane-1,2-diamine (3.56 g, 10.6 mmol) in dichloromethane (100 mL) was cooled to 0° C. Cyclohexyl isocyanate (3.00 mL, 23.5 mmol) was added over the course of a day, and the reaction was stirred at ambient temperature for three days. The solvent was removed under reduced pressure. Xylenes (3 cx 100 mL) were added and removed under reduced pressure to provide N-cyclohexyl-N'-[1,1-dimethyl-2-(3-nitro-7-phenylquinolin-4-ylamino)ethyl]urea as a yellow solid.

Part B

The method described in Part B of Examples 125-135 was used to convert N-cyclohexyl-N'-[1,1-dimethyl-2-(3-nitro-7-phenylquinolin-4-ylamino)ethyl]urea (4.88 g, 10.6 mmol) to 4.35 g of N-[2-(3-amino-7-phenylquinolin-4-ylamino)-1,1-dimethylethyl]-N'-cyclohexylurea, which was isolated as an orange powder.

Part C

N-cyclohexyl-N'-[2-(3-amino-7-phenylquinolin-4-ylamino)-1,1-dimethylethyl]urea was treated according to the methods described in Parts A-C Example 201. The product from amination was recrystallized twice from ethanol. The crystals were dissolved in dichloromethane, and the resulting solution was washed sequentially with water (2×) and brine, dried over sodium sulfate, filtered, concentrated under reduced pressure, and dried for two days under high vacuum at 65° C. to provide N-[2-(4-amino-2-ethoxymethyl-7-phenyl-1H-imidazo[4,5-c]quinolin-1-yl)-1,1-dimethylethyl]-N'-cyclohexylurea as an off-white powder, mp 152-156° C.

Anal. Calcd for $C_{30}H_{38}N_6O_2$: C, 70.01; H, 7.44; N, 16.33. Found: C, 69.78; H, 7.63; N, 16.24.

Examples 204

1-[3-(4-Amino-7-phenyl-1H-imidazo[4,5-c]quinolin-1-yl)propyl]pyrrolidin-2-one

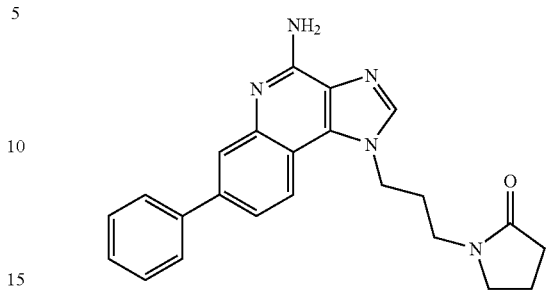

Part A

4-Chloro-3-nitro-7-phenylquinoline (3.51 g, 12.3 mmol) was treated with 1-(3-aminopropyl)pyrrolidin-2-one (2.3 mL, 16 mmol) according to the method described in Part E of Example 1 to provide 4.23 g of 1-[3-(3-nitro-7-phenylquinolin-4-ylamino)propyl]pyrrolidin-2-one as a yellow solid.

Part B

The method described in Part B of Examples 152-156 was used to convert 1-[3-(3-nitro-7-phenylquinolin-4-ylamino)propyl]pyrrolidin-2-one (4.25 g, 10.9 mmol) to 3.66 g of 1-[3-(3-amino-7-phenylquinolin-4-ylamino)propyl]pyrrolidin-2-one, which was obtained as a brown solid. In Part B, 1,1'-di-n-octyl-4,4'-bipyridinium dibromide was used instead of 1,1'-diethyl-4,4'-bipyridinium dibromide.

Part C

Triethyl orthoformate (2.50 mL, 15.0 mmol) was added to a solution of 1-[3-(3-amino-7-phenylquinolin-4-ylamino)propyl]pyrrolidin-2-one (3.59 g, 9.96 mmol) and pyridine hydrochloride (50 mg, 0.43 mmol) in anhydrous toluene (65 mL) and 1,2-dichloroethane (35 mL), and the reaction was heated at reflux overnight under a nitrogen atmosphere. The solution was then washed with saturated aqueous sodium carbonate (150 mL). The aqueous layer was extracted with dichloromethane (2×150 mL), and the combined organic fractions were washed with brine (150 mL), dried over magnesium sulfate, filtered, and concentrated under reduced pressure. The resulting solid was dissolved in dichloromethane (5 mL), and diethyl ether (100 mL) was added to form a solid, which was isolated by filtration and dried in a vacuum oven at 60° C. to provide 2.51 g of a light brown solid. A portion of the product was recrystallized from 25:75 ethyl acetate:heptane and dried in a vacuum oven at 60° C. to provide 1-[3-(7-phenyl-1H-imidazo[4,5-c]quinolin-1-yl)propyl]pyrrolidin-2-one as a light brown solid, mp 138-141

Anal. Calcd. for $C_{23}H_{22}N_4O$: C, 74.57; H, 5.99; N, 15.12. Found: C, 74.45; H, 6.17; N, 15.06.

Part D

1-[3-(7-Phenyl-1H-imidazo[4,5-c]quinolin-1-yl)propyl]pyrrolidin-2-one was oxidized and then aminated according to the methods described in Parts H and I of Example 1. The product from amination was purified twice by column chromatography on silica gel (eluting with chloroform:CMA in gradients from 100:0 to 70:30). The resulting solid was washed with diethyl ether, recrystallized from acetonitrile, and dried in a vacuum oven at 60° C. to provide 1-[3-(4-amino-7-phenyl-1H-imidazo[4,5-c]quinolin-1-yl)propyl]pyrrolidin-2-one as a light brown solid, mp 201-204° C.

Anal. Calcd. for $C_{23}H_{23}N_5O$: C, 71.67; H, 6.01; N, 18.17. Found: C, 71.64; H, 5.95; N, 18.48.

Example 205

1-[3-(4-Amino-2-ethoxymethyl-7-phenyl-1H-imidazo[4,5-c]quinolin-1-yl)propyl]pyrrolidin-2-one

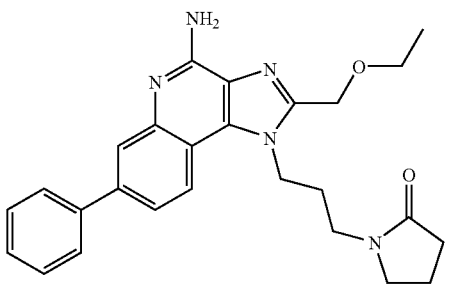

Part A

1-[3-(3-Amino-7-phenylquinolin-4-ylamino)propyl]pyrrolidin-2-one (2.21 g, 6.13 mmol) was treated with ethoxyacetyl chloride (0.95 mL, 8.76 mmol) according to the methods described in Parts C and D of Examples 152-156. Triethylamine (8.6 mmol) was added in Part C. The product from Part D was purified by column chromatography on silica gel (eluting with acetone and then chloroform:methanol in a gradient from 95:5 to 90:10) to provide 1.49 g of 1-[3-(2-ethoxymethyl-7-phenyl-1H-imidazo[4,5-c]quinolin-1-yl)propyl]pyrrolidin-2-one as a brown solid.

Part B

1-[3-(2-Ethoxymethyl-7-phenyl-1H-imidazo[4,5-c]quinolin-1-yl)propyl]pyrrolidin-2-one was oxidized and then aminated according to the methods described in Parts H and I of Example 1. The product from amination was purified by column chromatography on silica gel (eluting with chloroform:CMA in a gradient from 100:0 to 75:25) followed by recrystallization from acetonitrile and drying in a vacuum oven at 60° C. to provide 1-[3-(4-amino-2-ethoxymethyl-7-phenyl-1H-imidazo[4,5-c]quinolin-1-yl)propyl]pyrrolidin-2-one as a light brown solid, mp 199-203° C.

Anal. Calcd. for $C_{26}H_{29}N_5O_2$: C, 70.41; H, 6.59; N, 15.79. Found: C, 70.04; H, 6.55; N, 15.55.

Example 206

1-{3-[4-Amino-2-(2-methoxyethyl)-7-phenyl-1H-imidazo[4,5-c]quinolin-1-yl]propyl}pyrrolidin-2-one

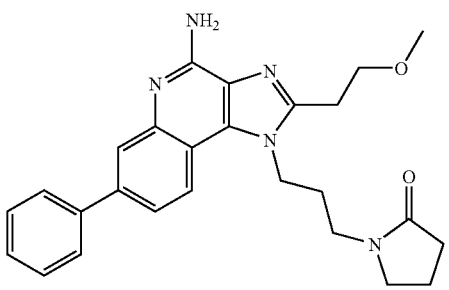

The methods described in Parts A of Example 204 were used to treat 1-[3-(3-amino-7-phenylquinolin-4-ylamino)propyl]pyrrolidin-2-one (1.19 g, 3.30 mmol) with 3-methoxypropionyl chloride (0.45 mL, 4.1 mmol) to afford 1-{3-[2-(2-methoxyethyl)-7-phenyl-1H-imidazo[4,5-c]quinolin-1-yl]propyl}pyrrolidin-2-one, which was oxidized and then aminated according to the methods described in Parts H and I of Example 1. The product from amination was recrystallized twice from acetonitrile and dried in a vacuum oven at 60° C. to provide 1-{3-[4-amino-2-(2-methoxyethyl)-7-phenyl-1H-imidazo[4,5-c]quinolin-1-yl]propyl}pyrrolidin-2-one as a light brown solid, mp 187-191° C.

Anal. Calcd. for $C_{26}H_{29}N_5O_2 \cdot 0.13H_2O$: C, 70.05; H, 6.61; N, 15.71. Found: C, 69.66; H, 6.73; N, 15.82.

Examples 207-243

7-Bromo-2-ethoxymethyl-1-(3-methoxypropyl)-1H-imidazo[4,5-c]quinolin-4-amine was coupled with the appropriate boronic acid or boronic acid ester according to the procedure described in Examples 20-65 and then purified by prep HPLC according to procedures described above. The table below shows the structure of the compound obtained in each example and the observed accurate mass for the isolated trifluoroacetate salt.

Examples 207-243

| Example | R | Measured Mass (M + H) |
|---|---|---|
| 207 | 3-furyl | 381.1920 |
| 208 | 2-thienyl | 397.1703 |
| 209 | 3-thienyl | 397.1696 |
| 210 | 4-methylphenyl | 405.2279 |
| 211 | 4-hydroxyphenyl | 407.2063 |

-continued
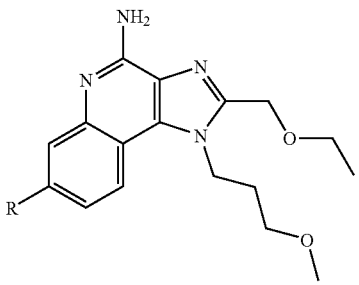
| Example | R | Measured Mass (M + H) |
|---|---|---|
| 212 | 3-hydroxyphenyl | 407.2091 |
| 213 | 3-cyanophenyl | 416.2078 |
| 214 | 4-cyanophenyl | 416.2076 |
| 215 | 3,5-dimethylphenyl | 419.2453 |
| 216 | 4-ethylphenyl | 419.2456 |
| 217 | 4-(hydroxymethyl)phenyl | 421.2240 |
| 218 | 4-methoxyphenyl | 421.2233 |
| 219 | 2,4-difluorophenyl | 427.1955 |
| 220 | 2-acetylphenyl | 433.2238 |
-continued
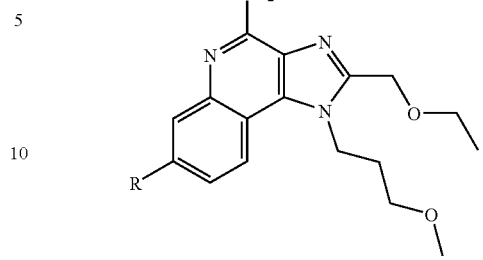
| Example | R | Measured Mass (M + H) |
|---|---|---|
| 221 | 3-acetylphenyl | 433.2244 |
| 222 | 4-acetylphenyl | 433.2226 |
| 223 | 3-carbamoylphenyl | 434.2203 |
| 224 | 3-ethoxyphenyl | 435.2425 |
| 225 | 2-acetamidophenyl | 448.2346 |
| 226 | 4-ethoxy-3-methylphenyl | 449.2544 |
| 227 | 2-isopropoxyphenyl | 449.2560 |

-continued
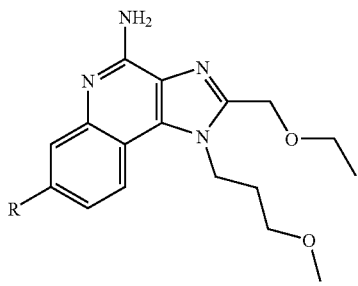
| Example | R | Measured Mass (M + H) |
|---|---|---|
| 228 | 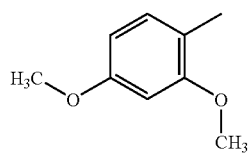 | 451.2355 |
| 229 | 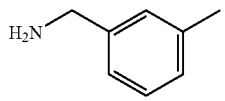 | 420.2405 |
| 230 | 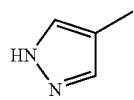 | 381.2043 |
| 231 | 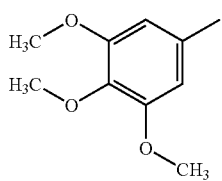 | 481.2441 |
| 232 | 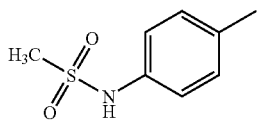 | 484.1996 |
| 233 | 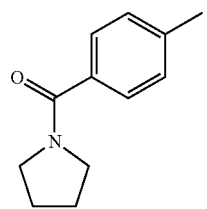 | 488.2650 |
| 234 | 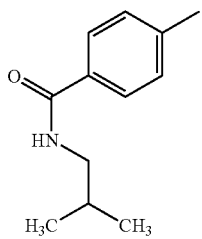 | 490.2800 |
-continued
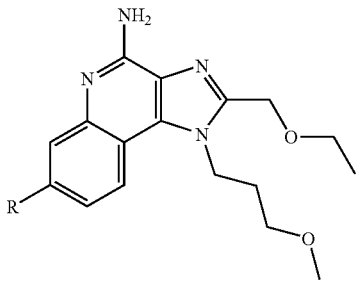
| Example | R | Measured Mass (M + H) |
|---|---|---|
| 235 | 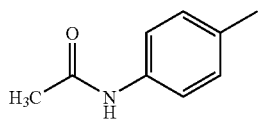 | 448.2330 |
| 236 | 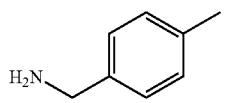 | 420.2382 |
| 237 | 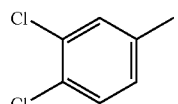 | 459.1323 |
| 238 | 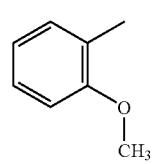 | 421.2232 |
| 239 | 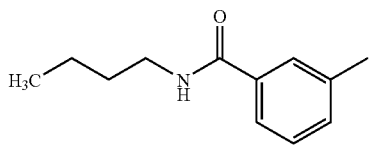 | 490.2826 |
| 240 | 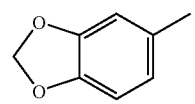 | 435.2045 |
| 241 | 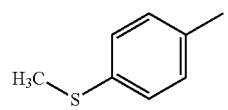 | 437.2012 |
| 242 | 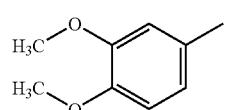 | 451.2355 |
| 243 | 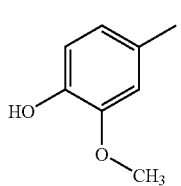 | 437.2174 |

Examples 244-323

A reagent from the table below, (0.064 mmol, 1.1 equivalents) was added to a test tube containing a solution of 2-ethoxymethyl-1-(piperidin-4-ylmethyl)-7-(pyridin-3-yl)-1H-imidazo[4,5-c]quinolin-4-amine trihydrochloride (30 mg, 0.057 mmol) and N,N-diisopropylethylamine (0.048 mL, 0.27 mmol, 4.8 equivalents) in chloroform (2 mL). The test tube was capped placed on a shaker at ambient temperature overnight. One drop of deionized water was then added to each test tube, and the solvent was removed by vacuum centrifugation. For Example 323, the capped test tube was heated at 60° C. overnight in a sand bath, and then lithium trifluoromethanesulfonimide (3 mg) was added followed by shaking for an additional four hours. The products were purified by prep HPLC according to the methods described above. The table below shows the reagent used for each example, the structure of the resulting compound, and the observed accurate mass for the isolated trifluoroacetate salt.

Examples 244-323

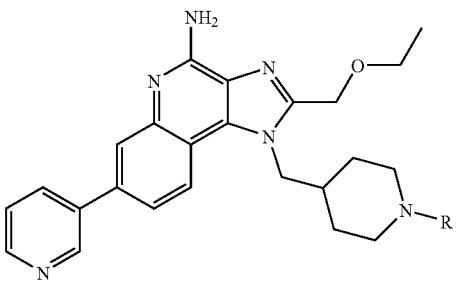

| Example | Reagent | R | Measured Mass (M + H) |
|---|---|---|---|
| 244 | Acetyl chloride | | 459.2510 |
| 250 | Isobutyryl chloride | | 487.2840 |
| 245 | Isovaleryl chloride | | 501.2990 |
| 246 | Pentanoyl chloride | | 501.2957 |
| 247 | Isoxazole-5-carbonyl chloride | | 512.2435 |
| 248 | Benzoyl chloride | | 521.2667 |
| 249 | Cyclohexane-carbonyl chloride | | 527.3166 |
| 250 | m-Toluoyl chloride | | 535.2848 |
| 251 | Phenylacetyl chloride | | 535.2853 |
| 252 | Thiophene-2-acetyl chloride | | 541.2407 |

-continued

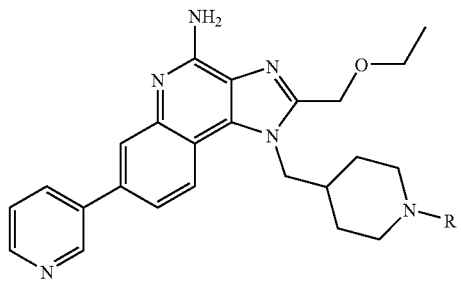

| Example | Reagent | R | Measured Mass (M + H) |
|---|---|---|---|
| 253 | 3-Cyclopentyl-propionyl chloride | (3-oxobutyl)cyclopentane group | 541.3304 |
| 254 | Cinnamoyl chloride | cinnamyl ketone group | 547.2837 |
| 255 | Hydrocinnamoyl chloride | 4-phenyl-2-butanone group | 549.3021 |
| 256 | 2-Methoxy-benzoyl chloride | 2-methoxyphenyl ketone | 551.2809 |
| 257 | m-Anisoyl chloride | 3-methoxyphenyl ketone | 551.2786 |
| 258 | 2-Chloro-benzoyl chloride | 2-chlorophenyl ketone | 555.2264 |

-continued

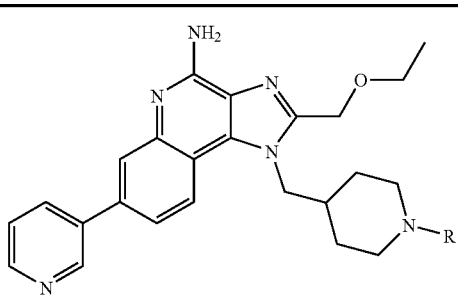

| Example | Reagent | R | Measured Mass (M + H) |
|---|---|---|---|
| 259 | 3-Chloro-benzoyl chloride | 3-chlorophenyl ketone | 555.2272 |
| 260 | 4-Chloro-benzoyl chloride | 4-chlorophenyl ketone | 555.2281 |
| 261 | trans-2-Phenyl-1-cyclopropanecarbonyl chloride | trans-2-phenylcyclopropyl ketone | 561.2970 |
| 262 | Benzyloxyacetyl chloride | benzyloxyacetyl group | 565.2938 |
| 263 | 1-Naphthoyl chloride | 1-naphthyl ketone | 571.2817 |

-continued

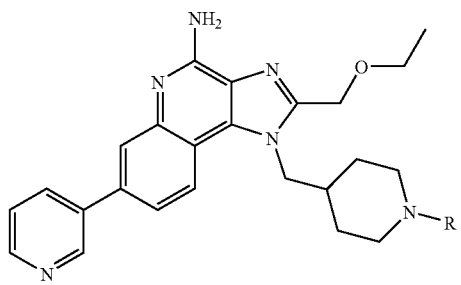

| Example | Reagent | R | Measured Mass (M + H) |
|---|---|---|---|
| 264 | 2-Naphthoyl chloride | (2-naphthyl C(=O)–) | 571.2817 |
| 265 | Methyl 4-chlorocarbonyl-benzoate | (4-(CO2CH3)C6H4–C(=O)–) | 579.2716 |
| 266 | 3-(Trifluoromethyl)benzoyl chloride | (3-CF3-C6H4–C(=O)–) | 589.2557 |
| 267 | 4-(Trifluoromethyl)benzoyl chloride | (4-CF3-C6H4–C(=O)–) | 589.2585 |

-continued

| Example | Reagent | R | Measured Mass (M + H) |
|---|---|---|---|
| 268 | 2,4-Dichlorobenzoyl chloride | (2,4-Cl2-C6H3–C(=O)–) | 589.1870 |
| 269 | 3,4-Dichlorobenzoyl chloride | (3,4-Cl2-C6H3–C(=O)–) | 589.1912 |
| 270 | 4-(Trifluoromethoxy)-benzoyl chloride | (4-OCF3-C6H4–C(=O)–) | 605.2531 |
| 271 | Ethanesulfonyl chloride | (CH3CH2–SO2–) | 509.2364 |
| 272 | Isopropylsulfonyl chloride | ((CH3)2CH–SO2–) | 523.2523 |
| 273 | Dimethylsulfamoyl chloride | ((CH3)2N–SO2–) | 524.2463 |

-continued

Common structure (Examples 274–280): 4-amino-2-(ethoxymethyl)-7-(pyridin-3-yl)-1H-imidazo[4,5-c]quinoline with 1-(piperidin-4-ylmethyl), piperidine N–R

| Example | Reagent | R | Measured Mass (M + H) |
|---|---|---|---|
| 274 | Benzenesulfonyl chloride | –SO₂–C₆H₅ | 557.2380 |
| 275 | 2-Thiophenesulfonyl chloride | –SO₂–(2-thienyl) | 563.1921 |
| 276 | α-Toluenesulfonyl chloride | –SO₂–CH₂–C₆H₅ | 571.2524 |
| 277 | m-Toluenesulfonyl chloride | –SO₂–(3-methylphenyl) | 571.2509 |
| 278 | 2-Cyanobenzenesulfonyl chloride | –SO₂–(2-cyanophenyl) | 582.2325 |
| 279 | 3-Cyanobenzenesulfonyl chloride | –SO₂–(3-cyanophenyl) | 582.2301 |
| 280 | 4-Cyanobenzenesulfonyl chloride | –SO₂–(4-cyanophenyl) | 582.2322 |

-continued

Common structure (Examples 281–287): same scaffold as above

| Example | Reagent | R | Measured Mass (M + H) |
|---|---|---|---|
| 281 | trans-β-Styrenesulfonyl chloride | –SO₂–CH=CH–C₆H₅ | 583.2543 |
| 282 | 4-Methoxybenzenesulfonyl chloride | –SO₂–(4-methoxyphenyl) | 587.2435 |
| 283 | 2-Chlorobenzenesulfonyl chloride | –SO₂–(2-chlorophenyl) | 591.1967 |
| 284 | 3-Chlorobenzenesulfonyl chloride | –SO₂–(3-chlorophenyl) | 591.1970 |
| 285 | 2,4-Difluorobenzenesulfonyl chloride | –SO₂–(2,4-difluorophenyl) | 593.2180 |
| 286 | 2,6-Difluorobenzenesulfonyl chloride | –SO₂–(2,6-difluorophenyl) | 593.2167 |
| 287 | 3-Nitrobenzenesulfonyl chloride | –SO₂–(3-nitrophenyl) | 602.2214 |

-continued

161

[Structure: 4-amino-2-(ethoxymethyl)-7-(pyridin-3-yl)-1H-imidazo[4,5-c]quinoline with 1-N-CH2-piperidine-N-R substituent]

| Example | Reagent | R | Measured Mass (M + H) |
|---|---|---|---|
| 288 | 8-Quinoline-sulfonyl chloride | 8-quinolinylsulfonyl | 608.2483 |
| 289 | 3,4-Dimethoxy-benzene-sulfonyl chloride | 3,4-dimethoxyphenylsulfonyl | 617.2534 |
| 290 | 2-(Trifluoromethyl)-benzene-sulfonyl chloride | 2-(trifluoromethyl)phenylsulfonyl | 625.2228 |
| 291 | 3-(Trifluoromethyl)-benzene-sulfonyl chloride | 3-(trifluoromethyl)phenylsulfonyl | 625.2214 |
| 292 | 2,4-Dichloro-benzene-sulfonyl chloride | 2,4-dichlorophenylsulfonyl | 625.1567 |
| 293 | (1R)-(−)-10-Camphor-sulfonyl chloride | (1R)-camphorsulfonyl | 631.3110 |

162

-continued

[Structure: 4-amino-2-(ethoxymethyl)-7-(pyridin-3-yl)-1H-imidazo[4,5-c]quinoline with 1-N-CH2-piperidine-N-R substituent]

| Example | Reagent | R | Measured Mass (M + H) |
|---|---|---|---|
| 294 | (1S)-(−)-10-Camphor-sulfonyl chloride | (1S)-camphorsulfonyl | 631.3090 |
| 295 | 4-Biphenyl-sulfonyl chloride | 4-biphenylsulfonyl | 633.2662 |
| 296 | 4-(Trifluoromethoxy)-benzene-sulfonyl chloride | 4-(trifluoromethoxy)phenylsulfonyl | 641.2178 |
| 297 | Isopropyl isocyanate | isopropylaminocarbonyl | 502.2964 |
| 298 | n-Propyl isocyanate | n-propylaminocarbonyl | 502.2924 |
| 299 | tert-Butyl isocyanate | tert-butylaminocarbonyl | 516.3080 |
| 300 | Dimethyl-carbamyl chloride | dimethylaminocarbonyl | 488.2809 |

-continued

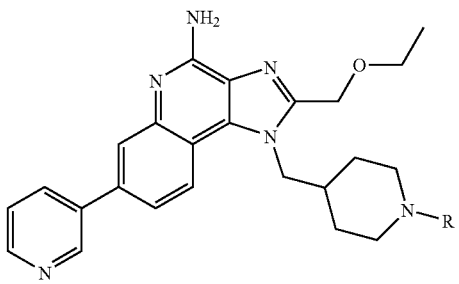

| Example | Reagent | R | Measured Mass (M + H) |
|---|---|---|---|
| 301 | Phenyl isocyanate | -C(O)NH-phenyl | 536.2817 |
| 302 | Cyclohexyl isocyanate | -C(O)NH-cyclohexyl | 542.3281 |
| 303 | Benzyl isocyanate | -C(O)NH-CH2-phenyl | 550.2914 |
| 304 | m-Tolyl isocyanate | -C(O)NH-(3-methylphenyl) | 550.2971 |
| 305 | o-Tolyl isocyanate | -C(O)NH-(2-methylphenyl) | 550.2964 |
| 306 | p-Tolyl isocyanate | -C(O)NH-(4-methylphenyl) | 550.2953 |

-continued

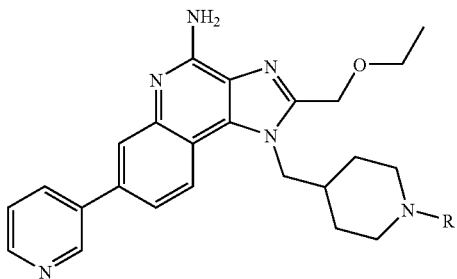

| Example | Reagent | R | Measured Mass (M + H) |
|---|---|---|---|
| 307 | 3-Fluorophenyl isocyanate | -C(O)NH-(3-fluorophenyl) | 554.2717 |
| 308 | 3-Cyanophenyl isocyanate | -C(O)NH-(3-cyanophenyl) | 561.2725 |
| 309 | 4-Cyanophenyl isocyanate | -C(O)NH-(4-cyanophenyl) | 561.2756 |
| 310 | Phenethyl isocyanate | -C(O)NH-CH2CH2-phenyl | 564.3129 |
| 311 | 1-Piperidine-carbonyl chloride | -C(O)-piperidinyl | 528.3115 |
| 312 | 3-Methoxyphenyl isocyanate | -C(O)NH-(3-methoxyphenyl) | 566.2924 |

-continued

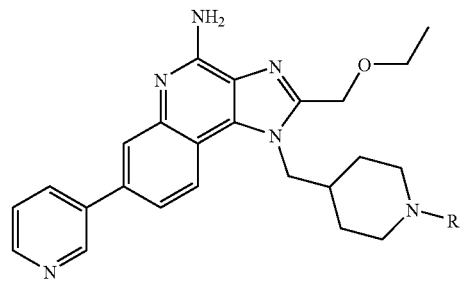

| Example | Reagent | R | Measured Mass (M + H) |
|---|---|---|---|
| 313 | 4-Methoxyphenyl isocyanate | —C(O)NH-(4-methoxyphenyl) | 566.2906 |
| 314 | 2-Chlorophenyl isocyanate | —C(O)NH-(2-chlorophenyl) | 570.2419 |
| 315 | trans-2-Phenylcyclopropyl isocyanate | —C(O)NH-(trans-2-phenylcyclopropyl) | 576.3120 |
| 316 | 3-Acetylphenyl isocyanate | —C(O)NH-(3-acetylphenyl) | 578.2910 |
| 317 | Benzoyl Isothiocyanate | —C(S)NH-C(O)-phenyl | 580.2478 |
| 318 | N-Methyl-N-phenyl-carbamoyl chloride | —C(O)N(CH₃)-phenyl | 550.2927 |

-continued

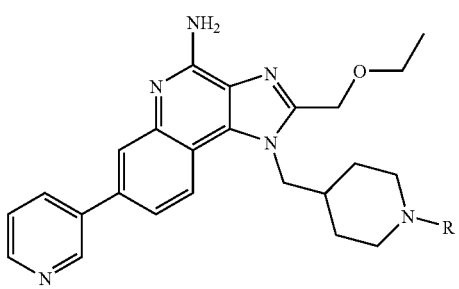

| Example | Reagent | R | Measured Mass (M + H) |
|---|---|---|---|
| 319 | Methyl 3-Isocyanatobenzoate | —C(O)NH-(3-methoxycarbonylphenyl) | 594.2820 |
| 320 | 2-(Trifluoromethyl)phenyl isocyante | —C(O)NH-(2-trifluoromethylphenyl) | 604.2616 |
| 321 | 3-(Trifluoromethyl)phenyl isocyante | —C(O)NH-(3-trifluoromethylphenyl) | 604.2638 |
| 322 | 4-(Trifluoromethyl)phenyl isocyante | —C(O)NH-(4-trifluoromethylphenyl) | 604.2658 |
| 323 | Benzyl glycidyl ether | —CH₂CH(OH)CH₂OCH₂-phenyl | 581.3278 |

Examples 323-331

1-(2-Amino-2-methylpropyl)-2-ethoxymethyl-7-phenyl-1H-imidazo[4,5-c]quinolin-4-amine was prepared from N$^1$-(3-nitro-7-phenylquinolin-4-yl)-2-methylpropane-1,2-diamine according to the methods described in Part C of Example 200 and Parts A-C of Example 201. A reagent from the table below, (0.051-0.058 mmol, 1.1 equivalents) was added to a test tube containing a solution of 1-(2-amino-2-methylpropyl)-2-ethoxymethyl-7-phenyl-1H-imidazo[4,5-c]quinolin-4-amine (20 mg, 0.051 mmol) and N,N-diisopropylethylamine (0.018 mL, 0.10 mmol, 2 equivalents) in chloroform (2 mL). The test tube was capped placed on a shaker at ambient temperature overnight. For Examples 324 and 327, the test tubes were then heated on a sand bath for two hours at 50° C. Ammonium hydroxide (2 drops) was added to the other reactions, and they were placed back on the shaker. The solvent was removed by vacuum centrifugation, and the products were purified by prep HPLC according to the methods described above. The table below shows the reagent used for each example, the structure of the resulting compound, and the observed accurate mass for the isolated trifluoroacetate salt.

Examples 324-331

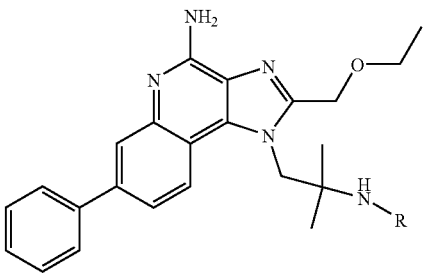

| Example | Reagent | R | Measured Mass (M + H) |
|---|---|---|---|
| 324 | Dimethylcarbamyl chloride | | 475.2825 |
| 325 | Cyclohexyl isocyanate | | 515.3126 |
| 326 | Methyl malonyl chloride | | 490.2459 |
| 327 | Dimethylsulfamoyl chloride | | 497.2338 |
| 328 | Phenylacetyl chloride | | 508.2685 |
| 329 | 3-Cyclopentyl-propionyl chloride | | 514.3140 |
| 330 | m-Anisolyl chloride | | 524.2621 |
| 331 | 3-Chlorobenzoyl chloride | | 528.2164 |

Examples 332-362

Part A tert-Butyl 4-[(4-amino-7-bromo-2-ethoxymethyl-1H-imidazo[4,5-c]quinolin-1-yl)methyl]piperidine-1-carboxylate (11.83 g, 22.82 mmol) was treated according to the method described in Example 177 to provide 9.73 g of 7-bromo-2-ethoxymethyl-1-(piperidin-4-ylmethyl)-1H-imidazo[4,5-c]quinolin-4-amine dihydrochloride as a white, crystalline solid, mp>300° C.

Part B

The method described in Examples 178-181 was used to treat 7-bromo-2-ethoxymethyl-1-(piperidin-4-ylmethyl)-1H-imidazo[4,5-c]quinolin-4-amine dihydrochloride (4.95 g, 10.1 mmol) with methanesulfonic anhydride (1.76 g, 10.1 mmol). The reaction was carried out in dichloromethane (150 mL). Following chromatographic purification (eluting with chloroform:CMA in a gradient from 100:0 to 90:10), the product was recrystallized from ethyl acetate to provide 2.37 g of 7-bromo-2-ethoxymethyl-1-{[1-(methanesulfonyl)piperidin-4-yl]methyl}-1H-imidazo[4,5-c]quinolin-4-amine as a white, crystalline solid, mp 233-234° C.

Anal. Calcd for $C_{20}H_{26}BrN_5O_3S$: C, 47.87; H, 5.34; N, 13.96. Found: C, 48.14; H, 5.28; N, 13.56.

Part C

7-Bromo-2-ethoxymethyl-1-{[1-(methanesulfonyl)piperidin-4-yl]methyl}-1H-imidazo[4,5-c]quinolin-4-amine was coupled with the appropriate boronic acid or boronic acid ester according to the procedure described in Examples 20-65. The preoducts were purifed by prep HPLC according to the methods described above. The table below shows the structure of the compound obtained in each example and the observed accurate mass for the isolated trifluoroacetate salt.

Examples 332-362

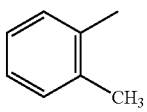

| Example | R | Measured Mass (M + H) |
|---|---|---|
| 332 | 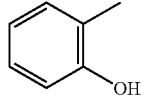 | 494.2178 |
| 333 | 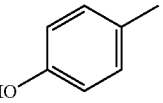 | 500.1795 |
| 334 | 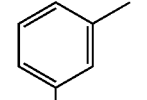 | 500.1746 |
| 335 | 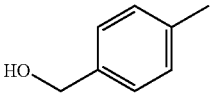 | 524.2994 |
| 336 | 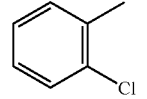 | 508.2383 |
| 337 | 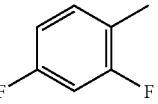 | 508.2341 |
| 338 | 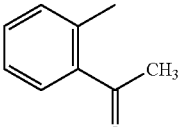 | 510.2195 |
| 339 | 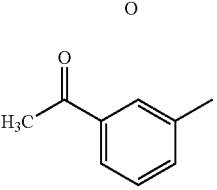 | 510.2144 |
| 340 | 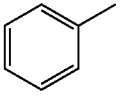 | 519.2164 |
| 341 | 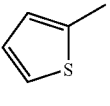 | 524.2298 |
| 342 | 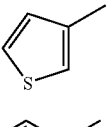 | 528.1834 |
| 343 | 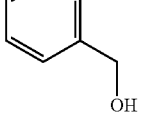 | 530.1990 |
| 344 | 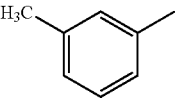 | 536.2293 |
| 345 |  | 536.2316 |

-continued
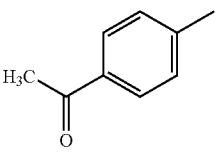
| Example | R | Measured Mass (M + H) |
|---|---|---|
| 346 | 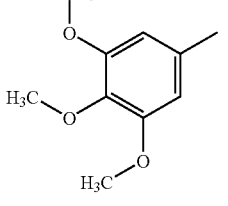 | 536.2313 |
| 347 | 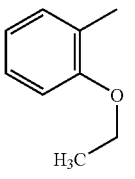 | 538.2466 |
| 348 | 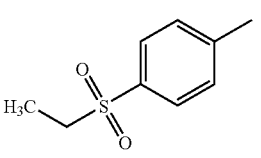 | 538.2468 |
| 349 | 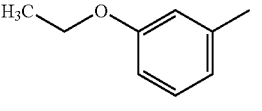 | 593.2872 |
| 350 | 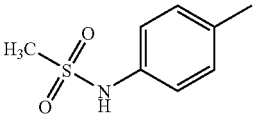 | 554.2466 |
| 351 | 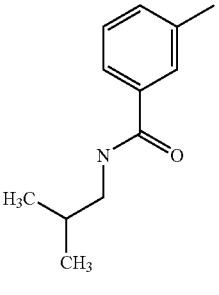 | 566.2402 |
| 352 | 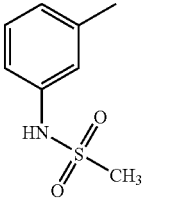 | 572.1982 |
-continued
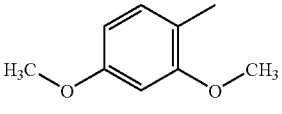
| Example | R | Measured Mass (M + H) |
|---|---|---|
| 353 | 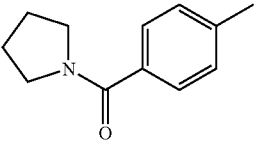 | 584.2515 |
| 354 | 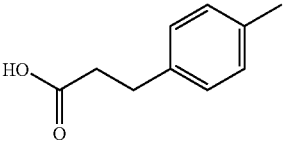 | 586.2136 |
| 355 | 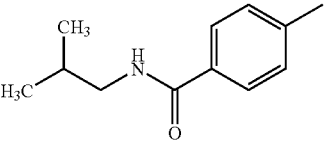 | 587.2072 |
| 356 | 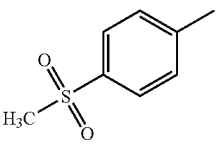 | 587.2101 |
| 357 | 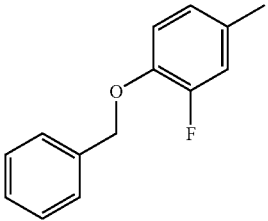 | 591.2743 |
| 358 | | 593.2916 |
| 359 | | 618.2496 |

-continued

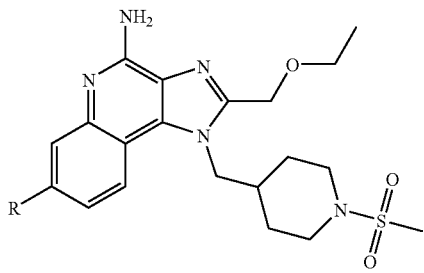

| Example | R | Measured Mass (M + H) |
|---|---|---|
| 360 | (4-methylbenzyl with NH2) | 523.2438 |
| 361 | (3-substituted benzyl with pyrrolidine carbonyl) | 591.2751 |
| 362 | (methylenedioxy methylphenyl) | 538.2087 |

Example 363

2-Ethoxymethyl-1-{2-[2-(methanesulfonyl)ethoxy]-2-methylpropyl}-7-(pyridin-3-yl)-1H-imidazo[4,5-c]quinolin-4-amine

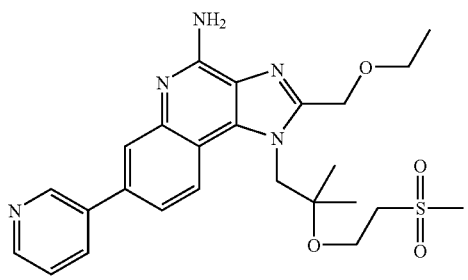

Part A

A solution of methyl vinyl sulfone (3.0 g, 29 mmol) and 1-(7-bromo-2-ethoxymethyl-1H-imidazo[4,5-c]quinolin-1-yl)-2-methylpropan-2-ol (5.4 g, 14 mmol) in anhydrous THF (57 mL) was purged with nitrogen; solid sodium hydride (available as a 60% dispersion in mineral oil, 57 mg, 1.4 mmol) was added. The reaction was stirred for 70 minutes at ambient temperature, at which time an analysis by HPLC indicated a ratio of product to starting material of 3:1. The reaction mixture was combined with material from another run, and water (100 mL) was added. The aqueous layer was separated and extracted with ethyl acetate (100 mL, 50 mL). The combined organic fractions were washed with brine (50 mL), dried over sodium sulfate, filtered, and concentrated under reduced pressure. The residue was purified by column chromatography on silica gel (eluting with 95:5 dichloromethane:methanol) to provide 7-bromo-2-ethoxymethyl-1-{2-[2-(methanesulfonyl)ethoxy]-2-methylpropyl}-1H-imidazo[4,5-c]quinoline.

Part B

A modification of the method described in Example 1 Part H was used to oxidize 7-bromo-2-ethoxymethyl-1-{2-[2-(methanesulfonyl)ethoxy]-2-methylpropyl}-1H-imidazo[4,5-c]quinoline (3.65 g, 7.53 mmol) with 3-chloroperoxybenzoic acid (2.2 g of 60% pure material, 7.53 mmol). The reaction was carried out in chloroform (38 mL) and allowed to proceed for one hour. The crude product was used without purification.

Part C

The material from Part B was aminated according to the method described in Part I of Example 1. The crude product was recrystallized from acetonitrile (35 mL), and the crystals were isolated by filtration, washed with acetonitrile, and dried for four hours under vacuum at 65° C. to provide 7-bromo-2-ethoxymethyl-1-{2-[2-(methanesulfonyl)ethoxy]-2-methylpropyl}-1H-imidazo[4,5-c]quinolin-4-amine as gold, crystalline plates, mp 198-201° C.

Anal. Calcd for $C_{20}H_{27}BrN_4O_4S$: C, 48.10; H, 5.45; N, 11.22. Found: C, 47.96; H, 5.34; N, 11.20.

Part D

7-Bromo-2-ethoxymethyl-1-{2-[2-(methanesulfonyl)ethoxy]-2-methylpropyl}-1H-imidazo[4,5-c]quinolin-4-amine (1.2 g, 2.4 mmol) and pyridine-3-boronic acid 1,3-propanediol cyclic ester (0.47 g, 2.9 mmol) were coupled according to the method described in Part J of Example 1. The work-up procedure used in Part F of Examples 125-135 was followed. The crude product was purified by column chromatography on silica gel (eluting sequentially with 95:5 and 90:10 dichloromethane:methanol) followed by recrystallization from acetonitrile (52 mL/g). The crystals were isolated by filtration, washed with acetonitrile, and dried for four hours under vacuum at 65° C. to provide 0.70 g of 2-ethoxymethyl-1-{2-[2-(methanesulfonyl)ethoxy]-2-methylpropyl}-7-(pyridin-3-yl)-1H-imidazo[4,5-c]quinolin-4-amine as white, crystalline plates, mp 202-204° C.

Anal. Calcd for $C_{25}H_{31}N_5O_4S$: C, 60.34; H, 6.28; N, 14.07. Found: C, 60.19; H, 6.45; N, 14.02.

Example 364

2-Ethoxymethyl-1-{2-[2-(methanesulfonyl)ethoxy]-2-methylpropyl}-7-(5-methoxypyridin-3-yl)-1H-imidazo[4,5-c]quinolin-4-amine

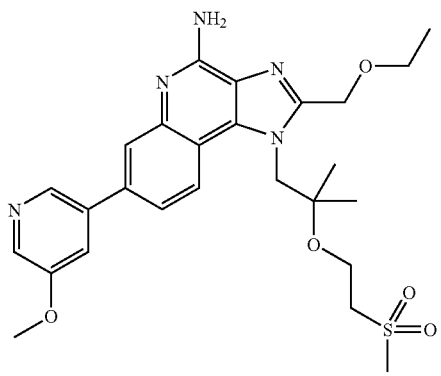

7-Bromo-2-ethoxymethyl-1-{2-[2-(methanesulfonyl)ethoxy]-2-methylpropyl}-1H-imidazo[4,5-c]quinolin-4-amine (1.1 g, 2.2 mmol) and pyridine-5-methoxy-3-boronic acid pinacol ester (0.63 g, 2.7 mmol) were coupled according to the method described in Part J of Example 1. The work-up procedure used in Part F of Examples 125-135 was followed. The crude product was purified by HPFC (eluting with dichloromethane:methanol in a gradient from 99:1 to 85:15) followed by trituration with ethyl acetate. The crystals were isolated by filtration and dried for four hours under vacuum at 65° C. to provide 0.1 g of 2-ethoxymethyl-1-{2-[2-(methanesulfonyl)ethoxy]-2-methylpropyl}-7-(5-methoxypyridin-3-yl)-1H-imidazo[4,5-c]quinolin-4-amine as a white powder, mp 186-188° C.

Anal. Calcd for $C_{26}H_{33}N_5O_5S$: C, 59.18; H, 6.30; N, 13.27. Found: C, 58.96; H, 6.64; N, 13.09.

Example 365

Dimethyl 4-[4-amino-2-ethoxymethyl-7-(pyridin-3-yl)-1H-imidazo[4,5-c]quinolin-1-yl]butane-1-sulfonamide

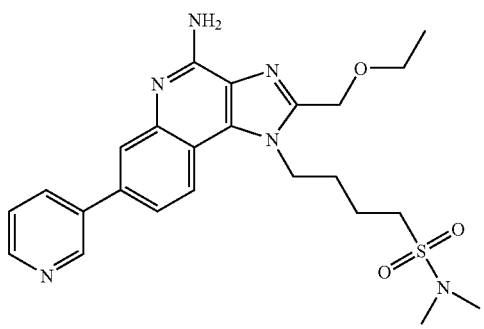

Part A

A modification of the method described in Part E of Example 1 was used to treat 7-bromo-4-chloro-3-nitroquinoline (20.0 g, 69.6 mmol) with 4-amino-1-butanol (6.9 mL, 76.5 mmol). The addition of 4-amino-1-butanol was carried out at ambient temperature. The product, 4-(7-bromo-3-nitroquinolin-4-ylamino)butan-1-ol (21.1 g) was isolated as a yellow solid and used without purification.

Part B

A suspension of 4-(7-bromo-3-nitroquinolin-4-ylamino)butan-1-ol (20.75 g, 61.0 mmol) in dichloromethane (220 mL) was cooled to 0° C.; thionyl chloride (4.90 mL, 67.1 mmol) was added dropwise over a period of ten minutes. The reaction was stirred at 0° C. for five minutes, allowed to warm to ambient temperature, and stirred overnight. Aqueous sodium bicarbonate (500 mL of 50%) was slowly added. The aqueous layer was separated and extracted with dichloromethane (3×100 mL). The combined organic fractions were dried over magnesium sulfate, filtered, and concentrated under reduced pressure to yield an orange semi-solid. An analysis by LCMS indicated the presence of starting material, and the semi-solid was dissolved in dichloromethane (150 mL) and treated with thionyl chloride (3.0 mL) as described above. Following the work-up procedure, the crude product was purified by column chromatography on silica gel (eluting with dichloromethane:methanol in a gradient from 100:0 to 95:5) to provide 8.3 g of (7-bromo-3-nitroquinolin-4-yl)-(4-chlorobutyl)amine as a yellow solid.

Part C

A suspension of (7-bromo-3-nitroquinolin-4-yl)-(4-chlorobutyl)amine (8.05 g, 22.5 mmol) in methanol (250 mL) was cooled to 0° C.; a solution of sodium hydrosulfite (19.5 g, 112 mmol) in water (80 mL) was added dropwise over a period of 30 minutes. The reaction was stirred at ambient temperature for two hours and then concentrated under reduced pressure. The residue was partitioned between dichloromethane (300 mL) and aqueous sodium bicarbonate (150 mL of 50%). The aqueous layer was separated and extracted with dichloromethane (2×50 mL). The combined organic fractions were dried over magnesium sulfate, filtered, and concentrated under reduced pressure to provide 7.25 g of crude 7-bromo-$N^4$-(4-chlorobutyl)quinoline-3,4-diamine as a light brown semi-solid.

Part D

A modification of the method described in Part C of Examples 125-135 was used to treat 7-bromo-$N^4$-(4-chlorobutyl)quinoline-3,4-diamine (7.25 g, 22.1 mmol) with ethoxyacetyl chloride (2.76 mL, 24.3 mmol). After the reaction was stirred for one hour, it was concentrated under reduced pressure to provide N-[7-bromo-4-(4-chlorobutylamino)quinolin-3-yl]-2-ethoxyacetamide hydrochloride as a yellow solid.

Part E

Aqueous sodium hydroxide (16.6 mL of 2 M, 33.2 mmol) was added to a suspension of the material from Part D in ethanol (100 mL), and the reaction was heated to 60° C. over a period of 30 minutes and stirred at 60° C. for one hour. The reaction was allowed to cool to ambient temperature and then concentrated under reduced pressure. The residue was partitioned between water (150 mL) and dichloromethane (300 mL). The aqueous layer was separated and extracted with dichloromethane (2×75 mL). The combined organic fractions were washed with brine (100 mL), dried over magnesium sulfate, filtered, and concentrated under reduced pressure. The crude product was purified by column chromatography on silica gel (eluting with ethyl acetate:chloroform in a gradient from 20:80 to 100:0) to provide 4.46 g of 7-bromo-1-(4-chlorobutyl)-2-ethoxymethyl-1H-imidazo[4,5-c]quinoline as a tan solid.

Part F

Potassium thioacetate (1.70 g, 14.9 mmol) was added in one portion to a stirred solution of 7-bromo-1-(4-chlorobutyl)-2-ethoxymethyl-1H-imidazo[4,5-c]quinoline (5.37 g, 13.5 mmol) in DMF (65 mL), and the reaction was stirred at ambient temperature for 21 hours. The DMF was removed under reduced pressure, and the residue was partitioned between dichloromethane (300 mL) and water (150 mL). The organic layer was separated, washed with brine (120 mL), dried over magnesium sulfate, filtered, and concentrated to provide 6.09 g of thioacetic acid S-[4-(7-bromo-2-ethoxymethyl-1H-imidazo[4,5-c]quinolin-1-yl)butyl]ester as a brown solid.

Part G

Nitrogen was bubbled through a solution of thioacetic acid S-[4-(7-bromo-2-ethoxymethyl-1H-imidazo[4,5-c]quinolin-1-yl)butyl]ester (1.93 g, 4.42 mmol) in methanol (45 mL), and then sodium methoxide (2.5 mL of 25% by weight in methanol, 11.1 mmol) was added dropwise over a period of three minutes. The yellow solution was stirred at ambient temperature for one hour and then concentrated under reduced pressure. The residue was partitioned between dichloromethane (250 mL) and water (125 mL), and hydrochloric acid (~3 mL of 2 M) was added to adjust the mixture to pH 7. The aqueous layer was separated and extracted with dichloromethane (50 mL); the combined organic fractions were washed with brine (100 mL), dried over magnesium sulfate, filtered, and concentrated under reduced pressure to provide 1.73 g of 4-(7-bromo-2-ethoxymethyl-1H-imidazo[4,5-c]quinolin-1-yl)butane-1-thiol as a tan solid.

Part H

A solution of 4-(7-bromo-2-ethoxymethyl-1H-imidazo[4,5-c]quinolin-1-yl)butane-1-thiol (1.73 g, 4.39 mmol) in concentrated hydrochloric acid (7.5 mL) and water (5 mL) was cooled to 0° C. A solution of sodium chlorate (0.61 g, 5.7 mmol) in water (2.5 mL) was added dropwise with vigourous stirring over a period of three minutes. The reaction was stirred at 0° C. for 90 minutes then diluted with dichloromethane (50 mL). Aqueous potassium carbonate (8 mL of 6M) was slowly added to adjust the mixture to pH 5. Dichloromethane (100 mL) and water (75 mL) were added, and the reaction was allowed to warm to ambient temperature with stirring. The aqueous layer was separated and extracted with dichloromethane (3×40 mL). The combined organic fractions were dried over magnesium sulfate, filtered, and concentrated under reduced pressure to provide 1.61 g of 4-(7-bromo-2-ethoxymethyl-1H-imidazo[4,5-c]quinolin-1-yl)butane-1-sulfonyl chloride as a tan solid.

Part I

Dimethylamine hydrochloride (0.60 g, 7.3 mmol) and aqueous potassium carbonate (1.46 mL of 6 M, 8.7 mmol) were sequentially added to a stirred solution of 4-(7-bromo-2-ethoxymethyl-1H-imidazo[4,5-c]quinolin-1-yl)butane-1-sulfonyl chloride (1.61 g, 3.49 mmol) in dichloromethane (35 mL), and the reaction was stirred at ambient temperature for 80 minutes. Dichloromethane (180 mL) and aqueous sodium bicarbonate (60 mL) were added. The aqueous layer was separated and extracted with dichloromethane (2×40 mL); the combined organic fractions were dried over magnesium sulfate, filtered, and concentrated under reduced pressure to provide 1.49 g of dimethyl 4-(7-bromo-2-ethoxymethyl-1H-imidazo[4,5-c]quinolin-1-yl)butane-1-sulfonamide as a tan solid.

Part J

3-Chloroperoxybenzoic acid (0.126 g of 70% pure material, 0.73 mmol) was added in one portion to a stirred solution of dimethyl 4-(7-bromo-2-ethoxymethyl-1H-imidazo[4,5-c]quinolin-1-yl)butane-1-sulfonamide (0.30 g, 0.63 mmol) in chloroform (7 mL), and the solution was stirred for two hours at ambient temperature. Ammonium hydroxide (2 mL) and p-toluenesulfonyl chloride (0.15 g, 0.76 mmol) were sequentially added, and the mixture was stirred at ambient temperature for one hour. Dichloromethane (100 mL) was added, and the mixture was washed sequentially with 2 M aqueous sodium hydroxide (2×30 mL), saturated aqueous sodium bicarbonate (2×30 mL), and brine (30 mL); dried over magnesium sulfate; filtered; and concentrated under reduced pressure. The crude product was purified by column chromatography on silica gel (eluting with ethyl acetate:ethanol in a gradient from 100:0 to 80:20) followed by recrystallization from dichloromethane:heptane. The crystals were dried for two hours under vacuum at 40° C. to provide 0.185 g of dimethyl 4-(4-amino-7-bromo-2-ethoxymethyl-1H-imidazo[4,5-c]quinolin-1-yl)butane-1-sulfonamide as a white solid, mp 193° C.

Anal. Calcd for $C_{19}H_{26}BrN_5O_3S$: C, 47.11; H, 5.41; N, 14.46. Found: C, 46.85; H, 5.48; N, 14.14.

Part K

Dimethyl 4-(4-amino-7-bromo-2-ethoxymethyl-1H-imidazo[4,5-c]quinolin-1-yl)butane-1-sulfonamide (1.00 g, 2.06 mmol), which was prepared in a separate run, and pyridine-3-boronic acid 1,3-propanediol ester (0.40 g, 2.5 mmol) were coupled according to the method described in Part J of Example 1. The reaction was heated at reflux for 14 hours, and the work-up procedure used in Part F of Examples 125-135 was followed. The crude product was purified by column chromatography on silica gel (eluting with chloroform:CMA in a gradient from 95:5 to 80:20) and then triturated sequentially with dichloromethane and methanol, isolated by filtration, and dried for two days under high vacuum at 140° C. to provide 0.695 g of dimethyl 4-[4-amino-2-ethoxymethyl-7-(pyridin-3-yl)-1H-imidazo[4,5-c]quinolin-1-yl]butane-1-sulfonamide as yellow needles, mp 205-206° C.

Anal. Calcd for $C_{24}H_{30}N_6O_3S$: C, 59.73; H, 6.27; N, 17.41. Found: C, 59.49; H, 6.24; N, 17.36.

Example 366

Dimethyl 4-[4-amino-2-ethoxymethyl-7-phenyl-1H-imidazo[4,5-c]quinolin-1-yl]butane-1-sulfonamide

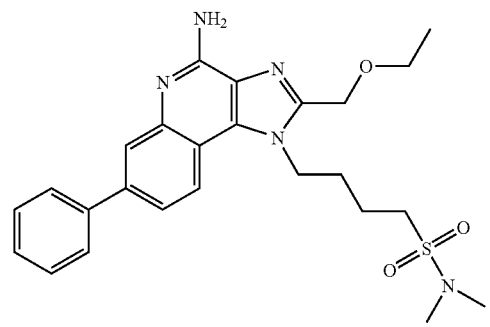

Dimethyl 4-(4-amino-7-bromo-2-ethoxymethyl-1H-imidazo[4,5-c]quinolin-1-yl)butane-1-sulfonamide (0.66 g, 1.4 mmol) and phenyl boronic acid (0.20 g, 1.6 mmol) were coupled according to the method described in Part J of Example 1. The reaction was heated at reflux for 14 hours, and the work-up procedure used in Part F of Examples 125-135 was followed. The crude product was recrystallized from methanol and then purified by column chromatography on silica gel (eluting with chloroform:CMA in a gradient from 100:0 to 90:10). The solid was then purified by HPFC to provide 0.14 g of dimethyl 4-[4-amino-2-ethoxymethyl-7-phenyl-1H-imidazo[4,5-c]quinolin-1-yl]butane-1-sulfonamide as Off-white needles, mp 207-208° C.

Anal. Calcd for $C_{25}H_{31}N_5O_3S$: C, 61.56; H, 6.55; N, 14.36. Found: C, 61.65; H, 6.67; N, 14.30.

Example 367

4-Methoxybenzyl 4-[4-amino-2-ethoxymethyl-7-(pyridin-3-yl)-1H-imidazo[4,5-c]quinolin-1-yl]butane-1-sulfonamide

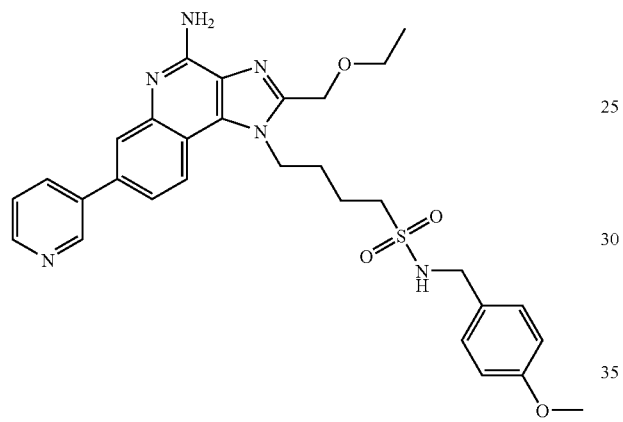

Part A

Over a period of three minutes, p-methoxybenzylamine (1.9 mL, 15 mmol) was added dropwise to a stirred solution of 4-(7-bromo-2-ethoxymethyl-1H-imidazo[4,5-c]quinolin-1-yl)butane-1-sulfonyl chloride (2.9 g, 6.1 mmol), prepared according to the methods described in Parts A-H of Example 365, in dichloromethane (60 mL). The reaction was stirred at ambient temperature for 90 minutes then diluted with dichloromethane (150 mL) and brine (100 mL). The aqueous layer was separated and extracted with dichloromethane (2×30 mL); the combined organic fractions were dried over magnesium sulfate, filtered, and concentrated under reduced pressure. The residue was triturated with dichloromethane (30 mL) to provide a white solid, which was isolated by filtration. The filtrate was concentrated under reduced pressure, and the residue was purified by column chromatography on silica gel (eluting with chloroform:CMA in a gradient from 90:10 to 20:80) to provide a white solid, which was triturated with dichloromethane and isolated by filtration. The solids were combined to yield 1.92 g of 4-methoxybenzyl 4-(7-bromo-2-ethoxymethyl-1H-imidazo[4,5-c]quinolin-1-yl)butane-1-sulfonamide as a white solid.

Part B

4-Methoxybenzyl 4-(7-bromo-2-ethoxymethyl-1H-imidazo[4,5-c]quinolin-1-yl)butane-1-sulfonamide was oxidized and then aminated according to the general method described in Part J of Example 365. The oxidation reaction was stirred for five hours, and the amination reaction was stirred overnight. The crude product was purified twice by column chromatography on silica gel (eluting with chloroform:CMA in a gradient from 95:5 to 80:20) to provide 0.80 g of 4-methoxybenzyl 4-(4-amino-7-bromo-2-ethoxymethyl-1H-imidazo[4,5-c]quinolin-1-yl)butane-1-sulfonamide. This material was mixed with material from another run.

Part C

4-Methoxybenzyl 4-(4-amino-7-bromo-2-ethoxymethyl-1H-imidazo[4,5-c]quinolin-1-yl)butane-1-sulfonamide (1.16 g, 2.0 mmol) and pyridine-3-boronic acid (0.30 g, 2.4 mmol) were coupled according to the method described in Part J of Example 1. The reaction was heated at reflux for 14 hours, at which time additional pyridine-3-boronic acid (0.3 equivalent) was added and the reaction was heated for an additional five hours. The work-up procedure used in Part F of Examples 125-135 was followed. The crude product was purified by column chromatography on silica gel (eluting with chloroform:CMA in a gradient from 100:0 to 80:20) and then triturated with methanol, isolated by filtration, and dried for 20 hours under high vacuum at 140° C. to provide 0.62 g of 4-methoxybenzyl 4-[4-amino-2-ethoxymethyl-7-(pyridin-3-yl)-1H-imidazo[4,5-c]quinolin-1-yl]butane-1-sulfonamide as a beige powder, mp 230-231.5° C.

Anal. Calcd for $C_{30}H_{34}N_6O_4S$: C, 62.70; H, 5.96; N, 14.62. Found: C, 62.39; H, 6.06; N, 14.56.

Example 368

4-[4-Amino-2-ethoxymethyl-7-(pyridin-3-yl)-1H-imidazo[4,5-c]quinolin-1-yl]butane-1-sulfonamide

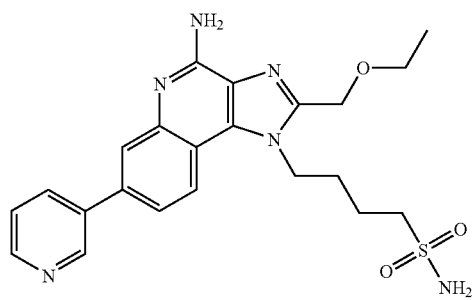

A solution of 4-methoxybenzyl 4-[4-amino-2-ethoxymethyl-7-(pyridin-3-yl)-1H-imidazo[4,5-c]quinolin-1-yl]butane-1-sulfonamide (0.50 g, 0.88 mmol) in trifluoroacetic acid (5 mL) was stirred at ambient temperature for four hours and then concentrated under reduced pressure. The residue was dissolved in methanol and concentrated under reduced pressure; this process was repeated three times. The residue was then suspended in water, and 2 M aqueous sodium hydroxide was added to adjust to pH 7. The mixture was stirred for 30 minutes, and the resulting solid was isolated by filtration, washed with water, and purified by HPFC (eluting with chloroform:CMA in a gradient from 100:0 to 30:70). The purified product was dried overnight under high vacuum at 80° C. to provide 0.31 g of 4-[4-amino-2-ethoxymethyl-7-(pyridin-3-yl)-1H-imidazo[4,5-c]quinolin-1-yl]butane-1-sulfonamide as tan needles, mp 250-251.5° C.

Anal. Calcd for $C_{22}H_{26}N_6O_3S$: C, 58.13; H, 5.77; N, 18.49. Found: C, 57.89; H, 5.44; N, 18.16.

Example 369

Methyl 4-[4-amino-2-ethoxymethyl-7-(pyridin-3-yl)-1H-imidazo[4,5-c]quinolin-1-yl]butane-1-sulfonamide

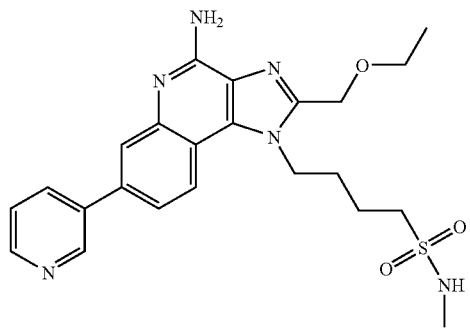

Part A

The method described in Part I of Example 365 was used to treat 4-(7-bromo-2-ethoxymethyl-1H-imidazo[4,5-c]quinolin-1-yl)butane-1-sulfonyl chloride (1.61 g, 3.49 mmol), prepared according to the methods described in Parts A-H of Example 365, with methylamine hydrochloride (0.50 g, 7.3 mmol) and aqueous potassium carbonate (1.3 mL of 6 M, 7.7 mmol) to provide 1.4 g of methyl 4-[7-bromo-2-ethoxymethyl-1H-imidazo[4,5-c]quinolin-1-yl]butane-1-sulfonamide as a tan solid.

Part B

Methyl 4-(7-bromo-2-ethoxymethyl-1H-imidazo[4,5-c]quinolin-1-yl)butane-1-sulfonamide was oxidized and then aminated according to the general method described in Part J of Example 365. The oxidation reaction was stirred for three hours, and the amination reaction was stirred for 90 minutes. The crude product was recrystallized from a mixture of dichloromethane, heptane, and a trace of methanol and isolated by filtration. The mother liquor was concentrated and purified by column chromatography on silica gel (eluting with chloroform:CMA in a gradient from 95:5 to 80:20) and then triturated with dichloromethane and isolated by filtration. The products were dried overnight under high vacuum at 140° C. to provide a total of 0.86 g of methyl 4-(4-amino-7-bromo-2-ethoxymethyl-1H-imidazo[4,5-c]quinolin-1-yl)butane-1-sulfonamide as a white solid, mp 199-200° C.

Anal. Calcd for $C_{18}H_{24}BrN_5O_3S$: C, 45.96; H, 5.14; N, 14.89. Found: C, 46.02; H, 4.85; N, 14.65.

Part C

Methyl 4-(4-amino-7-bromo-2-ethoxymethyl-1H-imidazo[4,5-c]quinolin-1-yl)butane-1-sulfonamide (0.78 g, 1.7 mmol) and pyridine-3-boronic acid 1,3-propanediol cyclic ester (0.33 g, 2.0 mmol) were coupled according to the method described in Part J of Example 1. The reaction was heated at reflux for 15 hours, at which time additional pyridine-3-boronic acid 1,3-propanediol cyclic ester, palladium acetate, and triphenylphosphine were added, and the reaction was heated for an additional three hours. The work-up procedure used in Part F of Examples 125-135 was followed. The crude product was purified twice by column chromatography on silica gel (eluting with chloroform:CMA in a gradient from 95:5 to 70:30) and then triturated with methanol, isolated by filtration, and dried for eight hours under high vacuum at 100° C. to provide 0.78 g of methyl 4-[4-amino-2-ethoxymethyl-7-(pyridin-3-yl)-1H-imidazo[4,5-c]quinolin-1-yl]butane-1-sulfonamide as off-white needles, mp 216-218° C.

Anal. Calcd for $C_{23}H_{28}N_6O_3S \cdot 0.23 H_2O$: C, 58.44; H, 6.07; N, 17.78. Found: C, 58.08; H, 5.97; N, 17.71.

Example 370

Dimethyl 5-[4-amino-2-ethoxymethyl-7-(pyridin-3-yl)-1H-imidazo[4,5-c]quinolin-1-yl]pentane-1-sulfonamide

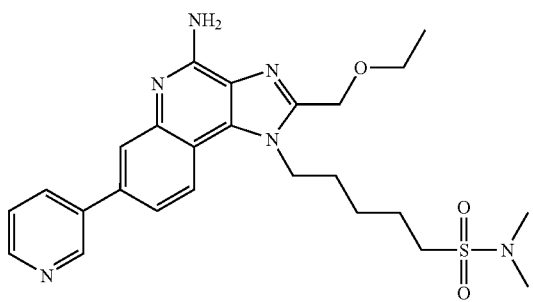

Part A

The method described in Part A of Example 365 was used to treat 7-bromo-4-chloro-3-nitroquinoline (20.0 g, 69.5 mmol) with 4-amino-1-pentanol (7.9 g, 76 mmol) to provide 24.0 g of 5-(7-bromo-3-nitroquinolin-4-ylamino)pentan-1-ol as a yellow solid.

Part B

A suspension of 5-(7-bromo-3-nitroquinolin-4-ylamino)pentan-1-ol (0.92 g, 2.6 mmol) in dichloromethane (13 mL) was cooled to 0° C.; thionyl chloride was added dropwise. The reaction was stirred for five minutes at 0° C. then allowed to warm to ambient temperature and stirred overnight. Saturated aqueous sodium bicarbonate (25 mL) was slowly added followed by water (25 mL). The aqueous layer was separated and extracted with dichloromethane (3×50 mL), and the combined organic fractions were dried over magnesium sulfate and concentrated under reduced pressure to provide 0.91 g of (7-bromo-3-nitroquinolin-4-yl)-(5-chloropentyl)amine as a yellow semisolid.

Part C

The methods described in Parts C-E of Example 365 were used to convert (7-bromo-3-nitroquinolin-4-yl)-(5-chloropentyl)amine to 7-bromo-1-(5-chloropentyl)-2-ethoxymethyl-1H-imidazo[4,5-c]quinoline. The crude product was purified twice by column chromatography on silica gel (eluting with chloroform:methanol in a gradient from 100:0 to 90:10).

Part D

Thiourea (0.29 g, 3.8 mmol) and potassium iodide (0.052 g, 3.1 mmol) were sequentially added to a suspension of 7-bromo-1-(5-chloropentyl)-2-ethoxymethyl-1H-imidazo[4,5-c]quinoline (1.3 g, 3.2 mmol) in DMF (15 mL), and the reaction was heated at 110° C. for 24 hours. The DMF was removed under reduced pressure, and the residue was partitioned between saturated aqueous sodium bicarbonate (40 mL) and dichloromethane (50 mL). The mixture was adjusted to pH 7 with the addition of 10% hydrochloric acid. Product remained on the walls of the reaction flask and was dissolved with methanol. The resulting solution was concentrated under reduced pressure to provide a solid. The aqueous layer was concentrated under reduced pressure, and the resulting solid was triturated with methanol and isolated by filtration. The filtrate was concentrated under reduced pressure, and the residue was triturated and isolated as described above. The isolated solids were combined and dried under high vacuum to provide 1.49 g of 2-[5-(7-bromo-2-ethoxymethyl-1H-imidazo[4,5-c]quinolin-1-yl)pentyl]isothiourea hydrochloride as a yellow solid.

Part E

A solution of 2-[5-(7-bromo-2-ethoxymethyl-1H-imidazo[4,5-c]quinolin-1-yl)pentyl]isothiourea hydrochloride (1.49 g, 3.16 mmol) in 7 M hydrochloric acid (8 mL) was cooled to 0° C. A solution of sodium chlorate (0.44 g, 4.1 mmol) in water (1.0 mL) was added dropwise with stirring, and the reaction was stirred at 0° C. for one hour. A precipitate formed and was isolated by filtration, washed with ice-cold water (4×4 mL), and dried under high vacuum to provide 0.92 g of 5-(7-bromo-2-ethoxymethyl-1H-imidazo[4,5-c]quinolin-1-yl)pentane-1-sulfonyl chloride as a yellow solid.

Part F

The method described in Part I of Example 365 was used to treat 5-(7-bromo-2-ethoxymethyl-1H-imidazo[4,5-c]quinolin-1-yl)pentane-1-sulfonyl chloride (0.91 g, 1.9 mmol) with dimethylamine hydrochloride (0.33 g, 4.0 mmol). The crude product was purified by HPFC (eluting with ethyl acetate:methanol in a gradient from 100:0 to 90:10) to provide 0.57 g of dimethyl 5-(7-bromo-2-ethoxymethyl-1H-imidazo[4,5-c]quinolin-1-yl)pentane-1-sulfonamide as a yellow solid.

Part G

Dimethyl 5-(7-bromo-2-ethoxymethyl-1H-imidazo[4,5-c]quinolin-1-yl)pentane-1-sulfonamide was oxidized and aminated according to the methods described in Part J of Example 365. The crude product was purified twice by HPFC (eluting with chloroform:CMA in a gradient from 100:0 to 90:10) and then triturated with ethyl acetate, isolated by filtration, washed with ethyl acetate (2×1 mL), and dried for several hours under high vacuum at 150° C. to provide dimethyl 5-(4-amino-7-bromo-2-ethoxymethyl-1H-imidazo[4,5-c]quinolin-1-yl)pentane-1-sulfonamide as a yellow solid.

Part H

Dimethyl 5-(4-amino-7-bromo-2-ethoxymethyl-1H-imidazo[4,5-c]quinolin-1-yl)pentane-1-sulfonamide (0.26 g, 0.53 mmol) and pyridine-3-boronic acid (0.78 g, 0.63 mmol) were coupled according to the method described in Part J of Example 1. The reaction was heated at 100° C. for 31 hours, at which time additional palladium acetate (0.002 equivalent) was added. Heating was resumed for 14 hours, and then additional pyridine-3-boronic acid (0.3 equivalent) was added. The reaction was heated for another 22 hours. The work-up procedure used in Part F of Examples 125-135 was followed. The crude product was purified twice by HPFC (eluting with chloroform:CMA in a gradient from 100:0 to 80:20) and then triturated with ethyl acetate and isolated by filtration. The product was finally recrystallized from isopropanol, isolated by filtration, and dried for eight hours under high vacuum at 100° C. to provide 0.090 g of dimethyl 5-[4-amino-2-ethoxymethyl-7-(pyridin-3-yl)-1H-imidazo[4,5-c]quinolin-1-yl]pentane-1-sulfonamide as a white powder, mp 159-160° C.

Anal. Calcd for $C_{25}H_{32}N_6O_3S$: C, 60.46; H, 6.49; N, 16.92. Found: C, 60.33; H, 6.56; N, 16.81.

Example 371

Methyl 5-[4-amino-2-ethoxymethyl-7-(pyridin-3-yl)-1H-imidazo[4,5-c]quinolin-1-yl]pentane-1-sulfonamide

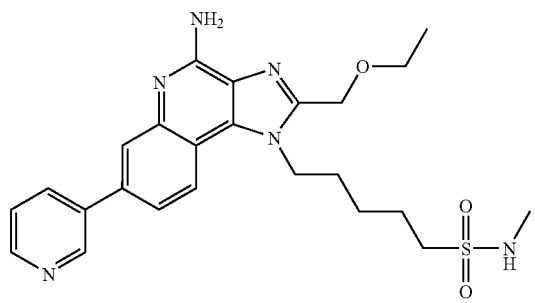

Part A

The method described in Part I of Example 365 was used to treat 5-(7-bromo-2-ethoxymethyl-1H-imidazo[4,5-c]quinolin-1-yl)pentane-1-sulfonyl chloride (1.11 g, 2.33 mmol) with methylamine hydrochloride (0.33 g, 4.9 mmol). The reaction was stirred overnight, and additional methylamine hydrochloride (0.3 equivalent) and 6 M potassium carbonate (0.4 equivalent) were added. The reaction was stirred for an additional four hours. The crude product was purified by HPFC (eluting with chloroform:CMA in a gradient from 100:0 to 80:20) to provide 0.80 g of methyl 5-(7-bromo-2-ethoxymethyl-1H-imidazo[4,5-c]quinolin-1-yl)pentane-1-sulfonamide as a white solid.

Part B

Methyl 5-(7-bromo-2-ethoxymethyl-1H-imidazo[4,5-c]quinolin-1-yl)pentane-1-sulfonamide was oxidized and aminated according to the methods described in Part J of Example 365. The oxidation reaction was stirred for three hours, and the amination reaction was stirred for 90 minutes. The product precipitated from the reaction mixture and was isolated by filtration. The crude product was purified by HPFC (eluting with chloroform:CMA in a gradient from 100:0 to 80:20) to provide methyl 5-(4-amino-7-bromo-2-ethoxymethyl-1H-imidazo[4,5-c]quinolin-1-yl)pentane-1-sulfonamide as a white solid.

Part C

Methyl 5-(4-amino-7-bromo-2-ethoxymethyl-1H-imidazo[4,5-c]quinolin-1-yl)pentane-1-sulfonamide (0.47 g, 0.97 mmol) was coupled with pyridine-3-boronic acid (0.14 g, 1.2 mmol) according to the methods described in Part J of Example 1 and Part H of Example 370. The crude product was purified twice by HPFC (eluting with chloroform:CMA in a gradient from 100:0 to 70:30) and then recrystallized from methanol, isolated by filtration, and dried for 5 days under high vacuum at 100-140° C. to provide 0.13 g of methyl 5-[4-amino-2-ethoxymethyl-7-(pyridin-3-yl)-1H-imidazo[4,5-c]quinolin-1-yl]pentane-1-sulfonamide as a white powder, mp 191-192° C.

Anal. Calcd for $C_{24}H_{30}N_6O_3S$: C, 59.73; H, 6.27; N, 17.41. Found: C, 59.48; H, 6.58; N, 17.56.

Examples 372-376

Part A

A solution of tert-butyl {4-[4-amino-2-ethoxymethyl-7-(pyridin-3-yl)-1H-imidazo[4,5-c]quinolin-1-yl]butyl}carbamate (40.35 g, 82.24 mmol) in concentrated hydrochloric acid (400 mL) was stirred for one hour, filtered, and concentrated under reduced pressure. The residue was dissolved in a minimal amount of water, and 50% aqueous sodium hydroxide was added to adjust the solution to pH 14. Chloroform (1.2 L) and a mixture of saturated aqueous sodium bicarbonate and 1% aqueous sodium carbonate (600 mL) were added; the mixture was stirred for 30 minutes. The organic layer was separated, dried over sodium sulfate, and concentrated under reduced pressure to provide 36.48 g of 1-(4-aminobutyl)-2-ethoxymethyl-7-(pyridin-3-yl)-1H-imidazo[4,5-c]quinolin-4-amine as a light yellow solid.

Part B

Triethylamine (1.39 mL, 10.0 mmol) was added to a solution of 1-(4-aminobutyl)-2-ethoxymethyl-7-(pyridin-3-yl)-1H-imidazo[4,5-c]quinolin-4-amine (3.00 g, 7.70 mmol) in chloroform (150 mL); the reagent (1.1 equivalents) listed in the table below was then added. The reaction was stirred for one hour or until completion; additional triethylamine and the indicated reagent were added as need until the reaction was complete. Deionized water (15-20 mL) was added, and the mixture was stirred for five minutes. The organic layer was separated, washed with 1% aqueous sodium carbonate, optionally dried with sodium sulfate and filtered, and concentrated under reduced pressure. The crude product was recrystallized from the solvent listed in the table below and dried overnight in a drying oven to provide the compound with the structure shown below.

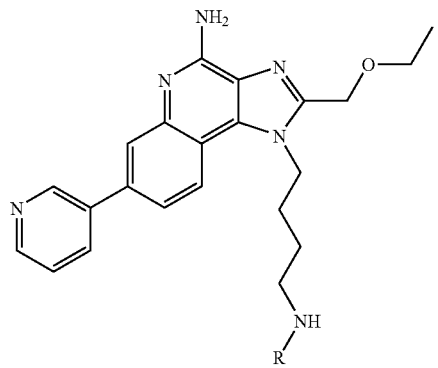

| Example | Reagent | Recrystallization solvent | R |
|---|---|---|---|
| 372 | Butyryl chloride | Acetonitrile:water 83:17 | H₃C-CH₂-CH₂-C(=O)- |
| 373 | Isobutyryl chloride | Isopropanol then acetonitrile:water | (CH₃)₂CH-C(=O)- |
| 374 | Cyclopentanecarbonyl chloride | Acetonitrile:water, isopropanol, methyl acetate, then isopropanol | cyclopentyl-C(=O)- |
| 375 | Methanesulfonic anhydride | Precipitated during work-up, no recrystallization done | H₃C-S(=O)₂- |
| 376 | 1-Propanesulfonyl chloride | Isopropanol then acetonitrile:water 75:25 | H₃C-CH₂-CH₂-S(=O)₂- |

| Example | Name | Form | mp (°C.) | Anal. |
|---|---|---|---|---|
| 372 | N-{4-[4-Amino-2-ethoxymethyl-7-(pyridin-3-yl)-1H-imidazo[4,5-c]quinolin-1-yl]butyl}butyramide | White solid | 150-152 | Calcd for $C_{26}H_{32}N_6O_2$: C, 67.80; H, 7.00; N, 18.25. Found: C, 67.51; H, 7.29; N, 18.18. |
| 373 | N-{4-[4-Amino-2-ethoxymethyl-7-(pyridin-3-yl)-1H-imidazo[4,5-c]quinolin-1-yl]butyl}-2-methylpropanamide | White solid | 200-202 | Calcd for $C_{26}H_{32}N_6O_2$: C, 67.80; H, 7.00; N, 18.25. Found: C, 67.47; H, 7.09; N, 18.16. |
| 374 | N-{4-[4-Amino-2-ethoxymethyl-7-(pyridin-3-yl)-1H-imidazo[4,5-c]quinolin-1-yl]butyl}cyclopentanecarboxamide | White solid | 196-198 | Calcd for $C_{28}H_{34}N_6O_2 \cdot 0.25H_2O$: C, 68.48; H, 7.08; N, 17.11. Found: C, 68.28; H, 7.36; N, 17.00. |
| 375 | N-{4-[4-Amino-2-ethoxymethyl-7-(pyridin-3-yl)-1H-imidazo[4,5-c]quinolin-1-yl]butyl}methanesulfonamide | White solid | 186-188 | Calcd for $C_{23}H_{28}N_6O_3S \cdot 0.25H_2O$: C, 58.39; H, 6.07; N, 17.76. Found: C, 58.31; H, 5.75; N, 17.72. |
| 376 | N-{4-[4-Amino-2-ethoxymethyl-7-(pyridin-3-yl)-1H-imidazo[4,5-c]quinolin-1-yl]butyl}propane-1-sulfonamide | Off-white solid | 178-180 | Calcd for $C_{25}H_{32}N_6O_3S$: C, 60.46; H, 6.49; N, 16.92. Found: C, 60.22; H, 6.42; N, 16.77. |

Examples 377-379

The isocyanate indicated in the table below was added slowly to a solution of 1-(4-aminobutyl)-2-ethoxymethyl-7-(pyridin-3-yl)-1H-imidazo[4,5-c]quinolin-4-amine (1 equivalent) in chloroform (20-50 mL/g). A precipitate formed within five minutes or formed upon cooling the reaction mixture to ~0° C. after 15 minutes. The precipitate was isolated by filtration and dried overnight in an oven. The solid was slurried with the solvent(s) listed in the table below, isolated by filtration, and dried overnight in an oven to provide the product with the structure shown in the table below.

Examples 377-379

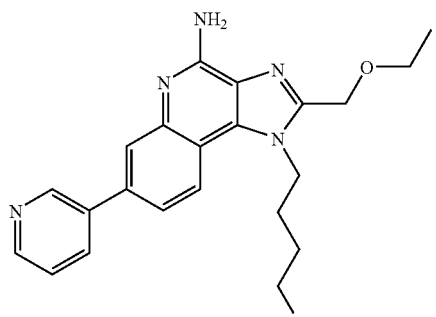

| Example | Isocyanate | Purification Solvent | R |
|---|---|---|---|
| 377 | Cyclopentyl isocyanate | Acetonitrile:water 75:25 | cyclopentyl-NHC(O)- |
| 378 | Propyl isocyanate | Not used | $H_3C$-CH$_2$CH$_2$-NHC(O)- |
| 379 | Isopropyl isocyanate | Hot isopropanol | (CH$_3$)$_2$CH-NHC(O)- |

| Example | Name | Form | mp (° C.) | Anal. |
|---|---|---|---|---|
| 377 | N-{4-[4-Amino-2-ethoxymethyl-7-(pyridin-3-yl)-1H-imidazo[4,5-c]quinolin-1-yl]butyl}-N'-cyclopentylurea | White solid | 190-192 | Calcd for $C_{28}H_{35}N_7O_2$: C, 67.04; H, 7.03; N, 19.55. Found: C, 66.76; H, 7.01; N, 19.46. |
| 378 | N-{4-[4-Amino-2-ethoxymethyl-7-(pyridin-3-yl)-1H-imidazo[4,5-c]quinolin-1-yl]butyl}-N'-propylurea | White solid | 191-193 | Calcd for $C_{26}H_{33}N_7O_2$: C, 65.66; H, 6.99; N, 20.62. Found: C, 65.84; H, 7.43; N, 20.66. |
| 379 | N-{4-[4-Amino-2-ethoxymethyl-7-(pyridin-3-yl)-1H-imidazo[4,5-c]quinolin-1-yl]butyl}-N'-(1-methylethyl)urea | White solid | 192-194 | Calcd for $C_{26}H_{33}N_7O_2$: C, 65.66; H, 6.99; N, 20.62. Found: C, 65.83; H, 7.39; N, 20.52. |

Examples 380-382

A solution of tert-butyl {4-[4-amino-2-propyl-7-(pyridin-3-yl)-1H-imidazo[4,5-c]quinolin-1-yl]butyl}carbamate (41.92 g, 88.32 mmol) in concentrated hydrochloric acid (210 mL) was stirred for ten minutes, and 50% aqueous sodium hydroxide was added to adjust the solution to pH 14. Chloroform (2.0 L) and a mixture of saturated aqueous sodium bicarbonate and 1% aqueous sodium carbonate (300 mL) were added. The organic layer was separated, dried over sodium sulfate, and concentrated under reduced pressure to provide a yellow solid. The aqueous phase was treated with sodium chloride and chloroform (400 mL), and the mixture was stirred overnight. The organic layer was separated, dried over sodium sulfate, and concentrated under reduced pressure to provide a yellow solid. The two solids were combined to yield 28.77 g of 1-(4-aminobutyl)-2-propyl-7-(pyridin-3-yl)-1H-imidazo[4,5-c]quinolin-4-amine as a light yellow solid.

Triethylamine (1.34 mL, 9.61 mmol) was added to a solution of 1-(4-aminobutyl)-2-propyl-7-(pyridin-3-yl)-1H-imidazo[4,5-c]quinolin-4-amine (3.00 g, 8.01 mmol) in chloroform (141 mL); the solution was then cooled to 0° C. A cold solution of the reagent (1.0 equivalent) listed in the table below in chloroform (9 mL) was then added. The reaction was stirred for 15 or 90 minutes, and deionized water (25 mL) was added. A precipitate formed and was isolated by filtration and dried overnight in a drying oven. The crude product was triturated with the solvent(s) listed in the table below, isolated by filtration, and dried overnight in a drying oven to provide the compound with the structure shown below.

Examples 380-382

| Example | Reagent | Purification solvent | R |
|---|---|---|---|
| 380 | Butyryl chloride | Chloroform (10 mL/g) and 1% aqueous sodium carbonate (3 mL/g) | 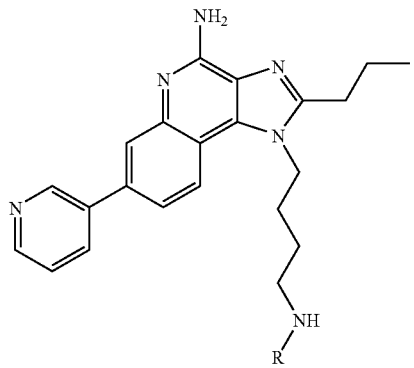 |

-continued

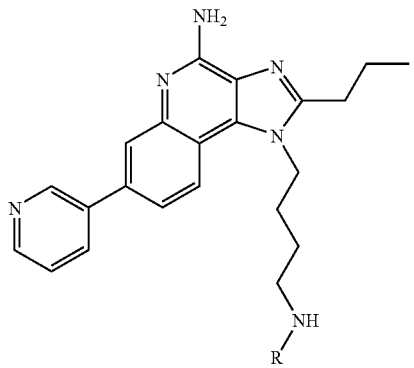

| Example | Reagent | Purification solvent | R |
|---|---|---|---|
| 381 | Isobutyryl chloride | Not used | (isopropyl ketone group) |
| 382 | Cyclopentanecarbonyl chloride | Chloroform (10 mL/g) then recrystallized from isopropanol (6 mL/g) | (cyclopentyl ketone group) |

| Example | Name | Form | mp (° C.) | Anal. |
|---|---|---|---|---|
| 380 | N-{4-[4-Amino-2-propyl-7-(pyridin-3-yl)-1H-imidazo[4,5-c]quinolin-1-yl]butyl}butyramide | White solid | 144–146 | Calcd for $C_{26}H_{32}N_6O \cdot 2\ H_2O$: C, 64.98; H, 7.55; N, 17.49. Found: C, 64.53; H, 7.08; N, 17.44. |
| 381 | N-{4-[4-Amino-2-propyl-7-(pyridin-3-yl)-1H-imidazo[4,5-c]quinolin-1-yl]butyl}-2-methylpropanamide | White solid | 168–170 | Calcd for $C_{26}H_{32}N_6O \cdot 0.25\ H_2O$: C, 69.54; H, 7.29; N, 18.71. Found: C, 69.45; H, 7.67; N, 18.65. |
| 382 | N-{4-[4-Amino-2-propyl-7-(pyridin-3-yl)-1H-imidazo[4,5-c]quinolin-1-yl]butyl}cyclopentanecarboxamide | White solid | 180–182 | Calcd for $C_{28}H_{34}N_6O \cdot 1.5\ H_2O$: C, 67.58; H, 7.49; N, 16.89. Found: C, 67.51; H, 7.72; N, 17.09. |

Examples 383–385

A solution of 1-(4-aminobutyl)-2-propyl-7-(pyridin-3-yl)-1H-imidazo[4,5-c]quinolin-4-amine (1 equivalent) in chloroform (18 mL/g) was cooled to 0° C.; a cold solution of the isocyanate indicated in the table below (1.05 equivalents) in chloroform (2 mL/g) was added. A precipitate formed within ten minutes or formed upon cooling the reaction mixture to ~0° C. for 30 minutes. The precipitate was isolated by filtration and dried overnight in an oven. The solid was from 1:1 acetonitrile:water, isolated by filtration, and dried for five days in an oven at 63° C. to provide the product with the structure shown in the table below.

Examples 383-385

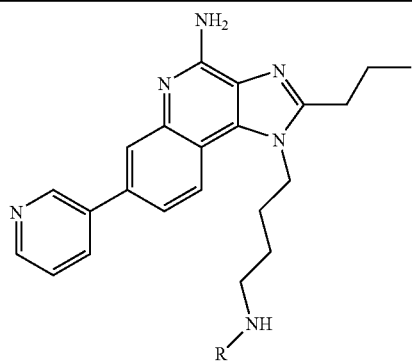

| Example | Isocyanate | R |
|---|---|---|
| 383 | Cyclopentyl isocyanate | cyclopentyl-NH-C(O)- |
| 384 | Propyl isocyanate | H3C-CH2-CH2-NH-C(O)- |
| 385 | Isopropyl isocyanate | (CH3)2CH-NH-C(O)- |

| Example | Name | Form | mp (° C.) | Anal. |
|---|---|---|---|---|
| 383 | N-{4-[4-Amino-2-propyl-7-(pyridin-3-yl)-1H-imidazo[4,5-c]quinolin-1-yl]butyl}-N'-cyclopentylurea | White solid | 181-183 | Calcd for $C_{28}H_{35}N_7O \cdot 1.5H_2O$: C, 65.60; H, 7.47; N, 19.13. Found: C, 65.44; H, 7.61; N, 19.09. |
| 384 | N-{4-[4-Amino-2-propyl-7-(pyridin-3-yl)-1H-imidazo[4,5-c]quinolin-1-yl]butyl}-N'-propylurea | White solid | 184-185 | Calcd for $C_{26}H_{33}N_7O \cdot 0.25H_2O$: C, 67.29; H, 7.28; N, 21.13. Found: C, 67.15; H, 7.56; N, 21.41. |
| 385 | N-{4-[4-Amino-2-propyl-7-(pyridin-3-yl)-1H-imidazo[4,5-c]quinolin-1-yl]butyl}-N'-(1-methylethyl)urea | White solid | 173-175 | Calcd for $C_{26}H_{33}N_7O \cdot 1.25H_2O$: C, 64.77; H, 7.42; N, 20.34. Found: C, 64.36; H, 7.78; N, 20.21. |

Example 386

N-{2-[4-Amino-2-ethoxymethyl-7-(pyridin-3-yl)-1H-imidazo[4,5-c]quinolin-1-yl]ethyl}-2-methylpropanamide

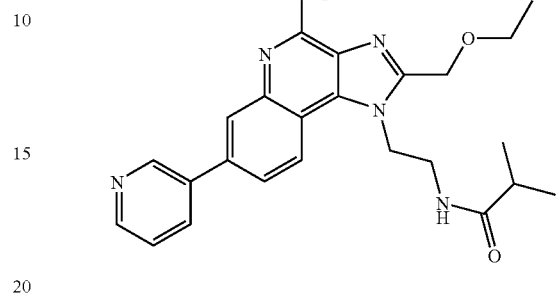

Part A

A solution of 7-bromo-4-chloro-3-nitroquinoline (140.00 g, 486.96 mmol) in chloroform (2.8 L) was cooled to 0° C. Triethylamine (82.0 mL, 588 mol) and ethylenediamine (35.75 mL, 535.6 mmol) were sequentially added; the resulting mixture was stirred for one hour at 0° C. then allowed to warm to ambient temperature and stirred for two hours. Additional ethylenediamine (0.1 equivalent) was added, and the reaction was stirred for an additional 1.75 hours. Additional triethylamine (88.0 mL, 631 mmol) followed by a solution of di-tert-butyl dicarbonate (180.0 mL, 779.1 mmol) in chloroform (320 mL) were added, and the reaction was stirred overnight at ambient temperature. Water (750 mL) was added, and the mixture was stirred for 15 minutes. The organic layer was separated and washed with 1% aqueous sodium carbonate (2×750 mL), dried over sodium sulfate, filtered through a layer of CELITE filter aid, and concentrated under reduced pressure. The resulting solid was triturated with hot acetonitrile (5 mL/g at 95° C.), cooled in an ice bath, and isolated by filtration to provide 165.0 g of tert-butyl [2-(7-bromo-3-nitroquinolin-4-ylamino)ethyl]carbamate as a light yellow solid.

Part B

A solution of tert-butyl [2-(7-bromo-3-nitroquinolin-4-ylamino)ethyl]carbamate (165.0 g, 401.2 mmol) in acetonitrile (3.3 L) and isopropanol (990 mL) and 5% platinum on carbon (13.2 g) were added to a Parr vessel, which was placed under hydrogen pressure (50 psi, $3.4 \times 10^5$ Pa) overnight. The mixture was filtered through a layer of CELITE filter aid, and the filtrate was concentrated under reduced pressure to provide 139.29 g of tert-butyl [2-(3-amino-7-bromoquinolin-4-ylamino)ethyl]carbamate as a yellow solid. The product was suspended in a mixture of dichloromethane (4 mL/g) and chloroform (8 mL/g), and the suspension was divided into two equal portions.

Part C

Ethoxyacetyl chloride (25.44 g, 182.7 mmol) in chloroform (50 mL) was added to one portion of the suspension from Part B. The resulting brown solution was stirred for 30 minutes and then concentrated under reduced pressure.

Part D

Triethylamine (101.85 mL, 730.7 mmol) was added to a suspension of the material from Part C in ethanol (1.1 L); the mixture was heated at reflux for two hours, allowed to stand over three days, and concentrated under reduced pressure. The residue was partitioned between chloroform (1.2 L) and water (400 mL). The organic layer was separated, washed with brine (2×400 mL), dried over sodium sulfate, filtered, and concentrated under reduced pressure. The crude product was triturated with acetonitrile (10 mL/g) at 95° C., isolated by filtration, and dried for three days to provide 51.48 g of tert-butyl [2-(7-bromo-2-ethoxymethyl-1H-imidazo[4,5-c]quinolin-1-yl)ethyl]carbamate as a white solid.

Part E

A modification of the method described in Example 1 Part H was used to oxidize tert-butyl [2-(7-bromo-2-ethoxymethyl-1H-imidazo[4,5-c]quinolin-1-yl)ethyl]carbamate (36.48 g, 81.18 mmol) with 3-chloroperoxybenzoic acid (36.31 g of 77% pure material, 105.5 mmol). The reaction was carried out in chloroform (370 mL) and allowed to proceed for 30 minutes. The crude product was used without purification.

Part F

The material from Part E was aminated according to the method described in Part I of Example 1; the reaction was complete after one hour. The crude product was triturated with acetonitrile (7 mL/g) at 95° C., and the resulting solid was isolated by filtration to provide 26.89 g of tert-butyl [2-(4-amino-7-bromo-2-ethoxymethyl-1H-imidazo[4,5-c]quinolin-1-yl)ethyl]carbamate as a fluffy, white solid.

Part G tert-Butyl [2-(4-amino-7-bromo-2-ethoxymethyl-1H-imidazo[4,5-c]quinolin-1-yl)ethyl]carbamate (21.80 g, 46.94 mmol) and 3-pyridylboronic acid (6.64 g, 54.0 mmol) were coupled according to the method described in Part J of Example 1. Palladium (II) acetate was added as a 5 mg/mL solution in toluene. The reaction was terminated after 4.5 hours, and the work-up procedure described in Part F of Examples 125-135 was followed. The crude product was recrystallized from acetonitrile (12 mL/g) to provide 10.80 g of tert-butyl {2-[2-ethoxymethyl-7-(pyridin-3-yl)-1H-imidazo[4,5-c]quinolin-1-yl]ethyl}carbamate as a white solid.

Part H

The method described in Part A of Examples 372-376 was used to convert tert-butyl {2-[2-ethoxymethyl-7-(pyridin-3-yl)-1H-imidazo[4,5-c]quinolin-1-yl]ethyl}carbamate (10.80 g, 23.34 mmol) to 8.38 g of 1-(2-aminoethyl)-2-ethoxymethyl-7-(pyridin-3-yl)-1H-imidazo[4,5-c]quinolin-4-amine as a white solid.

Part I 1-(2-Aminoethyl)-2-ethoxymethyl-7-(pyridin-3-yl)-1H-imidazo[4,5-c]quinolin-4-amine (2.00 g, 5.50 mmol) was treated with triethylamine (1.00 mL, 7.20 mmol) and isobutyryl chloride (0.64 mL, 6.10 mmol) according to the method described in Part B of Examples 372-376. The crude product was recrystallized from 93:7 acetonitrile:water and then from isopropanol (7.3 mL/g) and dried for two hours in a drying oven to provide 0.78 g of N-{2-[4-amino-2-ethoxymethyl-7-(pyridin-3-yl)-1H-imidazo[4,5-c]quinolin-1-yl]ethyl}-2-methylpropanamide as a white solid, mp 213-215° C.

Anal. Calcd for $C_{24}H_{28}N_6O_2 \cdot 0.75H_2O$: C, 64.63; H, 6.67; N, 18.84. Found: C, 64.66; H, 6.54; N, 18.71.

Example 387

N-{2-[4-Amino-2-ethoxymethyl-7-(pyridin-3-yl)-1H-imidazo[4,5-c]quinolin-1-yl]ethyl}methanesulfonamide

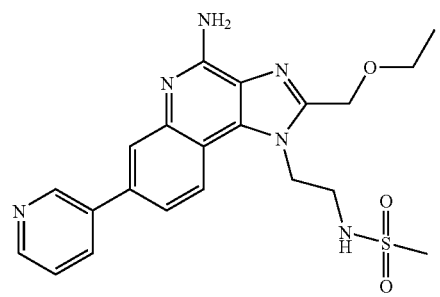

A solution of 1-(2-aminoethyl)-2-ethoxymethyl-7-(pyridin-3-yl)-1H-imidazo[4,5-c]quinolin-4-amine (2.00 g, 5.50 mmol) in chloroform (40 mL) was treated with triethylamine (1.62 mL, 11.6 mmol) and methanesulfonyl chloride (0.47 mL, 6.05 mmol). The reaction was stirred for 1.5 hours, and additional methanesulfonyl chloride (2 equivalents) was added. The reaction was stirred for 30 minutes, and then deionized water (15 mL) was added. A precipitate formed and was isolated by filtration, triturated once with methanol and twice with chloroform and 1% aqueous sodium carbonate, isolated by filtration, and dried overnight in an oven to provide 0.65 g of N-{2-[4-amino-2-ethoxymethyl-7-(pyridin-3-yl)-1H-imidazo[4,5-c]quinolin-1-yl]ethyl}methanesulfonamide as a white solid, mp 233-235° C.

Anal. Calcd for $C_{21}H_{24}N_6O_3S \cdot 0.5H_2O$: C, 56.11; H, 5.61; N, 18.69. Found: C, 56.02; H, 5.71; N, 18.64.

Example 388

N-{2-[4-Amino-2-ethoxymethyl-7-(pyridin-3-yl)-1H-imidazo[4,5-c]quinolin-1-yl]ethyl}-N'-(1-methylethyl)urea

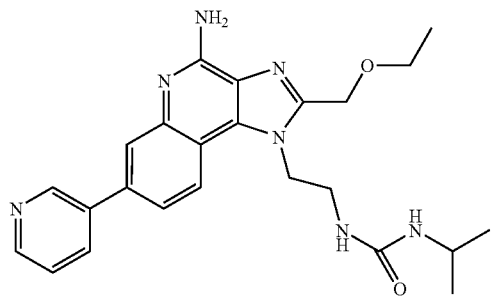

A solution of 1-(2-aminoethyl)-2-ethoxymethyl-7-(pyridin-3-yl)-1H-imidazo[4,5-c]quinolin-4-amine (2.50 g, 6.90 mmol) in chloroform (50 mL) was treated with isopropyl isocyanate (0.65 mL, 6.9 mmol) according to the method described in Examples 377-379. The crude product was purified by column chromatography on silica gel (eluting with 94:6 chloroform:methanol) followed by trituration with acetonitrile (15 mL/g) at 95° C. The mixture was cooled in an ice bath, isolated by filtration, and dried for one hour in a vacuum oven at 100° C. to provide 0.88 g of N-{2-[4-amino-2-ethoxymethyl-7-(pyridin-3-yl)-1H-imidazo[4,5-c]quinolin-1-yl]ethyl}-N'-(1-methylethyl)urea as a white solid, mp 194-196° C.

Anal. Calcd for $C_{24}H_{29}N_7O_2$: C, 64.41; H, 6.53; N, 21.91. Found: C, 64.34; H, 6.82; N, 22.05.

Example 389

1-[2-(1,1-Dioxo-1-isothiazolidin-2-yl)ethyl]-2-ethoxymethyl-7-(pyridin-3-yl)-1H-imidazo[4,5-c]quinolin-4-amine

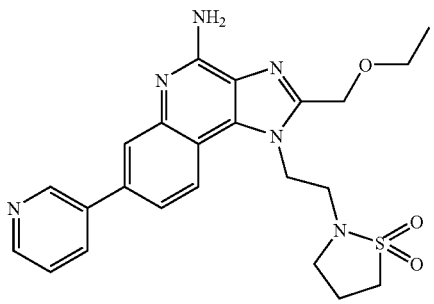

3-Chloropropanesulfonyl chloride (2.52 mL, 20.7 mmol) was added to a solution of 1-(2-aminoethyl)-2-ethoxymethyl-7-(pyridin-3-yl)-1H-imidazo[4,5-c]quinolin-4-amine (2.50 g, 6.90 mmol) in chloroform (50 mL) in two portions over a period of two hours, and the reaction was stirred overnight at ambient temperature. Additional 3-chloropropanesulfonyl chloride (1.72 mL, 14.1 mmol) was added followed by triethylamine (2.02 mL, 14.9 mmol) to drive the reaction to completion. Chloroform (50 mL) and water (30 mL) were added, and the mixture was stirred for five minutes. A precipitate formed, was isolated by filtration, and was mixed with DMF (66 mL) and DBU (2.06 mL, 13.8 mmol). The resulting solution was stirred for three days at ambient temperature and then combined with water (660 mL) and chloroform (400 mL). The organic layer was separated and dried over sodium sulfate, filtered, and concentrated under reduced pressure. The crude product was purified by column chromatography on silica gel (eluting with 95:5 chloroform:methanol). The resulting solid was triturated with methanol at 80° C., cooled in an ice bath, isolated by filtration, and dried overnight in a vacuum oven to provide 0.28 g of 1-[2-(1,1-dioxo-1-isothiazolidin-2-yl)ethyl]-2-ethoxymethyl-7-(pyridin-3-yl)-1H-imidazo[4,5-c]quinolin-4-amine as a white solid, mp 244-246° C.

Anal. Calcd for $C_{23}H_{26}N_6O_3S \cdot 0.11 H_2O$: C, 58.96; H, 5.64; N, 17.94. Found: C, 58.86; H, 5.69; N, 17.90.

Example 390

N-{2-[4-Amino-2-butyl-7-(pyridin-3-yl)-1H-imidazo[4,5-c]quinolin-1-yl]ethyl}-2-methylpropanamide

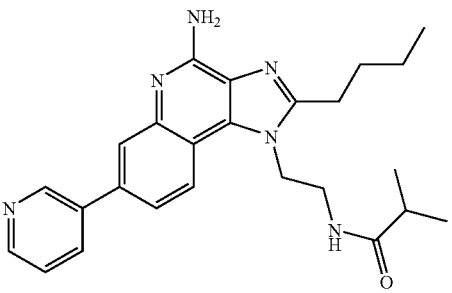

Part A

Valeryl chloride (21.68 mL, 182.6 mmol) in chloroform (50 mL) was added to one portion of the suspension from Part B of Example 386. The resulting brown solution was stirred for 30 minutes and then concentrated under reduced pressure.

Part B

A solution of sodium hydroxide (21.92 g, 274.0 mmol) in water (110 mL) was added to a suspension of the material from Part A in ethanol (640 mL); the mixture was heated at reflux for four hours and then concentrated under reduced pressure. The residue was partitioned between chloroform (1.2 L) and deionized water (400 mL). The mixture was stirred for 30 minutes. The organic fraction was separated, dried over sodium sulfate, filtered, and concentrated under reduced pressure. The resulting solid was triturated with isopropanol at 95° C., isolated by filtration, and dried on the filter funnel to provide 39.78 g of tert-butyl [2-(7-bromo-2-butyl-1H-imidazo[4,5-c]quinolin-1-yl)ethyl]carbamate as a pinkish-gray solid.

Part C tert-Butyl [2-(7-bromo-2-butyl-1H-imidazo[4,5-c]quinolin-1-yl)ethyl]carbamate (24.78 g, 55.4 mmol) was oxidized and then aminated according to the methods described in Parts E and F of Example 386. After purification 19.13 g of tert-butyl [2-(4-amino-7-bromo-2-butyl-1H-imidazo[4,5-c]quinolin-1-yl)ethyl]carbamate was obtained as a gray solid.

Part D tert-Butyl [2-(4-amino-7-bromo-2-butyl-1H-imidazo[4,5-c]quinolin-1-yl)ethyl]carbamate (14.09 g, 30.5 mmol) and 3-pyridylboronic acid (4.31 g, 35.0 mmol) were coupled according to the method described in Part G of Example 386. The reaction was heated for 2.5 hours. The crude product was triturated with toluene (15 mL/g) at 123° C. and isolated by filtration to provide 11.31 g of tert-butyl {2-[2-butyl-7-(pyridin-3-yl)-1H-imidazo[4,5-c]quinolin-1-yl]ethyl}carbamate as a white solid.

Part E

The method described in Part A of Examples 372-376 was used to convert tert-butyl {2-[2-butyl-7-(pyridin-3-yl)-1H-imidazo[4,5-c]quinolin-1-yl]ethyl}carbamate (11.31 g, 24.56 mmol) to 1-(2-aminoethyl)-2-butyl-7-(pyridin-3-yl)-1H-imidazo[4,5-c]quinolin-4-amine.

Part F 1-(2-Aminoethyl)-2-butyl-7-(pyridin-3-yl)-1H-imidazo[4,5-c]quinolin-4-amine (2.00 g, 5.50 mmol) was treated with triethylamine (1.01 mL, 7.26 mmol) and isobutyryl chloride (0.64 mL, 6.10 mmol) according to the method described in Part B of Examples 372-376. The crude product was recrystallized from isopropanol (4 mL/g) and then triturated with acetonitrile (12.5 mL/g), isolated by filtration, and dried overnight in a drying oven to provide 0.61 g of N-{2-[4-amino-2-butyl-7-(pyridin-3-yl)-1H-imidazo[4,5-c]quinolin-1-yl]ethyl}-2-methylpropanamide as a white solid, mp 228-230° C.

Anal. Calcd for $C_{25}H_{30}N_6O$: C, 69.74; H, 7.02; N, 19.52. Found: C, 69.37; H, 6.97; N, 19.60.

Example 391

N-{2-[4-Amino-2-butyl-7-(pyridin-3-yl)-1H-imidazo[4,5-c]quinolin-1-yl]ethyl}methanesulfonamide

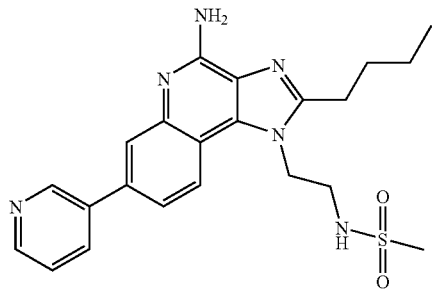

The method described in Example 387 was used to convert 1-(2-aminoethyl)-2-butyl-7-(pyridin-3-yl)-1H-imidazo[4,5-c]quinolin-4-amine to N-{2-[4-amino-2-butyl-7-(pyridin-3-yl)-1H-imidazo[4,5-c]quinolin-1-yl]ethyl}methanesulfonamide.

Example 392

N-{2-[4-Amino-2-butyl-7-(pyridin-3-yl)-1H-imidazo[4,5-c]quinolin-1-yl]ethyl}-N'-(1-methylethyl)urea

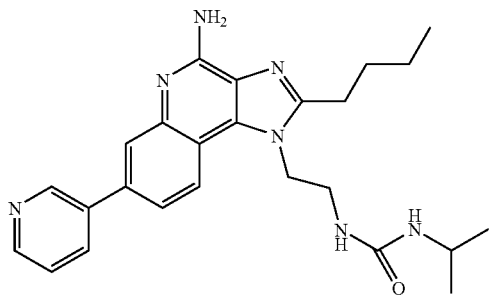

Isopropyl isocyanate (0.29 mL, 3.1 mmol) was added slowly to a suspension of 1-(2-aminoethyl)-2-butyl-7-(pyridin-3-yl)-1H-imidazo[4,5-c]quinolin-4-amine (1.13 g, 3.1 mmol) in chloroform (113 mL). A precipitate formed within 15 minutes, was isolated by filtration, and was dried overnight in an oven to provide 0.66 g of N-{2-[4-amino-2-butyl-7-(pyridin-3-yl)-1H-imidazo[4,5-c]quinolin-1-yl]ethyl}-N'-(1-methylethyl)urea as a white solid, mp 240-241° C.

Anal. Calcd for $C_{25}H_{31}N_7O$: C, 67.39; H, 7.01; N, 22.00. Found: C, 67.24; H, 7.08; N, 21.90.

Example 393

1-[2-(1,1-Dioxo-1-isothiazolidin-2-yl)ethyl]-2-butyl-7-(pyridin-3-yl)-1H-imidazo[4,5-c]quinolin-4-amine

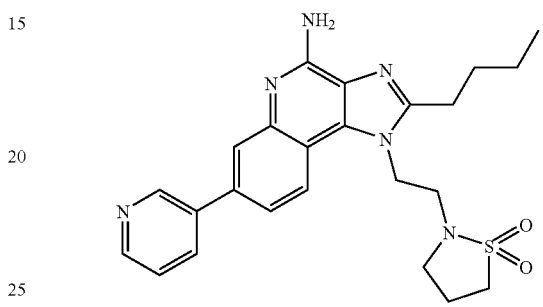

The method described in Example 389 was used to convert 1-(2-aminoethyl)-2-butyl-7-(pyridin-3-yl)-1H-imidazo[4,5-c]quinolin-4-amine (4.00 g, 11.1 mmol) to 1.05 g of 1-[2-(1,1-dioxo-1-isothiazolidin-2-yl)ethyl]-2-butyl-7-(pyridin-3-yl)-1H-imidazo[4,5-c]quinolin-4-amine, which was isolated as a white solid, mp 290-292° C.

Anal. Calcd for $C_{24}H_{28}N_6O_2S \cdot 0.06H_2O$: C, 61.90; H, 6.09; N, 18.05. Found: C, 61.52; H, 6.03; N, 18.05.

Examples 394-403

The methods described in Parts C, D, and E of Examples 125-135 were used to convert 1-(3-amino-7-bromoquinolin-4-ylamino)-2-methylpropan-2-ol to 1-(4-amino-7-bromo-2-methoxymethyl-1H-imidazo[4,5-c]quinolin-1-yl)-2-methylpropan-2-ol. Methoxyacetyl chloride was used in lieu of ethoxyacetyl chloride in Part C.

1-(4-Amino-7-bromo-2-methoxymethyl-1H-imidazo[4,5-c]quinolin-1-yl)-2-methylpropan-2-ol and the boronic acid or boronic acid ester from the table below were coupled according to the procedure described in Part F of Examples 125-135. After the work-up procedure, the crude product was purified by HPFC (eluting with chloroform:methanol in a gradient from 100:0 to 70:30). The resulting product was dissolved in dichloromethane and concentrated under reduced pressure until a precipitate began to form. Hexanes were added, and the resulting solid was isolated by filtration and dried overnight under vacuum at 70° C. to provide the compound shown in the table below. For Example 399, the solid isolated by filtration was triturated with hot acetonitrile, isolated by filtration, and dried under vacuum. For Example 402, the product from the coupling reaction was deprotected according to the method described in Part C of Example 150 to provide the product shown in the table below. The purification and characterization of Example 403 is given below the following tables.

Examples 394-403

| Example | Boronic acid | R |
|---|---|---|
| 394 | 2-Ethoxyphenylboronic acid | 2-ethoxyphenyl |
| 395 | Pyrimidine-5-boronic acid | pyrimidin-5-yl |
| 396 | Pyridine-3-boronic acid | pyridin-3-yl |
| 397 | 2-Methoxypyrimidine-5-boronic acid | 2-methoxypyrimidin-5-yl |
| 398 | 2-Methoxy-5-pyridineboronic acid | 6-methoxypyridin-3-yl |
| 399 | 4-Methoxy-3-pyridineboronic acid | 4-methoxypyridin-3-yl |
| 400 | 3-Methoxypyridine-5-boronic acid pinacol ester | 5-methoxypyridin-3-yl |
| 401 | 3-(Morpholine-4-carbonyl)phenylboronic acid | 3-(morpholine-4-carbonyl)phenyl |
| 402 | 5-(tert-Butyldimethyl-silanyloxymethyl)pyridine-3-boronic acid | 5-(hydroxymethyl)pyridin-3-yl |
| 403 | 5-Ethoxymethylpyridin-3-ylboronic acid | 5-(ethoxymethyl)pyridin-3-yl |

The characterization data for Examples 394-402 are shown in the table below.

Examples 394-403

| Example | Name | Form | mp (° C.) | Anal. |
|---|---|---|---|---|
| 394 | 1-[4-Amino-7-(2-ethoxyphenyl)-2-methoxymethyl-1H-imidazo[4,5-c]quinolin-1-yl]-2-methylpropan-2-ol | White solid | 173-175 | Calcd for $C_{24}H_{28}N_4O_3$: C, 68.55; H, 6.71; N, 13.32. Found: C, 68.38; H, 6.92; N, 13.47. |
| 395 | 1-[4-Amino-2-methoxymethyl-7-(pyrimidin-5-yl)-1H-imidazo[4,5-c]quinolin-1-yl]-2-methylpropan-2-ol | White powder | 220-220.5 | Calcd for $C_{20}H_{22}N_6O_2$: C, 63.48; H, 5.86; N, 22.21. Found: C, 63.30; H, 5.72; N, 22.21. |
| 396 | 1-[4-Amino-2-methoxymethyl-7-(pyridin-3-yl)-1H-imidazo[4,5-c]quinolin-1-yl]-2-methylpropan-2-ol | White solid | 225-225.5 | Calcd for $C_{21}H_{23}N_5O_2$: C, 65.70; H, 6.23; N, 18.24. Found: C, 65.30; H, 5.57; N, 17.99. |

-continued

| Example | Name | Form | mp (° C.) | Anal. |
|---|---|---|---|---|
| 397 | 1-[4-Amino-2-methoxymethyl-7-(2-methoxypyrimidin-5-yl)-1H-imidazo[4,5-c]quinolin-1-yl]-2-methylpropan-2-ol | White solid | 241-242 | Calcd for $C_{21}H_{24}N_6O_3$: C, 59.17; H, 6.14; N, 19.71. Found: C, 59.33; H, 6.12; N, 19.73. |
| 398 | 1-[4-Amino-2-methoxymethyl-7-(6-methoxypyridin-3-yl)-1H-imidazo[4,5-c]quinolin-1-yl]-2-methylpropan-2-ol | White powder | 190-190.5 | Calcd for $C_{22}H_{25}N_5O_3$: C, 64.85; H, 6.18; N, 17.19. Found: C, 64.61; H, 5.97; N, 17.13. |
| 399 | 1-[4-Amino-2-methoxymethyl-7-(4-methoxypyridin-3-yl)-1H-imidazo[4,5-c]quinolin-1-yl]-2-methylpropan-2-ol | White powder | 220.5-222 | Calcd for $C_{22}H_{25}N_5O_3$: C, 64.85; H, 6.18; N, 17.19. Found: C, 64.54; H, 5.90; N, 17.11. |
| 400 | 1-[4-Amino-2-methoxymethyl-7-(5-methoxypyridin-3-yl)-1H-imidazo[4,5-c]quinolin-1-yl]-2-methylpropan-2-ol | Yellow powder | 234-236 | Calcd for $C_{22}H_{25}N_5O_3 \cdot 0.13\ CH_2Cl_2$: C, 63.51; H, 6.08; N, 16.73. Found: C, 63.26; H, 5.83; N, 16.61. |
| 401 | {3-[4-Amino-1-(2-hydroxy-2-methylpropyl)-2-methoxymethyl-1H-imidazo[4,5-c]quinolin-7-yl]phenyl}morpholin-4-ylmethanone | White solid | 176-177 | Calcd for $C_{27}H_{31}N_5O_4 \cdot 1.0\ H_2O$: C, 63.89; H, 6.55; N, 13.80. Found: C, 63.50; H, 6.44; N, 13.64. |
| 402 | 1-[4-Amino-7-(5-hydroxymethylpyridin-3-yl)-2-methoxymethyl-1H-imidazo[4,5-c]quinolin-1-yl]-2-methylpropan-2-ol | White powder | 224-225 | Calcd for $C_{22}H_{25}N_5O_3 \cdot 1.5\ H_2O$: C, 60.82; H, 6.50; N, 16.12. Found: C, 60.81; H, 6.51; N, 16.14. |

Example 403

1 [4-Amino-7-(5-ethoxymethylpyridin-3-yl)-2-methoxymethyl-1H-imidazo[4,5-c]quinolin-1-yl]-2-methylpropan-2-ol The product from the coupling reaction was further purified by recrystallizing twice from acetonitrile:isopropanol followed by a second chromatographic purification on silica gel (eluting with chloroform:CMA in a gradient from 99:1 to 70:30) to provide the products as a white powder.

$^1$H NMR (300 mHz, DMSO-$d_6$ @45° C.) δ 8.90 (d, J=2.2 Hz, 1H), 8.54 (d, J=1.9 Hz, 1H), 8.40 (d, J=8.6 Hz, 1H), 8.07 (t, J=2.1 Hz, 1H), 7.91 (d, J=2.0 Hz, 1H), 7.57 (dd, J=8.6, 2.0 Hz, 1H), 6.54 (br s, 2H), 4.89 (br s, 2H), 4.83 (br s, 1H), 4.69 (br s, 2H), 4.60 (br s, 2H), 3.58 (q, J=7.0 Hz, 2H), 3.34 (s, 3H), 1.22-1.17 (m, 9H);

MS (ESI) m/z 436.2361 (436.2349 calcd for $C_{24}H_{29}N_5O_3$, M+H).

Example 404 tert-Butyl 4-{[4-amino-2-ethyl-7-(pyridin-3-yl)-1H-imidazo[4,5-c]quinolin-1-yl]methyl}piperidine-1-carboxylate

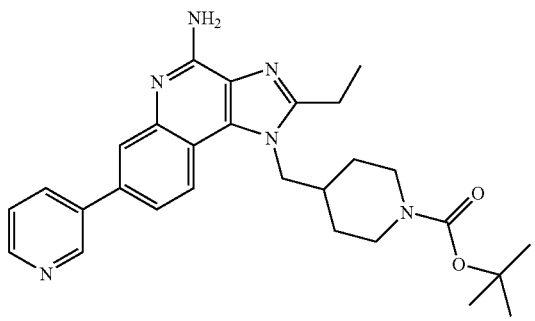

Part A

The method described in Part A of Examples 142-144 was used to treat tert-butyl 4-[(3-amino-7-bromoquinolin-4-ylamino)methyl]piperidine-1-carboxylate (15.0 g, 34.5 mmol) with triethyl orthopropionate (6.68 g, 37.9 mmol). After completion, the reaction mixture was concentrated under reduced pressure, and the residue was purified by flash column chromatography on silica gel (eluting with 95:5 chloroform:CMA) followed by recrystallization from ethyl acetate to provide 12.6 g of tert-butyl 4-[(7-bromo-2-ethyl-1H-imidazo[4,5-c]quinolin-1-yl)methyl]piperidine-1-carboxylate as a white powder, mp 208-209° C.

Anal. Calcd for $C_{23}H_{29}BrN_4O_2$: C, 58.35; H, 6.17; N, 11.83. Found: C, 58.13; H, 5.85; N, 11.69.

Part B tert-Butyl 4-[(7-bromo-2-ethyl-1H-imidazo[4,5-c]quinolin-1-yl)methyl]piperidine-1-carboxylate was oxidized and then aminated according to the methods described in Parts H and I of Example 1. The oxidation product was not recrystallized; the amination reaction was stirred for 16 hours. The product from amination was purified by column chromatography on silica gel (eluting with 90:10 chloroform:CMA) followed by recrystallization from ethyl acetate to provide tert-butyl 4-[(4-amino-7-bromo-2-ethyl-1H-imidazo[4,5-c]quinolin-1-yl)methyl]piperidine-1-carboxylate as an off-white powder, mp 131-132° C.

Anal. Calcd for $C_{23}H_{30}BrN_5O_2$: C, 56.56; H, 6.19; N, 14.34. Found: C, 56.30; H, 6.14; N, 14.06.

Part C tert-Butyl 4-[(4-amino-7-bromo-2-ethyl-1H-imidazo[4,5-c]quinolin-1-yl)methyl]piperidine-1-carboxylate (9.24 g, 18.9 mmol) and pyridine-3-boronic acid 1,3-propanediol cyclic ester (3.39 g, 20.8 mmol) were coupled according to the method described in Examples 118-121. Additional reagents were added after the reaction was heated for 16 hours, and the reaction was continued for 16 hours. Water (20 mL) was added, and the n-propanol was removed under reduced pressure. The remaining mixture was extracted with chloroform (2×200 mL), and the combined organic fractions were purified by column chromatography on silica gel (eluting with chloroform and chloroform:CMA). The resulting solid was recrystallized from acetonitrile to provide 5.44 g of tert-butyl 4-{[4-amino-2-ethyl-7-(pyridin-3-yl)-1H-imidazo[4,5-c]quinolin-1-yl]methyl}piperidine-1-carboxylate as a white, fluffy solid, mp 229-231° C.

Anal. Calcd for $C_{28}H_{34}N_6O_2$: C, 69.11; H, 7.04; N, 17.27. Found: C, 69.18; H, 7.07; N, 17.36.

Example 405

2-Ethyl-1-(piperidin-4-ylmethyl)-7-(pyridin-3-yl)-1H-imidazo[4,5-c]quinolin-4-amine trihydrochloride

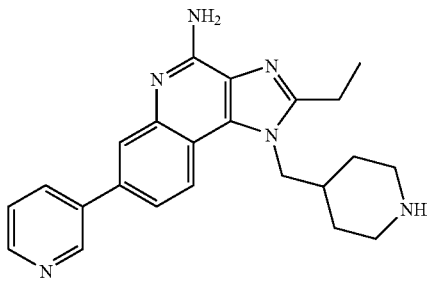

The method described in Example 177 was used to convert tert-butyl 4-{[4-amino-2-ethyl-7-(pyridin-3-yl)-1H-imidazo[4,5-c]quinolin-1-yl]methyl}piperidine-1-carboxylate (5.22 g, 10.7 mmol) to 5.15 g of 2-ethyl-1-(piperidin-4-ylmethyl)-7-(pyridin-3-yl)-1H-imidazo[4,5-c]quinolin-4-amine trihydrochloride, which was obtained as a white solid, mp>250° C.

Anal. Calcd for $C_{23}H_{26}N_6 \cdot 3HCl \cdot 1.4H_2O$: C, 53.01; H, 6.15; N, 16.13. Found: C, 53.40; H, 6.53; N, 16.15.

Examples 406-408

A solution of 2-ethyl-1-(piperidin-4-ylmethyl)-7-(pyridin-3-yl)-1H-imidazo[4,5-c]quinolin-4-amine trihydrochloride (1.50 g, 2.88 mmol) and triethylamine (5 or 10 equivalents) in chloroform (100 mL for Example 406 and 250 mL for Examples 407 and 408) and pyridine (60 mL for Example 406 and 100 mL for Examples 407 and 408) was cooled to 4° C. The reagent from the table below (1 equivalent) was added dropwise, and the reaction was allowed to warm to ambient temperature and stirred for between 12 and 48 hours, with additional reagents added in Example 406. For Example 406, the reaction mixture was diluted with chloroform, and the resulting solution was washed sequentially with water (100 mL), 4% aqueous sodium carbonate (2×50 mL), water (50 mL), and brine (50 mL) and then concentrated under reduced pressure. For Examples 407 and 408, the reaction mixture was concentrated under reduced pressure and then triturated with 5 N aqueous sodium hydroxide to afford a solid that was isolated by filtration. The crude products were purified by flash column chromatography on silica gel (eluting with chloroform and chloroform:CMA) followed by recrystallization from acetonitrile to provide the products shown in the table below. The following table contains characterization data for these compounds.

Examples 406-408

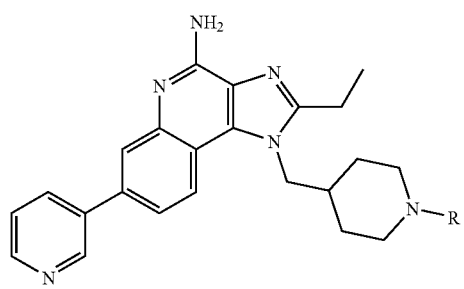

| Example | Reagent | R |
|---|---|---|
| 406 | Methanesulfonyl chloride | 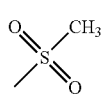 |
| 407 | Isobutyryl chloride | 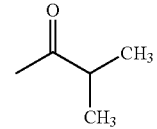 |
| 408 | Isopropyl isocyanate | 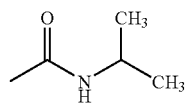 |

Examples 406-408

| Example | Name | Form | mp (° C.) | Anal. |
|---|---|---|---|---|
| 406 | 2-Ethyl-1-{[1-(methanesulfonyl)piperidin-4-yl]methyl}-7-(pyridin-3-yl)-1H-imidazo[4,5-c]quinolin-4-amine | White crystalline solid | 228-229 | Calcd for $C_{24}H_{28}N_6O_2S \cdot 0.86\,H_2O$: C, 60.04; H, 6.24; N, 17.50. Found: C, 60.21; H, 6.51; N, 17.43. |
| 407 | 1-{4-[4-Amino-2-ethyl-7-(pyridin-3-yl)-1H-imidazo[4,5-c]quinolin-1- | White crystalline solid | 189-191 | Calcd for $C_{27}H_{32}N_6O \cdot 0.5\,H_2O$: C, 69.65; H, 7.14; N, 18.05. Found: C, |

| Example | Name | Form | mp (° C.) | Anal. |
|---|---|---|---|---|
| | ylmethyl]piperidin-1-yl}-2-methylpropan-1-one | | | 69.58; H, 7.26; N, 18.11. |
| 408 | 4-[4-Amino-2-ethyl-7-(pyridin-3-yl)-1H-imidazo[4,5-c]quinolin-1-ylmethyl]piperidin-1-carboxylic acid isopropylamide | White solid | 255-256 | Calcd for $C_{27}H_{33}N_7O$•1.25 $H_2O$: C, 65.63; H, 7.24; N, 19.84. Found: C, 65.58; H, 7.03; N, 19.85. |

Example 409 tert-Butyl 4-{[4-amino-2-propyl-7-(pyridin-3-yl)-1H-imidazo[4,5-c]quinolin-1-yl]methyl}piperidine-1-carboxylate

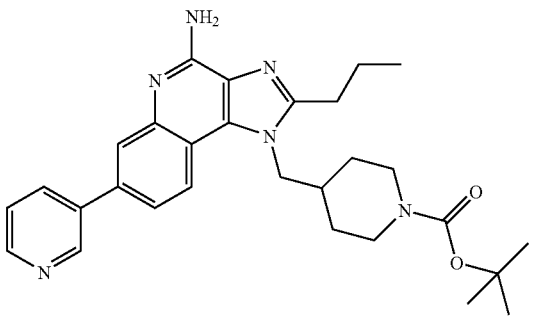

Part A

The method described in Part A of Examples 142-144 was used to treat tert-butyl 4-[(3-amino-7-bromoquinolin-4-ylamino)methyl]piperidine-1-carboxylate (15.0 g, 34.5 mmol) with trimethyl orthobutyrate (5.62 g, 37.9 mmol). After completion, the reaction mixture was concentrated under reduced pressure, and the residue was purified by flash column chromatography on silica gel (eluting with 95:5 chloroform:CMA) followed by recrystallization from ethyl acetate to provide 13.1 g of tert-butyl 4-[(7-bromo-2-propyl-1H-imidazo[4,5-c]quinolin-1-yl)methyl]piperidine-1-carboxylate as a white solid, mp 215-216° C.

Anal. Calcd for $C_{24}H_{31}BrN_4O_2$: C, 59.14; H, 6.41; N, 11.49. Found: C, 59.06; H, 6.24; N, 11.42.

Part B tert-Butyl 4-[(7-bromo-2-propyl-1H-imidazo[4,5-c]quinolin-1-yl)methyl]piperidine-1-carboxylate was oxidized and then aminated according to the methods described in Parts H and I of Example 1. The oxidation product was not recrystallized; the amination reaction was stirred for 16 hours. The product from amination was purified by column chromatography on silica gel (eluting with 90:10 chloroform:CMA) followed by recrystallization from ethyl acetate to provide tert-butyl 4-[(4-amino-7-bromo-2-propyl-1H-imidazo[4,5-c]quinolin-1-yl)methyl]piperidine-1-carboxylate as off-white needles, mp 134-137° C.

Anal. Calcd for $C_{24}H_{32}BrN_5O_2$: C, 57.37; H, 6.42; N, 13.94. Found: C, 57.14; H, 6.41; N, 13.52.

Part C tert-Butyl 4-[(4-amino-7-bromo-2-propyl-1H-imidazo[4,5-c]quinolin-1-yl)methyl]piperidine-1-carboxylate (8.02 g, 15.9 mmol) and pyridine-3-boronic acid 1,3-propanediol cyclic ester (2.86 g, 17.6 mmol) were coupled according to the method described in Part C of Example 404 to provide, after purification, 4.12 g of tert-butyl 4-{[4-amino-2-propyl-7-(pyridin-3-yl)-1H-imidazo[4,5-c]quinolin-1-yl]methyl}piperidine-1-carboxylate as an off-white solid, mp 209-211° C.

Anal. Calcd for $C_{29}H_{36}N_6O_2$.0.6$H_2O$: C, 68.10; H, 7.33; N, 16.43. Found: C, 67.72; H, 7.26; N, 16.31.

Example 410

1-(Piperidin-4-ylmethyl)-2-propyl-7-(pyridin-3-yl)-1H-imidazo[4,5-c]quinolin-4-amine trihydrochloride

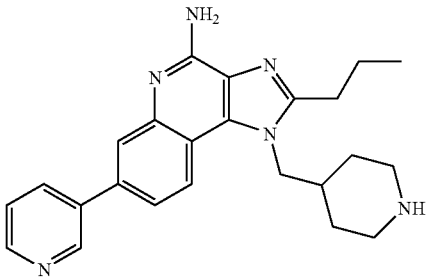

The method described in Example 177 was used to convert tert-butyl 4-{[4-amino-2-propyl-7-(pyridin-3-yl)-1H-imidazo[4,5-c]quinolin-1-yl]methyl}piperidine-1-carboxylate (4.00 g, 7.99 mmol) to 3.84 g of 1-(piperidin-4-ylmethyl)-2-propyl-7-(pyridin-3-yl)-1H-imidazo[4,5-c]quinolin-4-amine trihydrochloride, which was obtained as a white solid, mp>250° C.

Anal. Calcd for $C_{24}H_{28}N_6$.3HCl.0.59$H_2O$: C, 55.39; H, 6.23; N, 16.15. Found: C, 55.35; H, 6.52; N, 16.08.

Examples 411-413

The methods described for Examples 406, 407, and 408 were carried out for Examples 411, 412, and 413 respectively to provide the products shown in the table below.

Examples 411-413

| Example | Reagent | R |
|---|---|---|
| 411 | Methanesulfonyl chloride | 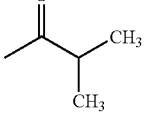 |
| 412 | Isobutyryl chloride | 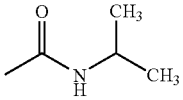 |
| 413 | Isopropyl isocyanate | |

Characterization data for Examples 411-413 are shown in the table below.

Examples 411-413

Example 414

2-Ethoxymethyl-1-(2-piperazin-1-ylethyl)-7-(pyridin-3-yl)-1H-imidazo[4,5-c]quinolin-4-amine

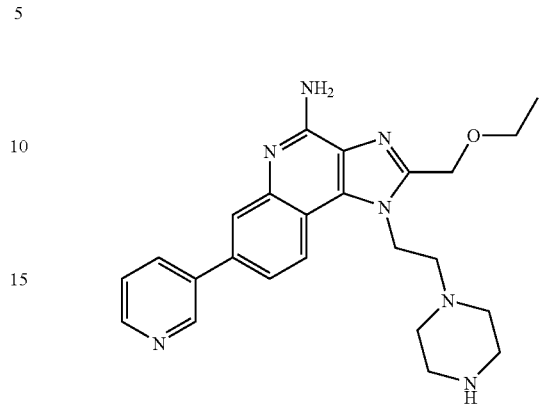

Part A

7-Bromo-4-chloro-3-nitroquinoline (33.0 g, 115 mmol) was treated with 4-(2-aminoethyl)-1-(tert-butoxycarbonyl)piperazine (26.4 mL, 115 mmol) according to the method described in Part E of Example 1. The reaction was stirred overnight. The crude product was triturated with diethyl ether and isolated by filtration to provide 33.05 g of tert-butyl 4-[2-(7-bromo-3-nitroquinolin-4-ylamino)ethyl]piperazine-1-carboxylate as a yellow solid.

Part B tert-Butyl 4-[2-(7-bromo-3-nitroquinolin-4-ylamino)ethyl]piperazine-1-carboxylate was treated according to the methods described in Parts B through D of Examples 152-156. Triethylamine (1.1 equivalents) was added to the reaction in Part C, and the reaction in Part D was heated at reflux overnight. Following chromatographic purification in Part D (eluting with chloroform:CMA in a gradient from 100:0 to

| Example | Name | Form | mp (° C.) | Anal. |
|---|---|---|---|---|
| 411 | 1-{[1-(Methanesulfonyl)piperidin-4-yl]methyl}-2-propyl-7-(pyridin-3-yl)-1H-imidazo[4,5-c]quinolin-4-amine | White solid | >250 | Calcd for $C_{25}H_{30}N_6O_2S \cdot 0.8$ HCl$\cdot 1.0$ $H_2O$: C, 57.11; H, 6.29; N, 15.98; Cl, 5.39. Found: C, 56.87; H, 6.68; N, 15.77; Cl, 5.02. |
| 412 | 1-{4-[4-Amino-2-propyl-7-(pyridin-3-yl)-1H-imidazo[4,5-c]quinolin-1-ylmethyl]piperidin-1-yl}-2-methylpropan-1-one | White solid | 248-249 | Calcd for $C_{28}H_{34}N_6O$: C, 71.46; H, 7.28; N, 17.86. Found: C, 71.21; H, 7.33; N, 17.55. |
| 413 | 4-[4-Amino-2-ethyl-7-(pyridin-3-yl)-1H-imidazo[4,5-c]quinolin-1-ylmethyl]piperidin-1-carboxylic acid isopropylamide | Off-white solid | 240-242 | Calcd for $C_{28}H_{35}N_7O$: C, 69.25; H, 7.26; N, 20.19. Found: C, 68.98; H, 7.20; N, 20.35. |

211

94:6), tert-butyl 4-[2-(7-bromo-2-ethoxymethyl-1H-imidazo[4,5-c]quinolin-1-yl)ethyl]piperazine-1-carboxylate was obtained as a white solid, mp 140-143° C.

Anal. Calcd for $C_{24}H_{32}BrN_5O_3$: C, 55.60; H, 6.22; N, 13.51. Found: C, 55.62; H, 6.31; N, 13.40.

Part C tert-Butyl 4-[2-(7-bromo-2-ethoxymethyl-1H-imidazo[4,5-c]quinolin-1-yl)ethyl]piperazine-1-carboxylate (21.5 g, 41.5 mmol) was oxidized with three equivalents of 3-chloroperoxybenzoic acid (28.63 g of 75% pure material, 124.4 mmol) according to the method described Part H of Example 1 to provide tert-butyl 4-[2-(7-bromo-2-ethoxymethyl-5-oxido-1H-imidazo[4,5-c]quinolin-1-yl)ethyl]-4-oxidopiperazine-1-carboxylate, which was used without purification.

Part D tert-Butyl 4-[2-(7-bromo-2-ethoxymethyl-5-oxido-1H-imidazo[4,5-c]quinolin-1-yl)ethyl]-4-oxidopiperazine-1-carboxylate was aminated according to the method described in Part I of Example 1. The reaction was stirred overnight, and the crude product was purified by flash column chromatography on silica gel (eluting with chloroform:CMA in a gradient from 95:5 to 70:30) to provide 10.84 g of tert-butyl 4-[2-(4-amino-7-bromo-2-ethoxymethyl-1H-imidazo[4,5-c]quinolin-1-yl)ethyl]-4-oxidopiperazine-1-carboxylate as a white solid.

Part E

A solution of tert-butyl 4-[2-(4-amino-7-bromo-2-ethoxymethyl-1H-imidazo[4,5-c]quinolin-1-yl)ethyl]-4-oxidopiperazine-1-carboxylate (8.84 g, 16.1 mmol) in chloroform (400 mL) was cooled to 4° C. Phosphorous trichloride (9.82 mL, 113 mmol) was added dropwise, and the reaction was stirred for 45 minutes at 4° C. Water (one drop) was added to the reaction, which was allowed to warm to ambient temperature. The chloroform was removed under reduced pressure, and the residue was dissolved in ethanol (150 mL). Hydrogen chloride (21.5 mL of a 3 M solution in ethanol) was added, and the reaction was heated at reflux for 25 minutes. The reaction was allowed to cool to room temperature; a precipitate formed and was isolated by filtration to provide 6.86 g of 7-bromo-2-ethoxymethyl-1-(2-piperazin-1-ylethyl)-1H-imidazo[4,5-c]quinolin-4-amine dihydrochloride as a light yellow solid.

Part F

Under a nitrogen atmosphere, triphenylphosphine (0.0409 g, 0.156 mmol), 2 M aqueous sodium carbonate (18.3 mL, 36.5 mmol) and a solution of palladium (II) acetate (0.0117 g, 0.52 mmol) in warm toluene were added to a solution of 7-bromo-2-ethoxymethyl-1-(2-piperazin-1-ylethyl)-1H-imidazo[4,5-c]quinolin-4-amine dihydrochloride (5.28 g, 10.4 mmol) and pyridine-3-boronic acid 1,3-propanediol cyclic ester (1.87 g, 11.5 mmol) in n-propanol (8 mL). The reaction was heated at reflux under nitrogen for three hours then allowed to cool to ambient temperature. Deionized water was added, and organic solvent was removed under reduced pressure. The aqueous mixture was extracted with ethyl acetate (3×), and the combined organic fractions were washed sequentially with 2 M aqueous sodium carbonate and brine, dried over sodium sulfate, filtered, and concentrated under reduced pressure. The crude product was combined with material from another run and purified by flash column chromatography on silica gel (eluting with chloroform:methanol in a gradient from 90:10 to 50:50 and 50:50 chloroform:CMA) to provide 3.54 g of 2-ethoxymethyl-1-(2-piperazin-1-ylethyl)-7-(pyridin-3-yl)-1H-imidazo[4,5-c]quinolin-4-amine as a white solid, mp 208-211° C.

212

Anal. Calcd for $C_{24}H_{29}N_7O \cdot 0.5H_2O$: C, 65.43; H, 6.86; N, 22.26. Found: C, 65.59; H, 7.09; N, 22.53.

Examples 415-417

A 0.015 M solution of 2-ethoxymethyl-1-(2-piperazin-1-ylethyl)-7-(pyridin-3-yl)-1H-imidazo[4,5-c]quinolin-4-amine (1.00 g, 2.32 mmol) and triethylamine (1.3-1.4 equivalents) in chloroform was cooled to 4° C. The reagent from the table below (1.1-1.2 equivalents) was added dropwise, and the reaction was allowed to warm to ambient temperature and stirred for two or three hours. In Examples 415 and 417, additional triethylamine and the reagent indicated in the table were added at 4° C., and the reaction was stirred overnight. The work-up procedure described in Examples 178 to 181 was carried out. The crude product was purified by flash column chromatography on silica gel or by HPFC (eluting with chloroform:CMA in a gradient from about 100:0 to 75:25) followed by recrystallization from acetonitrile to provide the products shown in the table below.

Examples 415-417

| Example | Reagent | R |
|---------|---------|---|
| 415 | Methanesulfonyl chloride | −S(=O)₂CH₃ |
| 416 | Isobutyryl chloride | −C(=O)CH(CH₃)₂ |
| 417 | 4-Morpholinecarbonyl chloride | −C(=O)-morpholin-4-yl |

The characterization data for Examples 415-417 are provided in the table below.

Examples 415-417

| Example | Name | Form | mp (° C.) | Anal. |
|---|---|---|---|---|
| 415 | 2-Ethoxymethyl-1-{2-[4-(methanesulfonyl)piperazin-1-yl]ethyl}-7-(pyridin-3-yl)-1H-imidazo[4,5-c]quinolin-4-amine | White solid | 205-207 | Calcd for $C_{25}H_{31}N_7O_3S \cdot 0.65\ H_2O$: C, 57.60; H, 6.25; N, 18.81. Found: C, 57.51; H, 6.22; N, 18.79. |
| 416 | 1-(4-{2-[4-Amino-2-ethoxymethyl-7-(pyridin-3-yl)-1H-imidazo[4,5-c]quinolin-1-yl]ethyl}piperazin-1-yl)-2-methylpropan-1-one | White solid | 190-192 | Calcd for $C_{28}H_{35}N_7O_2 \cdot 0.5\ H_2O$: C, 65.86; H, 7.11; N, 19.20. Found: C, 65.90; H, 7.07; N, 19.34. |
| 417 | 1-(4-{2-[4-Amino-2-ethoxymethyl-7-(pyridin-3-yl)-1H-imidazo[4,5-c]quinolin-1-yl]ethyl}piperazin-1-yl)morpholin-4-ylmethanone | Light yellow solid | 212-214 | $C_{29}H_{36}N_8O_3 \cdot 0.5\ H_2O$: C, 62.91; H, 6.74; N, 20.24. Found: C, 63.02; H, 6.69; N, 20.26. |

Examples 418-420

Part A

Trimethyl orthobutyrate (11.61 mL, 72.6 mmol) and catalytic pyridine hydrochloride were added to a solution of 1-(3-amino-7-bromoquinolin-4-ylamino)-2-methylpropan-2-ol (22.51 g, 72.6 mmol) in anhydrous toluene (120 mL), and the reaction was heated at reflux for two hours. The solvent was removed under reduced pressure, and the residue was dissolved in dichloromethane and washed with water. The dichloromethane was removed under reduced pressure until a precipitate began to form. Hexanes were added, and the precipitate was isolated by filtration to provide 20.17 g of 1-(7-bromo-2-propyl-1H-imidazo[4,5-c]quinolin-1-yl)-2-methylpropan-2-ol.

Part B 1-(7-Bromo-2-propyl-1H-imidazo[4,5-c]quinolin-1-yl)-2-methylpropan-2-ol was oxidized and then aminated according to the methods described in Part E of Examples 125-135 to provide 14.6 g of 1-(4-amino-7-bromo-2-propyl-1H-imidazo[4,5-c]quinolin-1-yl)-2-methylpropan-2-ol as a white solid, which was used without purification.

Part C 1-(4-Amino-7-bromo-2-propyl-1H-imidazo[4,5-c]quinolin-1-yl)-2-methylpropan-2-ol and the boronic acid from the table below were coupled according to the general procedure described in Part J of Example 1. Example 420 was heated at reflux overnight. The purification and characterization of each compound is described below the table.

Examples 418-420

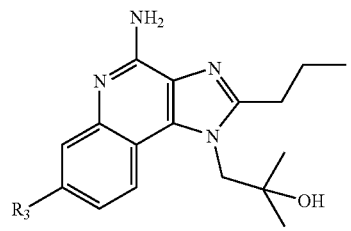

| Example | Boronic acid or ester | $R_3$ |
|---|---|---|
| 418 | Pyridine-3-boronic acid | 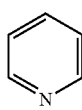 |
| 419 | Phenylboronic acid | 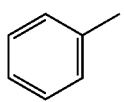 |
| 420 | 5-(tert-Butyldimethylsilanyloxymethyl) pyridine-3-boronic acid | 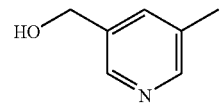 |

Example 418

1-[4-Amino-2-propyl-7-(pyridin-3-yl)-1H-imidazo[4,5-c]quinolin-1-yl]-2-methylpropan-2-ol The reaction mixture was concentrated under reduced pressure, and hexanes were added to form a precipitate. The precipitate was isolated by filtration and purified by HPFC (eluting with chloroform:CMA in a gradient from 100:0 to 70:30) to provide the product as an off-white solid, mp 238.5-241° C.

$^1$H NMR (300 MHz, DMSO-$d_6$) δ 8.97 (s, 1H), 8.57 (d, J=3.6 Hz, 1H), 8.38 (d, J=8.7 Hz, 1H), 8.14 (d, J=7.8 Hz, 1H), 7.9 (s, 1H), 7.55-7.47 (m, 2H), 6.39 (s, 2H), 4.71 (s, 1H), 4.56 (br s, 2H), 3.01 (t, J=7.2 Hz, 2H), 1.86 (sextet, J=7.5 Hz, 2H), 1.2 (s, 6H), 1.01 (t, J=7.5 Hz, 3H);

MS (APCI) m/z 376 (M+H)$^+$;

Anal. Calcd for $C_{22}H_{25}N_5O.0.33H_2O$: C, 69.28; H, 6.78; N, 18.36. Found: C, 69.68; H, 7.24; N, 18.58.

Example 419

1-[4-Amino-7-phenyl-2-propyl-1H-imidazo[4,5-c] quinolin-1-yl]-2-methylpropan-2-ol The isolated solid was recrystallized from methanol:water and then purified by HPFC (eluting with chloroform:CMA in a gradient from 100:0 to 70:30). A second recrystallization was carried out with acetonitrile:isopropanol to provide the product as a white solid.

$^1$H NMR (300 mHz, DMSO-$d_6$) δ 8.35 (d, J=8.7 Hz, 1H), 7.85 (d, J=2.0 Hz, 1H), 7.77-7.74 (m, 2H), 7.52-7.47 (m, 3H), 7.39-7.34 (m, 1H), 6.32 (br s, 2H), 4.71 (s, 1H), 4.57 (br s, 2H), 3.02 (t, J=7.4 Hz, 2H), 1.86 (sextet, J=7.6 Hz, 2H), 1.21 (br s, 6H), 1.02 (t, J=7.3 Hz, 3H);

MS (ESI) 375.2180 (375.2185 calcd for $C_{23}H_{26}N_4O$).

Example 420

1-[4-Amino-7-(5-hydroxymethylpyridin-3-yl)-2-propyl-1H-imidazo[4,5-c]quinolin-1-yl]-2-methyl-propan-2-ol The crude product was purified by HPFC (eluting with ethyl acetate and then chloroform:CMA in a gradient from 90:10 to 70:30) and then deprotected according to the method described in Part C of Example 150. The product from the deprotection was purified by HPFC (eluting with chloroform: CMA in a gradient from 100:0 to 60:40). The resulting product was mixed with dichloromethane and concentrated under reduced pressure until a solid began to form. The solid was isolated by filtration and dried under vacuum to provide 1-[4-amino-7-(5-hydroxymethylpyridin-3-yl)-2-propyl-1H-imidazo[4,5-c]quinolin-1-yl]-2-methylpropan-2-ol as a white solid, mp 225-226° C.

Anal. Calcd for $C_{23}H_{27}N_5O_2.0.67H_2O$: C, 66.17; H, 6.84; N, 16.78. Found: C, 65.86; H, 6.85; N, 16.66.

Example 421-424

Part A

The method described in Part A of Example 200 was used to treat 7-bromo-4-chloro-3-nitroquinoline (50.0 g, 174 mmol) with 1,2-diamino-2-methylpropane (36.5 mL, 348 mmol) and triethylamine (45 mL, 260 mmol). Following the work-up procedure, the solution of $N^1$-(3-nitro-7-bromo-quinolin-4-yl)-2-methylpropane-1,2-diamine in dichloromethane was concentrated to a volume of 1 L.

Part B

The solution from Part A was cooled to 0° C. under a nitrogen atmosphere. Triethylamine (48.5 mL, 348 mmol) was added followed by a solution of di-tert-butyl dicarbonate (41.8 g, 191 mmol) in dichloromethane (200 mL) over a period of 30 minutes. The reaction was allowed to warm to ambient temperature and stirred for three days. The reaction was washed with deionized water (2×500 mL) and brine (500 mL), dried over sodium sulfate and magnesium sulfate, filtered through a layer of CELITE filter aid, and concentrated under reduced pressure to provide 58 g of tert-butyl [2-(7-bromo-3-nitroquinolin-4-ylamino)-1,1-dimethylethyl]carbamate as a yellow solid.

Part C

The method described in Part B of Examples 125-135 was used to reduce tert-butyl [2-(7-bromo-3-nitroquinolin-4-ylamino)-1,1-dimethylethyl]carbamate (58.05 g, 132 mmol) to 23.74 g of tert-butyl [2-(3-amino-7-bromoquinolin-4-ylamino)-1,1-dimethylethyl]carbamate as an orange solid.

Part D

A modification of the method described in Part C of Examples 125-135 was used to treat tert-butyl [2-(3-amino-7-bromoquinolin-4-ylamino)-1,1-dimethylethyl]carbamate (23.7 g, 58.0 mmol) with ethoxyacetyl chloride (6.4 mL, 58 mmol). Triethylamine (12.1 mL, 87.0 mmol) was added to the reaction, which was stirred overnight. The reaction was washed with deionized water (2×) and brine, dried over sodium sulfate and magnesium sulfate, filtered, and concentrated under reduced pressure to provide 26.25 g of an orange solid.

Part E

The method described in Part D of Examples 152-156 was followed. The reaction was heated at reflux for four days. The crude product was purified first by HPFC (eluting with chloroform:CMA in a gradient from 85:15 to 80:20) and then by column chromatography on silica gel (eluting with 85:15 chloroform:CMA) to provide 15.94 g of tert-butyl [2-(7-bromo-2-ethoxymethyl-1H-imidazo[4,5-c]quinolin-1-yl)-1,1-dimethylethyl]carbamate as a brown solid.

Part F tert-Butyl [2-(7-bromo-2-ethoxymethyl-1H-imidazo[4,5-c]quinolin-1-yl)-1,1-dimethylethyl]carbamate (15.94 g, 33.39 mmol) was oxidized and then aminated according to the methods described in Parts H and I of Example 1. The oxidation reaction was carried out in chloroform and stirred overnight. The product was not recrystallized. The product from amination, tert-butyl [2-(4-amino-7-bromo-2-ethoxymethyl-1H-imidazo[4,5-c]quinolin-1-yl)-1,1-dimethylethyl] carbamate, was obtained as a brown solid after the work-up procedure and used without purification.

Part G

The material from Part F was deprotected according to the method described in Example 177. The work-up procedure described in Example 192 was followed with the exception that the aqueous solution was washed with twice dichloromethane before ammonium hydroxide was added. The crude product was purified by column chromatography on silica gel (eluting with dichloromethane:methanol in a gradient from 95:5 to 90:10) to provide 7.27 g of 1-(2-amino-2-methylpropyl)-7-bromo-2-ethoxymethyl-1H-imidazo[4,5-c] quinolin-4-amine as a tan solid.

Part H

A solution of 1-(2-amino-2-methylpropyl)-7-bromo-2-ethoxymethyl-1H-imidazo[4,5-c]quinolin-4-amine (1 equivalent, 4.5-5 mmol) in the solvent shown in the table below was cooled to −20° C. or 0° C.; triethylamine (2 equivalents) was added. The reagent shown in the table below (1.1 equivalents) was added slowly, and the reaction was stirred for between one hour and overnight. The reaction was washed

217 with deionized water (2×) and brine, dried over sodium sulfate, filtered, and concentrated under reduced pressure. The crude product was purified by HPFC (eluting with chloroform:CMA in a gradient from 100:0 to 70:30 for Examples 422 and 424 and with 90:10 dichloromethane:methanol for Example 423).

Part I

Under a nitrogen atmosphere, triphenylphosphine (0.015 equivalents), 2 M aqueous sodium carbonate (1.2 equivalents) and a solution of palladium (II) acetate in warm toluene (0.005 equivalents) were added to a solution of the material from Part G (Example 421) or Part H (Examples 422-424) (1 equivalent) and pyridine-3-boronic acid 1,3-propanediol cyclic ester (1.1 equivalents) in n-propanol (0.05-0.15 M). The reaction was heated at reflux under nitrogen for 1.5 to 3.5 hours. Deionized water was added, and organic solvent was removed under reduced pressure. The aqueous mixture was extracted twice with ethyl acetate, and the combined organic fractions were washed with 2 M aqueous sodium carbonate, dried over sodium sulfate, filtered, and concentrated under reduced pressure. The crude product was purified by HPFC (eluting with chloroform:CMA in a gradient from 100:0 to 70:30) to provide the product shown in the table below. Characterization data are shown after the table.

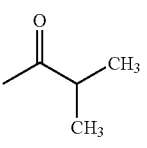

| Example | Solvent for Part H (concentration) | Reagent for Part H | R |
|---|---|---|---|
| 421 | Not used | Not used | H |
| 422 | NMP (0.17 M) | Isobutyryl chloride | 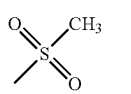 |
| 423 | Dichloromethane (0.1 M) | Methanesulfonic anhydride | 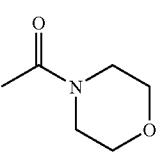 |
| 424 | Dichloromethane (0.1 M) | 4-Morpholine-carbonyl chloride | 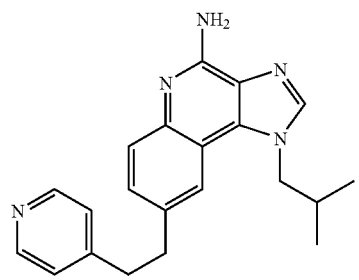 |

218

Example 421

1-(2-Amino-2-methylpropyl)-2-ethoxymethyl-7-(pyridin-3-yl)-1H-imidazo[4,5-c]quinolin-4-amine The product was obtained as an off-white powder. Anal. Calcd for $C_{22}H_{26}N_6O \cdot 0.25H_2O$: C, 66.90; H, 6.76; N, 21.28. Found: C, 66.62; H, 7.05, N, 21.34.

Example 422

N-{2-[4-Amino-2-ethoxymethyl-7-(pyridin-3-yl)-1H-imidazo[4,5-c]quinolin-1-yl]-1,1-dimethylethyl}-2-methylpropamide The product was obtained as a yellow powder. Anal. Calcd for $C_{26}H_{32}N_6O_2 \cdot 0.40H_2O$: C, 67.02; H, 7.05; N, 18.04. Found: C, 66.81; H, 7.25; N, 18.06.

Example 423

N-{2-[4-Amino-2-ethoxymethyl-7-(pyridin-3-yl)-1H-imidazo[4,5-c]quinolin-1-yl]-1,1-dimethylethyl}methanesulfonamide The product was obtained as a white powder. $^1$H NMR (300 MHz, DMSO-$d_6$) δ 8.99 (d, J=1.8 Hz, 1H), 8.59 (dd, J=4.7, 1.5 Hz, 1H), 8.41 (d, J=8.6 Hz, 1H), 8.19 (m, 1H), 7.91 (d, J=2.0 Hz, 1H), 7.59-7.50 (m, 2H), 7.33 (s, 1H), 6.73 (s, 2H), 4.90 (s, 4H), 3.57 (q, J=7.0 Hz, 2H), 3.01 (s, 3H), 1.32 (br s, 6H), 1.15 (t, J=7.0 Hz, 3H); MS (ESI) m/z 469.2018 (469.2022 calcd for $C_{23}H_{28}N_6O_3S$, M+H$^+$).

Example 424

N-{2-[4-Amino-2-ethoxymethyl-7-(pyridin-3-yl)-1H-imidazo[4,5-c]quinolin-1-yl]-1,1-dimethylethyl}morpholine-4-carboxamide The product was obtained as an off-white powder; $^1$H NMR (300 MHz, CDCl$_3$) δ 9.00 (d, J=2.1 Hz, 1H), 8.62 (m, 1H), 8.34 (d, J=8.6 Hz, 1H), 8.06-8.01 (m, 2H), 7.57 (m, 1H), 7.41 (m, 1H), 5.49 (s, 2H), 5.14 (s, 2H), 4.82 (br s, 2H), 4.44 (s, 1H), 3.62 (m, 6H), 3.22 (m, 4H), 1.41 (br s, 6H), 1.26 (m, 3H); MS (ESI) m/z 504.2734 (504.2723 calcd for $C_{27}H_{33}N_7O_3$, M+H$^+$).

Example 425

1-(2-Methylpropyl)-8-(2-pyridin-4-ylethyl)-1H-imidazo[4,5-c]quinolin-4-amine

Part A

A solution of 1-(2-methylpropyl)-1H-imidazo[4,5-c]quinolin-4-amine (30.0 g, 125 mmol) in chloroform (620 mL) was heated to 50° C., and N-bromosuccinimide (28.8 g, 162 mmol) was added in five portions over a period of five minutes. The resulting dark red solution was heated at reflux for 45 minutes, allowed to cool to ambient temperature, and stirred for one hour. A precipitate formed, was isolated by filtration, and was washed with water and diethyl ether to provide 9.0 g of 8-bromo-1-(2-methylpropyl)-1H-imidazo[4,5-c]-quinolin-4-amine as a solid.

Part B

Nitrogen was bubbled through a solution of 8-bromo-1-(2-methylpropyl)-1H-imidazo[4,5-c]-quinolin-4-amine (3.0 g, 9.4 mmol), 4-vinylpyridine (2.0 mL, 19 mmol), triphenylphosphine (246 mg, 0.94 mmol), and triethylamine (2.7 mL, 19 mmol) in acetonitrile (50 mL) for 15 minutes. Palladium (II) acetate (105 mg, 0.47 mmol) was added, and the reaction was heated at 100° C. for three days. The solvent was removed under reduced pressure, and the residue was adjusted to pH 2 with the addition of concentrated hydrochloric acid. Water was added, and the mixture was filtered through a layer of CELITE filter aid. Aqueous sodium carbonate (2 N) was added to the filtrate to adjust the solution to pH 10. The solution was then extracted with dichloromethane, and the combined extracts were dried over sodium sulfate, filtered, and concentrated under reduced pressure. The crude product was purified by flash column chromatography on silica gel (eluting with chloroform:CMA in a gradient from 95:5 to 80:20) to provide 2.1 g of 1-(2-methylpropyl)-8-(2-pyridin-4-ylvinyl)-1H-imidazo[4,5-c]-quinolin-4-amine as a yellow solid.

Part C 1-(2-Methylpropyl)-8-(2-pyridin-4-ylvinyl)-1H-imidazo[4,5-c]-quinolin-4-amine (2.1 g, 6.1 mmol) was treated according to the method described in Example 123; the reaction was allowed to run for seven days. An analysis by proton nuclear magnetic resonance spectroscopy indicated the presence of starting material in the purified product. The product mixture was dissolved in methanol (100 mL), and 10% palladium on carbon (200 mg) was added. The reaction was placed under hydrogen pressure (40 psi, $2.8 \times 10^5$ Pa) for four days, and the product was isolated as described in Example 123. The crude product was purified by flash column chromatography on silica gel (eluting with 90:10 chloroform:CMA) followed by recrystallization from acetonitrile to provide 380 mg of 1-(2-methylpropyl)-8-(2-pyridin-4-ylethyl)-1H-imidazo[4,5-c]-quinolin-4-amine as pale, yellow crystals, mp 221-224° C.

Anal. Calcd for $C_{21}H_{23}N_5$: C, 73.02; H, 6.71; N, 20.27. Found: C, 72.77; H, 6.39; N, 20.23.

Example 426

1-(2-Methylpropyl)-8-(4-phenylbutyl)-1H-imidazo[4,5-c]quinolin-4-amine

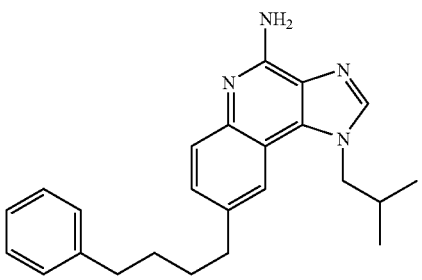

Part A

8-Bromo-1-(2-methylpropyl)-1H-imidazo[4,5-c]quinolin-4-amine (3.0 g, 9.4 mmol) was treated with 4-phenyl butene (4.2 mL, 28.2 mmol) according to the method described in Part B of Example 425. The reaction was heated overnight. Following chromatographic purification (eluting with 95:5 chloroform:methanol), 1.8 g of 1-(2-methylpropyl)-8-(4-phenylbut-1-enyl)-1H-imidazo[4,5-c]quinolin-4-amine were obtained as an off-white solid.

Part B 1-(2-Methylpropyl)-8-(4-phenylbut-1-enyl)-1H-imidazo[4,5-c]quinolin-4-amine (1.8 g, 4.8 mmol) was treated according to the method described in Example 123. The crude product was recrystallized from acetonitrile and then from methanol to provide 700 mg of 1-(2-methylpropyl)-8-(4-phenylbutyl)-1H-imidazo[4,5-c]quinolin-4-amine as white crystals, mp 176-177° C.

Anal. Calcd for $C_{24}H_{28}N_4$: C, 77.38; H, 7.58; N, 15.04. Found: C, 76.99; H, 7.45; N, 14.97.

Examples 427-429

Part A

A solution of (7-bromo-3-nitroquinolin-4-yl)-(2-methylpropyl)amine (30.9 g, 105 mmol) in acetonitrile (1.8 L) and isopropanol (200 mL) was added to a Parr vessel. A mixture of 5% platinum on carbon (3.0 g) and acetonitrile:isopropanol (20 mL) was added, and the vessel was purged with nitrogen. The vessel was placed under hydrogen pressure (40 psi, $2.8 \times 10^5$ Pa) for two hours. After one hour, the pressure had decreased to 20 psi ($1.4 \times 10^5$ Pa) and was readjusted to 40 psi ($2.8 \times 10^5$ Pa). The reaction mixture was filtered through a layer of CELITE filter aid, and the filter cake was washed with acetonitrile. The filtrate was concentrated under reduced pressure to provide 7-bromo-N-$^4$-(2-methylpropyl)quinoline-3,4-diamine as an oil.

Part B

Under a nitrogen atmosphere, a mixture of the material from Part A, triethyl orthoformate (20.9 mL, 126 mmol), and pyridine hydrochloride (3.1 g, 27 mmol) in acetonitrile was heated at reflux for 20 minutes. A Dean-Stark trap was used to collect the volatiles. The reaction mixture was concentrated under reduced pressure to provide 18.7 g of 7-bromo-1-(2-methylpropyl)-1H-imidazo[4,5-c]quinoline as a gold solid.

Part C

The method described in Part J of Example 365 was used to oxidize and aminate 7-bromo-1-(2-methylpropyl)-1H-imidazo[4,5-c]quinoline (18.7 g, 58.4 mmol). 3-Chloroperoxybenzoic acid (22.1 g of 50% pure material, 129 mmol) was added in five portions during the oxidation step, and the amination with ammonium hydroxide (146 mL) and p-toluenesulfonyl chloride (16.6 g, 87.6 mmol) proceeded overnight. The crude product was obtained as an oil, which was treated with acetonitrile to form a precipitate. The precipitate was isolated by filtration, washed with a small amount of acetonitrile, and recrystallized from acetonitrile to provide 4 g of 7-bromo-1-(2-methylpropyl)-1H-imidazo[4,5-c]quinolin-4-amine as off-white needeles, mp 218-220° C.

Anal. Calcd for $C_{14}H_{15}BrN_4$: C, 52.68; H, 4.74; N, 17.55. Found: C, 52.55; H, 4.99; N, 17.44.

Part D

7-Bromo-1-(2-methylpropyl)-1H-imidazo[4,5-c]quinolin-4-amine and the boronic acid indicated in the table below were coupled according to the general methods described in Part J of Example 1 and Part F of Examples 125-135. Palladium (II) acetate was added as a 5 mg/mL solution in toluene, and the reaction was heated overnight. The crude product was purified by flash column chromatography on silica gel (eluting with 90:10 chloroform:CMA for Examples 428 and 429 and chloroform:methanol in a gradient from 95:5 to 90:10 for Example 427). Examples 427 and 428 were recrystallized from the solvents shown in the table below, isolated by filtration, and dried under high vacuum.

Example 429 was dissolved in THF (20 mL), and tetrabutylammonium fluoride (4.0 mL of a 1.0 M solution in THF) was added. The reaction was stirred for 15 minutes and concentrated under reduced pressure. The resulting black oil was purified by flash column chromatography on silica gel (eluting with methanol:CMA in a gradient from 90:10 to 75:25) to provide an oil that was stirred with acetonitrile at 0° C. to provide a solid, which was recrystallized from acetonitrile/methanol to provide the compound shown in the following table.

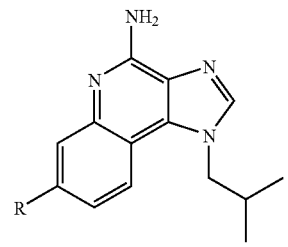

| Example | Boronic Acid | Recrystallization solvent(s) | R |
|---|---|---|---|
| 427 | trans-2-Phenylvinyl-boronic acid | Methanol | styryl |
| 428 | 3-Pyridine boronic acid | Acetonitrile | pyridin-3-yl |
| 429 | 5-(tert-Butyldimethyl-silanyloxymethyl) pyridine-3-boronic acid | Acetonitrile/methanol | 5-(hydroxymethyl)pyridin-3-yl |

Examples 427-429

| Example | Name | Form | mp (° C.) | Anal. |
|---|---|---|---|---|
| 427 | 1-(2-Methylpropyl)-7-styryl-1H-imidazo[4,5-c]quinolin-4-amine | Light brown needles | 257-258 | Calcd for $C_{22}H_{22}N_4$: C, 77.16; H, 6.48; N, 16.36. Found: C, 76.86; H, 6.40; N, 16.44. |
| 428 | 1-(2-Methylpropyl)-7-(pyridin-3-yl)-1H-imidazo[4,5-c]quinolin-4-amine | Gray needles | 125 | Calcd for $C_{19}H_{19}N_5$: C, 71.90; H, 6.03; N, 22.07. Found: C, 70.99; H, 6.20; N, 21.88. |
| 429 | 1-(2-Methylpropyl)-7-(5-hydroxymethylpyridin-3-yl)-1H-imidazo[4,5-c]quinolin-4-amine | Yellow crystals | 210-211 | Calcd for $C_{20}H_{21}N_5O$: C, 69.14; H, 6.09; N, 20.16. Found: C, 68.96; H, 6.26; N, 20.22. |

Example 430

1-(2-Methylpropyl)-7-phenethyl-1H-imidazo[4,5-c]quinolin-4-amine

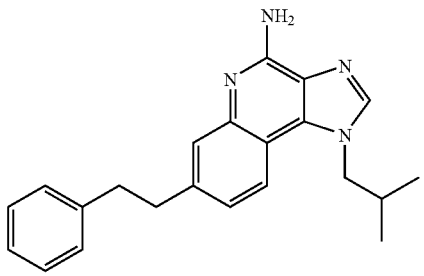

A modification of the method described in Example 123 was used to reduce 1-(2-methylpropyl)-7-styryl-1H-imidazo[4,5-c]quinolin-4-amine (1.2 g, 3.5 mmol). The reaction was carried out in methanol (100 mL) for seven days. The crude product was purified by flash column chromatography on silica gel (eluting with 90:10 chloroform:CMA) followed by recrystallization from acetonitrile to provide 1-(2-methylpropyl)-7-phenethyl-1H-imidazo[4,5-c]quinolin-4-amine as white crystals, mp 172-173° C.

Anal. Calcd for $C_{22}H_{24}N_4$: C, 76.71; H, 7.02; N, 16.27. Found: C, 76.56; H, 7.15; N, 16.24.

Examples 431-436

Part A

Triethyl orthoformate (10.0 mL, 60.1 mmol), Meldrum's acid (8.2 g, 57 mmol), and either 3-benzyl aniline or 4-benzyl aniline (10.0 g, 54.6 mmol) as indicated in the table below in methanol (303 mL) were combined and treated according to the method described in Part A of Example 1 to provide 5-[(3-benzylphenylamino)methylene]-2,2-dimethyl-[1,3]dioxane-4,6-dione (15.5 g) or 5-[(4-benzylphenylamino)methylene]-2,2-dimethyl-[1,3]dioxane-4,6-dione (15.2 g), respectively.

Part B

5-[(3-Benzylphenylamino)methylene]-2,2-dimethyl-[1,3]dioxane-4,6-dione (15.5 g, 46.0 mmol, Examples 431-433) or 5-[(4-benzylphenylamino)methylene]-2,2-dimethyl-[1,3]dioxane-4,6-dione (15.2 g, 45.0 mmol, Examples 434-436) was heated at 230° C. in DOWTHERM A heat transfer fluid for one hour, and then the reaction was allowed to cool to ambient temperature overnight.

For Examples 431-433, a 4.0 M solution of hydrogen chloride in 1,4-dioxane followed by diethyl ether were added to the reaction to precipitate a salt, which adhered to the sides of the reaction flask. The salt was washed with diethyl ether (3×) and dissolved in dichloromethane. Sodium carbonate (2 M) was added to adjust the solution to pH 11, and water was added. The aqueous layer was separated and extracted with dichloromethane, and the combined organic fractions were dried over sodium sulfate, filtered, and concentrated under reduced pressure. The residue was purified by HPFC (eluting with chloroform:CMA in a gradient from 97:3 to 40:60) to provide 4.0 g of 7-benzylquinolin-4-ol and 4.75 g of 5-benzylquinolin-4-ol.

For Examples 434-436, a precipitate formed upon cooling and was isolated by filtration and washed with diethyl ether to provide 6-benzylquinolin-4-ol as a light brown solid.

Part C

The method described in Part D of Example 10 was used to treat 7-benzylquinolin-4-ol or 6-benzylquinolin-4-ol with nitric acid to provide 7-benzyl-3-nitroquinolin-4-ol or 6-benzyl-3-nitroquinolin-4-ol, respectively, as solids.

Part D

The method described in Part E of Example 10 was used to treat 7-benzyl-3-nitroquinolin-4-ol or 6-benzyl-3-nitroquinolin-4-ol with phosphorous oxychloride to provide 7-benzyl-4-chloro-3-nitroquinoline as a light yellow powder or 6-benzyl-4-chloro-3-nitroquinoline as a tan powder, respectively.

Part E

Under a nitrogen atmosphere, 1-amino-2-methylpropan-2-ol (1.2 equivalents) was added to a 0.2 M solution of 7-benzyl-4-chloro-3-nitroquinoline or 6-benzyl-4-chloro-3-nitroquinoline (1 equivalent) and triethylamine (3 equivalents) in dichloromethane, and the reaction was stirred overnight at ambient temperature. The volatiles were removed under reduced pressure, and the residue was stirred with water (50 mL) for one hour. The resulting yellow solid was isolated by filtration and washed with water to provide 1-(7-benzyl-3-nitroquinolin-4-ylamino)-2-methylpropan-2-ol or 1-(6-benzyl-3-nitroquinolin-4-ylamino)-2-methylpropan-2-ol, respectively.

Part F

A modification of the method described in Part A of Examples 427-429 was used to reduce 1-(7-benzyl-3-nitroquinolin-4-ylamino)-2-methylpropan-2-ol or 1-(6-benzyl-3-nitroquinolin-4-ylamino)-2-methylpropan-2-ol. The reaction was shaken for one or two days to provide 1-(3-amino-7-benzylquinolin-4-ylamino)-2-methylpropan-2-ol or 1-(3-amino-6-benzylquinolin-4-ylamino)-2-methylpropan-2-ol.

Part G

For Examples 431 and 434, a modification of the method described in Part B of Examples 427-429 was used to treat 1-(3-amino-7-benzylquinolin-4-ylamino)-2-methylpropan-2-ol or 1-(3-amino-6-benzylquinolin-4-ylamino)-2-methylpropan-2-ol with triethyl orthoformate, as indicated in the table below. The reaction was heated at reflux for one hour and then stirred overnight at ambient temperature. A precipitate formed, which was isolated by filtration to provide 1-(7-benzyl-1H-imidazo[4,5-c]quinolin-1-yl)-2-methylpropan-2-ol or 1-(8-benzyl-1H-imidazo[4,5-c]quinolin-1-yl)-2-methylpropan-2-ol.

For Examples 432, 433, 435, and 436, 1-(3-amino-7-benzylquinolin-4-ylamino)-2-methylpropan-2-ol or 1-(3-amino-6-benzylquinolin-4-ylamino)-2-methylpropan-2-ol was treated with the acid chloride shown in the table below according to the method described in Part A of Example 9. The reaction was heated overnight, and after the work-up procedure, the crude product was purified by HPFC (eluting with chloroform:CMA in a gradient from 99:1 to 70:30).

Part H

The method described in Part J of Example 365 was used to oxidize and aminate the material from Part G. 3-Chloroperoxybenzoic acid (1-1.5 equivalents of 50% pure material) was added in two portions over a period of 30 minutes during the oxidation step. After the work-up procedure, the crude product was purified by HPFC (eluting with chloroform:CMA in a gradient from about 100:0 to about 60:40) followed by recrystallization from acetonitrile to provide the product shown in the table below. For Example 434, no chromatographic purification was carried out, and the product was recrystallized from acetonitrile:methanol.

Examples 431-436

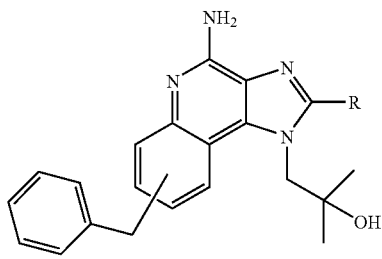

| Ex. | Starting material | Reagent in Part G | Product | R |
|---|---|---|---|---|
| 431 | 3-Benzyl aniline | Triethyl orthoformate | 7-Benzyl | —H |
| 432 | 3-Benzyl aniline | Butyryl chloride | 7-Benzyl | —$CH_2CH_2CH_3$ |
| 433 | 3-Benzyl aniline | Ethoxyacetyl chloride | 7-Benzyl | —$CH_2OCH_2CH_3$ |
| 434 | 4-Benzyl aniline | Triethyl orthoformate | 8-Benzyl | —H |
| 435 | 4-Benzyl aniline | Butyryl chloride | 8-Benzyl | —$CH_2CH_2CH_3$ |
| 436 | 4-Benzyl aniline | Ethoxyacetyl chloride | 8-Benzyl | —$CH_2OCH_2CH_3$ |

Examples 431-436

| Example | Name | Form | mp (° C.) | Anal. |
|---|---|---|---|---|
| 431 | 1-(4-Amino-7-benzyl-1H-imidazo[4,5-c]quinolin-1-yl)-2-methylpropan-2-ol | Brown crystals | 228-229 | Calcd for $C_{21}H_{22}N_4O$: C, 72.81; H, 6.40; N, 16.17. Found: C, 72.66; H, 6.37; N, 16.14. |
| 432 | 1-(4-Amino-7-benzyl-2-propyl-1H-imidazo[4,5-c]quinolin-1-yl)-2-methylpropan-2-ol | Tan crystals | 130-131 | Calcd for $C_{24}H_{28}N_4O\cdot 0.25 H_2O$: C, 73.35; H, 7.31; N, 14.26. Found: C, 73.04; H, 7.46; N, 14.30. |
| 433 | 1-(4-Amino-7-benzyl-2-ethoxymethyl-1H-imidazo[4,5-c]quinolin-1-yl)-2-methylpropan-2-ol | Light brown crystals | 166-167 | Calcd for $C_{24}H_{28}N_4O_2$: C, 71.26; H, 6.98; N, 13.85. Found: C, 70.92; H, 7.30; N, 14.05. |
| 434 | 1-(4-Amino-8-benzyl-1H-imidazo[4,5-c]quinolin-1-yl)-2-methylpropan-2-ol | Pale yellow crystals | 256-257 | Calcd for $C_{21}H_{22}N_4O$: C, 72.81; H, 6.40; N, 16.17. Found: C, 72.56; H, 6.21; N, 16.13. |
| 435 | 1-(4-Amino-8-benzyl-2-propyl-1H-imidazo[4,5-c]quinolin-1-yl)-2-methylpropan-2-ol | Tan powder | 191-192 | Calcd for $C_{24}H_{28}N_4O$: C, 74.20; H, 7.26; N, 14.42. Found: C, 73.93; H, 7.47; N, 14.26. |
| 436 | 1-(4-Amino-8-benzyl-2-ethoxymethyl-1H-imidazo[4,5-c]quinolin-1-yl)-2-methylpropan-2-ol | Yellow crystlas | 209-210 | Calcd for $C_{24}H_{28}N_4O_2$: C, 71.26; H, 6.98; N, 13.85. Found: C, 70.89; H, 6.87; N, 13.84. |

Examples 437-439

Part A

Under a nitrogen atmosphere, cyclohexylmethylamine (40.9 mL, 315 mmol) was added dropwise to a solution of 7-bromo-4-chloro-3-nitroquinoline (30.0 g, 105 mmol) in dichloromethane (524 mL). The reaction was stirred for 18 hours at ambient temperature and then concentrated under reduced pressure. Water (200 mL) was added to the residue, and the mixture was stirred for three hours. Acetonitrile was added; a precipitate formed. The solid was isolated by filtration, dried under a flow of air for two hours, and recrystallized from acetonitrile to provide 24.0 g of (7-bromo-3-nitroquinolin-4-yl)cyclohexylmethylamine as a yellow solid.

Part B

The method described in Part A of Examples 427-429 was used to reduce (7-bromo-3-nitroquinolin-4-yl)cyclohexylmethylamine (24.0 g, 65.9 mmol) to 21.0 g of 7-bromo-$N^4$-(cyclohexylmethyl)quinoline-3,4-diamine, obtained as a greenish solid.

Part C

A modification of the method described in Part A of Example 9 was used to treat 7-bromo-$N$-$^4$-(cyclohexylmethyl)quinoline-3,4-diamine (7.3 g, 22 mmol) with ethoxyacetyl chloride (2.75 mL, 24.0 mmol). The reaction was heated overnight at 90° C. and then concentrated under reduced pressure to provide 7-bromo-1-cylcohexylmethyl-2-ethoxymethyl-1H-imidazo[4,5-c]quinoline as a dark brown semi-solid.

Part D

The method described in Part J of Example 365 was used to oxidize and aminate 7-bromo-1-cylcohexylmethyl-2- ethoxymethyl-1H-imidazo[4,5-c]quinoline (7.58 g, 22.0 mmol). 3-Chloroperoxybenzoic acid (9.1 g of 50% pure material, 26.4 mmol) was added in five portions during the oxidation step, and the amination with ammonium hydroxide (55 mL) and p-toluenesulfonyl chloride (6.3 g, 33 mmol) proceeded overnight. The crude product was obtained as an oil, which was treated with acetonitrile to form a precipitate. The precipitate was isolated by filtration and washed with a small amount of acetonitrile. A portion of the brown solid was purified by flash column chromatography on silica gel (eluting with chloroform:CMA in a gradient from 95:5 to 85:15) to provide 7-bromo-1-cylcohexylmethyl-2-ethoxymethyl-1H-imidazo[4,5-c]quinolin-4-amine as a brown solid, mp 215-216° C.

Anal. Calcd for $C_{20}H_{25}BrN_4O$: C, 57.56; H, 6.04; N, 13.42. Found: C, 57.57; H, 5.93; N, 13.44.

Part E

7-Bromo-1-cylcohexylmethyl-2-ethoxymethyl-1H-imidazo[4,5-c]quinolin-4-amine and the boronic acid indicated in the table below were coupled according to the general methods described in Part J of Example 1 and Part F of Examples 125-135. Palladium (II) acetate was added as a 5 mg/mL solution in toluene, and the reaction was heated overnight. The crude product was purified by HPFC (eluting with chloroform:CMA in a gradient from 90:10 to 55:45 for Examples 437 and 438 and 95:5 to 85:15 for Example 439) followed by recrystallization from acetonitrile to provide the product shown in the table below.

Example 439 was treated as described in Example 429. The crude product was purified twice by flash column chromatography on silica gel (eluting with chloroform:CMA in a gradient from 90:10 to 70:30) followed by recrystallization from methanol to provide the compound shown in the following table.

Examples 437-439

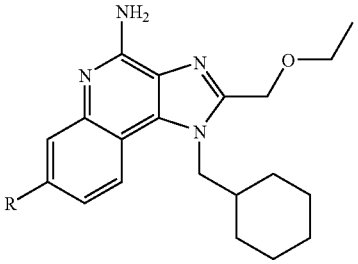

| Example | Boronic Acid | R |
|---|---|---|
| 437 | 3-(Morpholine-4-carbonyl)phenylboronic acid | 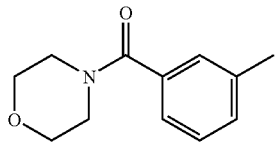 |
| 438 | 3-Pyridine boronic acid | 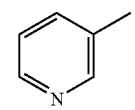 |
| 439 | 5-(tert-Butyldimethyl-silanyloxymethyl)pyridine-3-boronic acid | 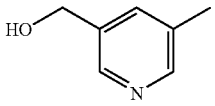 |

Examples 437-439

| Example | Name | Form | mp (° C.) | Anal. |
|---|---|---|---|---|
| 437 | 1-[3-(4-Amino-1-cyclohexylmethyl-2-ethoxymethyl-1H-imidazo[4,5-c]quinolin-7-yl)phenyl]morpholin-4-ylmethanone | Tan needles | 186-187 | Calcd for $C_{31}H_{37}N_5O_3$: C, 70.56; H, 7.07; N, 13.27. Found: C, 70.16; H, 7.24; N, 13.40. |
| 438 | 1-Cyclohexylmethyl-2-ethoxymethyl-7-(pyridin-3-yl)-1H-imidazo[4,5-c]quinolin-4-amine | Tan crystals | 146-148 | Calcd for $C_{25}H_{29}N_5O$: C, 71.95; H, 7.05; N, 16.78. Found: C, 71.60; H, 6.83; N, 16.65. |
| 439 | 1-Cyclohexylmethyl-2-ethoxymethyl-7-(5-hydroxymethylpyridin-3-yl)-1H-imidazo[4,5-c]quinolin-4-amine | Off-white crystals | 240-241 | Calcd for $C_{26}H_{31}N_5O_2$: C, 70.09; H, 7.01; N, 15.72. Found: C, 69.92; H, 6.97; N, 15.61. |

Examples 440-463

Part A (7-Bromo-3-nitroquinolin-4-yl)-(2-methylpropyl)amine (117 g) was dissolved in hot toluene (2 L) and poured into stainless steel Parr vessel. Additional toluene (2 L) and 5% platinum on carbon (12.5 g) were added. The vessel was evacuated, charged with hydrogen (54 psi, 3.7×10$^5$ Pa), and shaken overnight at room temperature. The reaction mixture evacuated, filtered through a layer of CELITE filter aid, and concentrated under reduced pressure to provide 7-bromo-N$^4$-(2-methylpropyl)quinoline-3,4-diamine, which was used without purification.

Part B

Butyryl chloride (1.1 equivalent) was slowly added to a stirred solution of 7-bromo-N-$^4$-(2-methylpropyl)quinoline-3,4-diamine (52.9 g, 0.18 mol.) in pyridine (700 mL) at room temperature. A pale yellow precipitate formed and then went into solution. The reaction mixture was heated at reflux for eight hours, and then allowed to slowly cool to room temperature over the weekend. The dark gold, turbid reaction mixture was concentrated under reduced pressure. The residue was dissolved in 1 N hydrochloric acid and then adjusted to pH 14 with the addition of 10% aqueous sodium hydroxide. A precipitate formed, was isolated by filtration, washed with water (3×100 mL), and dried overnight on the filter funnel to provide 7-bromo-1-(2-methylpropyl)-2-propyl-1H-imidazo[4,5-c]quinoline as an off-white solid.

Part C

To a stirred solution of 7-bromo-1-(2-methylpropyl)-2-propyl-1H-imidazo[4,5-c]quinoline (51.1 g, 0.148 mol) in dichloromethane (1 L) was slowly added 3-chloroperoxybenzoic acid (1.0 equivalent of 50% pure material) in small portions. The reaction was maintained at room temperature for one hour. Concentrated ammonium hydroxide (600 mL) was added with stirring. After 15 minutes, p-toluenesulfonyl chloride (1.1 equivalents.) was added in small portions. The reaction was stirred at room temperature overnight. The reaction was quenched by adding water (1 L) and stirred for an additional hour. A solid was present and was isolated by filtration to provide 7-bromo-1-(2-methylpropyl)-2-propyl-1H-imidazo[4,5-c]quinolin-4-amine as an off-white solid.

Part D

Triethylamine (3.0 equivalents), potassium vinyltrifluoroborate (1.0 equivalent) and dichloro[1,1'-bis(diphenylphosphino)ferrocene]palladium (II) dichloromethane adduct (0.2 equivalent) were added to a solution of 7-bromo-1-(2-methylpropyl)-2-propyl-1H-imidazo[4,5-c]quinolin-4-amine (1.0 equivalent) in n-propanol (30 ml/g). The reaction mixture was heated at reflux under a nitrogen atmosphere until it was complete (between four and 18 hours) and then poured into water (3 volumes). The pH of the mixture was monitored and adjusted to pH 12 with the addition of 10% aqueous sodium hydroxide if needed. The mixture was extracted with ethyl acetate, and the combined organic fractions were filtered and concentrated under reduced pressure. The crude product was purified by flash column chromatography on silica gel (eluting with chloroform:methanol in a gradient from 100:0 to 90:10), followed by recrystallization from acetonitrile to provide 1-(2-methylpropyl)-2-propyl-7-vinyl-1H-imidazo[4,5-c]quinolin-4-amine as an off-white solid.

Part E

A thick-walled glass tube, equipped with magnetic stir-bar, was charged with acetonitrile (20 mL/g), palladium (II) acetate (0.1 equivalent), tri-ortho-tolylphosphine (0.3 equivalent), triethylamine (3.0 equivalent), 1-(2-methylpropyl)-2-propyl-7-vinyl-1H-imidazo[4,5-c]quinolin-4-amine (1.0 equivalent), and the aryl- or heteroaryl-halide (1.5 equivalents) shown in the table below. The tube was purged with nitrogen and sealed. The reaction mixture was heated at 120° C. for between 24 and 48 hours and then allowed to cool to ambient temperature. The solvent was removed under reduced pressure. The solid was then partitioned between dichloromethane and water; the mixture was adjusted to pH 12 with the addition of 10% aqueous sodium hydroxide if needed. The organic layer was separated and was purified by flash column chromatography on silica gel (eluting with chloroform:methanol in a gradient from 100:0 to 90:10) followed by recrystallization from acetonitrile to provide the compound shown in the table below.

Examples 440-455

| Example | Aryl- or Heteroaryl halide | R |
|---|---|---|
| 440 | 3-Bromobenzene-sulfonamide | 3-sulfonamidephenyl |
| 441 | 5-Bromo-2-methylbenzothiazole | 2-methylbenzothiazol-5-yl |
| 442 | 2-Iodo-5-methylthiophene | 5-methylthiophen-2-yl |
| 443 | 3-Bromoanisole | 3-methoxyphenyl |
| 444 | 4-Bromoanisole | 4-methoxyphenyl |

-continued

Structure: 4-amino-1-(2-methylpropyl)-2-propyl-1H-imidazo[4,5-c]quinoline with (E)-vinyl-R substituent at position 7.

| Example | Aryl- or Heteroaryl halide | R |
|---|---|---|
| 445 | 2-Bromoanisole | 2-methoxyphenyl |
| 446 | 3-Bromopyridine | pyridin-3-yl |
| 447 | 4-Bromobenzenesulfonamide | 4-sulfamoylphenyl |
| 448 | 2-Bromopyridine | pyridin-2-yl |
| 449 | 2-Chlorobenzothiazole | benzothiazol-2-yl |
| 450 | 5-Bromonicotinonitrile | 5-cyanopyridin-3-yl |

-continued

| Example | Aryl- or Heteroaryl halide | R |
|---|---|---|
| 451 | 5-Bromonicotinamide | 5-carbamoylpyridin-3-yl |
| 452 | 2-Bromobenzamide | 2-carbamoylphenyl |
| 453 | 2-Acetyl-5-bromothiophene | 5-acetylthiophen-2-yl |
| 454 | 4-Bromotoluene | 4-methylphenyl |
| 455 | Ethyl 3-bromobenzoate | 3-(ethoxycarbonyl)phenyl |

The characterization data for Examples 440-446 and Example 452 are shown in the table below.

Examples 440-446, 450, 452

| Ex. | Name | Form | Mp (° C.) | Anal. |
|---|---|---|---|---|
| 440 | (E)-3-{2-[4-Amino-1-(2-methylpropyl)-2-propyl-1H-imidazo[4,5-c]quinolin-7-yl]vinyl}benzenesulfonamide | White solid | >250 | Calcd for $C_{25}H_{29}N_5O_2S$: C, 54.69; H, 5.60; N, 12.77. Found: C, 54.62; H, 5.44; N, 12.65. |
| 441 | (E)-7-[2-(2-Methylbenzothiazol-5-yl)vinyl]-1-(2-methylpropyl)-2-propyl-1H-imidazo[4,5-c]quinolin-4-amine | Off-white solid | 210-212 | Calcd for $C_{27}H_{29}N_5S \cdot 1.8$ $CH_4O$: C, 67.22; H, 7.46; N, 13.63. Found: C, 67.07; H, 7.18; N, 13.91. |
| 442 | (E)-1-(2-Methylpropyl)-7-[2-(5-methylthiophen-2-yl)vinyl]-2-propyl-1H-imidazo[4,5-c]quinolin-4-amine | Light tan crystals | 182-185 | Calcd for $C_{24}H_{28}N_4S$: C, 71.25; H, 6.98; N, 13.85. Found: C, 71.01; H, 6.80; N, 13.81. |

-continued

| Ex. | Name | Form | Mp (° C.) | Anal. |
|---|---|---|---|---|
| 443 | (E)-7-[2-(3-Methoxyphenyl)vinyl]-1-(2-methylpropyl)-2-propyl-1H-imidazo[4,5-c]quinolin-4-amine | Pale yellow crystals | 181-183 | Calcd for $C_{26}H_{30}N_4O$: C, 75.33; H, 7.29; N, 13.51. Found: C, 75.28; H, 7.52; N, 13.77. |
| 444 | (E)-7-[2-(4-Methoxyphenyl)vinyl]-1-(2-methylpropyl)-2-propyl-1H-imidazo[4,5-c]quinolin-4-amine | Off-white solid | 201-202 | Calcd for $C_{26}H_{30}N_4O$: C, 75.33; H, 7.29; N, 13.51. Found: C, 75.06; H, 7.44; N, 13.63. |
| 445 | (E)-7-[2-(2-Methoxyphenyl)vinyl]-1-(2-methylpropyl)-2-propyl-1H-imidazo[4,5-c]quinolin-4-amine | Tan needles | 214-216 | Calcd for $C_{26}H_{30}N_4O$: C, 75.33; H, 7.29; N, 13.51. Found: C, 75.12; H, 7.68; N, 13.53. |
| 446 | (E)-1-(2-Methylpropyl)-2-propyl-7-[2-(pyridin-3-yl)vinyl]-1H-imidazo[4,5-c]quinolin-4-amine | Yellow crystals | 190-192 | Calcd for $C_{24}H_{27}N_5 \cdot 0.5 H_2O$: C, 73.07; H, 7.15: N, 17.75. Found: C, 73.13; H, 7.33; N, 17.88. |
| 450 | (E)-3-{2-[4-Amino-1-(2-methylpropyl)-2-propyl-1H-imidazo[4,5-c]quinolin-7-yl]vinyl}nicotinonitrile | Yellow solid | 246-248 | Calcd for $C_{25}H_{26}N_6$: C, 73.14; H, 6.38: N, 20.47. Found: C, 73.15; H, 6.11; N, 20.42. |
| 452 | (E)-2-{2-[4-Amino-(2-methylpropyl)-2-propyl-1H-imidazo[4,5-c]quinolin-7-yl]vinyl}benzamide | Tan crystals | Not measured | Calcd for $C_{26}H_{29}N_5O$: C, 73.04; H, 6.84: N, 16.38. Found: C, 72.80; H, 6.79; N, 16.26. |

Examples 447-449, 451, 453-455

| Example | Name | MS (APCI) m/z $(M + H)^+$ |
|---|---|---|
| 447 | (E)-4-{2-[4-Amino-1-(2-methylpropyl)-2-propyl-1H-imidazo[4,5-c]quinolin-7-yl]vinyl}benzenesulfonamide | 464 |
| 448 | (E)-1-(2-Methylpropyl)-2-propyl-7-[2-(pyridin-2-yl)vinyl]-1H-imidazo[4,5-c]quinolin-4-amine | 386 |
| 449 | (E)-7-[2-(Benzothiazol-2-yl)vinyl]-1-(2-methylpropyl)-2-propyl-1H-imidazo[4,5-c]quinolin-4-amine | 442 |
| 451 | (E)-3-{2-[4-Amino-1-(2-methylpropyl)-2-propyl-1H-imidazo[4,5-c]quinolin-7-yl]vinyl}nicotinamide | 429.3 |
| 453 | (E)-7-[2-(2-Acetylthiophen-5-yl)vinyl]-1-(2-methylpropyl)-2-propyl-1H-imidazo[4,5-c]quinolin-4-amine | 433.3 |
| 454 | (E)-1-(2-Methylpropyl)-2-propyl-7-[2-(p-tolyl)vinyl]-1H-imidazo[4,5-c]quinolin-4-amine | 399.1 |
| 455 | (E)-Ethyl 3-{2-[4-amino-(2-methylpropyl)-2-propyl-1H-imidazo[4,5-c]quinolin-7-yl]vinyl}benzoate | 457.3 |

Examples 456-461

A Parr hydrogenation vessel was charged with the starting material indicated in the table below, a 1:1 mixture of methanol:ethanol (30 mL/g), and 10% palladium on carbon (50% wt./wt.). The reaction vessel was evacuated, charged with hydrogen (45 psi, $3.1 \times 10^5$ Pa), and shaken until the reaction was complete (24-48 hours). The reaction mixture was filtered through CELITE filter agent, concentrated under reduced pressure, and purified by flash column chromatography on silica gel (eluting with dichloromethane:methanol in a gradient from 100:0 to 90:10) followed by recrystallization from acetonitrile to provide the product shown in the table below.

Examples 456-461

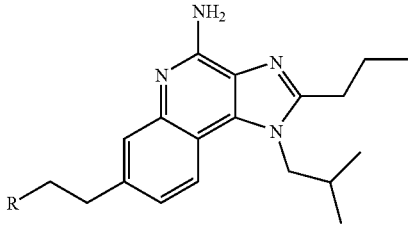

| Example | Starting Material | R |
|---|---|---|
| 456 | Example 440 | 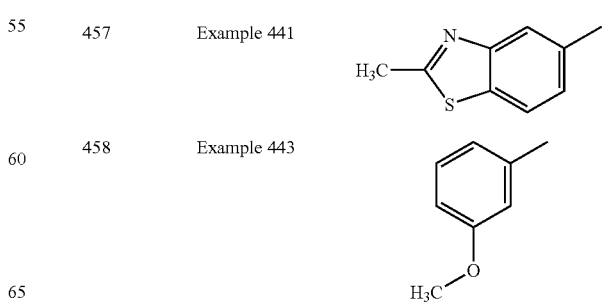 |
| 457 | Example 441 | |
| 458 | Example 443 | |

-continued

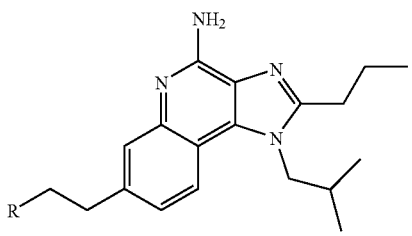

| Example | Starting Material | R |
|---|---|---|
| 459 | Example 444 | 4-methoxyphenyl-methyl |
| 460 | Example 445 | 2-methoxyphenyl-methyl |
| 461 | Example 442 | 5-methyl-2-thienyl-methyl (H₃C-thiophene-CH₃) |

The characterization data for Examples 456-461 are shown in the table below.

Examples 456-461

Examples 462-471

The procedure described in Examples 456-461 can also be used to hydrogenate the following compounds to provide the products shown in the table below.

Examples 462-471

| Example | Starting Material | R |
|---|---|---|
| 462 | Example 446 | 3-pyridyl |
| 463 | Example 454 | 4-methylphenyl |

| Example | Name | Form | mp (° C.) | Anal. |
|---|---|---|---|---|
| 456 | 3-{2-[4-Amino-1-(2-methylpropyl)-2-propyl-1H-imidazo[4,5-c]quinolin-7-yl]ethyl}benzenesulfonamide | Off-white solid | 250-251 | Calcd for $C_{25}H_{31}N_5O_2S$: C, 64.49; H, 6.71; N, 15.04. Found: C, 64.28; H, 6.76; N, 14.88. |
| 457 | 7-[2-(2-Methylbenzothiazol-5-yl)ethyl]-1-(2-methylpropyl)-2-propyl-1H-imidazo[4,5-c]quinolin-4-amine | White solid | >250 | Calcd for $C_{27}H_{31}N_5S\cdot HCl$: C, 65.63; H, 6.53; N, 14.17. Found: C, 65.68; H, 6.73; N, 13.96. |
| 458 | 7-[2-(3-Methoxyphenyl)ethyl]-1-(2-methylpropyl)-2-propyl-1H-imidazo[4,5-c]quinolin-4-amine | White crystals | 155-157 | Calcd for $C_{26}H_{32}N_4O$: C, 74.97; H, 7.74; N, 13.45. Found: C, 74.57; H, 7.65; N, 13.52. |
| 459 | 7-[2-(4-Methoxyphenyl)ethyl]-1-(2-methylpropyl)-2-propyl-1H-imidazo[4,5-c]quinolin-4-amine | White solid | >250 | Calcd for $C_{26}H_{32}N_4O\cdot HCl$: C, 68.93; H, 7.34; N, 12.37. Found: C, 68.67; H, 7.82; N, 12.33. |
| 460 | 7-[2-(2-Methoxyphenyl)ethyl]-1-(2-methylpropyl)-2-propyl-1H-imidazo[4,5-c]quinolin-4-amine | White solid | >250 | Calcd for $C_{26}H_{32}N_4O\cdot HCl$: C, 68.93; H, 7.34; N, 12.37. Found: C, 68.76; H, 7.69; N, 12.29. |
| 461 | 1-(2-Methylpropyl)-7-[2-(5-methylthiophen-2-yl)ethyl]-2-propyl-1H-imidazo[4,5-c]quinolin-4-amine | Off-white solid | 150-152 | Calcd for $C_{24}H_{30}N_4S$: C, 70.90; H, 7.44; N, 13.78. Found: C, 71.28; H, 7.70; N, 13.80. |

-continued

| Example | Starting Material | R |
|---|---|---|
| 464 | Example 447 | ![sulfonamide tolyl] |
| 465 | Example 448 | 2-methylpyridine |
| 466 | Example 449 | 2-methylbenzothiazole |
| 467 | Example 450 | 5-methyl-3-cyanopyridine |
| 468 | Example 451 | 5-methylnicotinamide |
| 469 | Example 452 | 2-methylbenzamide |
| 470 | Example 453 | 5-methyl-2-acetylthiophene |
| 471 | Example 455 | ethyl 3-methylbenzoate |

Example 472

2-Ethloxymethyl-1-(3-methoxypropyl)-7-(pyrazol-1-yl)-1H-imidazo[4,5-c]quinolin-4-amine

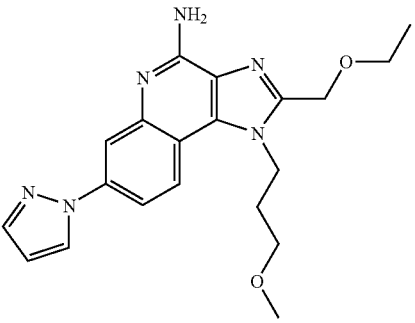

A 4 dram vial containing a stir bar was charged sequentially with copper(I) iodide (0.003 g), potassium phosphate (0.890 g), pyrazole (0.164 g), 7-bromo-2-ethoxymethyl-1-(3-methoxypropyl)-1H-imidazo[4,5-c]quinolin-4-amine (0.786 g), (1)-trans-1,2-diaminocyclohexane (0.030 mL), and anhydrous 1,4-dioxane (2 mL). The vial was flushed with nitrogen, capped, and placed in an oil bath at 110° C. After 15.5 hours, the reaction was cooled to room temperature and purified by flash column chromatography using a gradient of CMA/chloroform as the eluent. Subsequent recrystallization from acetonitrile yielded 0.190 g of 2-ethoxymethyl-1-(3-methoxypropyl)-7-(pyrazol-1-yl)-1H-imidazo[4,5-c]quinolin-4-amine as a white solid, mp 159.0-160.0° C.

Anal Calcd. for $C_{20}H_{24}N_6O_2$: % C, 63.14; % H, 6.36; % N, 22.09. Found: % C, 62.91; % H, 6.32; % N, 22.06.

Example 473

2-Ethoxymethyl-7-(imidazol-1-yl)-1-(3-methoxypropyl)-1H-imidazo[4,5-c]quinolin-4-amine

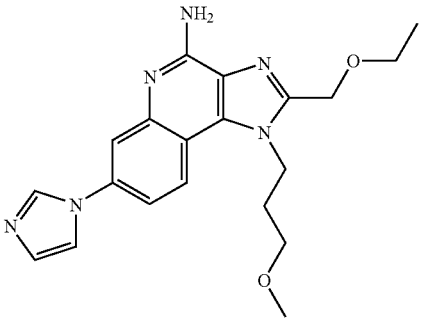

The general method described in Example 452 was followed with imidazole replacing pyrazole as a reactant. After cooling to room temperature, the reaction mixture was poured into water and diluted with dichloromethane. The mixture was stirred for 10 minutes, followed by separation of the layers. The aqueous fraction was extracted with dichloromethane and the combined organic fractions were concentrated. The residue was initially purified by HPFC eluting with a linear gradient of 1-30% CMA in chloroform. A final recrystallization from acetonitrile provided 0.070 g of 2-ethoxymethyl-7-(imidazol-1-yl)-1-(3-methoxypropyl)-1H-imidazo[4,5-c]quinolin-4-amine as an off-white solid, mp 167.5-169.0° C.

Anal Calcd. for $C_{20}H_{24}N_6O_2$: % C, 63.14; % H, 6.36; % N, 22.09. Found: % C, 63.11; % H, 6.30; % N, 22.16.

Example 474

1-(4-Amino-7-{4-[4-amino-2-ethoxymethyl-1-(2-hydroxy-2-methylpropyl)-1H-imidazo[4,5-c]quinolin-7-yl]phenyl}-2-ethoxymethyl-1H-imidazo[4,5-c]quinolin-1-yl)-2-methylpropan-2-ol

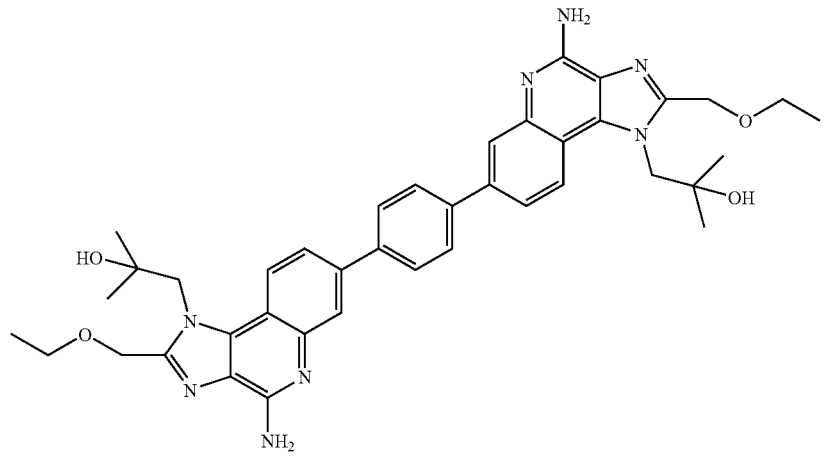

A mixture of 1-(4-amino-7-bromo-2-ethoxymethyl-1H-imidazo[4,5-c]quinolin-1-yl)-2-methylpropan-2-ol (2.18 g, 5.54 mmol), 1,4-phenylenebisboronic acid (0.44 g, 2.65 mmol), triphenylphosphine (42 mg, 0.16 mmol), n-propanol (36 mL), 2 M aqueous sodium carbonate (3.2 mL, 6.4 mmol), and water was degassed three times and placed under a nitrogen atmosphere. Palladium (II) acetate (12 mg, 0.050 mmol) in 250 μL of warm toluene was added, and reaction was degassed twice and placed under a nitrogen atmosphere. The reaction was heated at 100° C. for one hour and then allowed to cool to ambient temperature. A precipitate formed and was isolated by filtration, recrystallized from ethanol (300 mL), isolated by filtration, washed with ethanol, and dried in a vacuum oven at 60° C. to provide 286 mg of 1-(4-amino-7-{4-[4-amino-2-ethoxymethyl-1-(2-hydroxy-2-methylpropyl)-1H-imidazo[4,5-c]quinolin-7-yl]phenyl}-2-ethoxymethyl-1H-imidazo[4,5-c]quinolin-1-yl)-2-methylpropan-2-ol as off-white needles, mp 325-328° C.

Anal. Calcd for $C_{40}H_{46}N_8O_4 \cdot 1.4H_2O$: C, 65.99; H, 6.76; N, 15.39. Found: C, 65.86; H, 6.80; N, 15.39.

Example 475

1-(4-Amino-7-{7-[4-amino-2-ethoxymethyl-1-(2-hydroxy-2-methylpropyl)-1H-imidazo[4,5-c]quinolin-7-yl]-9,9-dihexyl-9H-fluoren-2-yl}-2-ethoxymethyl-1H-imidazo[4,5-c]quinolin-1-yl)-2-methylpropan-2-ol

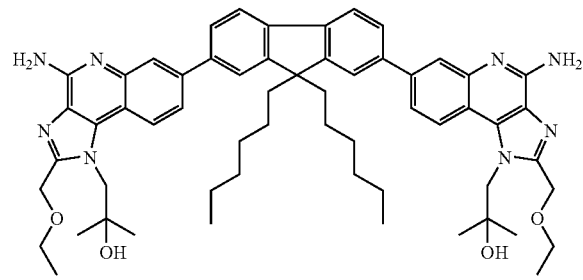

1-(4-Amino-7-bromo-2-ethoxymethyl-1H-imidazo[4,5-c]quinolin-1-yl)-2-methylpropan-2-ol (2.18 g, 5.54 mmol) and 9,9-dihexylfluorene-2,7-diboronic acid (1.12 g, 2.65 mmol) were coupled according to the method described in Example 474. At the completion of the reaction, the n-propanol was removed under reduced pressure, and the residue was dissolved in dichloromethane (150 mL). The resulting solution was washed sequentially with 2 M aqueous sodium carbonate (50 mL) and brine (50 mL), dried over magnesium sulfate, filtered, and concentrated under reduced pressure. The crude product was purified by HPFC (eluting with chloroform:CMA in a gradient from 100:0 to 75:25) followed by recrystallization from dichloromethane (15 mL) and heptane (30 mL). The solid was isolated by filtration, washed with heptane, and dried overnight in a vacuum oven at 60° C. to provide 0.68 g of 1-(4-amino-7-{7-[4-amino-2-ethoxymethyl-1-(2-hydroxy-2-methylpropyl)-1H-imidazo[4,5-c]quinolin-7-yl]-9,9-dihexyl-9H-fluoren-2-yl}-2-ethoxymethyl-1H-imidazo[4,5-c]quinolin-1-yl)-2-methylpropan-2-ol as off-white needles, mp 261-265° C.

Anal. Calcd for $C_{59}H_{74}N_8O_4 \cdot 1.1H_2O$: C, 72.35; H, 7.85; N, 11.44. Found: C, 72.24; H, 7.99; N, 11.47.

Example 476

1-[4-Amino-7-(7-{4-amino-2-(2-methoxyethyl)-1-[3-(pyrrolidin-2-one)propyl]-1H-imidazo[[4,5-c]quinolin-7-yl}-9,9-dihexyl-9H-fluoren-2-yl)-2-(2-methoxyethyl)-1H-imidazo[4,5-c]quinolin-1-yl]propyl}pyrrolidin-2-one

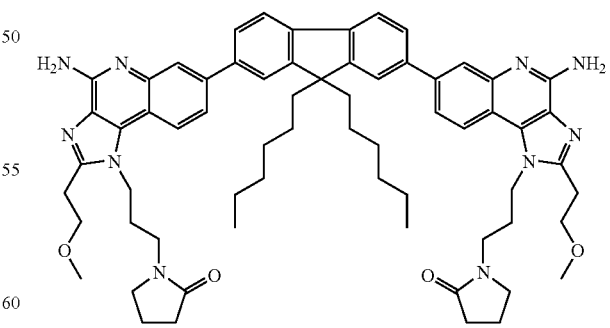

1-{3-[4-Amino-7-bromo-2-(2-methoxyethyl)-1H-imidazo[4,5-c]quinolin-1-yl]propyl}pyrrolidin-2-one (0.91 g, 2.0 mmol) and 9,9-dihexylfluorene-2,7-diboronic acid (0.41 g, 0.97 mmol) were coupled according to the method described in Example 474; the work-up procedure described

241 in Example 475 was followed. The crude product was purified by HPFC (eluting with chloroform:CMA in a gradient from 90:10 to 65:35) followed by recrystallization from isopropanol (40 mL). The solid was isolated by filtration, washed with isopropanol, and dried over three days in a vacuum oven at 60° C. to provide 0.45 g of 1-[4-amino-7-(7-{4-amino-2-(2-methoxyethyl)-1-[3-(pyrrolidin-2-one)propyl]-1H-imidazo[4,5-c]quinolin-7-yl}-9,9-dihexyl-9H-fluoren-2-yl)-2-(2-methoxyethyl)-1H-imidazo[4,5-c]quinolin-1-yl]propyl}pyrrolidin-2-one as off-white needles, mp 251-254° C.

Anal. calcd for $C_{65}H_{80}N_{10}O_4 \cdot 0.8H_2O$: C, 72.27; H, 7.62; N, 12.97. Found: C, 72.07; H, 7.84; N, 12.99.

Examples 477-480

Part A

Ammonium hydroxide (1 L) was added to a solution of methyl tetrahydropyranyl acetate (20 mL, 150 mmol) in methanol (500 mL), and the reaction was stirred overnight at ambient temperature. Additional ammonium hydroxide (500 mL) was added, and the reaction was stirred for four additional days. The methanol was removed under reduced pressure. Solid sodium chloride was added to the aqueous layer, which was extracted with chloroform (3×150 mL). The combined extracts were dried over sodium sulfate, filtered, and concentrated under reduced pressure to provide 11.4 g of tetrahydropyran-4-carboxamide as a white solid.

Part B

A solution of tetrahydropyran-4-carboxamide (11.4 g, 88.3 mmol) in THF (441 mL) was cooled to 0° C. Lithium aluminum hydride (10.0 g, 265 mmol) was added in six portions over a period of ten minutes. The reaction flask was purged with nitrogen between the additions. When the reaction mixture was no longer bubbling, it was heated at reflux for six hours. The reaction was then cooled to 0° C., and ethyl acetate was added dropwise until bubbling ceased. Methanol was then added dropwise until bubbling ceased. Water (10 mL), 15% aqueous sodium hydroxide (10 mL), and water (30 mL) were sequentially added. The organic fraction was decanted off, and the remaining gray solid was washed with chloroform. The combined organic fractions were dried over sodium sulfate, filtered, and concentrated under reduced pressure to provide C-(tetrahydropyran-4-yl)methylamine.

Part C

The method described in Part E of Examples 431-436 was used to treat 7-bromo-4-chloro-3-nitroquinoline (12.43 g, 43.45 mmol) with C-(tetrahydropyran-4-yl)methylamine (10 g, 87 mmol) to provide 15.0 g of (7-bromo-3-nitroquinolin-4-yl)(tetrahydropyran-4-ylmethyl)amine as a bright yellow solid.

Part D

The method described in Part A of Examples 427-429 was used to reduce (7-bromo-3-nitroquinolin-4-yl)(tetrahydropyran-4-ylmethyl)amine (15.0 g, 44.0 mmol) to 7-bromo-$N^4$-(tetrahydropyran-4-ylmethyl)quinoline-3,4-diamine, obtained as a greenish solid.

Part E

The material from Part D was treated with ethoxyacetyl chloride (5.5 mL, 48 mmol) according to the method described in Part A of Example 9. The reaction was heated overnight, and after the work-up procedure, the crude product was purified by HPFC (eluting with chloroform:CMA in a gradient from 100:0 to 80:20) to provide 9.3 g of 7-bromo-2-ethoxymethyl-1-(tetrahydropyran-4-ylmethyl)-1H-imidazo[4,5-c]quinoline as an oil.

Part F

The method described in Part J of Example 365 was used to oxidize and aminate 7-bromo-2-ethoxymethyl-1-(tetrahydropyran-4-ylmethyl)-1H-imidazo[4,5-c]quinoline (9.3 g, 23.0 mmol). 3-Chloroperoxybenzoic acid (7.9 g of 50% pure material, 23 mmol) was added in five portions during the oxidation step, which was stirred overnight. Additional 3-chloroperoxybenzoic acid (200 mg) was added, and the reaction was stirred for 20 mintues before ammonium hydroxide (60 mL) and p-toluenesulfonyl chloride (6.58 g, 34.5 mmol) were added. The crude product was obtained as an oil, which was treated with acetonitrile to form a precipitate. The precipitate was isolated by filtration and purified by HPFC (eluting with chloroform:CMA in a gradient from 100:0 to 80:20) to provide 6.0 g of 7-bromo-2-ethoxymethyl-1-(tetrahydropyran-4-ylmethyl)-1H-imidazo[4,5-c]quinolin-4-amine as a white solid, mp 186-188° C.

Part G

7-Bromo-2-ethoxymethyl-1-(tetrahydropyran-4-ylmethyl)-1H-imidazo[4,5-c]quinolin-4-amine and the boronic acid indicated in the table below were coupled according to the general methods described in Part J of Example 1 and Part F of Examples 125-135. Palladium (II) acetate was added as a 5 mg/mL solution in toluene, and the reaction was heated overnight. The crude product was purified by HPFC (eluting with chloroform:CMA in a gradient from 100:0 to 70:30). The resulting oil was stirred with a small amount of acetonitrile to provide a solid, which was isolated by filtration. For Examples 477 and 478, the solid was recrystallized twice from acetonitrile to provide the product shown in the table below. For Examples 479 and 480, the solid was allowed to dry in the filter funnel to provide the product shown in the table below.

Examples 477-480

| Example | Boronic Acid | R |
|---|---|---|
| 477 | 3-(Morpholine-4-carbonyl)phenylboronic acid | 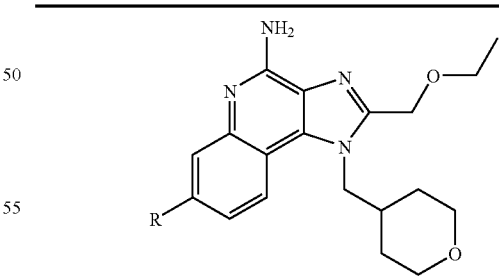 |

Examples 477-480

| Example | Boronic Acid | R |
|---|---|---|
| 478 | 2-Ethoxyphenylboronic acid | 2-ethoxyphenyl group |
| 479 | 3-Pyridine boronic acid | pyridin-3-yl group |
| 480 | 3-(Methylsulfonylamino)phenylboronic acid | 3-(methylsulfonylamino)phenyl group |

The characterization data for Examples 477-480 are provide in the table below.

Examples 477-480

| Example | Name | Form | mp (°C.) | Anal. |
|---|---|---|---|---|
| 477 | {3-[4-Amino-2-ethoxymethyl-1-(tetrahydropyran-4-ylmethyl)-1H-imidazo[4,5-c]quinolin-7-yl]phenyl}morpholin-4-ylmethanone | White crystals | 125-128 | Calcd for $C_{30}H_{35}N_5O_4 \cdot 0.2H_2O$: C, 66.67; H, 6.75; N, 12.96. Found: C, 66.34; H, 6.75; N, 12.99. |
| 478 | 2-Ethoxymethyl-7-(2-ethoxyphenyl)-1--(tetrahydropyran-4-ylmethyl)-1H-imidazo[4,5-c]quinolin-4-amine | Yellow crystals | 192-193 | Calcd for $C_{27}H_{32}N_4O_3 \cdot 0.06H_2O$: C, 70.25; H, 7.01; N, 12.14. Found: C, 69.85; H, 7.37; N, 12.32. |
| 479 | 2-Ethoxymethyl-7-(pyridin-3-yl)-1-(tetrahydropyran-4-ylmethyl)-1H-imidazo[4,5-c]quinolin-4-amine | White powder | 116-121 | Calcd for $C_{24}H_{27}N_5O_2 \cdot 0.09H_2O$: C, 68.78; H, 6.54; N, 16.71. Found: C, 68.89; H, 6.94; N, 16.73. |
| 480 | {3-[4-Amino-2-ethoxymethyl-1-(tetrahydropyran-4-ylmethyl)-1H-imidazo[4,5-c]quinolin-7-yl]phenyl}methanesulfonamide | White powder | 254-255 | Calcd for $C_{26}H_{31}N_5O_4S$: C, 61.28; H, 6.13; N, 13.74. Found: C, 60.96; H, 6.46; N, 13.99. |

Example 481

1-(2-Methylpropyl)-8-(1-pyrrolyl)-1H-imidazo[4,5-c]quinolin-4-amine

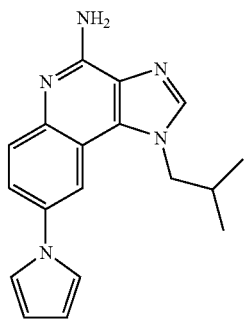

Part A

A solution of 1-(2-methylpropyl)-1H-imidazo[4,5-c]quinolin-4-amine (28.3 g, 0.118 mol) in concentrated sulfuric acid (150 mL) was cooled to 5° C. A solution of 70% nitric acid (8.4 mL, 0.130 mol) in sulfuric acid (30 mL) was added in portions over a period of one hour. The reaction temperature was maintained below 10° C. The solution was allowed to warm to ambient temperature, stirred for two hours, and then poured into 500 g of ice. The resulting solution was made basic with the addition of ammonium hydroxide while keeping the solution cold. A precipitate formed, was isolated by filtration, washed with water, and dried to provide 1-(2-methylpropyl)-8-nitro-1H-imidazo[4,5-c]quinolin-4-amine as a yellow solid.

Part B

The material from Part A was added slowly with stirring to a solution of 98% tin (II) chloride (114 g, 0.589 mmol) in concentrated hydrochloric acid (500 mL), and the reaction was heated at 100° C. for 15 minutes, allowed to cool to ambient temperature, and cooled to 0° C. A precipitate formed and was isolated by filtration, washed with a small amount of ethanol, and suspended in water. The suspension was adjusted to pH 13-14, and the resulting precipitate was isolated by filtration, washed with water, and mixed with water. The resulting suspension was made acidic with the addition of 6 N aqueous hydrochloric acid and then filtered. The filtrate was adjusted to pH 13-14 to form a precipitate, which was isolated by filtration, washed with water, and dried to provide 21.8 g of 8-amino-1-(2-methylpropyl)-1H-imidazo[4,5-c]quinolin-4-amine as a solid.

Part C 2,5-Dimethoxytetrahydrofuran (1.6 mL of 95%, 12 mmol) was added to a suspension of 8-amino-1-(2-methylpropyl)-1H-imidazo[4,5-c]quinolin-4-amine (3.0 g, 12 mmol) in acetic acid (60 mL), and the reaction was heated at reflux for one hour. The resulting dark brown solution was concentrated under reduced pressure, and the residue was mixed with water. The resulting mixture was made basic with the addition of ammonium hydroxide and stirred for 30 minutes. The resulting precipitate was isolated by filtration, washed with water, dried, and recrystallized from ethanol (100 mL). The crystals were collected in three crops. The first crop was dried for a day in a vacuum oven at 100° C. to provide 2.1 g of 1-(2-methylpropyl)-8-(1-pyrrolyl)-1H-imidazo[4,5-c]quinolin-4-amine as a solid, mp 227.5-231.5° C.

Anal. Calcd for $C_{18}H_{19}N_5$: C, 70.8; H, 6.3; N, 22.9. Found: C, 70.6; H, 6.3; N, 23.1.

Example 482

1-(2-Methylpropyl)-9-phenyl-1H-imidazo[4,5-c]quinolin-4-amine

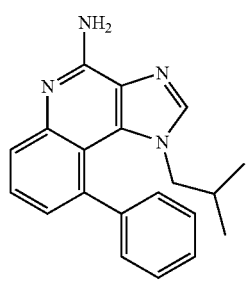

Part A

5-[(3-Bromophenylamino)methylene]-2,2-dimethyl-[1,3]dioxane-4,6-dione (32.6 g, 0.100 mol) was heated at 250° C. in DOWTHERM A heat transfer fluid for one hour, and then the reaction was allowed to cool to ambient temperature. A precipitate formed upon cooling and was isolated by filtration and washed with diethyl ether to provide 7-bromoquinolin-4-ol and 5-bromoquinolin-4-ol in a 2:1 ratio.

Part C

The method described in Part D of Example 10 was used to treat the material from Part A with nitric acid (10.3 mL of 11.74 M, 0.121 mmol) to provide 18.0 g of a 2:1 mixture of 7-bromo-3-nitroquinolin-4-ol and 5-bromo-3-nitroquinolin-4-ol.

Part D

The method described in Part D of Example 1 was used to treat 7-bromo-3-nitroquinolin-4-ol and 5-bromo-3-nitroquinolin-4-ol (10.0 g, 37.0 mmol) with phosphorous oxychloride (32.0 mL of 1.16 M) to provide a 2:1 mixture of 7-bromo-4-chloro-3-nitroquinoline and 5-bromo-4-chloro-3-nitroquinoline.

Part E

Under a nitrogen atmosphere, isobutylamine (11.0 mL, 0.111 mol) was added to the material from Part D and triethylamine (11.0 mL, 0.111 mol) in dichloromethane (15 mL). The reaction was stirred for 30 minutes at ambient temperature, and the volatiles were removed under reduced pressure to provide a 2:1 mixture of (7-bromo-3-nitroquinolin-4-yl)isobutylamine and (5-bromo-3-nitroquinolin-4-yl)isobutylamine containing some triethylamine.

Part F

A solution of sodium hydrosulfite (3.2 g, 185 mmol) in water (8 mL) was added to a solution of the material from Part E in 1:1 ethanol:acetonitrile (300 mL), and the reaction was stirred at ambient temperature for one hour. The solvents were removed under reduced pressure, and the resulting mixture was diluted with water. The aqueous mixture was extracted with chloroform (3×). The combined extracts were purified by HPFC (eluting with chloroform:CMA in a gradient from 100:0 to 80:20); the first compound to elute was 5-bromo-N-4-(2-methylpropyl)quinoline-3,4-diamine. Following the purification 2.2 g of this compound were isolated.

Part G

A mixture of 5-bromo-$N^4$-(2-methylpropyl)quinoline-3,4-diamine (1.0 g, 3.4 mmol), triethyl orthoformate (0.9 mL, 5 mmol), and pyridine hydrochloride (117 mg, 1.0 mmol) in acetonitrile (17 mL) was heated at reflux overnight. The reaction mixture was concentrated under reduced pressure, and the residue was purified by HPFC (eluting with chloroform:CMA in a gradient from 100:0 to 70:30) to provide 9-bromo-1-(2-methylpropyl)-1H-imidazo[4,5-c]quinoline as a dark oil.

Part H

9-Bromo-1-(2-methylpropyl)-1H-imidazo[4,5-c]quinoline (0.34 mmol) and benzene boronic acid (62 mg, 0.51 mmol) were coupled according to Part J of Example 1. The work-up procedure described in Parts 125-135 was followed. The crude product was purified by HPFC (eluting with chloroform:CMA in a gradient from 100:0 to 85:15) to provide 1-(2-methylpropyl)-9-phenyl-1H-imidazo[4,5-c]quinoline.

Part I

The method described in Part J of Example 365 was used to oxidize and aminate 1-(2-methylpropyl)-9-phenyl-1H-imidazo[4,5-c]quinoline (0.34 mmol). The crude product was purified by HPFC (eluting with chloroform:CMA in a gradient from 100:0 to 85:15) to provide 40 mg of 1-(2-methylpropyl)-9-phenyl-1H-imidazo[4,5-c]quinolin-4-amine as a pale yellow powder, mp 263-265° C.

$^1$H NMR (300 MHz, DMSO-$d_6$) δ 7.98 (s, 1H), 7.57 (d, J=8.1 Hz, 1H), 7.55-7.39 (m, 6H), 7.12 (d, J=7.2 Hz, 1H), 6.65 (broad s, 2H), 2.57 (d, J=7.6 Hz, 2H), 1.48 (m, 1H), 0.22 (d, J=6.7 Hz, 6H);

MS (ESI) m/z 317.1770 (calcd for $C_{20}H_{20}N_4$ 317.1766, M+H$^+$).

Example 483

1-(2-Methylpropyl)-9-(4-propoxyphenyl)-1H-imidazo[4,5-c]quinolin-4-amine

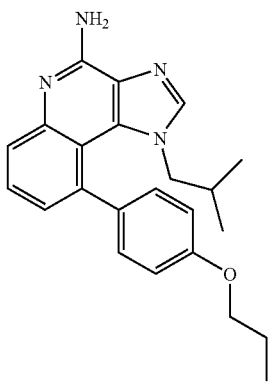

Part A

9-Bromo-1-(2-methylpropyl)-1H-imidazo[4,5-c]quinoline (1.0 g, 3.4 mmol) and 4-propoxyphenylboronic acid (1.0 g, 5.5 mmol) were coupled according to Part J of Example 1. The palladium (II) acetate (2.5 mg, 0.011 mmol) was added as a 5 mg/mL solution in toluene. The work-up procedure described in Parts 125-135 was followed. The crude product was purified by HPFC (eluting with chloroform:CMA in a gradient from 100:0 to 70:30) to provide 1.1 g of 1-(2-methylpropyl)-9-(4-propoxyphenyl)-1H-imidazo[4,5-c]quinoline as a dark brown oil.

Part I

The method described in Part J of Example 365 was used to oxidize and aminate 1-(2-methylpropyl)-9-(4-propoxyphenyl)-1H-imidazo[4,5-c]quinoline (1.1 g, 3.1 mmol). The amination reaction was stirred for 36 hours. The crude product was purified by HPFC (eluting with chloroform:CMA in a gradient from 100:0 to 70:30) to provide an oil, which was stirred with acetonitrile to provide a solid. The solid was isolated by filtration and recrystallized from acetonitrile to provide 165 mg of 1-(2-methylpropyl)-9-(4-propoxyphenyl)-1H-imidazo[4,5-c]quinolin-4-amine as light tan needles, mp 181-182° C.

Anal. Calcd for $C_{23}H_{26}N_4O \cdot 0.2H_2O$: C, 73.07; H, 7.04; N, 14.82. Found: C, 72.70; H, 6.90; N, 14.87.

Examples 484-486

Part A

Diethyl malonate (101 mL, 0.989 mol) and 2-bromoaniline (50.g, 0.291 mol) were combined and heated at 180° C. for six hours. A Dean-Stark trap was used to collect the volatiles. The reaction was allowed to cool to ambient temperature overnight; a precipitate formed. The precipitate was isolated by filtration and combined with methanol (160 mL), water (800 mL), and solid sodium carbonate (105 g). The mixture was heated at reflux for two hours, allowed to cool to ambient temperature, and then cooled to 0° C. The mixture was adjusted to pH 2 with the addition of 3 N hydrochloric acid; a white precipitate formed. The precipitate was isolated by filtration, washed with water, and dried overnight on the filter funnel to provide 43 g of N-(2-bromophenyl)malonamic acid as a white solid.

Part B

N-(2-Bromophenyl)malonamic acid (43 g, 170 mmol), polyphosphoric acid (334 mL of 0.5 M), and hydrochloric acid (444 mL of 1 N) were combined and heated at 140° C. for three hours. The solution was allowed to cool to ambient temperature, and additional hydrochloric acid (603 mL of 1 N) was added. The reaction was stirred for four hours and then adjusted to pH 4 with the addition of 20% aqueous sodium hydroxide. A precipitate formed and was isolated by filtration, washed with water, and dried to provide 37.4 g of 8-bromoquinoline-2,4-diol as a solid.

Part C

A modification of the method described in Part D of Example 10 was used to treat 8-bromoquinoline-2,4-diol (10.0 g, 41.6 mmol) with nitric acid (3.6 mL of 11.74 M, 54 mmol). The nitric acid was added at ambient temperature, and then the reaction was heated at 100° C. for one hour, at which time an exotherm occurred. The reaction was allowed to cool to ambient temperature; a precipitate formed and was isolated by filtration and washed with a small volume of water to provide 7.58 g of 8-bromo-3-nitroquinoline-2,4-diol as a yellow solid.

Part D

A mixture of phenylphosphonic dichloride (14.1 mL of 90% pure material, 99.3 mmol) and 8-bromo-3-nitroquinoline-2,4-diol (7.08 g, 24.8 mmol) was heated at 140° C. for three hours and then allowed to cool to ambient temperature. Ice water was added, and the mixture was stirred for 20 minutes to form a precipitate. The precipitate was isolated by filtration to provide 8-bromo-2,4-dichloro-3-nitroquinoline as a solid.

Part E

1-Amino-2-methylpropan-2-ol (2.08 g, 24.8 mmol) and triethylamine (10.4 mL, 74.4 mmol) were added to a solution of the material from Part D in dichloromethane (73 mL), and the reaction was stirred for 30 minutes. The solvent and some of the amines were removed under reduced pressure, and the residue was diluted with water. The aqueous layer was separated and extracted with chloroform, and the combined organic fractions were purified by HPFC (eluting with chloroform:CMA in a gradient from 100:0 to 80:20) to provide 1-(8-bromo-2-chloro-3-nitroquinolin-4-ylamino)-2-methylpropan-2-ol as a yellow solid.

Part F

The method described in Part F of Example 482 was used to reduce the material from Part E with sodium hydrosulfite (25.4 g, 124 mmol) to provide 5.15 g of 1-(3-amino-8-bromo-2-chloroquinolin-4-ylamino)-2-methylpropan-2-ol as a brown oil.

Part G

A solution of 1-(3-amino-8-bromo-2-chloroquinolin-4-ylamino)-2-methylpropan-2-ol (4.65 g, 14.4 mmol) and ethoxyacetyl chloride (1.9 mL, 15.8 mmol) in dichloromethane (72 mL) was stirred for one hour at ambient temperature. The solvent was removed under reduced pressure, and ethanol (43 mL), water (29 mL), and potassium carbonate (3.98 g, 28.8 mmol) were added. The reaction was stirred at 40° C. for 36 hours. The solvent was removed under reduce pressure, and the residue was diluted with water. The aqueous solution was extracted with chloroform, and the combined extracts were dried over sodium sulfate, filtered, and concentrated under reduced pressure to provide 4.4 g of 1-(6-bromo-2-ethoxymethyl-1H-imidazo[4,5-c]quinolin-1-yl)-2-methylpropan-2-ol as an orange solid.

Part H

Ammonia (50 mL of a 7 N solution in methanol) and 1-(6-bromo-2-ethoxymethyl-1H-imidazo[4,5-c]quinolin-1-yl)-2-methylpropan-2-ol (4.4 g, 11 mmol) were heated at 120° C. for 72 hours in a high-pressure vessel. The solvent was removed under reduced pressure to provide 3.5 g of a tan powder. The powder was dissolved in chloroform, washed with water, dried over sodium sulfate, filtered, and concentrated under reduced pressure to provide 1-(4-amino-6-bromo-2-ethoxymethyl-1H-imidazo[4,5-c]quinolin-1-yl)-2-methylpropan-2-ol as a tan solid.

Part I 1-(4-Amino-6-bromo-2-ethoxymethyl-1H-imidazo[4,5-c]quinolin-1-yl)-2-methylpropan-2-ol (842 mg, 2.14 mmol) and the boronic acid indicated in the table below (2.56 mmol) were coupled according to the procedure described in Part J of Example 1. Palladium (II) acetate was added as a 5 mg/mL solution in toluene. The reaction was heated for 15-17 hours at which time additional palladium (II) acetate (1.5 mg) and optionally additional boronic acid were added, and the reaction was heated for an additional 16 hours. The work-up procedure described in Examples 125-135 was followed. The crude product was purified by HPFC (eluting with chloroform:CMA in a gradient from 100:0 to 70:30) followed by recrystallization from the solvent indicated in the table below. For Example 484, a second purification by HPFC, and the resulting oil was triturated with acetonitrile to provide a solid. The structures of the products are shown in the table below.

Examples 484-486

| Example | Boronic Acid | Recrystallization Solvent | R |
|---|---|---|---|
| 484 | 3-(Methylsulfonylamino)-phenylboronic acid | Acetonitrile | |
| 485 | 3-Pyridine boronic acid | Methanol | |
| 486 | 3-(Morpholine-4-carbonyl)phenylboronic acid | Acetonitrile | |

The characterization data for Examples 484-486 are shown in the table below.

Examples 484-486

| Example | Name | Form | mp (° C.) | Anal. |
|---|---|---|---|---|
| 484 | {3-[4-Amino-2-ethoxymethyl-1-(2-hydroxy-2-methylpropyl)-1H-imidazo[4,5-c]quinolin-6-yl]phenyl}methanesulfonamide | White powder | 234-235 | Calcd for $C_{24}H_{29}N_5O_4S$: C, 59.61; H, 6.04; N, 14.48. Found: C, 59.56; H, 6.30; N, 14.55. |

-continued

| Example | Name | Form | mp (° C.) | Anal. |
|---|---|---|---|---|
| 485 | 1-[4-Amino-2-ethoxymethyl-6-(pyridin-3-yl)-1H-imidazo[4,5-c]quinolin-1-yl]-2-methylpropan-2-ol | Tan crystals | 199-201 | Calcd for $C_{22}H_{25}N_5O_2$: C, 67.50; H, 6.44; N, 17.89. Found: C, 67.38; H, 6.49; N, 17.92. |
| 486 | {3-[4-Amino-2-ethoxymethyl-1-(2-hydroxy-2-methylpropyl)-1H-imidazo[4,5-c]quinolin-6-yl]phenyl}morpholin-4-ylmethanone | Tan crystals | 164-166 | Calcd for $C_{28}H_{33}N_5O_4$: C, 66.78; H, 6.60; N, 13.91. Found: C, 66.61; H, 6.58; N, 13.91. |

Example 487

(R)-1-[(2,2-Dimethyl-1,3-dioxolan-4-yl)methyl]-2-ethoxymethyl-7-(pyridin-3-yl)-1H-imidazo[4,5-c]quinolin-4-amine

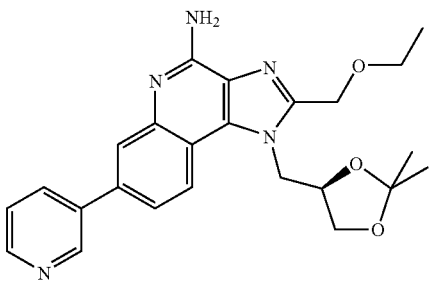

Part A

7-Bromo-4-chloro-3-nitroquinoline (22.00 g, 76.52 mmol) was treated with (R)-2,2-dimethyl-1,3-dioxolane-4-methanamine (11.61 g, 114.8 mmol) according to the method described in Part A of Examples 152-156. The crude product was triturated with water (200 mL), isolated by filtration, washed with water, dried, and suspended in diethyl ether (100 mL). The suspension was sonicated, and the resulting solid was isolated by filtration, and dried for four hours in a vacuum oven at 40° C. to provide 25.84 g of (R)-(7-bromo-3-nitroquinolin-4-yl)-(2,2-dimethyl-1,3-dioxolan-4-ylmethyl)amine as a yellow solid, mp 136-137° C.

Anal. Calcd for $C_{15}H_{16}BrN_3O_4$: C, 47.14; H, 4.22; N, 10.99. Found: C, 46.78; H, 3.93; N, 10.90.

Part B

The methods described in Parts B, C, and D of Examples 152-156 were used to treat (R)-(7-bromo-3-nitroquinolin-4-yl)-(2,2-dimethyl-1,3-dioxolan-4-ylmethyl)amine (25.8 g, 67.5 mmol). Triethylamine (11.3 mL, 81.2 mmol) was added in Part C, and after the reaction was stirred for four hours, it was concentrated under reduced pressure and used in Part D. Following chromatographic purification in Part D (eluting with 95:5 chloroform:CMA), the resulting white solid was recrystallized from acetonitrile to provide 17.37 g of (R)-7-bromo-1-[(2,2-dimethyl-1,3-dioxolan-4-yl)methyl]-2-ethoxymethyl-1H-imidazo[4,5-c]quinoline as a white, crystalline solid, mp 90-91° C.

Anal. Calcd for $C_{19}H_{22}BrN_3O_3$: C, 54.30; H, 5.28; N, 10.00. Found: C, 54.37; H, 5.06; N, 9.94.

Part C (R)-7-Bromo-1-[(2,2-dimethyl-1,3-dioxolan-4-yl)methyl]-2-ethoxymethyl-1H-imidazo[4,5-c]quinoline (17.37 g, 41.22 mmol) was oxidized and then aminated according to the methods described in Parts H and I of Example 1. The oxidation product was not recrystallized. The product from amination was purified by flash column chromatography on silica gel (eluting with chloroform:CMA in a gradient from 100:0 to 90:10) followed by recrystallization from acetonitrile to provide 7.48 g of (R)-7-bromo-1-[(2,2-dimethyl-1,3-dioxolan-4-yl)methyl]-2-ethoxymethyl-1H-imidazo[4,5-c]quinolin-4-amine as a white solid, mp 176-177° C.

Anal. Calcd for $C_{19}H_{23}BrN_4O_3 \cdot 0.25H_2O$: C, 51.89; H, 5.39; N, 12.74. Found: C, 52.10; H, 5.31; N, 12.88.

Part D (R)-7-Bromo-1-[(2,2-dimethyl-1,3-dioxolan-4-yl)methyl]-2-ethoxymethyl-1H-imidazo[4,5-c]quinolin-4-amine (3.0 g, 6.9 mmol) and pyridine-3-boronic acid (1.02 g, 8.27 mmol) were coupled according to the method described in Examples 118-121. The work-up procedure described in Part F of Examples 125-135 was followed. The crude product was purified by HPFC (eluting with chloroform:CMA in a gradient from 100:0 to 80:20) followed by recrystallization from acetonitrile to provide 1.96 g of (R)-1-[(2,2-dimethyl-1,3-dioxolan-4-yl)methyl]-2-ethoxymethyl-7-(pyridin-3-yl)-1H-imidazo[4,5-c]quinolin-4-amine as a white, crystalline solid, mp 155-156° C.

Anal. Calcd for $C_{24}H_{27}N_5O_3$: C, 66.50; H, 6.28; N, 16.15. Found: C, 66.37; H, 6.22; N, 16.37.

Example 488

(R)-3-[4-Amino-2-ethoxymethyl-7-(pyridin-3-yl)-1H-imidazo[4,5-c]quinolin-1-yl]propane-1,2-diol

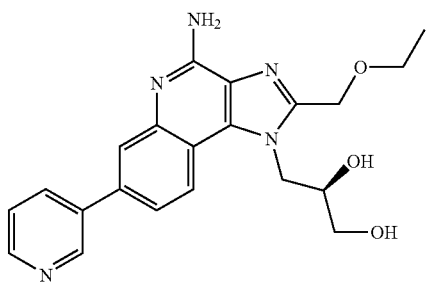

(R)-1-[(2,2-Dimethyl-1,3-dioxolan-4-yl)methyl]-2-ethoxymethyl-7-(pyridin-3-yl)-1H-imidazo[4,5-c]quinolin-4-amine (1.0 g, 2.3 mmol) was treated according to the method Example 162. The product was recrystallized from methanol to provide 0.60 g of (R)-3-[4-amino-2-ethoxymethyl-7-(pyridin-3-yl)-1H-imidazo[4,5-c]quinolin-1-yl]propane-1,2-diol as a white, crystalline solid, mp 202-204° C.

Anal. Calcd for $C_{21}H_{23}N_5O_3 \cdot 0.5H_2O$: C, 62.67; H, 6.01; N, 17.40. Found: C, 62.58; H, 5.99; N, 17.29.

Example 489

(S)-1-[(2,2-Dimethyl-1,3-dioxolan-4-yl)methyl]-2-ethoxymethyl-7-(pyridin-3-yl)-1H-imidazo[4,5-c]quinolin-4-amine

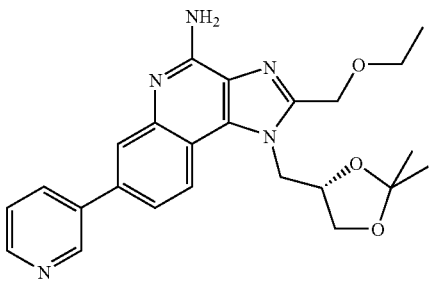

Part A

7-Bromo-4-chloro-3-nitroquinoline (11.00 g, 38.26 mmol) was reacted with (S)-2,2-dimethyl-[1,3]dioxolane-4-methanamine (5.81 g, 57.4 mmol) according to the method described in Part A of Examples 125-135. When the reaction was complete, it was concentrated under reduced pressure, and the residue was stirred with water (100 mL). The resulting solid was isolated by filtration, mixed twice with ethanol and concentrated under reduced pressure. The solid was then triturated with diethyl ether, isolated by filtration, and dissolved in dichloromethane. An insoluble impurity was removed by filtration, and the filtrate was concentrated under reduced pressure to provide 14.05 g of (S)-(7-bromo-3-nitroquinolin-4-yl)-(2,2-dimethyl-1,3-dioxolan-4-ylmethyl)amine as a yellow solid.

Part B

The methods described in Parts B, C, and D of Examples 152-156 were used to treat (S)-(7-bromo-3-nitroquinolin-4-yl)-(2,2-dimethyl-1,3-dioxolan-4-ylmethyl)amine (10.7 g, 30.4 mmol). Triethylamine (4.67 mL, 33.5 mmol) was added in Part C, and after the reaction was stirred for 1.5 hours, additional reagents were added. The reaction was stirred for an additional four hours before it was concentrated under reduced pressure and used in Part D. Following purification in Part D by HPFC (eluting with chloroform:CMA in a gradient from 100:0 to 78:22), the resulting white solid was mixed with diethyl ether to form a solid. The solid was isolated by filtration to provide 8.88 g of (S)-7-bromo-1-[(2,2-dimethyl-1,3-dioxolan-4-yl)methyl]-2-ethoxymethyl-1H-imidazo[4,5-c]quinoline as a white solid, mp 89-90° C.

Anal. Calcd for $C_{19}H_{22}BrN_3O_3$: C, 54.30; H, 5.28; N, 10.00. Found: C, 54.31; H, 5.25; N, 10.00.

Part C (S)-7-Bromo-1-[(2,2-dimethyl-1,3-dioxolan-4-yl)methyl]-2-ethoxymethyl-1H-imidazo[4,5-c]quinoline (8.74 g, 20.8 mmol) was oxidized and then aminated according to the methods described in Parts H and I of Example 1. The oxidation product was not recrystallized. The product from amination was purified by HPFC (eluting with chloroform:CMA in a gradient from 100:0 to 80:20) followed by recrystallization from acetonitrile to provide 4.28 g of (S)-7-bromo-1-[(2,2-dimethyl-1,3-dioxolan-4-yl)methyl]-2-ethoxymethyl-1H-imidazo[4,5-c]quinolin-4-amine as a white solid, mp 184-185° C.

Anal. Calcd for $C_{19}H_{23}BrN_4O_3$: C, 52.42; H, 5.33; N, 12.87. Found: C, 52.41; H, 5.13; N, 12.91.

Part D (S)-7-Bromo-1-[(2,2-dimethyl-1,3-dioxolan-4-yl)methyl]-2-ethoxymethyl-1H-imidazo[4,5-c]quinolin-4-amine (2.65 g, 6.09 mmol) and pyridine-3-boronic acid 1,3-propanediol cyclic ester (1.19 g, 7.30 mmol) were coupled according to the method described in Examples 118-121. The work-up procedure described in Part F of Examples 125-135 was followed. The crude product was purified by HPFC (eluting with chloroform:CMA in a gradient from 100:0 to 80:20) followed by recrystallization from acetonitriled to provide 1.43 g of (S)-1-[(2,2-dimethyl-1,3-dioxolan-4-yl)methyl]-2-ethoxymethyl-7-(pyridin-3-yl)-1H-imidazo[4,5-c]quinolin-4-amine as a white solid, mp 157-158° C.

Anal. Calcd for $C_{24}H_{27}N_5O_3 \cdot 0.3H_2O$: C, 65.68; H, 6.34; N, 15.96. Found: C, 65.76; H, 6.24; N, 16.05.

Example 490

(S)-3-[4-Amino-2-ethoxymethyl-7-(pyridin-3-yl)-1H-imidazo[4,5-c]quinolin-1-yl]propane-1,2-diol

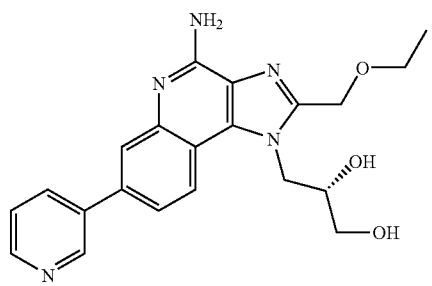

(S)-1-[(2,2-Dimethyl-1,3-dioxolan-4-yl)methyl]-2-ethoxymethyl-7-(pyridin-3-yl)-1H-imidazo[4,5-c]quinolin-4-amine (0.72 g, 1.66 mmol) was treated according to the method Example 162. The product was recrystallized from methanol to provide 0.38 g of (S)-3-[4-amino-2-ethoxymethyl-7-(pyridin-3-yl)-1H-imidazo[4,5-c]quinolin-1-yl]propane-1,2-diol as a white, crystalline solid, mp 203-204° C.

Anal. Calcd for $C_{21}H_{23}N_5O_3 \cdot 0.25H_2O$: C, 63.38; H, 5.95; N, 17.60. Found: C, 63.41; H, 6.02; N, 17.61.

Example 491

2-Ethoxymethyl-1-(piperidin-2-ylmethyl)-7-(pyridin-3-yl)-1H-imidazo[4,5-c]quinolin-4-amine trihydrochloride

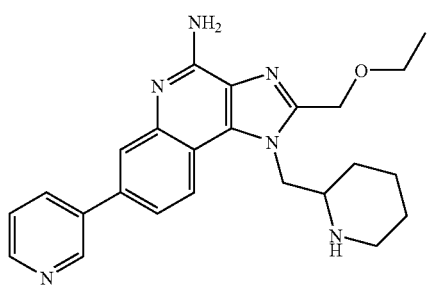

Part A

7-Bromo-4-chloro-3-nitroquinoline (12.08 g, 42.0 mmol) was treated according to the methods described in Parts A through D of Examples 152-156 using 1-(tert-butoxycarbonyl)-2-(aminomethyl)piperidine (10.0 g, 46.7 mmol) in Part A. The product from Part A was triturated with diethyl ether and isolated by filtration. Triethylamine (1.1 equivalents) was added to the reaction in Part C. At the completion of the reaction in Part C, the solvent was removed under reduced pressure, and the residue was used in Part D. Following chromatographic purification in Part D (eluting with chloroform:CMA in a gradient from 100:0 to 98:2), tert-butyl 2-[(7-bromo-2-ethoxymethyl-1H-imidazo[4,5-c]quinolin-1-yl)methyl]piperidine-1-carboxylate was obtained as a light yellow solid.

Part B tert-Butyl 2-[(7-bromo-2-ethoxymethyl-1H-imidazo[4,5-c]quinolin-1-yl)methyl]piperidine-1-carboxylate (8.68 g, 17.24 mmol) was oxidized and then aminated according to the methods described in Parts H and I of Example 1. The oxidation product was not recrystallized. The product from amination was purified by flash column chromatography on silica gel (eluting with chloroform:CMA in a gradient from 100:0 to 90:10) to provide tert-butyl 2-[(4-amino-7-bromo-2-ethoxymethyl-1H-imidazo[4,5-c]quinolin-1-yl)methyl]piperidine-1-carboxylate as a white solid, mp 190-192° C.

Anal. Calcd for $C_{24}H_{32}BrN_5O_3$: C, 55.60; H, 6.22; N, 13.51. Found: C, 55.52; H, 6.20; N, 13.31.

Part C tert-Butyl 2-[(4-amino-7-bromo-2-ethoxymethyl-1H-imidazo[4,5-c]quinolin-1-yl)methyl]piperidine-1-carboxylate (4.82 g, 9.30 mmol) and pyridine-3-boronic acid 1,3-propanediol cyclic ester (1.67 g, 10.2 mmol) were coupled according to the method described in Part F of Example 414. Palladium (II) acetate (0.0103 f, 0.046 mmol) was added as a solid. The reaction was heated for 15 hours. The crude product was purified by HPFC (eluting with chloroform:CMA in a gradient from 100:0 to 72:28) to provide 3.4 g of tert-butyl 2-{[4-amino-2-ethoxymethyl-7-(pyridin-3-yl)-1H-imidazo[4,5-c]quinolin-1-yl]methyl}piperidine-1-carboxylate as an off-white, crystalline solid.

Part D tert-Butyl 2-{[4-amino-2-ethoxymethyl-7-(pyridin-3-yl)-1H-imidazo[4,5-c]quinolin-1-yl]methyl}piperidine-1-carboxylate (3.15 g, 6.10 mmol) was deprotected according to the method described in Example 177 to provide 2.54 g of 2-ethoxymethyl-1-(piperidin-2-ylmethyl)-7-(pyridin-3-yl)-1H-imidazo[4,5-c]quinolin-4-amine trihydrochloride as an off-white solid, mp>250° C.

Anal. Calcd for $C_{24}H_{28}N_6O \cdot 3HCl \cdot 2H_2O$: C, 51.30; H, 6.28; N, 14.96. Found: C, 50.95; H, 6.38; N, 15.10.

Example 492

2-Ethoxymethyl-1-{[1-(methanesulfonyl)piperidin-2-yl]methyl}-7-(pyridin-3-yl)-1H-imidazo[4,5-c]quinolin-4-amine

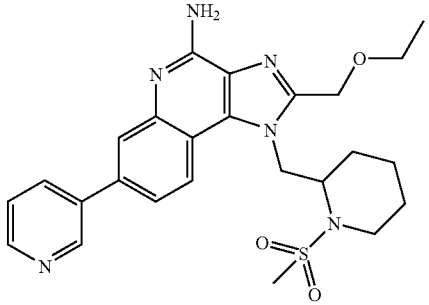

A solution of 2-ethoxymethyl-1-(piperidin-2-ylmethyl)-7-(pyridin-3-yl)-1H-imidazo[4,5-c]quinolin-4-amine trihydrochloride (0.60 g, 1.1 mmol) and triethylamine (0.79 mL, 5.7 mmol) in chloroform (50 mL) was cooled to 4° C. Methanesulfonyl chloride (0.12 mL, 1.5 mmol) was added, and the reaction was allowed to warm to ambient temperature and stirred overnight. Additional methanesulfonyl chloride (2.5 equivalents) was added at 4° C. over the course of several days. The work-up procedure described in Examples 178 to 181 was carried out. The crude product was purified by HPFC (eluting with chloroform:CMA in a gradient from about 100:0 to 70:30) followed by recrystallization from acetonitrile to provide 0.19 g of 2-ethoxymethyl-1-{[1-(methanesulfonyl)piperidin-2-yl]methyl}-7-(pyridin-3-yl)-1H-imidazo[4,5-c]quinolin-4-amine as a white solid, mp 152-154° C.

Anal. Calcd for $C_{25}H_{30}N_6O_3S \cdot 0.5H_2O$: C, 59.62; H, 6.20; N, 16.69. Found: C, 59.62; H, 6.44; N, 16.78.

Example 493

N-{4-[4-Amino-2-ethoxymethyl-7-(pyridin-3-yl)-1H-imidazo[4,5-c]quinolin-1-ylmethyl]benzyl}methanesulfonamide

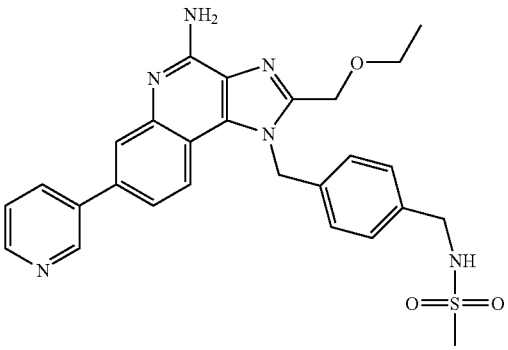

Part A 1-(N-BOC-aminomethyl)-4-(aminomethyl)benzene (5.0 g, 21 mmol) in dichloromethane (50 mL) was added dropwise to a mixture of 7-bromo-4-chloro-3-nitroquinoline (5.81 g, 20 mmol) and triethylamine (5.63 mL) in dichloromethane (60 mL). The reaction was stirred for 16 hours and then washed sequentially with water and saturated aqueous sodium chloride. The organic fraction was dried over sodium sulfate, filtered and concentrated to provide a yellow crystalline solid. Recrystallization from 2-propanol yielded 9.1 g of tert-butyl {4-[(7-bromo-3-nitroquinolin-4-ylamino)methyl]benzyl}carbamate as a yellow powder.

Part B

Ethyl viologen dibromide (0.069 g, 0.18 mmol), potassium carbonate (12.76 g, 92 mmol) in water (55 mL), and sodium hydrosulfite (11.25 g, 65 mmol) in water (55 mL) were added sequentially to a solution of tert-butyl {4-[(7-bromo-3-nitroquinolin-4-ylamino)methyl]benzyl}carbamate (9.0 g, 18.5 mmol) in dichloromethane (110 mL). The resulting biphasic mixture was stirred for 20 hours. The reaction was diluted with water (600 mL) and dichloromethane (500 mL). The layers were separated and the aqueous fraction was extracted with dichloromethane. The organic fractions were combined and washed sequentially with water and saturated aqueous sodium chloride. The organic fraction was dried over sodium sulfate, filtered, and concentrated under reduced pressure to yield 8.5 g of tert-butyl {4-[(3-amino-7-bromoquinolin-4-ylamino)methyl]benzyl}carbamate as a yellow-brown amorphous solid.

Part C.

tert-Butyl {4-[(3-amino-7-bromoquinolin-4-ylamino)methyl]benzyl}carbamate (8.46 g, 18.5 mmol), triethylamine (2.25 mL) and dichloromethane (92 mL) were combined. Ethoxyacetyl chloride (2.92 g, 24 mmol) was added dropwise to the mixture. The reaction was stirred for an additional 1.5 hours and then concentrated under reduced pressure. Ethanol (92 mL) and triethylamine (10.31 mL) were added to the residue and the reaction was heated at reflux temperature for 1.5 hours. A precipitate formed. The reaction was cooled to room temperature and then concentrated under reduced pressure. The residue was dissolved in dichloromethane and washed sequentially with water and saturated aqueous sodium chloride. The organic fraction was dried over magnesium sulfate, filtered, and concentrated under reduced pressure. An initial purification by flash column chromatography eluting with a gradient of CMA in chloroform (2-10%) was followed by recrystallization from acetonitrile to provide 3.4 g of tert-butyl [4-(7-bromo-2-ethoxymethyl-1H-imidazo[4,5-c]quinolin-1-ylmethyl)benzyl]carbamate as yellow-orange crystals.

Part D

3-Chloroperoxybenzoic acid (2.91 g, 9.3 mmol, 55% pure) was added to a solution of tert-butyl [4-(7-bromo-2-ethoxymethyl-1H-imidazo[4,5-c]quinolin-1-ylmethyl)benzyl]carbamate (3.2 g, 6.1 mmol) in chloroform (60 mL). The reaction was stirred for 1 hour and then cooled with an ice bath. Ammonium hydroxide (40 mL) was added and the reaction was stirred for 10 minutes. p-Toluenesulfonyl chloride (1.16 g, 6.1 mmol) was added in two portions. The cooling bath was removed and the mixture was stirred for an additional 16 hours. The layers were separated and the aqueous fraction was extracted with dichloromethane. The combined organic fractions were washed sequentially with water and saturated aqueous sodium chloride, dried over sodium sulfate, filtered, and concentrated under reduced pressure. Purification of the residue by flash column chromatography (CMA/chloroform) and subsequent recrystallization from acetonitrile yielded 1.15 g of tert-butyl [4-(4-amino-7-bromo-2-ethoxymethyl-1H-imidazo [4,5-c]quinolin-1-ylmethyl)benzyl]carbamate as a tan solid.

Part E.

tert-Butyl [4-(4-amino-7-bromo-2-ethoxymethyl-1H-imidazo[4,5-c]quinolin-1-ylmethyl) benzyl]carbamate (1.15 g, 2.1 mmol), triphenylphosphine (0.005 g), pyridine-3-boronic acid 1,3-propanediol cyclic ester (0.365 g, 2.2 mmol), and n-propanol (3.67 mL) were combined. Aqueous sodium carbonate (2M, 1.12 mL) and water (0.6 mL) were added to the mixture and the flask was flushed with nitrogen. Palladium (II) acetate (0.0013 g) in toluene (0.200 mL) was added, and the flask was again flushed with nitrogen. The flask was sealed and heated in an oil bath at a temperature of 105° C. for 16 hours. The reaction was allowed to cool to room temperature and the mixture was diluted with dichloromethane and water. The layers were separated and the aqueous fraction was extracted with dichloromethane. The organic fractions were combined, washed sequentially with water and saturated aqueous sodium chloride, dried over sodium sulfate, filtered, and concentrated under reduced pressure. Purification of the residue by flash column chromatography eluting with a gradient of CMA/chloroform and subsequent recrystallization from acetonitrile yielded 0.725 g of tert-butyl {4-[4-amino-2-ethoxymethyl-7-(pyridin-3-yl)-1H-imidazo[4,5-c]quinolin-1-ylmethyl]benzyl}carbamate as flocculent white crystals, m.p. 195.5-197.0° C.

Anal Calcd. for $C_{31}H_{34}N_6O_3$: % C, 69.13; % H, 6.36; % N, 15.60. Found: % C, 68.85; % H, 6.34; % N, 15.63.

Part F tert-Butyl {4-[4-amino-2-ethoxymethyl-7-(pyridin-3-yl)-1H-imidazo[4,5-c]quinolin-1-ylmethyl]benzyl}carbamate (0.660 g) was added to ethanolic hydrogen chloride (4M, 10 mL) and the solution was heated at reflux temperature for 30 minutes. The reaction was cooled to room temperature and concentrated under reduced pressure. Diethyl ether and water were added to the oily residue and the layers were separated. The aqueous fraction was brought to pH 13 with 10% aqueous sodium hydroxide and then extracted sequentially with dichloromethane and dichloromethane containing 5% methanol. The organic fractions were combined, washed sequentially with water and saturated aqueous sodium chloride, dried over sodium sulfate, filtered, and concentrated under reduced pressure to yield 0.526 g of 1-(4-aminomethylbenzyl)-2-ethoxymethyl-7-(pyridin-3-yl)-1H-imidazo[4,5-c]quinolin-4-amine as an off-white solid, mp 211.0-213.5° C.

Anal Calcd. for $C_{26}H_{26}N_6O$: % C, 71.21; % H, 5.98; % N, 19.16. Found: % C, 70.85; % H, 5.98; % N, 19.22.

Part G.

Methanesulfonyl chloride (0.13 mL, 1.7 mmol) was added dropwise to a mixture of 1-(4-aminomethylbenzyl)-2-ethoxymethyl-7-(pyridin-3-yl)-1H-imidazo[4,5-c]quinolin-4-amine (0.520 g, 1.2 mmol) in dichloromethane (10 mL). The reaction was stirred for 16 hours and then saturated aqueous sodium carbonate was added. The layers were separated and the aqueous fraction was extracted with 95:5 chloroform/methanol. The organic fractions were combined and washed sequentially with water and saturated aqueous sodium chloride, dried over sodium sulfate, filtered, and concentrated under reduced pressure. The resulting solid was purified by flash column chromatography with a gradient of CMA (2%-10%) in chloroform as the eluent. A final recrystallization from 2-propanol provided 0.240 g of N-{4-[4-amino-2-ethoxymethyl-7-(pyridin-3-yl)-1H-imidazo[4,5-c]

quinolin-1-ylmethyl]benzyl}methanesulfonamide as white granular crystals, mp 228.0-229.0° C.

Anal Calcd. for $C_{27}H_{28}N_6O_3S$: % C, 62.77; % H, 5.46; % N, 16.27; % S, 6.21. Found: % C, 62.55; % H, 5.13; % N, 16.15; % S, 6.11.

Example 494

N-[4-(4-Amino-2-ethoxymethyl-7-(pyridin-3-yl)imidazo[4,5-c]quinolin-1-yl)butyl]-4-[(2-dimethylaminoethoxy)phenylmethyl]benzamide

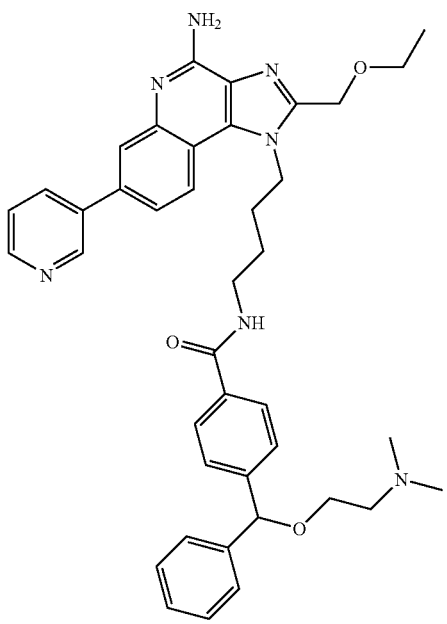

A mixture of 4-[(2-dimethylaminoethoxy)phenylmethyl]benzoic acid (0.433 g) and 1-hydroxybenzotriazole (0.196 g) in chloroform (7 mL) was cooled to 0° C. and 1-(3-dimethylaminopropyl)-3-ethylcarbodiimide hydrochloride (0.277 g) was added in small portions over a 2 minute period. The mixture was stirred for 1 hour and then added dropwise to a chilled (0° C.) solution of 1-(4-aminobutyl)-2-ethoxymethyl-7-(pyridin-3-yl)-1H-imidazo[4,5-c]quinolin-4-amine (0.400 g) in anhydrous dimethylacetamide (7 mL). The cooling bath was removed and the reaction was stirred for an additional 16 hours. Water was added and the mixture was made acidic by the addition of 4N hydrochloric acid. The aqueous fraction was extracted with diethyl ether (3×) to remove the dimethylacetamide. Sodium hydroxide (10% in water) was added to make the aqueous fraction basic and the aqueous fraction was subsequently extracted with multiple portions of dichloromethane. The organic fractions were combined, washed sequentially with water and brine, dried over sodium sulfate, filtered and concentrated under reduced pressure. The residue was purified by flash column chromatography using a gradient of CMA/chloroform as the eluent. A final recrystallization from acetonitrile provided 0.426 g of N-[4-(4-amino-2-ethoxymethyl-7-(pyridin-3-yl)imidazo[4,5-c]quinolin-1-yl)butyl]-4-[(2-dimethylaminoethoxy)phenylmethyl]benzamide as a white crystalline solid, mp 157.0-161.0° C.

Anal Calcd. for $C_{40}H_{45}N_7O_3 \cdot 1.0H_2O$: % C, 69.64; % H, 6.87; % N, 14.21. Found: % C, 69.81; % H, 7.07; % N, 14.25.

Example 495

N-[2-(4-Amino-2-butyl-7-vinyl-1H-imidazo[4,5-c]quinolin-1-yl)ethyl]methanesulfonamide

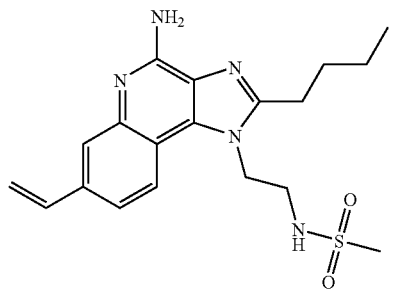

Part A

A solution of 7-bromo-4-chloro-3-nitroquinoline (143.8 g, 0.5 mol) in 800 mL warm DMF was added to a stirred solution of ethylenediamine in 200 mL DMF at room temperature; the reaction was stirred at room temperature overnight. The reaction was quenched with 2 L water and stirred for an additional hour. Additional water was added, and the mixture was stirred overnight. A precipitate formed and was isolated by filtration and air-dried overnight on the filter funnel to provide $N^1$-(7-bromo-3-nitroquinolin-4-yl)ethane-1,2-diamine as a yellow solid.

Part B

To a stirred solution of $N^1$-(7-bromo-3-nitroquinolin-4-yl)ethane-1,2-diamine (50 g, 0.167 mol) and triethylamine (2 equivalents) in 1500 mL dichloromethane, was slowly added methanesulfonic anhydride (1.2 equivalents), and the reaction was stirred overnight at room temperature. Water (1 L) was added, and the mixture was stirred vigorously for one hour. The organic layer was separated and concentrated under reduced pressure to provide N-[2-(7-bromo-3-nitroquinolin-4-ylamino)ethyl]methanesulfonamide.

Part C

An 8 L stainless steel Parr vessel was charged with N-[2-(7-bromo-3-nitroquinolin-4-ylamino)ethyl]methanesulfonamide (61 g), 5% Pt/C catalyst (6.0 g) and acetonitrile (3 L). The vessel was evacuated, filled with hydrogen (45 psi, $3.1 \times 10^5$ Pa), and shaken at ambient temperature overnight. The reaction mixture was filtered through CELITE filter agent and concentrated under reduced pressure to provide N-[2-(3-amino-7-bromoquinolin-4-ylamino)ethyl]methanesulfonamide.

Part D

To a stirred solution of N-[2-(3-amino-7-bromoquinolin-4-ylamino)ethyl]methanesulfonamide (46.4 g, 0.129 mol) in 1000 mL pyridine was slowly added valeryl chloride (1.1 equivalents). After 1.5 hours the mixture was yellow and turbid. The reaction mixture was then heated at reflux for 12 hours, allowed to cool to ambient temperature and concentrated under reduced pressure. The residue was mostly dissolved in 10% HCl to adjust to pH 1. The resulting suspension was adjusted to pH 12 with the addtion of 50% aqueous sodium hydroxide and stirred overnight. A precipitate formed and was isolated by filtration and air-dried to provide 45 g of N-[2-(7-bromo-2-butyl-1H-imidazo[4,5-c]quinolin-1-yl)ethyl]methanesulfonamide as a pale gray/green solid.

Part E

3-Chloroperoxybenzoic acid (1.0 equivalent of 50% pure material) was added to a solution of N-[2-(7-bromo-2-butyl-1H-imidazo[4,5-c]quinolin-1-yl)ethyl]methanesulfonamide (44 g, 103.4 mmol) in 1000 mL dichloromethane. After 2 hours, concentrated ammonium hydroxide solution (600 mL) was added. The reaction was stirred for 15 minutes before p-toluenesulfonyl chloride (1.1 equivalents) was slowly added in small portions. The reaction was stirred overnight at room temperature and then water and potassium carbonate were added with vigorous stirring. A precipitate formed and was isolated by filtration to provide N-[2-(4-amino-7-bromo-2-butyl-1H-imidazo[4,5-c]quinolin-1-yl)-ethyl]methanesulfonamide.

Part F

N-[2-(4-Amino-7-bromo-2-butyl-1H-imidazo[4,5-c]quinolin-1-yl)ethyl]methanesulfonamide was coupled with potassium vinyltrifluoroborate according to the procedure described in Part D of Examples 440-455 and recrystallized from acetonitrile to provide N-[2-(4-amino-2-butyl-7-vinyl-1H-imidazo[4,5-c]quinolin-1-yl)ethyl]methanesulfonamide as an off-white solid.

Example 496

1-[2-(4-Amino-2-ethoxymethyl-7-vinyl-1H-imidazo[4,5-c]quinolin-1-yl)ethyl]-3-(2-methylethyl)urea

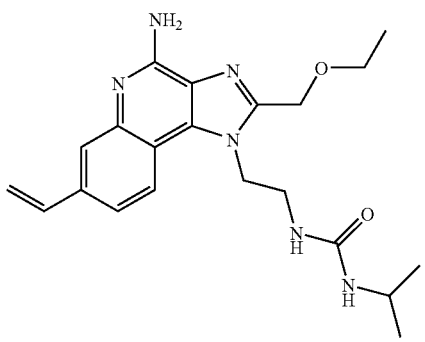

Part A

A mixture of N$^1$-(7-bromo-3-nitroquinolin-4-yl)ethane-1,2-diamine (40 g, 0.129 mol), triethylamine (3.0 equivalents) and 1 L dichloromethane was stirred vigorously as isopropyl isocyante (1.1 equivalents) was added dropwise. As the reaction progressed it became more homogeneous, and then a yellow precipitate formed. After 4 hours the volume of dichloromethane was reduced under reduced pressure. The yellow solid was isolated by filtration and air-dried overnight to provide 43 g 1-(2-methylethyl)-3-[2-(3-nitroquinolin-4-ylamino)ethyl]urea.

Part B

An 8 L stainless steel Parr vessel was charged with 1-(2-methylethyl)-3-[2-(3-nitroquinolin-4-ylamino)ethyl]urea (44 g, 0.111 mol), 5% platinum on carbon (5 g) and acetonitrile (4000 mL). The vessel was evacuated, charged with hydrogen, and shaken vigorously for six hours. An analysis by HPLC and TLC indicated the reaction was not complete. Additional catalyst (5 g) was added, and the vessel was placed under hydrogen pressure and shaken overnight. The reaction mixture was filtered and concentrated under reduced pressure to provide 1-[2-(3-amino-7-bromoquinolin-4-ylamino)ethyl]-3-(2-methylethyl)urea.

Part C

To a stirred solution of 1-[2-(3-amino-7-bromoquinolin-4-ylamino)ethyl]-3-(2-methylethyl)urea (27.2 g, 0.0743 mol) in 600 mL pyridine was slowly added ethoxyacetyl chloride (1.1 equivalents). After 1.5 hours the mixture was yellow and turbid. The reaction mixture was then heated at 80° C. for 12 hours and then concentrated under reduced pressure. The residue was dissolved in water and saturated aqueous potassium carbonate and stirred vigorously for three hours. A precipitate was present, was isolated by filtration, and air-dried for 48 hours to provide 32 g of 1-[2-(7-bromo-2-ethoxymethyl-1H-imidazo[4,5-c]quinolin-1-yl)ethyl]-3-(2-methylethyl)urea.

Part D

The method described in Part E of Example 495 was used to oxidize and aminate 1-[2-(7-bromo-2-ethoxymethyl-1H-imidazo[4,5-c]quinolin-1-yl)ethyl]-3-(2-methylethyl)urea (31 g, 71.4 mmol). The isolated product was recrystallized from acetonitrile to provide 1-[2-(4-amino-7-bromo-2-ethoxymethyl-1H-imidazo[4,5-c]quinolin-1-yl)ethyl]-3-(2-methylethyl)urea.

Part E

1-[2-(4-Amino-7-bromo-2-ethoxymethyl-1H-imidazo[4,5-c]quinolin-1-yl)ethyl]-3-(2-methylethyl)urea was coupled with potassium vinyltrifluoroborate according to the procedure described in Part D of Examples 440-455 to provide N-[2-(4-amino-2-butyl-7-vinyl-1H-imidazo[4,5-c]quinolin-1-yl)ethyl]-3-(2-methylethyl)urea as an off-white solid.

MS (APCI) m/z 397.2 (M+H)$^+$.

Examples 497-500

The bromide starting material indicated in the table below was coupled with potassium vinyltrifluoroborate according to the procedure described in Part D of Examples 440-463 and recrystallized from acetonitrile to provide the products shown in the table below.

Examples 497-500

| Example | Starting Material | Product Structure |
|---|---|---|
| 497 | 7-Bromo-2-ethoxymethyl-1-(2-methylpropyl)-1H-imidazo[4,5-c]quinolin-4-amine | |
| 498 | 1-[4-Amino-7-bromo-2-ethoxymethyl-1H-imidazo[4,5-c]quinolin-1-yl]-2-methylpropan-2-ol | |
| 499 | 8-Bromo-1-(2-methylpropyl)-1H-imidazo[4,5-c]quinolin-4-amine | |
| 500 | 7-Bromo-2-ethoxymethyl-1-(3-methoxypropyl)-1H-imidazo[4,5-c]quinolin-4-amine | |

| Example | Product Name | Form | MS (APCI) m/z (M + H)$^+$ | Anal. |
|---|---|---|---|---|
| 497 | 2-Ethoxymethyl-1-(2-methyl-propyl)-7-vinyl-1H-imidazo[4,5-c]quinolin-4-amine | Off-white solid | 325.1 | Calcd for $C_{19}H_{24}N_4O$: C, 70.34; H, 7.46; N, 17.27. Found: C, 69.99; H, 7.60; N, 17.36. |
| 498 | 1-[4-Amino-2-ethoxymethyl-7-vinyl-1H-imidazo[4,5-c]quinolin-1-yl]-2-methylpropan-2-ol | Off-white solid | 341.1 | Calcd for $C_{19}H_{24}N_4O_2$: C, 67.04; H, 7.11; N, 16.46. Found: C, 66.09; H, 7.41; N, 16.16. |
| 499 | 1-(2-Methyl-propyl)-8-vinyl-1H-imidazo[4,5-c]quinolin-4-amine | Off-white solid | 267.2 | Not measured |
| 500 | 2-Ethoxymethyl-1-(3-methoxy-propyl)-7-vinyl-1H-imidazo[4,5-c]quinolin-4-amine | Off-white solid | 341.1 | Not measured |

Examples 501-506

The method described in Part E of Example 440-455 was used to couple the vinyl compound indicated in the table below with 3-bromopyridine to provide the product shown and named in the table below.

Example 501-506

| Example | Starting Vinyl Compound | Product Structure | Product Name | Form | MS (APCI) m/z (M + H)+ |
|---|---|---|---|---|---|
| 501 | Example 495 | | (E)-N-{2-[4-Amino-2-butyl-7-(2-pyridin-3-ylvinyl)-1H-imidazo[4,5-c]quinolin-1-yl]ethyl}methanesulfonamide | Off-White solid | 465.0 |
| 502 | Example 496 | | (E)-N-{2-[4-Amino-2-ethoxymethyl-7-(2-pyridin-3-ylvinyl)-1H-imidazo[4,5-c]quinolin-1-yl]ethyl}-N'-(2-methylethyl)urea | Off-White solid | 474.1 |
| 503 | Example 497 | | (E)-2-Ethoxymethyl-1-(2-methylpropyl)-7-(2-pyridin-3-ylvinyl)-1H-imidazo[4,5-c]quinolin-4-amine | Off-White solid | 402.2 |
| 504 | Example 498 | | (E)-1-[4-Amino-2-ethoxymethyl-7-(2-pyridin-3-ylvinyl)-1H-imidazo[4,5-c]quinolin-1-yl]-2-methylpropan-2-ol | Off-White solid | 418.1 |

| Example | Starting Vinyl Compound | Product Structure | Product Name | Form | MS (APCI) m/z (M + H)+ |
|---|---|---|---|---|---|
| 505 | Example 499 | | (E)-1-(2-Methylpropyl)-8-(2-pyridin-3-ylvinyl)-1H-imidazo[4,5-c]quinolin-4-amine | Off-White solid | 344.0 |
| 506 | Example 500 | | (E)-2-Ethoxymethyl-1-(3-methoxypropyl)-7-(2-pyridin-3-ylvinyl)-1H-imidazo[4,5-c]quinolin-4-amine | Not reported | 418.0 |

Example 507

(E)-2-Ethoxymethyl-1-(3-methoxypropyl)-7-(2-pyridin-2-ylvinyl)-1H-imidazo[4,5-c]quinolin-4-amine

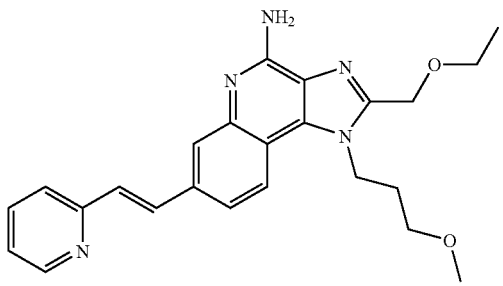

A thick walled glass tube, equipped with magnetic stir-bar, was charged with toluene (20 mL/g), palladium (II) acetate (0.1 equivalents), tri-ortho-tolylphosphine (0.3 equivalents), triethylamine (3.0 equivalents), 2-vinylpyridine (1.0 equivalent), and 7-bromo-2-ethoxymethyl-1-(3-methoxypropyl)-1H-imidazo[4,5-c]quinolin-4-amine (1.0 eq.). The tube was purged with nitrogen and sealed. The reaction mixture was heated at 120° C. for 24-48 hours. The reaction mixture was allowed to cool and then concentrated under reduced pressure. The solid residue was partitioned between dichloromethane and water, and the mixture was adjusted to pH 12 with the addition of 10% aqueous sodium hydroxide. The organic layer was separated and purified by flash chromatography on silica gel (eluting with chloroform:methanol in a gradient from 100:0 to 90:10) followed by recrystallization from acetonitrile to provide (E)-2-ethoxymethyl-1-(3-methoxypropyl)-7-(2-pyridin-2-ylvinyl)-1H-imidazo[4,5-c]quinolin-4-amine as an off-white solid.

MS (APCI) m/z 418.2 (M+H)$^+$.

Examples 508-557

Part A

Concentrated hydrochloric acid (~15 mL) was added to a suspension of tert-butyl [4-(4-amino-7-bromo-2-propyl-1H-imidazo[4,5-c]quinolin-1-yl)butyl]carbamate (3.19 g, 6.7 mmol) in ethanol (6.4 mL), and the reaction was stirred for 30 minutes. The reaction was adjusted to pH 13 with the addition of 50% aqueous sodium hydroxide. A precipitate formed, was isolated by filtration, washed with 1% sodium carbonate, and dried overnight on the filter funnel to provide 1-(4-aminobutyl)-7-bromo-2-propyl-1H-imidazo[4,5-c]quinolin-4-amine, which contained some water.

Part B

A suspension of 1-(4-aminobutyl)-7-bromo-2-propyl-1H-imidazo[4,5-c]quinolin-4-amine (2.00 g, 5.3 mmol) in chloroform (20 mL) was cooled to 0° C., and a solution of isopropyl isocyanate (5.3 mmol) in chloroform (3 mL/g) was added slowly over a period of eight minutes. After one hour, additional isopropyl isocyanate (0.53 mmol) in chloroform was added. Additional isopropyl isocyanate (2.15 mmol) was added again after an additional 2.5 hours. A precipitate was present and was isolated by filtration, washed with cold chloroform, and dried overnight on the filter funnel to provide 1.99 g of N-{4-[4-amino-7-bromo-2-propyl-1H-imidazo[4,5-c]quinolin-1-yl]butyl}-N'-(1-methylethyl)urea as a white solid.

Part C

N-{4-[4-Amino-7-bromo-2-propyl-1H-imidazo[4,5-c]quinolin-1-yl]butyl}-N'-(1-methylethyl)urea was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 508-557

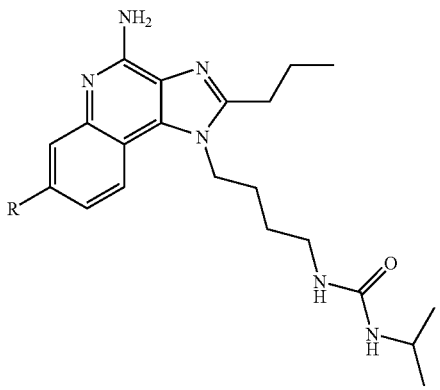

| Example | R | Measured Mass (M + H) |
|---|---|---|
| 508 | 3-furyl | 449.2651 |
| 509 | phenyl | 459.2888 |
| 510 | 3-pyridyl | 460.2821 |
| 511 | 4-pyridyl | 460.2820 |
| 512 | 2-thienyl | 465.2428 |
| 513 | 3-thienyl | 465.2402 |
| 514 | 2-(hydroxymethyl)phenyl | 489.3017 |
| 515 | 3-methylphenyl | 473.3035 |
| 516 | 4-methylphenyl | 473.3037 |
| 517 | 2-methylphenyl | 473.3009 |
| 518 | 2-hydroxyphenyl | 475.2831 |
| 519 | 4-hydroxyphenyl | 475.2809 |
| 520 | 3-hydroxyphenyl | 475.2786 |
| 521 | 3-cyanophenyl | 484.2824 |

| Example | R | Measured Mass (M + H) |
|---|---|---|
| 522 | 4-cyanophenyl | 484.2817 |
| 523 | (E)-2-phenylethenyl | 485.3011 |
| 524 | 3,5-dimethylphenyl | 487.3150 |
| 525 | 5-(hydroxymethyl)pyridin-3-yl | 490.2932 |
| 526 | 4-(hydroxymethyl)phenyl | 489.2955 |
| 527 | 4-methoxyphenyl | 489.2944 |
| 528 | 2-chlorophenyl | 493.2472 |
| 529 | 3-chlorophenyl | 493.2459 |
| 530 | 4-chlorophenyl | 493.2487 |
| 531 | 2,4-difluorophenyl | 495.2691 |
| 532 | 2-acetylphenyl | 501.2973 |
| 533 | 3-acetylphenyl | 501.2957 |
| 534 | 4-acetylphenyl | 501.2982 |
| 535 | 3-carbamoylphenyl | 502.2921 |
| 536 | 4-(dimethylamino)phenyl | 502.3275 |
| 537 | 3-ethoxyphenyl | 503.3109 |

| Example | R | Measured Mass (M + H) |
|---|---|---|
| 538 | 3-aminophenyl (H2N-C6H4-) | 474.2977 |
| 539 | 4-(methylthio)phenyl (H3C-S-C6H4-) | 505.2754 |
| 540 | 2-(acetylamino)phenyl | 516.3057 |
| 541 | 2-(isopropoxy)phenyl | 517.3257 |
| 542 | 4-(isopropoxy)phenyl | 517.3261 |
| 543 | 2,4-dimethoxyphenyl | 519.3101 |

| Example | R | Measured Mass (M + H) |
|---|---|---|
| 544 | 2,6-dimethoxyphenyl | 519.3092 |
| 545 | 3-(aminomethyl)phenyl | 488.3139 |
| 546 | 4-(2-carboxyethyl)phenyl | 531.3060 |
| 547 | 4-(methylsulfonyl)phenyl | 537.2693 |
| 548 | 3,4,5-trimethoxyphenyl | 549.3190 |
| 549 | 4-(ethylsulfonyl)phenyl | 551.2814 |
| 550 | 4-(methylsulfonylamino)phenyl | 552.2754 |

-continued

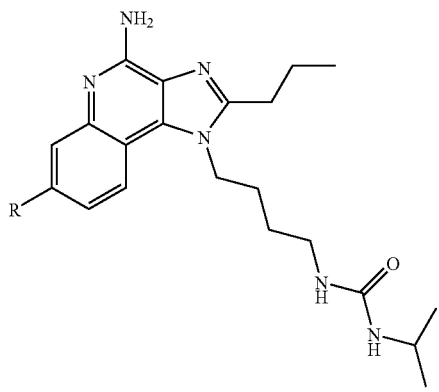

| Example | R | Measured Mass (M + H) |
|---|---|---|
| 551 |  | 552.2759 |
| 552 | 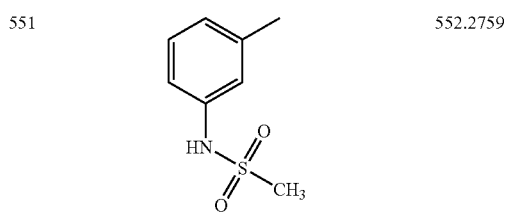 | 556.3423 |
| 553 |  | 558.3538 |
| 554 |  | 572.3351 |
| 555 |  | 516.3045 |
| 556 |  | 488.3117 |

-continued

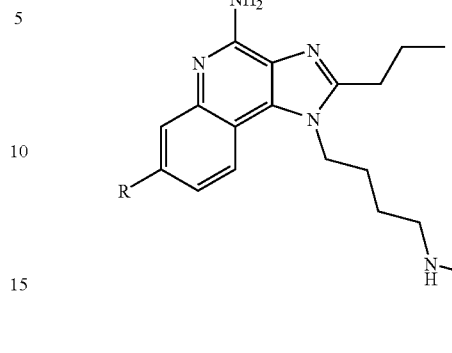

| Example | R | Measured Mass (M + H) |
|---|---|---|
| 557 | 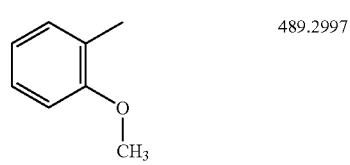 | 489.2997 |

Examples 558-582

Part A

A suspension of 1-(4-aminobutyl)-7-bromo-2-propyl-1H-imidazo[4,5-c]quinolin-4-amine (2.42 g, 6.4 mmol) and triethylamine (0.99 mL, 7.1 mmol) in chloroform (240 mL) was cooled to 0° C., and cyclopentanecarbonyl chloride (0.78 mL, 6.4 mmol) was added dropwise over a period of five minutes. The reaction was stirred for ten minutes, washed sequentially with water (50 mL) and 1% aqueous sodium carbonate (100 mL), dried over sodium sulfate, and concentrated under reduced pressure. The residue was triturated with isopropanol:water (10 mL/g and 1.7 mL/g) and isolated by filtration. The filtrate was concentrated under reduced pressure and recrystallized from isopropanol (5 mL/g). The two solids were combined and dried overnight in a vacuum oven to provide 1.51 g of N-{4-[4-amino-7-bromo-2-propyl-1H-imidazo[4,5-c]quinolin-1-yl]butyl}cyclopentanecarboxamide as a light yellow solid.

Part B

N-{4-[4-Amino-7-bromo-2-propyl-1H-imidazo[4,5-c]quinolin-1-yl]butyl}-cyclopentanecarboxamide was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 558-582
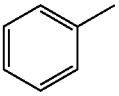
| Example | R | Measured Mass (M + H) |
|---|---|---|
| 558 | 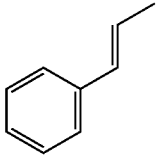 | 470.2917 |
| 559 | 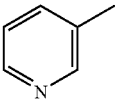 | 471.2877 |
| 560 | 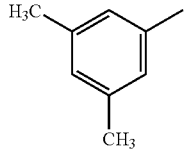 | 476.2485 |
| 561 | 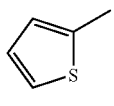 | 476.2503 |
| 562 | 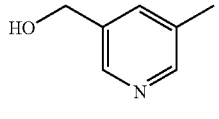 | 500.3024 |
| 563 | 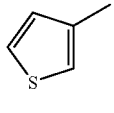 | 484.3093 |
| 564 | 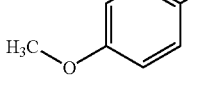 | 486.2841 |
| 565 | 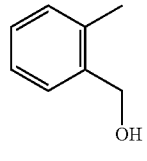 | 495.2852 |
-continued
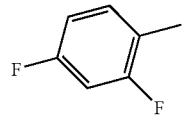
| Example | R | Measured Mass (M + H) |
|---|---|---|
| 566 | 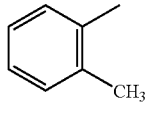 | 496.3090 |
| 567 | 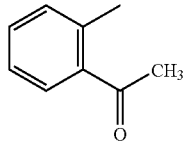 | 498.3227 |
| 568 | 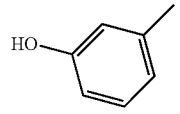 | 501.2946 |
| 569 | 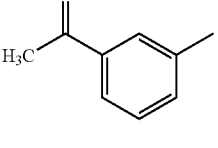 | 500.3015 |
| 570 | 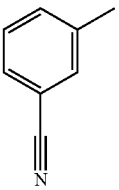 | 506.2754 |
| 571 |  | 512.3023 |
| 572 |  | 512.2994 |

-continued

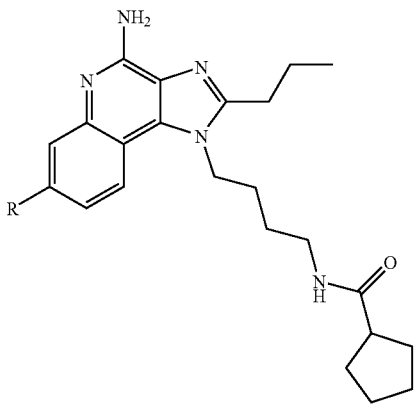

| Example | R | Measured Mass (M + H) |
|---|---|---|
| 573 | 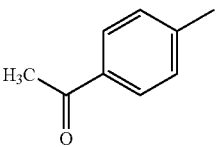 | 512.3024 |
| 574 | 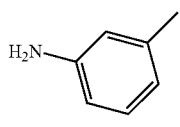 | 485.3015 |
| 575 | 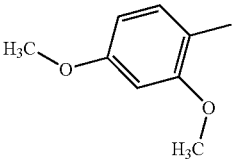 | 530.3084 |
| 576 | 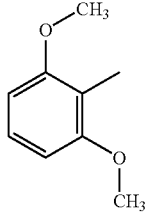 | 530.3101 |
| 577 | 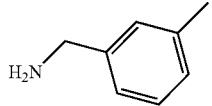 | 499.3166 |
| 578 | 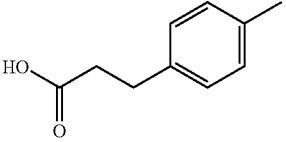 | 542.3149 |
| 579 | 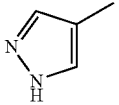 | 460.2821 |

-continued

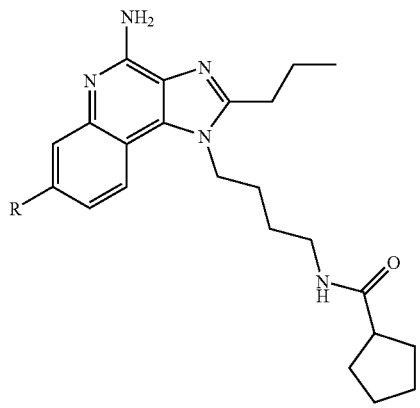

| Example | R | Measured Mass (M + H) |
|---|---|---|
| 580 | 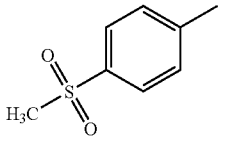 | 548.2672 |
| 581 | 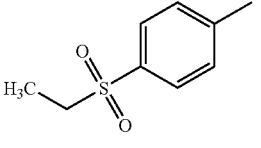 | 562.2844 |
| 582 | 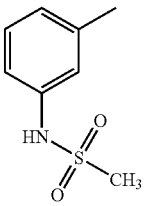 | 563.2784 |

Examples 583-611

Part A

A solution of 7-bromo-2-ethoxymethyl-1-(piperidin-4-yl-methyl)-1H-imidazo[4,5-c]quinolin-4-amine dihydrochloride (4.0 g, 8.1 mmol) and triethylamine (5.67 mL, 40.7 mmol) in chloroform (300 mL) was cooled to 0° C., and 4-morpholinecarbonyl chloride (0.95 mL, 8.1 mmol) was added dropwise. The reaction was allowed to warm to ambient temperature and stirred overnight before it was diluted with chloroform (200 mL); washed sequentially with water (200 mL), 2 M sodium carbonate (2×200 mL), water (200 mL), and brine (200 mL); and concentrated under reduced pressure. The residue was triturated with ethyl acetate and subsequently recrystallized from acetonitrile to provide 3.64 g of 7-bromo-2-ethoxymethyl-1-{[1-(morpholin-4-ylcarbonyl)piperidin-4-yl]methyl}-1H-imidazo[4,5-c]quinolin-4-amine as a white solid, mp 198-199° C.

Anal. Calcd for $C_{24}H_{31}BrN_6O_3$: C, 54.24; H, 5.88; N, 15.81. Found: C, 54.27; H, 5.64; N, 15.87.

Part B

7-Bromo-2-ethoxymethyl-1-{[1-(morpholin-4-ylcarbonyl)piperidin-4-yl]methyl}-1H-imidazo[4,5-c]quinolin-4-amine was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 583-611

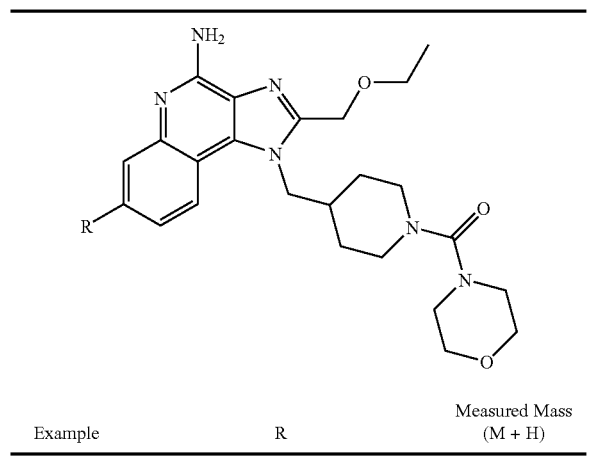

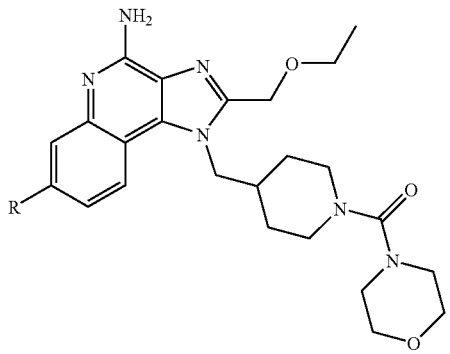

| Example | R | Measured Mass (M + H) |
|---|---|---|
| 583 | phenyl | 529.2931 |
| 584 | pyridin-3-yl | 530.2852 |
| 585 | pyridin-4-yl | 530.2841 |
| 586 | thien-2-yl | 535.2465 |
| 587 | thien-3-yl | 535.2465 |
| 588 | 3,5-dimethylphenyl | 543.3043 |
| 589 | 4-methylphenyl | 543.3057 |
| 590 | 2-methylphenyl | 543.3105 |
| 591 | 2-hydroxyphenyl | 545.2865 |
| 592 | 3-hydroxyphenyl | 545.2874 |
| 593 | 3-cyanophenyl | 554.2842 |
| 594 | 4-cyanophenyl | 554.2849 |
| 595 | (E)-styryl | 555.3068 |
| 596 | 4-methoxyphenyl | 559.3006 |
| 597 | 2-chlorophenyl | 563.2570 |

-continued
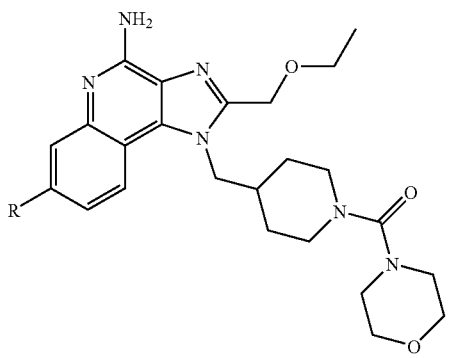
| Example | R | Measured Mass (M + H) |
|---|---|---|
| 598 | 3-chlorophenyl | 563.2519 |
| 599 | 4-chlorophenyl | 563.2496 |
| 600 | 2,4-difluorophenyl | 565.2722 |
| 601 | 2-acetylphenyl | 571.3003 |
| 602 | 3-acetylphenyl | 571.3016 |
| 603 | 4-acetylphenyl | 571.3063 |
| 604 | 3-carbamoylphenyl | 572.2994 |
-continued
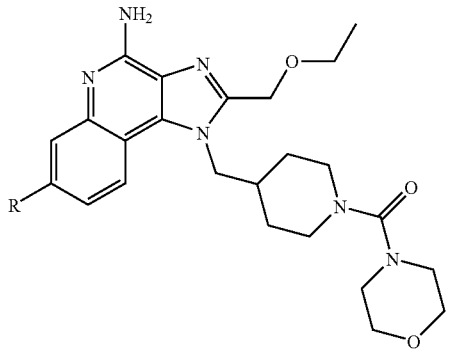
| Example | R | Measured Mass (M + H) |
|---|---|---|
| 605 | 3-(N-isobutylcarbamoyl)phenyl | 628.3633 |
| 606 | 2-(acetylamino)phenyl | 586.3104 |
| 607 | 3-(aminomethyl)phenyl | 558.3211 |
| 608 | 4-(2-carboxyethyl)phenyl | 601.3146 |
| 609 | 4-(methylsulfonyl)phenyl | 607.2709 |
| 610 | 4-(ethylsulfonyl)phenyl | 621.2830 |
| 611 | 3-(methylsulfonylamino)phenyl | 622.2778 |

Examples 612-642

Part A

Hydrogen chloride (100 mL of a 4 M solution in 1,4-dioxane) was added to tert-butyl [4-(4-amino-7-bromo-2-ethoxymethyl-1H-imidazo[4,5-c]quinolin-1-yl)butyl]carbamate (10.0 g, 20.3 mmol), and the reaction was stirred for one hour. The reaction was adjusted to pH 11 with the addition of sodium hydroxide pellets in a small amount of water. Chloroform (300 mL) was added followed by saturated aqueous sodium bicarbonate (50 mL). The organic layer was separated, dried over sodium sulfate, filtered, concentrated under reduced pressure, and dried overnight in a drying oven to provide 5.60 g of 1-(4-aminobutyl)-7-bromo-2-ethoxymethyl-1H-imidazo[4,5-c]quinolin-4-amine as a light yellow solid.

Part B

Methanesulfonyl chloride (0.44 mL, 5.7 mmol) was added to a suspension of 1-(4-aminobutyl)-7-bromo-2-ethoxymethyl-1H-imidazo[4,5-c]quinolin-4-amine (2.04 g, 5.2 mmol) and triethylamine (0.94 mL, 6.8 mmol) in chloroform (100 mL), and the reaction was stirred for four hours. Water was added; a precipitate formed. The aqueous layer was adjusted to pH 10 with the addition of 50% aqueous sodium hydroxide. The precipitate was isolated by filtration, washed with cold chloroform, and dried overnight on the filter funnel. Material from another run was added, and entire procedure was repeated to eliminate unreacted starting material. N-{4-[4-Amino-7-bromo-2-ethoxymethyl-1H-imidazo[4,5-c]quinolin-1-yl]butyl}methanesulfonamide (2.95 g) was obtained as a white solid.

Part C

N-{4-[4-Amino-7-bromo-2-ethoxymethyl-1H-imidazo[4,5-c]quinolin-1-yl]butyl}methanesulonamide was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 612-642

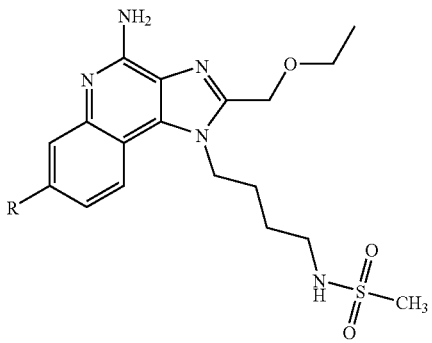

| Example | R | Measured Mass (M + H) |
|---|---|---|
| 612 | (phenyl) | 468.2072 |
| 613 | (3-methylphenyl, H₃C-) | 482.2245 |
| 614 | (2-methylphenyl, -CH₃) | 482.2243 |
| 615 | (2-hydroxyphenyl, -OH) | 484.2014 |
| 616 | (3-hydroxyphenyl, HO-) | 484.2051 |
| 617 | (4-cyanophenyl, N≡C-) | 493.2035 |
| 618 | (4-vinylphenyl) | 494.2239 |
| 619 | (3,5-dimethylphenyl, H₃C-, CH₃) | 496.2400 |
| 620 | (4-ethylphenyl, H₃C-) | 496.2396 |

287

-continued

[Structure: 4-amino-2-(ethoxymethyl)-1-[4-(methanesulfonamido)butyl]-imidazoquinoline with R group on benzene ring]

| Example | R | Measured Mass (M + H) |
|---|---|---|
| 621 | 5-(hydroxymethyl)pyridin-3-yl | 499.2145 |
| 622 | 4-(hydroxymethyl)phenyl | 498.2190 |
| 623 | 4-methoxyphenyl | 498.2167 |
| 624 | 2-chlorophenyl | 502.1650 |
| 625 | 3-chlorophenyl | 502.1717 |
| 626 | 2,5-difluorophenyl | 504.1894 |
| 627 | 3-acetylphenyl | 510.2177 |
| 628 | 4-acetylphenyl | 510.2184 |

288

-continued

[Structure: same scaffold as 287]

| Example | R | Measured Mass (M + H) |
|---|---|---|
| 629 | 2-ethoxyphenyl | 512.2349 |
| 630 | 3-ethoxyphenyl | 512.2345 |
| 631 | 3-(isobutylcarbamoyl)phenyl | 567.2750 |
| 632 | 2-(acetamido)phenyl | 525.2305 |
| 633 | 4-ethoxy-3-methylphenyl | 526.2516 |
| 634 | 4-(isopropoxy)phenyl | 526.2512 |

-continued

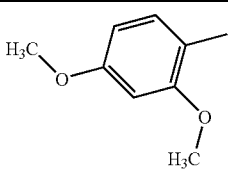

| Example | R | Measured Mass (M + H) |
|---|---|---|
| 635 | 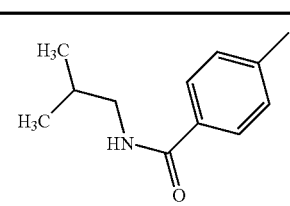 | 528.2282 |
| 636 | 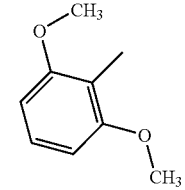 | 528.2320 |
| 637 | 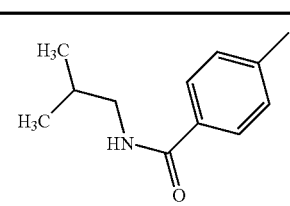 | 540.2274 |
| 638 | 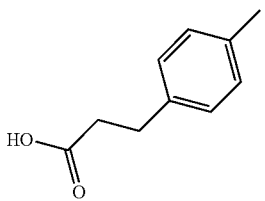 | 561.1957 |
| 639 | 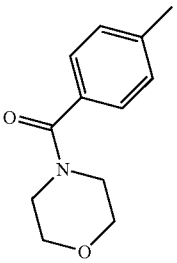 | 561.1987 |
| 640 | 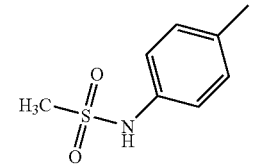 | 565.2621 |

-continued

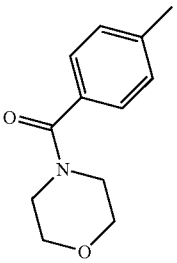

| Example | R | Measured Mass (M + H) |
|---|---|---|
| 641 | 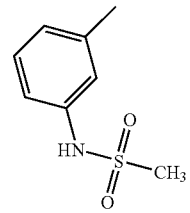 | 567.2791 |
| 642 | 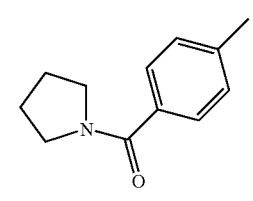 | 581.2590 |

Example 643-663

Part A

A solution of 1-(4-aminobutyl)-7-bromo-2-ethoxymethyl-1H-imidazo[4,5-c]quinolin-4-amine (2.00 g, 5.1 mmol) in chloroform (36 mL) was cooled to 0° C., and a cold solution of isopropyl isocyanate (0.50 mL, 5.4 mmol) in chloroform (4 mL) was added slowly. A precipitate formed, and the reaction was stirred for 45 minutes. The reaction mixture was triturated with ethyl acetate (200 mL), and the precipitate was isolated by filtration and dried for three days in a drying oven to provide 1.86 g of N-{4-[4-amino-7-bromo-2-ethoxymethyl-1H-imidazo[4,5-c]quinolin-1-yl]butyl}-N'-(1-methylethyl)urea as a white solid, mp 211° C.

Anal. Calcd for $C_{21}H_{29}BrN_6O_2$: C, 52.83; H, 6.12; N, 17.60. Found: C, 52.52; H, 6.13; N, 17.29.

Part B

N-{4-[4-Amino-7-bromo-2-ethoxymethyl-1H-imidazo[4,5-c]quinolin-1-yl]butyl}-N'-(1-methylethyl)urea was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Example 643-663

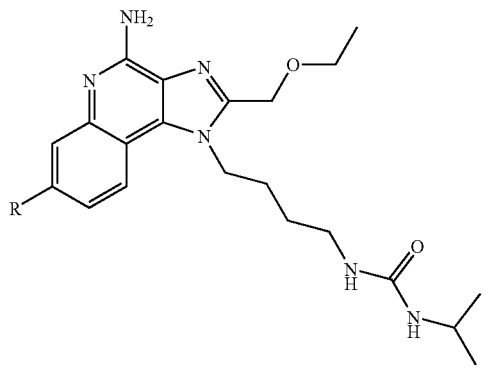

| Example | R | Measured Mass (M + H) |
|---|---|---|
| 643 | phenyl | 475.2793 |
| 644 | pyridin-3-yl | 476.2749 |
| 645 | thiophen-2-yl | 481.2385 |
| 646 | thiophen-3-yl | 481.2366 |
| 647 | 2-(hydroxymethyl)phenyl | 505.2915 |
| 648 | 4-methylphenyl | 489.2940 |
| 649 | 2-methylphenyl | 489.2956 |
| 650 | 2-hydroxyphenyl | 491.2746 |
| 651 | 4-hydroxyphenyl | 491.2772 |
| 652 | 3-hydroxyphenyl | 491.2758 |
| 653 | 4-(hydroxymethyl)phenyl | 505.2906 |
| 654 | 2-acetylphenyl | 517.2902 |
| 655 | 3-carbamoylphenyl | 518.2886 |
| 656 | 4-(dimethylamino)phenyl | 518.3214 |
| 657 | 3-(isobutylcarbamoyl)phenyl | 574.3497 |
| 658 | 1H-pyrazol-4-yl | 465.2721 |

-continued

| Example | R | Measured Mass (M + H) |
|---|---|---|
| 659 | 4-(methanesulfonamido)phenyl | 568.2730 |
| 660 | 3-(methanesulfonamido)phenyl | 568.2715 |
| 661 | 4-(pyrrolidine-1-carbonyl)phenyl | 572.3354 |
| 662 | 4-(isobutylaminocarbonyl)phenyl | 574.3502 |
| 663 | 4-(morpholine-4-carbonyl)phenyl | 588.3318 |

Examples 664-703

1-{3-[4-Amino-7-bromo-2-(2-methoxyethyl)-1H-imidazo[4,5-c]quinolin-1-yl]propyl}pyrrolidin-2-one was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 664-703

| Example | R | Measured Mass (M + H) |
|---|---|---|
| 664 | phenyl | 444.2367 |
| 665 | pyridin-3-yl | 445.2348 |
| 666 | pyridin-4-yl | 445.2376 |
| 667 | thiophen-2-yl | 450.1961 |
| 668 | thiophen-3-yl | 450.1949 |
| 669 | 2-(hydroxymethyl)phenyl | 474.2487 |
| 670 | 3,5-dimethylphenyl | 458.2561 |
| 671 | 4-methylphenyl | 458.2533 |
| 672 | 2-methylphenyl | 458.2528 |

-continued

Common structure (both columns): 4-amino-2-(2-methoxyethyl)-1-[3-(2-oxopyrrolidin-1-yl)propyl]imidazo[4,5-c]quinoline with R substituent on the benzene ring.

| Example | R | Measured Mass (M + H) |
|---|---|---|
| 673 | 2-hydroxyphenyl | 460.2343 |
| 674 | 3-hydroxyphenyl | 460.2322 |
| 675 | 3-cyanophenyl | 469.2308 |
| 676 | 4-cyanophenyl | 469.2344 |
| 677 | 4-(hydroxymethyl)phenyl | 474.2486 |
| 678 | 4-methoxyphenyl | 474.2510 |
| 679 | 2-chlorophenyl | 478.1996 |
| 680 | 2-acetylphenyl | 486.2490 |
| 681 | 3-acetylphenyl | 486.2463 |
| 682 | 4-acetylphenyl | 486.2488 |
| 683 | 4-(dimethylamino)phenyl | 487.2797 |
| 684 | 3-carboxyphenyl | 488.2299 |
| 685 | 3-(isobutylcarbamoyl)phenyl | 543.3068 |
| 686 | 3-aminophenyl | 459.2486 |
| 687 | 2-acetamidophenyl | 501.2592 |
| 688 | 4-(isopropoxy)phenyl | 502.2805 |

-continued

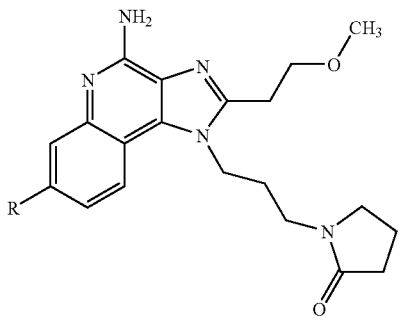

| Example | R | Measured Mass (M + H) |
|---|---|---|
| 689 | H₂N-CH₂-(3-methylphenyl) | 473.2643 |
| 690 | HO-CO-CH₂CH₂-(4-methylphenyl) | 516.2563 |
| 691 | H₃C-SO₂-(4-methylphenyl) | 522.2159 |
| 692 | H₃C-SO₂-NH-(4-methylphenyl) | 537.2263 |
| 693 | (3-methylphenyl)-NH-SO₂-CH₃ | 537.2266 |
| 694 | pyrrolidine-CO-(4-methylphenyl) | 541.2872 |
| 695 | (CH₃)₂CHCH₂-NH-CO-(4-methylphenyl) | 543.3067 |

-continued

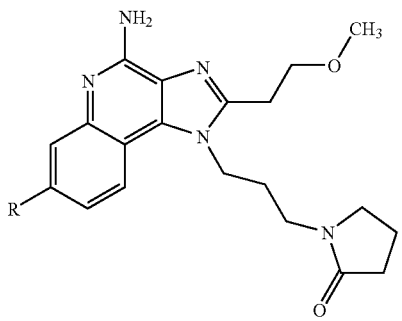

| Example | R | Measured Mass (M + H) |
|---|---|---|
| 696 | morpholine-CO-(4-methylphenyl) | 557.2853 |
| 697 | H₂N-CH₂-(4-methylphenyl) | 473.2643 |
| 698 | (2-methoxyphenyl)-CH₃ | 474.2495 |
| 699 | 4-oxopiperidine-CO-(4-methylphenyl) | 569.2845 |
| 700 | HO-CH₂CH₂CH₂-(3-methylphenyl) | 502.2812 |

-continued

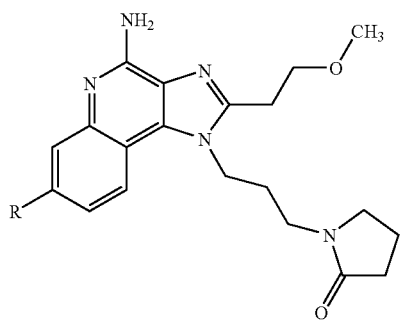

| Example | R | Measured Mass (M + H) |
|---|---|---|
| 701 | 2-carbamoylphenyl | 487.2454 |
| 702 | 3-(furan-2-ylmethylcarbamoyl)phenyl | 567.2703 |
| 703 | 3-(cyanomethyl)phenyl | 483.2511 |

Examples 704-738

1-{3-[4-Amino-8-bromo-2-(2-methoxyethyl)-1H-imidazo[4,5-c]quinolin-1-yl]propyl}pyrrolidin-2-one was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 704-738

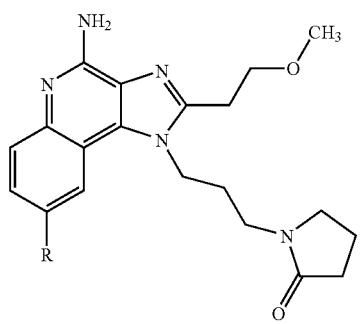

| Example | R | Measured Mass (M + H) |
|---|---|---|
| 704 | furan-3-yl | 434.2216 |
| 705 | phenyl | 444.2412 |
| 706 | pyridin-4-yl | 445.2380 |
| 707 | thiophen-2-yl | 450.1968 |
| 708 | thiophen-3-yl | 450.1963 |
| 709 | 3-methylphenyl | 458.2571 |
| 710 | 4-methylphenyl | 458.2547 |

-continued
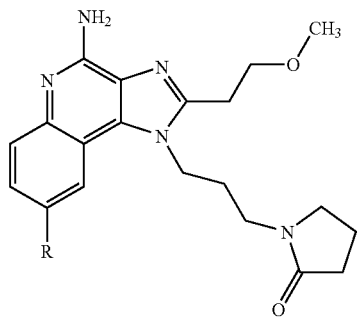
| Example | R | Measured Mass (M + H) |
|---|---|---|
| 711 | 2-methylphenyl | 458.2563 |
| 712 | 2-hydroxyphenyl | 460.2370 |
| 713 | 4-hydroxyphenyl | 460.2324 |
| 714 | 3-hydroxyphenyl | 460.2359 |
| 715 | (E)-2-phenylethenyl | 470.2581 |
| 716 | 5-(hydroxymethyl)pyridin-3-yl | 475.2460 |
-continued
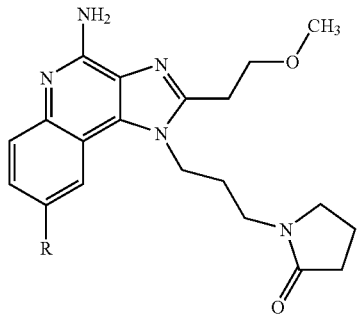
| Example | R | Measured Mass (M + H) |
|---|---|---|
| 717 | 4-(hydroxymethyl)phenyl | 474.2530 |
| 718 | 4-methoxyphenyl | 474.2484 |
| 719 | 2-chlorophenyl | 478.2023 |
| 720 | 3-chlorophenyl | 478.2005 |
| 721 | 4-chlorophenyl | 478.1989 |
| 722 | 2-acetylphenyl | 486.2513 |

-continued

[Structure: 4-amino-2-(2-methoxyethyl)-1-(3-(2-oxopyrrolidin-1-yl)propyl)-1H-imidazo[4,5-c]quinoline with R substituent at 8-position]

| Example | R | Measured Mass (M + H) |
|---|---|---|
| 723 | 3-acetylphenyl | 486.2530 |
| 724 | 4-acetylphenyl | 486.2545 |
| 725 | 3-carbamoylphenyl | 487.2502 |
| 726 | 3-aminophenyl | 459.2529 |
| 727 | 4-(methylthio)phenyl | 490.2287 |
| 728 | 2-(acetylamino)phenyl | 501.2592 |

-continued

[Same core structure]

| Example | R | Measured Mass (M + H) |
|---|---|---|
| 729 | 3-(aminomethyl)phenyl | 473.2639 |
| 730 | 4-(methylsulfonyl)phenyl | 522.2183 |
| 731 | 4-(methylsulfonylamino)phenyl | 537.2275 |
| 732 | 3-(methylsulfonylamino)phenyl | 537.2269 |
| 733 | 4-(pyrrolidin-1-ylcarbonyl)phenyl | 541.2952 |

Example 739-762

Part A

A solution of 7-bromo-2-ethoxymethyl-1-(piperidin-4-yl-methyl)-1H-imidazo[4,5-c]quinolin-4-amine dihydrochloride (4.0 g, 8.1 mmol) and triethylamine (5.67 mL, 40.7 mmol) in chloroform (300 mL) was treated with isobutyryl chloride (0.85 mL, 8.1 mmol) according to the method described in Part A of Examples 583-611. The reaction was complete after one hour. Following trituration with ethyl acetate, the solid was recrystallized from ethyl acetate and then triturated with hot acetonitrile and isolated by filtration to provide 3.63 g of 7-bromo-2-ethoxymethyl-1-{[1-(2-methylpropylcarbonyl)piperidin-4-yl]methyl}-1H-imidazo[4,5-c]quinolin-4-amine as a white solid, mp 199-200° C.

Anal. Calcd for $C_{23}H_{30}BrN_5O_2$: C, 56.56; H, 6.19; N, 14.34. Found: C, 56.49; H, 6.33; N, 14.12.

Part B

7-Bromo-2-ethoxymethyl-1-{[1-(2-methylpropylcarbonyl)piperidin-4-yl]methyl}-1H-imidazo[4,5-c]quinolin-4-amine was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Example 739-762

| Example | R | Measured Mass (M + H) |
|---------|---|------------------------|
| 739 | phenyl | 486.2873 |
| 740 | pyridin-3-yl | 487.2845 |
| 741 | pyridin-4-yl | 487.2839 |
| 742 | thiophen-2-yl | 492.2446 |

-continued

| Example | R | Measured Mass (M + H) |
|---------|---|------------------------|
| 734 | 4-methyl-N-isobutylbenzamide | 543.3086 |
| 735 | 4-methyl-morpholinobenzamide | 557.2878 |
| 736 | 4-methyl-N-(4-acetamidophenyl) | 501.2599 |
| 737 | 4-methylbenzylamine | 473.2668 |
| 738 | 2-methoxy-3-methylphenyl | 474.2533 |

-continued

| Example | R | Measured Mass (M + H) |
|---|---|---|
| 743 | 3-thienyl | 492.2407 |
| 744 | 3,5-dimethylphenyl | 500.3025 |
| 745 | 3,4-dimethylphenyl | 500.3015 |
| 746 | 2,3-dimethylphenyl | 500.3022 |
| 747 | 4-hydroxyphenyl | 502.2812 |
| 748 | 3-hydroxyphenyl | 502.2826 |
| 749 | 2-cyano-4-methylpyridyl | 511.2816 |
| 750 | 4-cyanophenyl | 511.2824 |
| 751 | 4-methoxyphenyl | 516.3008 |

-continued

| Example | R | Measured Mass (M + H) |
|---|---|---|
| 752 | 2-chlorophenyl | 520.2502 |
| 753 | 3-chlorophenyl | 520.2512 |
| 754 | 4-chlorophenyl | 520.2506 |
| 755 | 2,4-difluorophenyl | 522.2695 |
| 756 | 3-acetylphenyl | 528.2963 |
| 757 | 4-acetylphenyl | 528.2943 |
| 758 | 3-(N-isobutylcarbamoyl)phenyl | 585.3572 |
| 759 | 4-(methylsulfonyl)phenyl | 564.2650 |

Examples 763-785

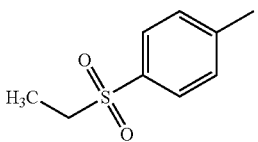

| Example | R | Measured Mass (M + H) |
|---|---|---|
| 760 | 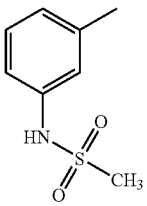 | 578.2791 |
| 761 | 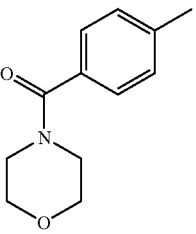 | 579.2740 |
| 762 | 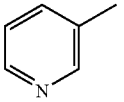 | 599.3309 |

Examples 763-785

Part A

Cyclopentanecarbonyl chloride (0.80 mL, 6.6 mmol) was added dropwise over a period of five minutes to a suspension of 1-(4-aminobutyl)-7-bromo-2-ethoxymethyl-1H-imidazo[4,5-c]quinolin-4-amine (2.00 g, 5.1 mmol) and triethylamine (0.78 mL, 5.6 mmol) in chloroform (200 mL). The reaction was stirred for 2.5 hours and then stored for three days in a refrigerator. Additional cyclopentanecarbonyl chloride (0.18 mL) was added, and the reaction was stirred for 30 minutes and treated as described for Examples 558-583. The crude product was recrystallized from isopropanol (13 mL/g), isolated by filtration, and dried overnight on the filter funnel to provide 1.60 g of N-{4-[4-amino-7-bromo-2-ethoxymethyl-1H-imidazo[4,5-c]quinolin-1-yl]butyl}cyclopentanecarboxamide as a white solid.

Part B

N-{4-[4-Amino-7-bromo-2-ethoxymethyl-1H-imidazo[4,5-c]quinolin-1-yl]butyl}-cyclopentanecarboxamide was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 763-785

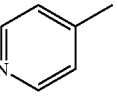

| Example | R | Measured Mass (M + H) |
|---|---|---|
| 763 | 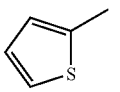 | 487.2841 |
| 764 | 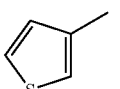 | 487.2839 |
| 765 | 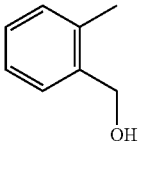 | 492.2468 |
| 766 | 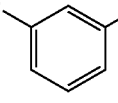 | 492.2411 |
| 767 | 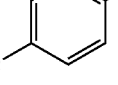 | 516.3013 |
| 768 | 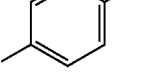 | 500.3054 |
| 769 |  | 500.3050 |
| 770 |  | 502.2824 |

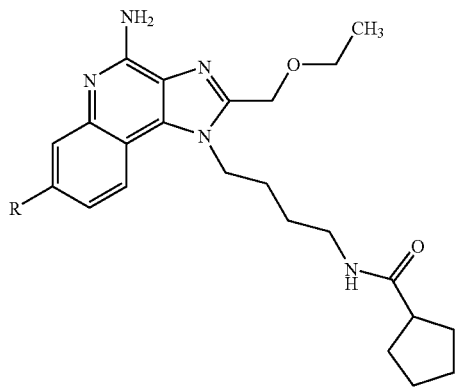
| Example | R | Measured Mass (M + H) |
|---|---|---|
| 771 | 3-HO-C6H4- | 502.2812 |
| 772 | 3-NC-C6H4- | 511.2804 |
| 773 | 4-NC-C6H4- | 511.2807 |
| 774 | 5-(hydroxymethyl)pyridin-3-yl | 517.2941 |
| 775 | 4-(HOCH2)-C6H4- | 516.3018 |
| 776 | 4-(CH3O)-C6H4- | 516.2982 |
| 777 | 2-Cl-C6H4- | 520.2447 |
| 778 | 3-Cl-C6H4- | 520.2510 |
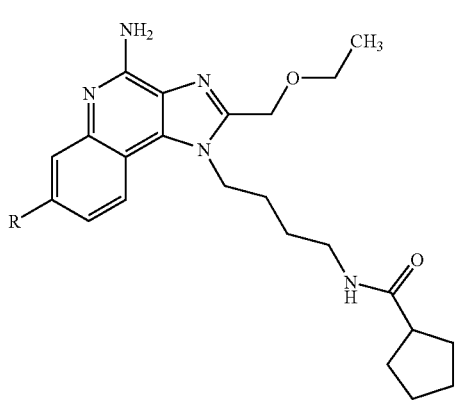
| Example | R | Measured Mass (M + H) |
|---|---|---|
| 779 | 4-Cl-C6H4- | 520.2469 |
| 780 | 3-[(isobutyl)NHC(O)]-C6H4- | 585.3587 |
| 781 | 3-(H2NCH2)-C6H4- | 515.3151 |
| 782 | 4-(CH3SO2)-C6H4- | 564.2663 |
| 783 | 4-(CH3SO2NH)-C6H4- | 579.2753 |
| 784 | 3-(CH3SO2NH)-C6H4- | 579.2776 |

-continued

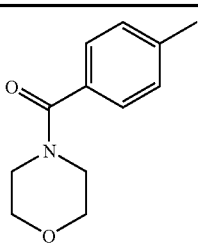

| Example | R | Measured Mass (M + H) |
|---|---|---|
| 785 | 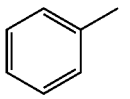 | 599.3339 |

Example 786-806

Part A

A suspension of 1-(4-aminobutyl)-7-bromo-2-propyl-1H-imidazo[4,5-c]quinolin-4-amine (3.27 g, 8.7 mmol) and triethylamine (3.82 mL, 11.3 mmol) in chloroform (165 mL) was cooled to 0° C. A cold solution of methanesulfonyl chloride (1.37 mL, 9.6 mmol) in chloroform (10 mL) was slowly added. The reaction was allowed to warm to ambient temperature after 15 minutes. Additional triethylamine (3.74 mL) and methanesulfonyl chloride (2.12 mL) were added over the course of several days to drive the reaction to completion. The reaction was concentrated under reduced pressure, and the residue was partitioned between 1% aqueous sodium carbonate and chloroform. The aqueous layer was adjusted to pH 13 with the addition of saturated aqueous sodium bicarbonate and 50% aqueous sodium hydroxide. The precipitate was isolated by filtration, air-dried, and combined with material from another run. The crude product was recrystallized from isopropanol:water (15 mL/g:1.5 mL/g) and dried in a drying oven for several days to provide 1.48 g of N-{4-[4-amino-7-bromo-2-propyl-1H-imidazo[4,5-c]quinolin-1-yl]butyl}methanesulfonamide as a white solid.

Part B

N-{4-[4-Amino-7-bromo-2-propyl-1H-imidazo[4,5-c]quinolin-1-yl]butyl}methanesulfonamide was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 786-806

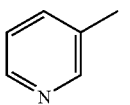

| Example | R | Measured Mass (M + H) |
|---|---|---|
| 786 | 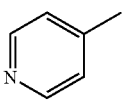 | 452.2107 |
| 787 | 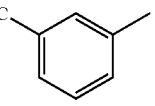 | 453.2040 |
| 788 | 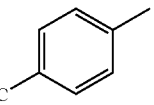 | 453.2061 |
| 789 | 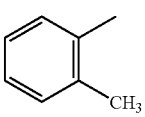 | 466.2274 |
| 790 | 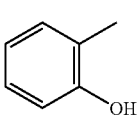 | 466.2247 |
| 791 | 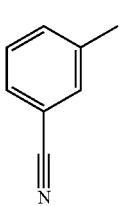 | 466.2280 |
| 792 |  | 468.2050 |
| 793 |  | 477.2056 |

-continued

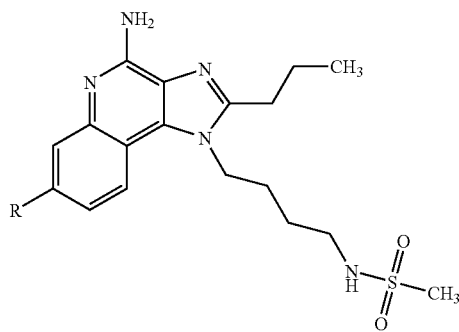

| Example | R | Measured Mass (M + H) |
|---|---|---|
| 794 | 5-(hydroxymethyl)pyridin-3-yl | 483.2149 |
| 795 | 4-methoxyphenyl | 482.2186 |
| 796 | 2-chlorophenyl | 486.1711 |
| 797 | 3-chlorophenyl | 486.1713 |
| 798 | 4-chlorophenyl | 486.1720 |
| 799 | 3-(aminocarbonyl)phenyl | 495.2148 |
| 800 | 3-(isobutylaminocarbonyl)phenyl | 551.2762 |
| 801 | 4-(1-methylethoxy)phenyl | 510.2527 |

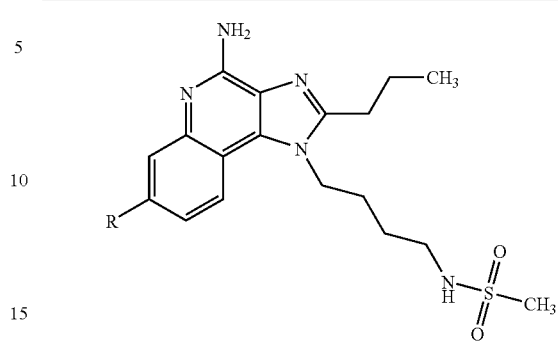

| Example | R | Measured Mass (M + H) |
|---|---|---|
| 802 | 3-(aminomethyl)phenyl | 481.2388 |
| 803 | 4-(methylsulfonyl)phenyl | 530.1874 |
| 804 | 4-(methylsulfonylamino)phenyl | 545.1954 |
| 805 | 4-(pyrrolidin-1-ylcarbonyl)phenyl | 549.2600 |
| 806 | 4-(isobutylaminocarbonyl)phenyl | 551.2773 |

Examples 807-860

1-(4-Amino-8-bromo-2-ethoxymethyl-1H-imidazo[4,5-c]quinolin-1-yl)-2-methylpropan-2-ol was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Example 807-860

| Example | R | Measured Mass (M +H) |
|---|---|---|
| 807 | phenyl | 391.2158 |
| 808 | pyridin-3-yl | 392.2117 |
| 809 | pyridin-4-yl | 392.2101 |
| 810 | thiophen-2-yl | 397.1702 |
| 811 | thiophen-3-yl | 397.1716 |
| 812 | 2-(hydroxymethyl)phenyl | 421.2254 |
| 813 | 3-methylphenyl | 405.2313 |
| 814 | 4-methylphenyl | 405.2303 |
| 815 | 2-methylphenyl | 405.2323 |
| 816 | 2-hydroxyphenyl | 407.2123 |
| 817 | 4-hydroxyphenyl | 407.2115 |
| 818 | 3-hydroxyphenyl | 407.2117 |
| 819 | 3-cyanophenyl | 416.2117 |
| 820 | 4-cyanophenyl | 416.2068 |

319
-continued
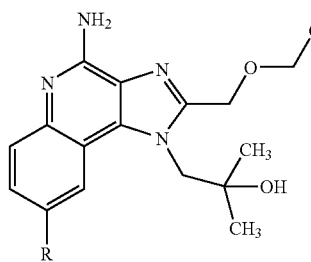
| Example | R | Measured Mass (M +H) |
|---|---|---|
| 821 | (E)-styryl | 417.2311 |
| 822 | 3,5-dimethylphenyl | 419.2468 |
| 823 | 5-(hydroxymethyl)pyridin-3-yl | 422.2206 |
| 824 | 4-(hydroxymethyl)phenyl | 421.2281 |
| 825 | 4-methoxyphenyl | 421.2275 |
| 826 | 2-chlorophenyl | 425.1750 |
320
-continued
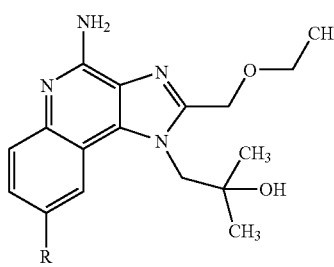
| Example | R | Measured Mass (M +H) |
|---|---|---|
| 827 | 3-chlorophenyl | 425.1758 |
| 828 | 4-chlorophenyl | 425.1772 |
| 829 | 2-acetylphenyl | 433.2227 |
| 830 | 3-acetylphenyl | 433.2268 |
| 831 | 4-acetylphenyl | 433.2265 |
| 832 | 3-carbamoylphenyl | 434.2209 |

| Example | R | Measured Mass (M +H) |
|---|---|---|
| 833 | 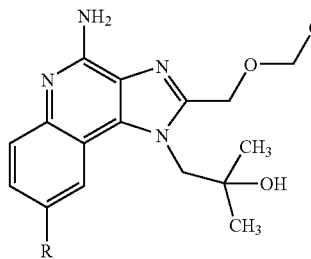 | 434.2561 |
| 834 | 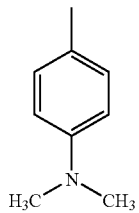 | 490.2814 |
| 835 | 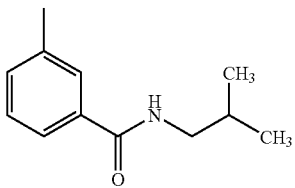 | 406.2247 |
| 836 | 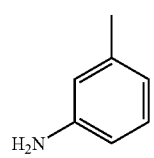 | 448.2364 |
| 837 | 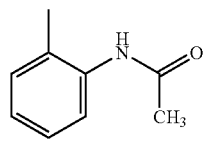 | 449.2564 |
| 838 | 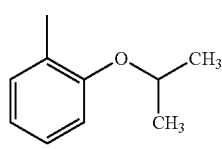 | 449.2574 |
| Example | R | Measured Mass (M +H) |
|---|---|---|
| 839 | 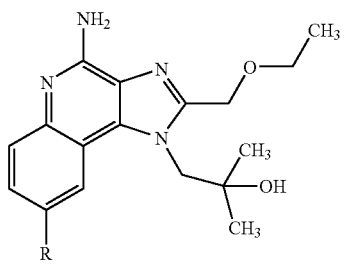 | 420.2432 |
| 840 | 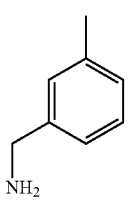 | 381.2046 |
| 841 | 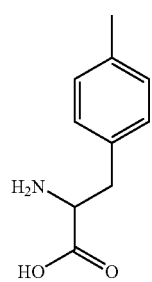 | 478.2410 |
| 842 | 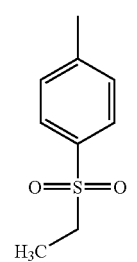 | 483.2058 |
| 843 | 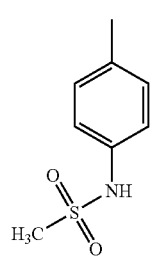 | 484.2024 |

323
-continued
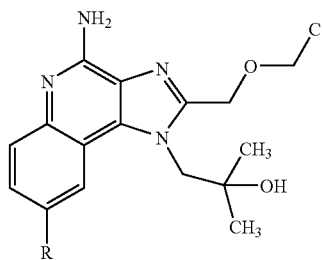
| Example | R | Measured Mass (M +H) |
|---|---|---|
| 844 | 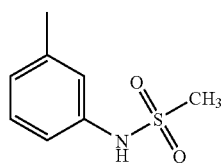 | 484.2026 |
| 845 | 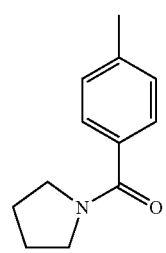 | 488.2686 |
| 846 | 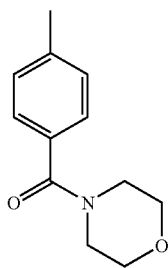 | 504.2607 |
| 847 | 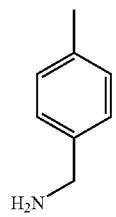 | 420.2394 |
| 848 | 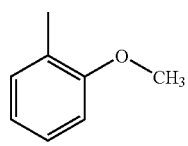 | 421.2247 |
324
-continued
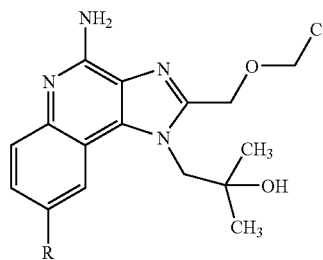
| Example | R | Measured Mass (M +H) |
|---|---|---|
| 849 | 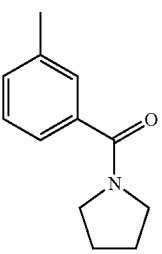 | 488.2662 |
| 850 | 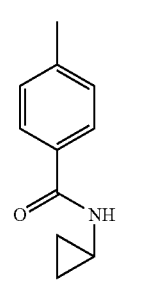 | 474.2520 |
| 851 | 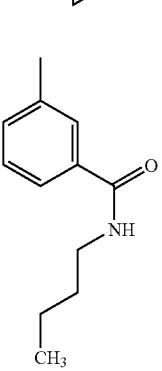 | 490.2816 |
| 852 | 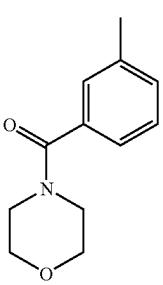 | 504.2585 |

-continued

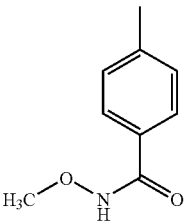

| Example | R | Measured Mass (M+H) |
|---|---|---|
| 853 | 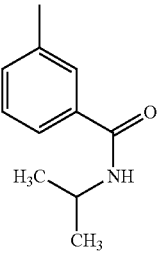 | 464.2324 |
| 854 | 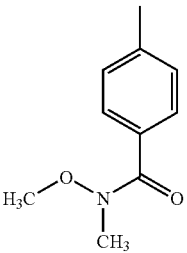 | 478.2449 |
| 855 | 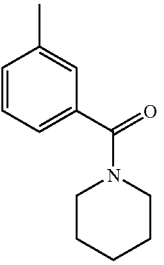 | 502.2843 |
| 856 | 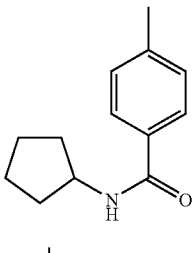 | 462.2492 |
| 857 | 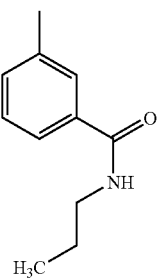 | 524.2639 |

-continued

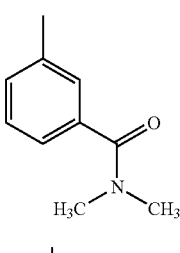

| Example | R | Measured Mass (M+H) |
|---|---|---|
| 858 | 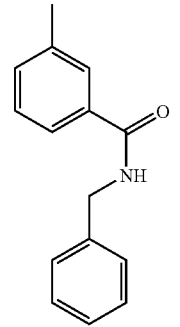 | 476.2647 |
| 859 | | 502.2809 |
| 860 | | 476.2672 |

Examples 861-921

1-(4-Amino-7-bromo-2-ethoxymethyl-1H-imidazo[4,5-c]quinolin-1-yl)-2-methylpropan-2-ol was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 861-921
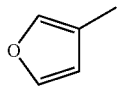
| Example | R | Measured Mass (M + H) |
|---|---|---|
| 861 | 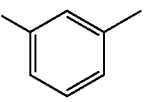 | 381.1925 |
| 862 | 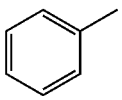 | 391.2139 |
| 863 | 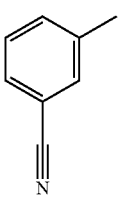 | 392.2069 |
| 864 | 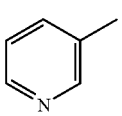 | 392.2050 |
| 865 | 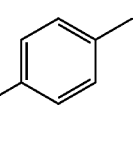 | 397.1667 |
| 866 | 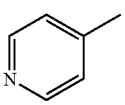 | 397.1695 |
| 867 | 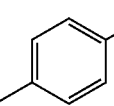 | 405.2259 |
| 868 | 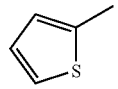 | 405.2269 |
| 869 | 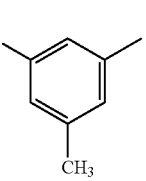 | 405.2283 |
| 870 | 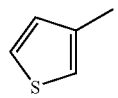 | 407.2066 |
| 871 | 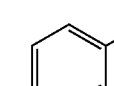 | 407.2051 |
-continued
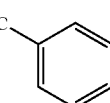
| Example | R | Measured Mass (M + H) |
|---|---|---|
| 872 | 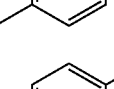 | 407.2068 |
| 873 | 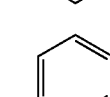 | 416.2070 |
| 874 | 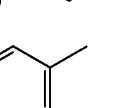 | 416.2066 |
| 875 | 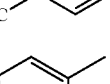 | 417.2247 |
| 876 | 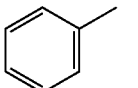 | 419.2472 |
| 877 | 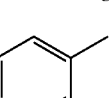 | 419.2413 |
| 878 | 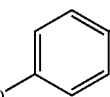 | 421.2206 |
| 879 | | 425.1762 |
| 880 | | 425.1763 |

-continued
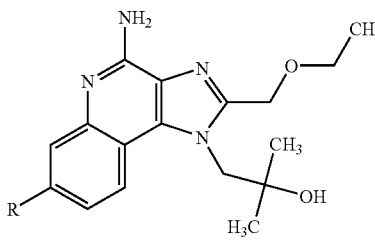
| Example | R | Measured Mass (M + H) |
|---|---|---|
| 881 | 4-chlorophenyl | 425.1725 |
| 882 | 2,4-difluorophenyl | 427.1958 |
| 883 | 2-acetylphenyl | 433.2243 |
| 884 | 3-acetylphenyl | 433.2263 |
| 885 | 4-acetylphenyl | 433.2231 |
| 886 | 3-carbamoylphenyl | 434.2170 |
| 887 | 2-(ethoxy)phenyl | 435.2352 |
| 888 | 3-(ethoxymethoxy)phenyl | 435.2393 |
-continued
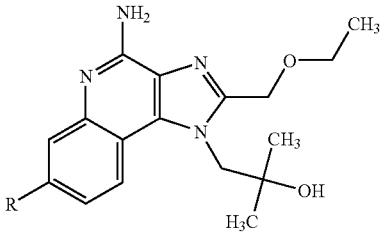
| Example | R | Measured Mass (M + H) |
|---|---|---|
| 889 | 3-(isobutylcarbamoyl)phenyl | 490.2780 |
| 890 | 4-(methylthio)phenyl | 437.1983 |
| 891 | 4-ethoxy-3-methylphenyl | 449.2522 |
| 892 | 2-(isopropoxy)phenyl | 449.2562 |
| 893 | 4-(1-methylethoxy)phenyl | 449.2521 |
| 894 | 2,4-dimethoxyphenyl | 451.2303 |
| 895 | 2,6-dimethoxyphenyl | 451.2195 |

-continued

| Example | R | Measured Mass (M + H) |
|---|---|---|
| 896 | 4-methyl-1H-pyrazole | 381.2039 |
| 897 | 4-(methylsulfonyl)phenyl | 469.1895 |
| 898 | 2-amino-3-(4-methylphenyl)propanoic acid | 478.2435 |
| 899 | 3,4,5-trimethoxyphenyl | 481.2317 |
| 900 | 4-(ethylsulfonyl)phenyl | 483.2026 |
| 901 | N-(4-methylphenyl)methanesulfonamide | 484.2015 |
| 902 | (4-methylphenyl)(pyrrolidin-1-yl)methanone | 488.2650 |
| 903 | N-isobutyl-4-methylbenzamide | 490.2784 |

-continued

| Example | R | Measured Mass (M + H) |
|---|---|---|
| 904 | N-(4-methylphenyl)acetamide | 448.2361 |
| 905 | (4-methylphenyl)methanamine | 420.2409 |
| 906 | 2-methoxyphenyl | 421.2241 |
| 907 | (3-methylphenyl)(pyrrolidin-1-yl)methanone | 488.2619 |
| 908 | N-butyl-3-methylbenzamide | 490.2794 |
| 909 | (3-methylphenyl)(morpholin-4-yl)methanone | 504.2563 |
| 910 | N-methoxy-4-methylbenzamide | 464.2296 |

-continued

| Example | R | Measured Mass (M + H) |
|---|---|---|
| 911 | 4-methyl-N-cyclopentylbenzamide group | 502.2782 |
| 912 | 3-methyl-N,N-dimethylbenzamide group | 462.2493 |
| 913 | 3-methyl-N-benzylbenzamide group | 524.2609 |
| 914 | 3-methyl-N-isopropylbenzamide group | 476.2669 |
| 915 | 3-methyl-piperidinyl benzamide group | 502.2786 |
| 916 | 3-methyl-N-(2-cyanoethyl)benzamide group | 487.2453 |

-continued

| Example | R | Measured Mass (M + H) |
|---|---|---|
| 917 | 3-methyl-(3-hydroxypropyl)phenyl group | 449.2572 |
| 918 | 2-methylbenzamide group | 434.2215 |
| 919 | 2,3-dimethylphenyl group | 419.2444 |
| 920 | 3-methyl-N-(furan-2-ylmethyl)benzamide group | 514.2440 |
| 921 | 3-methyl-(cyanomethyl)phenyl group | 430.2249 |

Example 922-955

A reagent from the table below, (0.11 mmol, 1.1 equivalents) was added to a test tube containing a solution of 1-(4-aminobutyl)-2-ethoxymethyl-7-(pyridin-3-yl)-1H-imidazo[4,5-c]quinolin-4-amine (39 mg, 0.10 mmol) and N,N-diisopropylethylamine (0.024 mL, 0.14 mmol, 1.4 equivalents) in chloroform (2 mL). The test tube was capped and placed on a shaker at ambient temperature overnight. One drop of deionized water was then added to each test tube, and the solvent was removed by vacuum centrifugation. The products were purified by prep HPLC according to the methods described above. The table below shows the reagent used for each example, the structure of the resulting compound, and the observed accurate mass for the isolated trifluoroacetate salt.

Examples 922-955

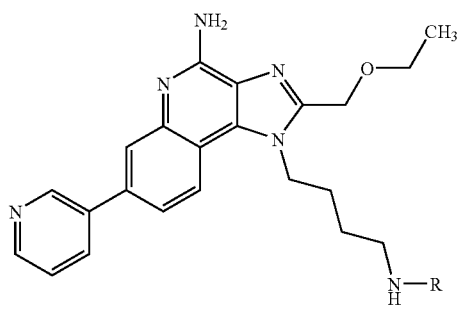

| Example | Reagent | R | Measured Mass (M + H) |
|---|---|---|---|
| 922 | Acetyl chloride | —C(O)CH₃ | 433.2328 |
| 923 | Cyclopropanecarbonyl chloride | —C(O)-cyclopropyl | 459.2498 |
| 924 | Butyryl chloride | —C(O)CH₂CH₂CH₃ | 461.2625 |
| 925 | Methoxyacetyl chloride | —C(O)CH₂OCH₃ | 463.2431 |
| 926 | Cyclobutanecarbonyl chloride | —C(O)-cyclobutyl | 473.2641 |
| 927 | 2-Furoyl chloride | —C(O)-2-furyl | 485.2261 |

-continued
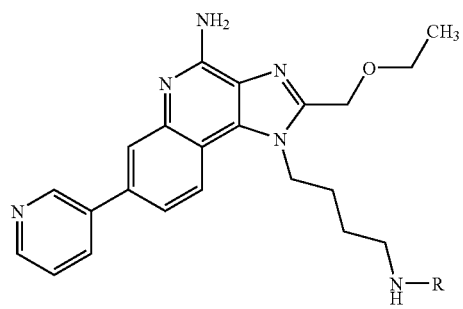
| Example | Reagent | R | Measured Mass (M + H) |
|---|---|---|---|
| 928 | 3-Furoyl chloride | 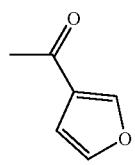 | 485.2284 |
| 929 | Hexanoyl chloride | 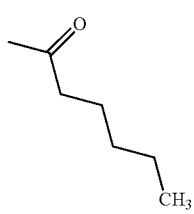 | 489.2979 |
| 930 | Methyl malonyl chloride | 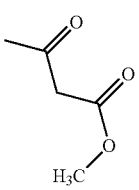 | 491.2390 |
| 931 | Benzoyl chloride | 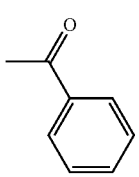 | 495.2462 |
| 932 | Thiophene-2-carbonyl chloride | 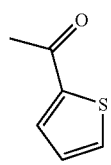 | 501.2066 |
| 933 | Isonicotinoyl chloride hydrochloride | 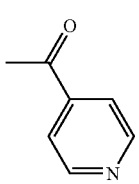 | 496.2431 |

-continued

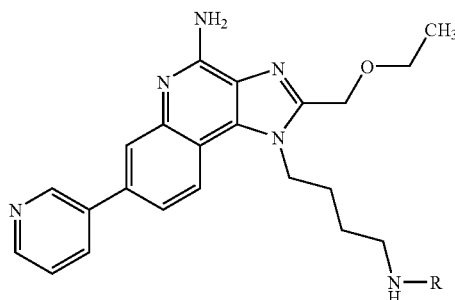

| Example | Reagent | R | Measured Mass (M + H) |
|---|---|---|---|
| 934 | Nicotinoyl chloride hydrochloride | 3-acetylpyridine group | 496.2466 |
| 935 | Picolinoyl chloride hydrochloride | 2-acetylpyridine group | 496.2476 |
| 936 | Methanesulfonyl chloride | —S(O)$_2$—CH$_3$ | 469.2018 |
| 937 | Ethanesulfonyl chloride | —S(O)$_2$—CH$_2$CH$_3$ | 483.2137 |
| 938 | Isopropylsulfonyl chloride | —S(O)$_2$—CH(CH$_3$)$_2$ | 497.2370 |
| 939 | Dimethylsulfamoyl chloride | —S(O)$_2$—N(CH$_3$)$_2$ | 498.2243 |
| 940 | Benzenesulfonyl chloride | —S(O)$_2$—phenyl | 531.2141 |
| 941 | 1-Methylimidazole-4-sulfonyl chloride | —S(O)$_2$—(1-methylimidazol-4-yl) | 535.2206 |
| 942 | 3-Methylbenzenesulfonyl chloride | —S(O)$_2$—(3-methylphenyl) | 545.2297 |

-continued
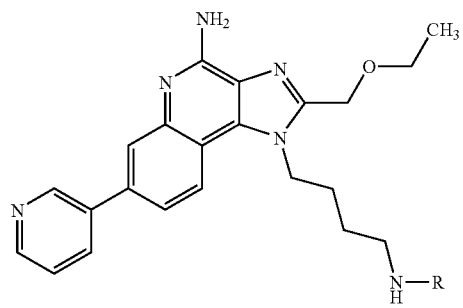
| Example | Reagent | R | Measured Mass (M + H) |
|---|---|---|---|
| 943 | 3,5-Dimethylisooxazole-4-sulfonyl chloride | | 550.2181 |
| 944 | 3-Methoxybenzenesulfonyl chloride | | 561.2244 |
| 945 | 4-Methoxybenzenesulfonyl chloride | | 561.2260 |
| 946 | 3,4-Dimethoxybenzenesulfonyl chloride | | 591.2353 |
| 947 | Ethyl isothiocyanate | | 478.2372 |
| 948 | Pentyl isocyanate | | 504.3038 |
| 949 | Phenyl isocyanate | | 510.2595 |

-continued

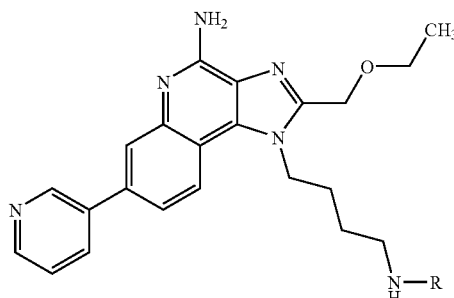

| Example | Reagent | R | Measured Mass (M + H) |
|---|---|---|---|
| 950 | Phenyl isothiocyanate | -C(=S)-NH-phenyl | 526.2362 |
| 951 | 3-Pyridyl isothiocyanate | -C(=S)-NH-(3-pyridyl) | 527.2310 |
| 952 | Cyclohexyl isothiocyanate | -C(=S)-NH-cyclohexyl | 532.2814 |
| 953 | 2-Oxo-1-imidazolidinecarbonyl chloride | -C(=O)-(2-oxoimidazolidin-1-yl) | 503.2503 |
| 954 | 1-Naphthyl isocyanate | -C(=O)-NH-(1-naphthyl) | 560.2722 |
| 955 | 2-Morpholinoethyl isothiocyanate | -C(=S)-NH-CH2CH2-morpholino | 563.2881 |

Examples 956-981

Part A 1-(4-Amino-7-bromo-2-ethoxymethyl-1H-imidazo[4,5-c]quinolin-1-yl)-2-methylpropan-2-ol (2.62 g, 6.67 mmol) and 3-(N-tert-butoxycarbonylaminomethyl)phenylboronic acid (2.0 g, 8.0 mmol) were coupled according to the procedure described in Part J of Example 1. Palladium (II) acetate was added as a 5 mg/mL solution in toluene. The reaction was heated for four hours, and the work-up procedure described in Examples 125-135 was followed. The crude product was purified by HPFC (eluting with chloroform:CMA in a gradient from 100:0 to 80:20) to provide 2.94 g of tert-butyl {3-[4-amino-2-ethoxymethyl-1-(2-hydroxy-2-methylpropyl)-1H-imidazo[4,5-c]quinolin-7-yl]benzyl}carbamate as a white solid.

Part B

Hydrogen chloride (30 mL of a 3 M solution in ethanol) was added to the material from Part A, and the reaction was heated at reflux for 30 minutes. A precipitate formed. Diethyl ether was added, and the precipitate was isolated by filtration, washed with diethyl ether, and air-dried to provide an off-white solid. The solid was partitioned between 2 M aqueous sodium carbonate, brine, and chloroform. The aqueous layer was extracted with chloroform. The combined organic fractions were dried over magnesium sulfate, filtered, and concentrated under reduced pressure. The residue was purified by HPFC (eluting with chloroform:CMA in a gradient from 100:0 to 50:50). The resulting white solid was recrystallized from acetonitrile, isolated by filtration, washed with cold acetonitrile, and air-dried to provide 1.7 g of 1-[4-amino-7-(3-aminomethylphenyl)-2-ethoxymethyl-1H-imidazo[4,5-c]quinolin-1-yl]-2-methylpropan-2-ol as a white solid.

Part C

A reagent from the table below, (0.11 mmol, 1.1 equivalents) was added to a test tube containing a solution of 1-[4-amino-7-(3-aminomethylphenyl)-2-ethoxymethyl-1H-imidazo[4,5-c]quinolin-1-yl]-2-methylpropan-2-ol (40 mg, 0.097 mmol) and N,N-diisopropylethylamine (0.022 mL, 0.12 mmol, 1.25 equivalents) in chloroform (2 mL). The test tube was capped and placed on a shaker at ambient temperature overnight. The solvent was removed by vacuum centrifugation. The products were purified by prep HPLC according to the methods described above. The table below shows the reagent used for each example, the structure of the resulting compound, and the observed accurate mass for the isolated trifluoroacetate salt.

Examples 956-981

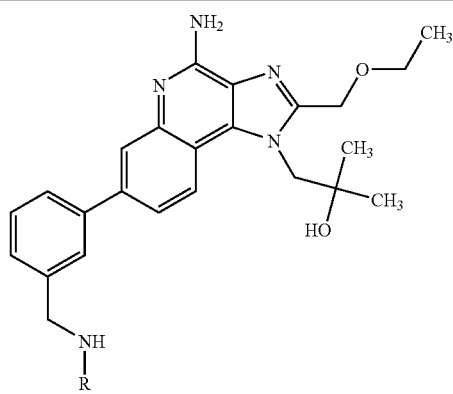

| Example | Reagent | R | Measured Mass (M + H) |
|---|---|---|---|
| 956 | None | H | 420.2386 |
| 957 | Acetyl chloride | H₃C−C(=O)− | 462.2499 |
| 958 | Cyclopropanecarbonyl chloride | cyclopropyl−C(=O)− | 488.2661 |
| 959 | 3-Furoyl chloride | 3-furyl−C(=O)− | 514.2431 |
| 960 | Benzoyl chloride | phenyl−C(=O)− | 524.2619 |
| 961 | Cyclopentylacetyl chloride | cyclopentyl−CH₂−C(=O)− | 530.3090 |

-continued
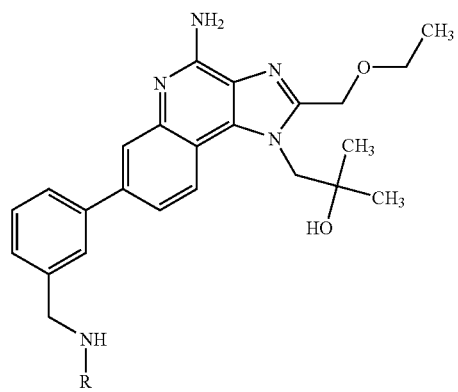
| Example | Reagent | R | Measured Mass (M + H) |
|---|---|---|---|
| 962 | Hydrocinnamoyl chloride | | 552.2921 |
| 963 | 3-Methoxybenzoyl chloride | | 554.2740 |
| 964 | Ethanesulfonyl chloride | | 512.2318 |
| 965 | Isopropylsulfonyl chloride | | 526.2449 |
| 966 | Dimethylsulfamoyl chloride | | 527.2409 |
| 967 | Trifluoromethanesulfonyl chloride | | 552.1876 |
| 968 | Benzenesulfonyl chloride | | 560.2306 |

-continued
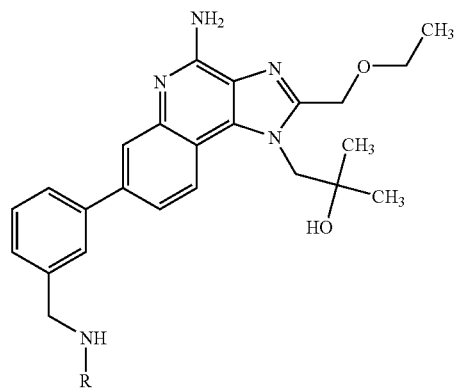
| Example | Reagent | R | Measured Mass (M + H) |
|---|---|---|---|
| 969 | 1-Methylimidazole-4-sulfonyl chloride | (1-methyl-1H-imidazol-4-yl)sulfonyl | 564.2360 |
| 970 | 3-Methylbenzenesulfonyl chloride | (3-methylphenyl)sulfonyl | 574.2455 |
| 971 | 3-Fluorobenzenesulfonyl chloride | (3-fluorophenyl)sulfonyl | 578.2197 |
| 972 | 3-Cyanobenzenesulfonyl chloride | (3-cyanophenyl)sulfonyl | 585.2266 |
| 973 | 3-Methoxybenzenesulfonyl chloride | (3-methoxyphenyl)sulfonyl | 590.2421 |

-continued
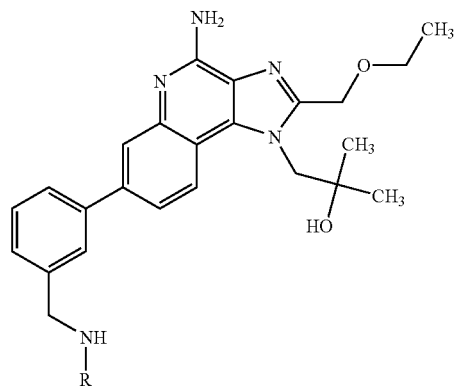
| Example | Reagent | R | Measured Mass (M + H) |
|---|---|---|---|
| 974 | 8-Quinolinesulfonyl chloride | | 611.2408 |
| 975 | Ethyl isocyanate | | 491.2751 |
| 976 | N,N-Dimethylcarbamoyl chloride | | 491.2740 |
| 977 | Benzyl isocyanate | | 553.2889 |
| 978 | m-Tolyl isocyanate | | 553.2903 |
| 979 | 2-Tetrahydrofurfuryl isothiocyanate | | 563.2772 |
| 980 | 2-Oxo-1-imidazolidinecarbonyl chloride | | 532.2656 |

-continued

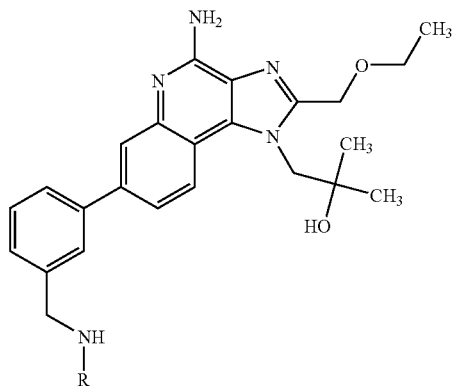

| Example | Reagent | R | Measured Mass (M + H) |
|---|---|---|---|
| 981 | 3-Methoxyphenyl isocyanate | 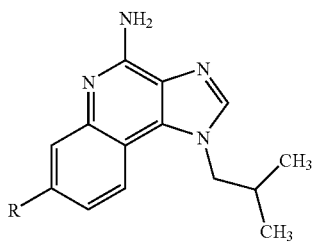 | 569.2869 |

Examples 982-1020

7-Bromo-1-(2-methylpropyl)-1H-imidazo[4,5-c]quinolin-4-amine was coupled with the appropriate boronic acid or boronic acid ester according to the procedure described in Examples 20-65. The products were purified by prep HPLC according to the methods described above. The table below shows the structure of the compound obtained in each example and the observed accurate mass for the isolated trifluoroacetate salt.

Examples 982-1020

| Example | R | Measured Mass (M + H) |
|---|---|---|
| 982 | ![phenyl] | 317.1781 |
| 983 | ![4-pyridyl] | 318.1737 |
| 984 | ![2-thienyl] | 323.1358 |
| 985 | ![3-thienyl] | 323.1355 |
| 986 | ![3-methylphenyl] | 331.1947 |

-continued
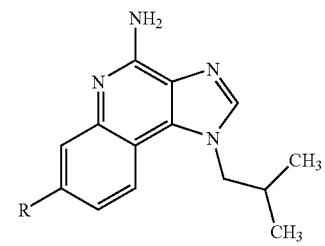
| Example | R | Measured Mass (M + H) |
|---|---|---|
| 987 | 4-methylphenyl (H₃C-C₆H₄-) | 331.1948 |
| 988 | 2-methylphenyl | 331.1940 |
| 989 | 2-hydroxyphenyl | 333.1740 |
| 990 | 3-hydroxyphenyl | 333.1720 |
| 991 | 3-cyanophenyl | 342.1749 |
| 992 | 4-vinylphenyl | 343.1926 |
| 993 | 3,5-dimethyl... (trimethylphenyl) | 345.2101 |
| 994 | 4-ethylphenyl | 345.2080 |
| 995 | 4-methoxyphenyl | 347.1886 |
-continued
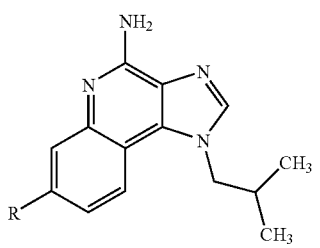
| Example | R | Measured Mass (M + H) |
|---|---|---|
| 996 | 2-chlorophenyl | 351.1398 |
| 997 | 3-chlorophenyl | 351.1399 |
| 998 | 2,4-difluorophenyl | 353.1572 |
| 999 | 2-acetylphenyl | 359.1885 |
| 1000 | 3-acetylphenyl | 359.1897 |
| 1001 | 4-acetylphenyl | 359.1907 |
| 1002 | 3-carbamoylphenyl | 360.1859 |
| 1003 | 2-ethoxyphenyl | 361.2050 |

-continued
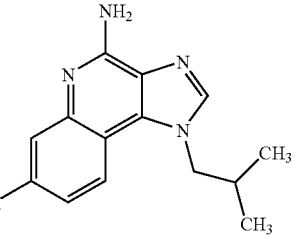
| Example | R | Measured Mass (M + H) |
|---|---|---|
| 1004 | 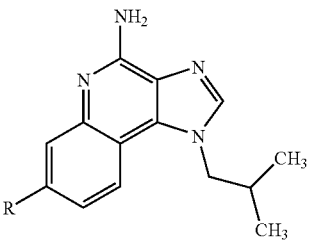 | 416.2472 |
| 1005 | 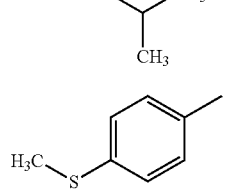 | 363.1660 |
| 1006 | 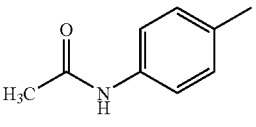 | 375.2195 |
| 1007 | 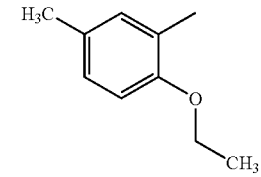 | 375.2171 |
| 1008 | 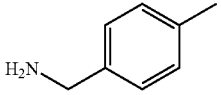 | 377.2009 |
| 1009 | 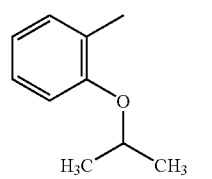 | 377.2013 |
| 1010 | 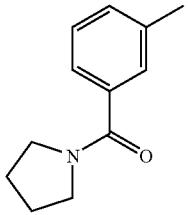 | 410.1660 |
-continued
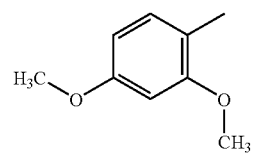
| Example | R | Measured Mass (M + H) |
|---|---|---|
| 1011 | 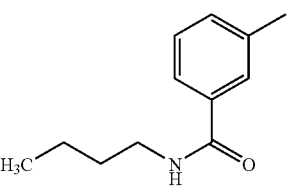 | 410.1689 |
| 1012 | 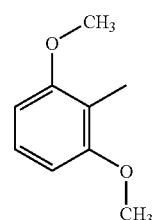 | 374.2006 |
| 1013 | 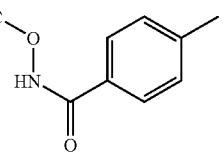 | 346.2040 |
| 1014 | 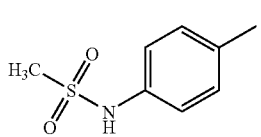 | 414.2326 |
| 1015 | | 416.2472 |
| 1016 | 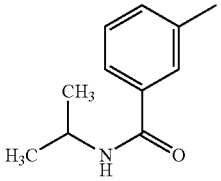 | 390.1950 |
| 1017 | | 402.2324 |

-continued

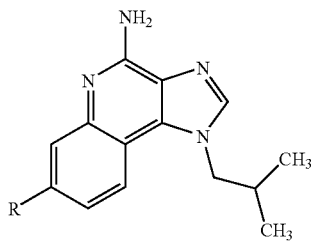

| Example | R | Measured Mass (M + H) |
|---|---|---|
| 1018 | (3-methylphenyl)-C(O)-N-piperidinyl | 428.2479 |
| 1019 | (3-methylphenyl)-C(O)-NH-CH₂CH₂-C≡N | 413.2098 |
| 1020 | (3-methylphenyl)-C(O)-NH-CH₂CH₂-CH₃ (H₃C-CH₂-CH₂-NH-C(O)-) | 402.2303 |

Cytokine Induction in Human Cells

Many compounds of the invention have been found to modulate cytokine biosynthesis by inducing the production of interferon α and/or tumor necrosis factor α when tested using the method described below. Particular examples include but are not limited to the compounds of Examples 1-10, 12, 16, 18-21, 24-31, 43, 44, 51, 54, 55, 63, 66-101, 103-117, 119, 121-203, 205-390, 392-400, 403-407, 409-412, 414-418, 420, 425, 426, 428, 430-440, 442-446, 464-466, 468, 472-474, 476, 493, 494, 508-663, 807-830, 832-837, 839-841, 843, 844, 847-849, 852, 856, 858, 860-916, and 922-955.

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10⁶ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30-0.014 μM). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

TNF-α Inhibition in Mouse Cells

Certain compounds of the invention have been found to modulate cytokine biosynthesis by inhibiting production of tumor necrosis factor α (TNF-α) when tested using the method described below. Particular examples include but are not limited to the compounds of Examples 14, 15, and 481.

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to 3×10⁵ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4\times10^5$ cells/mL in RPMI with 10% FBS. Cell suspension (250 μL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Exemplary Compounds

Certain exemplary compounds, including some of those described above in the Examples, have the following Formula (XLV) wherein $R_1$, $R_2$, and $R_3$ are defined immediately below.

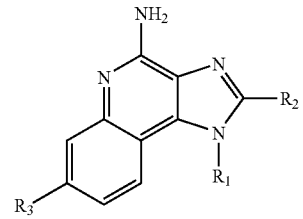

XLV $R_1$ Substituents:

4-methanesulfonylaminobutyl (As Shown with Only a Portion of the Ring System)

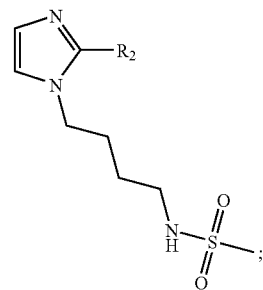

2-hydroxy-2-methylpropyl (As Shown with Only a Portion of the Ring System)

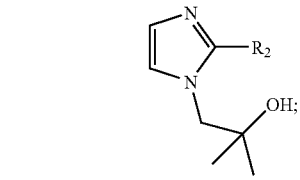

2-methylpropyl (As Shown with Only a Portion of the Ring System)

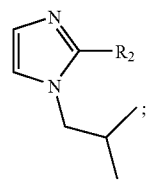

363

2-methanesulfonylamino-2-methylpropyl (As Shown with Only a Portion of the Ring System)

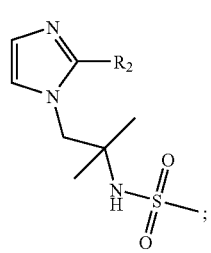

3-methoxypropyl (As Shown with Only a Portion of the Ring System)

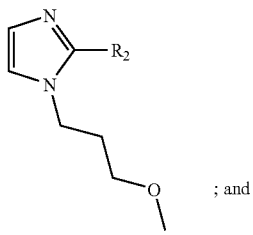
; and

2-[3-(1-methylethyl)ureido]ethyl (As Shown with Only a Portion of the Ring System)

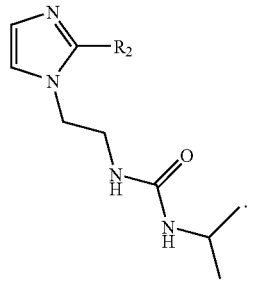

R$_2$ Substituents:

ethoxymethyl (As Shown with Only a Portion of the Ring System)

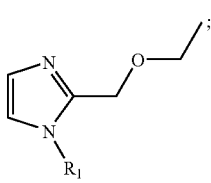

364 methoxymethyl (As Shown with Only a Portion of the Ring System)

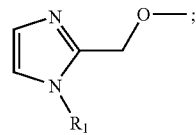

ethyl (As Shown with Only a Portion of the Ring System)

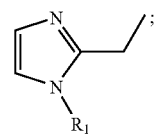

hydrogen (As Shown with Only a Portion of the Ring System)

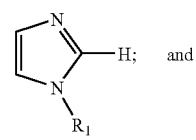 and 2-methoxyethyl (As Shown with Only a Portion of the Ring System)

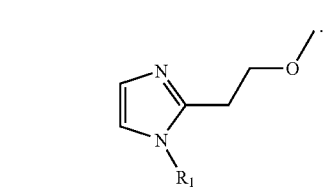

R$_3$ Substituents:

pyridin-3-yl (As Shown Attached to the Ring System)

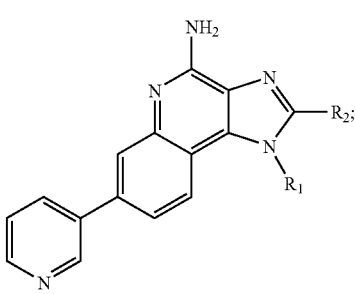

5-hydroxymethylpyridin-3-yl (As Shown Attached to the Ring System)

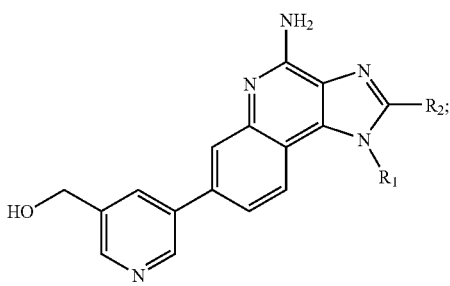

pyridin-4-yl (As Shown Attached to the Ring System)

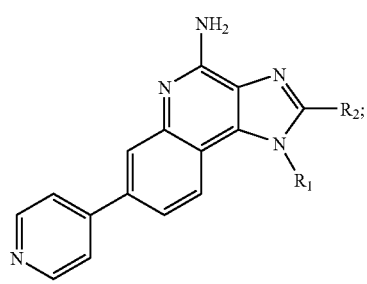

2-ethoxyphenyl (As Shown Attached to the Ring System)

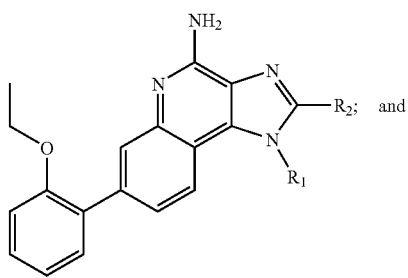

3-(morpholine-4-carbonyl)phenyl (As Shown Attached to the Ring System)

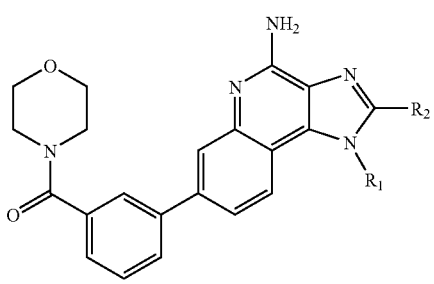

Certain exemplary compounds have the above Formula (XLV) and the following substituents, wherein each line of the table represents a specific compound.

| $R_1$ | $R_2$ | $R_3$ |
|---|---|---|
| 4-methanesulfonylaminobutyl | ethoxymethyl | pyridin-3-yl |
| 4-methanesulfonylaminobutyl | ethoxymethyl | 5-hydroxymethylpyridin-3-yl |
| 4-methanesulfonylaminobutyl | ethoxymethyl | pyridin-4-yl |
| 4-methanesulfonylaminobutyl | ethoxymethyl | 2-ethoxyphenyl |
| 4-methanesulfonylaminobutyl | ethoxymethyl | 3-(morpholine-4-carbonyl)phenyl |
| 4-methanesulfonylaminobutyl | methoxymethyl | pyridin-3-yl |
| 4-methanesulfonylaminobutyl | methoxymethyl | 5-hydroxymethylpyridin-3-yl |
| 4-methanesulfonylaminobutyl | methoxymethyl | pyridin-4-yl |
| 4-methanesulfonylaminobutyl | methoxymethyl | 2-ethoxyphenyl |
| 4-methanesulfonylaminobutyl | methoxymethyl | 3-(morpholine-4-carbonyl)phenyl |
| 4-methanesulfonylaminobutyl | ethyl | pyridin-3-yl |
| 4-methanesulfonylaminobutyl | ethyl | 5-hydroxymethylpyridin-3-yl |
| 4-methanesulfonylaminobutyl | ethyl | pyridin-4-yl |
| 4-methanesulfonylaminobutyl | ethyl | 2-ethoxyphenyl |
| 4-methanesulfonylaminobutyl | ethyl | 3-(morpholine-4-carbonyl)phenyl |
| 4-methanesulfonylaminobutyl | hydrogen | pyridin-3-yl |
| 4-methanesulfonylaminobutyl | hydrogen | 5-hydroxymethylpyridin-3-yl |
| 4-methanesulfonylaminobutyl | hydrogen | pyridin-4-yl |
| 4-methanesulfonylaminobutyl | hydrogen | 2-ethoxyphenyl |
| 4-methanesulfonylaminobutyl | hydrogen | 3-(morpholine-4-carbonyl)phenyl |
| 4-methanesulfonylaminobutyl | 2-methoxyethyl | pyridin-3-yl |
| 4-methanesulfonylaminobutyl | 2-methoxyethyl | 5-hydroxymethylpyridin-3-yl |
| 4-methanesulfonylaminobutyl | 2-methoxyethyl | pyridin-4-yl |
| 4-methanesulfonylaminobutyl | 2-methoxyethyl | 2-ethoxyphenyl |
| 4-methanesulfonylaminobutyl | 2-methoxyethyl | 3-(morpholine-4-carbonyl)phenyl |
| 2-hydroxy-2-methylpropyl | ethoxymethyl | pyridin-3-yl |
| 2-hydroxy-2-methylpropyl | ethoxymethyl | 5-hydroxymethylpyridin-3-yl |
| 2-hydroxy-2-methylpropyl | ethoxymethyl | pyridin-4-yl |
| 2-hydroxy-2-methylpropyl | ethoxymethyl | 2-ethoxyphenyl |
| 2-hydroxy-2-methylpropyl | ethoxymethyl | 3-(morpholine-4-carbonyl)phenyl |
| 2-hydroxy-2-methylpropyl | methoxymethyl | pyridin-3-yl |
| 2-hydroxy-2-methylpropyl | methoxymethyl | 5-hydroxymethylpyridin-3-yl |
| 2-hydroxy-2-methylpropyl | methoxymethyl | pyridin-4-yl |
| 2-hydroxy-2-methylpropyl | methoxymethyl | 2-ethoxyphenyl |
| 2-hydroxy-2-methylpropyl | methoxymethyl | 3-(morpholine-4-carbonyl)phenyl |
| 2-hydroxy-2-methylpropyl | ethyl | pyridin-3-yl |
| 2-hydroxy-2-methylpropyl | ethyl | 5-hydroxymethylpyridin-3-yl |
| 2-hydroxy-2-methylpropyl | ethyl | pyridin-4-yl |
| 2-hydroxy-2-methylpropyl | ethyl | 2-ethoxyphenyl |
| 2-hydroxy-2-methylpropyl | ethyl | 3-(morpholine-4-carbonyl)phenyl |
| 2-hydroxy-2-methylpropyl | hydrogen | pyridin-3-yl |
| 2-hydroxy-2-methylpropyl | hydrogen | 5-hydroxymethylpyridin-3-yl |
| 2-hydroxy-2-methylpropyl | hydrogen | pyridin-4-yl |
| 2-hydroxy-2-methylpropyl | hydrogen | 2-ethoxyphenyl |
| 2-hydroxy-2-methylpropyl | hydrogen | 3-(morpholine-4-carbonyl)phenyl |
| 2-hydroxy-2-methylpropyl | 2-methoxyethyl | pyridin-3-yl |
| 2-hydroxy-2-methylpropyl | 2-methoxyethyl | 5-hydroxymethylpyridin-3-yl |
| 2-hydroxy-2-methylpropyl | 2-methoxyethyl | pyridin-4-yl |
| 2-hydroxy-2-methylpropyl | 2-methoxyethyl | 2-ethoxyphenyl |
| 2-hydroxy-2-methylpropyl | 2-methoxyethyl | 3-(morpholine-4-carbonyl)phenyl |
| 2-methylpropyl | ethoxymethyl | pyridin-3-yl |
| 2-methylpropyl | ethoxymethyl | 5-hydroxymethylpyridin-3-yl |
| 2-methylpropyl | ethoxymethyl | pyridin-4-yl |
| 2-methylpropyl | ethoxymethyl | 2-ethoxyphenyl |
| 2-methylpropyl | ethoxymethyl | 3-(morpholine-4-carbonyl)phenyl |

-continued

| R₁ | R₂ | R₃ |
|---|---|---|
| 2-methylpropyl | methoxymethyl | pyridin-3-yl |
| 2-methylpropyl | methoxymethyl | 5-hydroxymethylpyridin-3-yl |
| 2-methylpropyl | methoxymethyl | pyridin-4-yl |
| 2-methylpropyl | methoxymethyl | 2-ethoxyphenyl |
| 2-methylpropyl | methoxymethyl | 3-(morpholine-4-carbonyl)phenyl |
| 2-methylpropyl | ethyl | pyridin-3-yl |
| 2-methylpropyl | ethyl | 5-hydroxymethylpyridin-3-yl |
| 2-methylpropyl | ethyl | pyridin-4-yl |
| 2-methylpropyl | ethyl | 2-ethoxyphenyl |
| 2-methylpropyl | ethyl | 3-(morpholine-4-carbonyl)phenyl |
| 2-methylpropyl | hydrogen | pyridin-3-yl |
| 2-methylpropyl | hydrogen | 5-hydroxymethylpyridin-3-yl |
| 2-methylpropyl | hydrogen | pyridin-4-yl |
| 2-methylpropyl | hydrogen | 2-ethoxyphenyl |
| 2-methylpropyl | hydrogen | 3-(morpholine-4-carbonyl)phenyl |
| 2-methylpropyl | 2-methoxyethyl | pyridin-3-yl |
| 2-methylpropyl | 2-methoxyethyl | 5-hydroxymethylpyridin-3-yl |
| 2-methylpropyl | 2-methoxyethyl | pyridin-4-yl |
| 2-methylpropyl | 2-methoxyethyl | 2-ethoxyphenyl |
| 2-methylpropyl | 2-methoxyethyl | 3-(morpholine-4-carbonyl)phenyl |
| 2-methanesulfonylamino-2-methylpropyl | ethoxymethyl | pyridin-3-yl |
| 2-methanesulfonylamino-2-methylpropyl | ethoxymethyl | 5-hydroxymethylpyridin-3-yl |
| 2-methanesulfonylamino-2-methylpropyl | ethoxymethyl | pyridin-4-yl |
| 2-methanesulfonylamino-2-methylpropyl | ethoxymethyl | 2-ethoxyphenyl |
| 2-methanesulfonylamino-2-methylpropyl | ethoxymethyl | 3-(morpholine-4-carbonyl)phenyl |
| 2-methanesulfonylamino-2-methylpropyl | methoxymethyl | pyridin-3-yl |
| 2-methanesulfonylamino-2-methylpropyl | methoxymethyl | 5-hydroxymethylpyridin-3-yl |
| 2-methanesulfonylamino-2-methylpropyl | methoxymethyl | pyridin-4-yl |
| 2-methanesulfonylamino-2-methylpropyl | methoxymethyl | 2-ethoxyphenyl |
| 2-methanesulfonylamino-2-methylpropyl | methoxymethyl | 3-(morpholine-4-carbonyl)phenyl |
| 2-methanesulfonylamino-2-methylpropyl | ethyl | pyridin-3-yl |
| 2-methanesulfonylamino-2-methylpropyl | ethyl | 5-hydroxymethylpyridin-3-yl |
| 2-methanesulfonylamino-2-methylpropyl | ethyl | pyridin-4-yl |
| 2-methanesulfonylamino-2-methylpropyl | ethyl | 2-ethoxyphenyl |
| 2-methanesulfonylamino-2-methylpropyl | ethyl | 3-(morpholine-4-carbonyl)phenyl |
| 2-methanesulfonylamino-2-methylpropyl | hydrogen | pyridin-3-yl |
| 2-methanesulfonylamino-2-methylpropyl | hydrogen | 5-hydroxymethylpyridin-3-yl |
| 2-methanesulfonylamino-2-methylpropyl | hydrogen | pyridin-4-yl |
| 2-methanesulfonylamino-2-methylpropyl | hydrogen | 2-ethoxyphenyl |
| 2-methanesulfonylamino-2-methylpropyl | hydrogen | 3-(morpholine-4-carbonyl)phenyl |
| 2-methanesulfonylamino-2-methylpropyl | 2-methoxyethyl | pyridin-3-yl |
| 2-methanesulfonylamino-2-methylpropyl | 2-methoxyethyl | 5-hydroxymethylpyridin-3-yl |
| 2-methanesulfonylamino-2-methylpropyl | 2-methoxyethyl | pyridin-4-yl |
| 2-methanesulfonylamino-2-methylpropyl | 2-methoxyethyl | 2-ethoxyphenyl |

-continued

| R₁ | R₂ | R₃ |
|---|---|---|
| 2-methanesulfonylamino-2-methylpropyl | 2-methoxyethyl | 3-(morpholine-4-carbonyl)phenyl |
| 3-methoxypropyl | ethoxymethyl | pyridin-3-yl |
| 3-methoxypropyl | ethoxymethyl | 5-hydroxymethylpyridin-3-yl |
| 3-methoxypropyl | ethoxymethyl | pyridin-4-yl |
| 3-methoxypropyl | ethoxymethyl | 2-ethoxyphenyl |
| 3-methoxypropyl | ethoxymethyl | 3-(morpholine-4-carbonyl)phenyl |
| 3-methoxypropyl | methoxymethyl | pyridin-3-yl |
| 3-methoxypropyl | methoxymethyl | 5-hydroxymethylpyridin-3-yl |
| 3-methoxypropyl | methoxymethyl | pyridin-4-yl |
| 3-methoxypropyl | methoxymethyl | 2-ethoxyphenyl |
| 3-methoxypropyl | methoxymethyl | 3-(morpholine-4-carbonyl)phenyl |
| 3-methoxypropyl | ethyl | pyridin-3-yl |
| 3-methoxypropyl | ethyl | 5-hydroxymethylpyridin-3-yl |
| 3-methoxypropyl | ethyl | pyridin-4-yl |
| 3-methoxypropyl | ethyl | 2-ethoxyphenyl |
| 3-methoxypropyl | ethyl | 3-(morpholine-4-carbonyl)phenyl |
| 3-methoxypropyl | hydrogen | pyridin-3-yl |
| 3-methoxypropyl | hydrogen | 5-hydroxymethylpyridin-3-yl |
| 3-methoxypropyl | hydrogen | pyridin-4-yl |
| 3-methoxypropyl | hydrogen | 2-ethoxyphenyl |
| 3-methoxypropyl | hydrogen | 3-(morpholine-4-carbonyl)phenyl |
| 3-methoxypropyl | 2-methoxyethyl | pyridin-3-yl |
| 3-methoxypropyl | 2-methoxyethyl | 5-hydroxymethylpyridin-3-yl |
| 3-methoxypropyl | 2-methoxyethyl | pyridin-4-yl |
| 3-methoxypropyl | 2-methoxyethyl | 2-ethoxyphenyl |
| 3-methoxypropyl | 2-methoxyethyl | 3-(morpholine-4-carbonyl)phenyl |
| 2-[3-(1-methylethyl)ureido]ethyl | ethoxymethyl | pyridin-3-yl |
| 2-[3-(1-methylethyl)ureido]ethyl | ethoxymethyl | 5-hydroxymethylpyridin-3-yl |
| 2-[3-(1-methylethyl)ureido]ethyl | ethoxymethyl | pyridin-4-yl |
| 2-[3-(1-methylethyl)ureido]ethyl | ethoxymethyl | 2-ethoxyphenyl |
| 2-[3-(1-methylethyl)ureido]ethyl | ethoxymethyl | 3-(morpholine-4-carbonyl)phenyl |
| 2-[3-(1-methylethyl)ureido]ethyl | methoxymethyl | pyridin-3-yl |
| 2-[3-(1-methylethyl)ureido]ethyl | methoxymethyl | 5-hydroxymethylpyridin-3-yl |
| 2-[3-(1-methylethyl)ureido]ethyl | methoxymethyl | pyridin-4-yl |
| 2-[3-(1-methylethyl)ureido]ethyl | methoxymethyl | 2-ethoxyphenyl |
| 2-[3-(1-methylethyl)ureido]ethyl | methoxymethyl | 3-(morpholine-4-carbonyl)phenyl |
| 2-[3-(1-methylethyl)ureido]ethyl | ethyl | pyridin-3-yl |
| 2-[3-(1-methylethyl)ureido]ethyl | ethyl | 5-hydroxymethylpyridin-3-yl |
| 2-[3-(1-methylethyl)ureido]ethyl | ethyl | pyridin-4-yl |
| 2-[3-(1-methylethyl)ureido]ethyl | ethyl | 2-ethoxyphenyl |
| 2-[3-(1-methylethyl)ureido]ethyl | ethyl | 3-(morpholine-4-carbonyl)phenyl |
| 2-[3-(1-methylethyl)ureido]ethyl | hydrogen | pyridin-3-yl |
| 2-[3-(1-methylethyl)ureido]ethyl | hydrogen | 5-hydroxymethylpyridin-3-yl |
| 2-[3-(1-methylethyl)ureido]ethyl | hydrogen | pyridin-4-yl |
| 2-[3-(1-methylethyl)ureido]ethyl | hydrogen | 2-ethoxyphenyl |
| 2-[3-(1-methylethyl)ureido]ethyl | hydrogen | 3-(morpholine-4-carbonyl)phenyl |

-continued

| R₁ | R₂ | R₃ |
|---|---|---|
| 2-[3-(1-methylethyl)ureido]ethyl | 2-methoxyethyl | pyridin-3-yl |
| 2-[3-(1-methylethyl)ureido]ethyl | 2-methoxyethyl | 5-hydroxymethylpyridin-3-yl |
| 2-[3-(1-methylethyl)ureido]ethyl | 2-methoxyethyl | pyridin-4-yl |
| 2-[3-(1-methylethyl)ureido]ethyl | 2-methoxyethyl | 2-ethoxyphenyl |
| 2-[3-(1-methylethyl)ureido]ethyl | 2-methoxyethyl | 3-(morpholine-4-carbonyl)phenyl |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of formula (III):

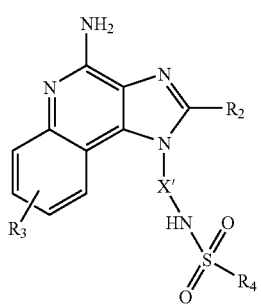

III wherein:
$R_2$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$,
—Z—Ar'—X—Y—$R_4$,
—Z—Ar'—$R_5$, and
—Z—Ar'—X—$R_5$;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

X' is $C_{2-8}$ alkylene;

each Y is independently selected from the group consisting of:

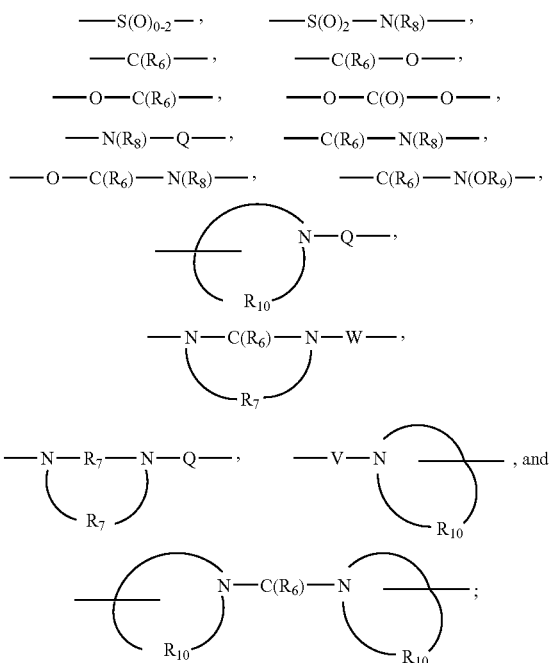

Z is selected from the group consisting of a bond, alkylene, alkenylene, and alkynylene;

each $R_4$ is independently selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

each $R_5$ is independently selected from the group consisting of:

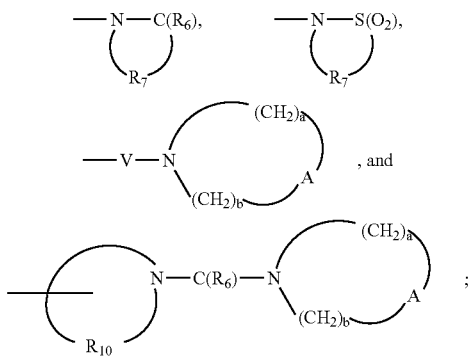

each $R_6$ is independently selected from the group consisting of =O and =S;
each $R_7$ is independently $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
each $R_{10}$ is independently $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.

2. The compound or salt of claim 1 wherein X' is —CH$_2$—C(CH$_3$)$_2$—.

3. The compound or salt of claim 1 wherein $R_2$ is selected from the group consisting of hydrogen, $C_{1-4}$ alkyl, and $C_{1-4}$ alkyl-O—$C_{1-4}$ alkylenyl.

4. The compound or salt of claim 1 wherein $R_4$ is selected from the group consisting of alkyl, aryl, and heteroaryl.

5. The compound or salt of claim 1 wherein $R_3$ is phenyl or pyridyl, either of which can be unsubstituted or can be substituted by one or more substituents selected from the group consisting of halogen, alkyl, hydroxy, hydroxyalkyl, alkoxy, alkylsulfonylamino, arylsulfonylamino, alkylcarbonylamino, arylcarbonylamino, alkylsulfonylaminoalkylenyl, arylsulfonylaminoalkylenyl, alkylcarbonylaminoalkylenyl, and arylcarbonylaminoalkylenyl.

6. A pharmaceutical composition comprising a therapeutically effective amount of a compound or salt of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,598,382 B2 | Page 1 of 1 |
| APPLICATION NO. | : 11/275553 | |
| DATED | : October 6, 2009 | |
| INVENTOR(S) | : Hays et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 135 days Delete the phrase "by 135 days" and insert -- by 401 days --

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,598,382 B2 Page 1 of 1
APPLICATION NO. : 11/275553
DATED : October 6, 2009
INVENTOR(S) : Hays et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 667 days.

Signed and Sealed this

Twenty-eighth Day of September, 2010

David J. Kappos
*Director of the United States Patent and Trademark Office*